(12) United States Patent
Gjesdal et al.

(10) Patent No.: US 9,046,589 B2
(45) Date of Patent: Jun. 2, 2015

(54) DYNAMIC MR IMAGING OF PATIENTS WITH BREAST CANCER—ESTABLISHMENT AND COMPARISON OF DIFFERENT ANALYTICAL METHODS FOR TISSUE PERFUSION AND CAPILLARY PERMEABILITY

(71) Applicants: Kjell-Inge Gjesdal, Ålesund (NO); Endre Grøvik, Ikomnes (NO)

(72) Inventors: Kjell-Inge Gjesdal, Ålesund (NO); Endre Grøvik, Ikomnes (NO)

(73) Assignee: SUNNMORE MR-KLINIKK AS, Alesund (NO)

( * ) Notice: Subject to any disclaimer, the term of this patent is extended or adjusted under 35 U.S.C. 154(b) by 0 days.

(21) Appl. No.: 14/068,734

(22) Filed: Oct. 31, 2013

(65) Prior Publication Data
US 2014/0107469 A1    Apr. 17, 2014

Related U.S. Application Data

(63) Continuation of application No. 13/941,652, filed on Jul. 15, 2013, now abandoned, which is a continuation of application No. 13/900,266, filed on May 22, 2013, now abandoned, which is a continuation-in-part of application No. PCT/NO2011/000330, filed on Nov. 22, 2011.

(30) Foreign Application Priority Data

Nov. 22, 2010   (NO) .................................. 201011638

(51) Int. Cl.
  *G06K 9/00*   (2006.01)
  *G01R 33/56*   (2006.01)
  (Continued)

(52) U.S. Cl.
  CPC ............ *G01R 33/5602* (2013.01); *A61B 5/055* (2013.01); *A61B 5/4312* (2013.01);
  (Continued)

(58) Field of Classification Search
  CPC ................. G01R 33/5601; G06T 2207/10088; A61K 49/06; A61M 5/007
  See application file for complete search history.

(56) References Cited

U.S. PATENT DOCUMENTS

2010/0296714 A1*  11/2010  Schmainda et al. .......... 382/131

FOREIGN PATENT DOCUMENTS

| WO | WO 2008/144539 A1 | 11/2008 |
| WO | WO 2008/147921 A1 | 12/2008 |
| WO | WO 2009/135923 A1 | 11/2009 |

OTHER PUBLICATIONS

Schuman et al., A demonstration of the feasibility of DSC in evaluating breast tumor blood volume, 2007, Proc. Intl. Soc. Mag. Reson. Med., vol. 15, p. 2947.*

(Continued)

*Primary Examiner* — Elmer Chao
(74) *Attorney, Agent, or Firm* — Finnegan, Henderson, Farabow, Garrett & Dunner LLP

(57) ABSTRACT

The present invention encompasses methods, apparatus, and computer based systems for identifying benign and malignant tumors in tissues such as soft tissues and particularly breast tissue using dynamic contrast-enhanced magnetic resonance imagining (DCE-MRI) and dynamic susceptibility contrast-enhanced magnetic resonance (DSC) imagining of the tumors. Some embodiments encompass the use of two dynamic MRI pulse sequences in intercalating mode during parenteral administration of an MR contrast substance, wherein one of said pulse sequences is optimized for spatial information and the other pulse sequence is adjusted for high temporal solution, the high-temporal dissolved sequence further comprising a double echo-collection sensitive towards both DCE and DSC for generating a number of different biomarker data such as pharmacokinetic biomarker data, descriptive DCE biomarkers and descriptive DSC biomarkers, and subsequently normalizing and comparing said data with corresponding data from corresponding benign and malign tumors, respectively.

10 Claims, 54 Drawing Sheets

(51) Int. Cl.
  A61B 5/055   (2006.01)
  A61B 5/00    (2006.01)
  G01R 33/563  (2006.01)
  G01R 33/28   (2006.01)
  G01R 33/48   (2006.01)
(52) U.S. Cl.
  CPC ...... *G01R33/5601* (2013.01); *G01R 33/56366* (2013.01); *A61B 5/742* (2013.01); *G01R 33/281* (2013.01); *G01R 33/4828* (2013.01); *G01R 33/5608* (2013.01)

(56) References Cited

OTHER PUBLICATIONS

PCT Notification of Transmittal of the International Search Report and the Written Opinion of the International Searching Authority, or the Declaration, mailed Apr. 27, 2012, International Application No. PCT/NO2011/000330.
Gjesdal, E. et al., "Preliminary Results using a split dynamic time series for DCE MR-mamography," Proceedings of the International Society for Magnetic Resonance in Medicine, 18$^{th}$ Scientific Meeting and Exhibition, Stockholm, Sweden, May 1-7, 2010, Apr. 17, 2010, p. 2478, XP55024768, as cited in PCT International Search Report for International Application No. PCT/NO2011/000330.
Grovik, E. et al., "DSC MR-mammography: Tumor characterization using quantitative R2* analysis," Proceedings of the International Society for Magnetic Resonance in Medicine, 18$^{th}$ Scientific Meeting and Exhibition, Stockholm, Sweden, May 1-7, 2010, Apr. 17, 2010, p. 2485, XP55024786, as cited in PCT International Search Report for International Application No. PCT/NO2011/000330.
Grovik, E. et al., "Influence of spatial heterogeneity on the diagnostic accuracy of DCE-MRI in breast tumor characterization," Proceedings of the International Society for Magnetic Resonance in Medicine, 18$^{th}$ Scientific Meeting and Exhibition, Stockholm, Sweden, May 1-7, 2010, Apr. 17, 2010, p. 2483, XP55024784, as cited in PCT International Search Report for International Application No. PCT/NO2011/000330.
Grovik, E. et al., "Improved diagnostic accuracy in DCE MR-mammography by normalization of kinetic parameters following AIF deconvolution," Proceedings of the International Society for Magnetic Resonance in Medicine, 18$^{th}$ Scientific Meeting and Exhibition, Stockholm, Sweden, May 1-7, 2010, Apr. 17, 2010, XP55024766, as cited in PCT International Search Report for International Application No. PCT/NO2011/000330.
Sourbon, S. et al., "Bolus-Tracking MRI with a Simultaneous $T_1$- and $T_2$*- Measurement", Magnetic, *Resonance in Medicine*, 62: 672-681, 2009.
Bloch, F. et al., "Nuclear induction," *Phys Rev*, vol. 70, pp. 460-474, 1946.
Purcell, E.M. et al., "Resonance absorption by nuclear magnetic moments in a solid," *Phys Rev*, vol. 69, p. 37, 1946.
Proctor, W.G., et al., "The dependence of a nuclear magnetic resonance frequency upon chemical Compound," *Phy. Rev*, vol. 77, p. 717, 1950.
Damadian, R., "Tumor detection by nuclear magnetic resonance," *Science*, vol. 171, pp. 1151-1153, 1971.
Garroway. A.N, et al., "Image formation in NMR by a selective irradiative process," *J Phys. C*, vol. 7, pp. L457-L462, 1974.
Kumar, D et al., "NMR Fourier Zeugmatography," *J Magn Res*, vol. 18, pp. 69-83, 1975.
Mansfield, P., "Multi-planar image formation using NMR spin echoes," *J Phys C*, Solid state phys., vol. 10, pp. L55-L58, 1977.
Vlaardingerbroek, M., et al., *Magnetic Resonance Imaging*, (Table of Contents), 2nd ed., Berlin, Springer 1999.
Haacke, E.M., *Magnetic resonance imaging: Physical principles and sequence design*, (Table of Contents), New York, Wiley, 1999.
Bjørnerud, A., *The physics of magnetic resonance imaging*, Kompendium for FYS-KJM 4740, Universitetet i Oslo, 2008.

Padhani, A. R. et al., "Dynamic contrast-enhanced MRI studies in human tumours," *Br J Radial*, vol. 72, pp. 427-431, 1999.
Pacihani A. R. et al. "Dynamic contrast-enhanced MRI in clinical oncology. Current status and future directions," *J Magn Res Imaging*, 16, p. 407-422, 2002.
Kuhl, C. K. et al., "Breast neoplasms: T2* susceptibliity-contrast, first-pass perfusion MR imaging," *Radiology*, vol. 202, pp. 87-95, 1997.
Kuhl, C. K. et al., "Do T2-weighted pulse sequences help with the differential diagnosis of enhancing lesions in dynamic breast MRI?," *J Magn Res Imaging*, vol. 9, pp. 187-196, 1999.
Kuhl, C. K. et al., "Dynamic breast MR imaging: Are signal intensity time course data useful for differential diagnosis of enhancing lesions?," *Radiology*, vol. 211, pp. 101-110, 1999.
Orel, S. G. et al., "MR imaging of the breast for the detection, diagnosis, and staging of breast cancer," *Radiology*, vol. 220, pp. 13-30, 2001.
Kvistad et al., "Differentiating benign and malignant breast lesions with T2*-weighted first pass perfusion imaging," *Acta Radiology*, vol. 40, pp. 45-51, 1999.
Knopp at al., "Pathopnysiologic basis of contrast enhancement in breast tumors," *J Magn Res*, vol. 10, pp. 260-266, 1999.
Bhujwalla, Z. M. et al., "Tumor angiogenesis, vascularization, and contrast-enhanced magnetic resonance imaging," *Top Magn Res Imaging*, vol. 10(2), pp. 92-103, 1999.
Brix, G. et al., "Pharmacokinetic parameters in CNS Gd-DTPA enhanced R imaging," *J Comp Assist Tomogr*, vol. 15, pp. 621-528, 1991.
Buckley, D. L. et al., "Quantitative analysis of multi-slice Gd-DTPA enhanced dynamic MR images using an automated simplex minimization procedure," *Magn Res Med*, vol. 32, pp. 646-651, 1994.
Hoffmann, U. et al., Pharmacokinetic mapping of the breast: a new method of dynamic MR mammography, Magn Res Med, vol. 33(4), pp. 506-514, 1995.
Villringer, A. et al., Dynamic imaging with lanthanide chelstes in normal brain: contrast due to magnetic-susceptibility effects, *Magn Res Med*, vol. 6, pp. 164-174, 1988.
Kassner, A. et al., "Abnormalities of the contrast re-circulation phase in cerebral tumors demonstrated using dynamic susceptibility contrast-enhanced imaging: a possible marker of vascular tortuosity," *J Magn Res Imaging*, vol. 11, pp. 103-113, 2000.
Tofts, P. S. et al., "Estimating kinetic parameters from dynamic contrast-enhanced $T_1$-weighted MRI of a diffusable tracer: standardized quantities and symbols," *J Magn Res Imaging*, vol. 10, pp. 223-232, 1999.
Tofts, P. S. et al., G, "Measurement of the blood brain barrier permeability and leakage space using dynamic MR imaging. 1. Fundamental concepts," *Magn Res Med*, vol. 17, pp. 357-367, 1991.
Buckley, D. L, "Uncertainty in the analysis of tracer kinetics using dynamic contrast-enhanced $T_1$-weighted MRI," *Magn Red Med*, vol. 47, pp. 601-606, 2002.
Bjørnerud, A., "Analyse av diagnostisk, dynamisk bildeinformasjon: Tracer-kinetikk," Forelesningsnotater for FYS-4780, Universitetet i Oslo, 2009.
Jackson, A. et al., "Dynamic contrast-enhanced magnetic resonance imaging in oncology," *Medical Radiology: Diagnostic Imaging and Radiation Oncology*, (Table of Contents), Springer-Verlag, 2005.
Reeder, S. B, et al., "Clinical Application of MR diffusion and perfusion imaging," *Magnetic resonance imaging clinics*, vol. 12, No. 2, Pennsylvania, Saunders, 2009.
Evelhoch, J. L., "Key factors in the acquisition of contrast kinetic data for oncology," *J Magn Res Imaging*, vol. 10, pp. 254-259, 1999.
Moate, P. J. et al., "A modified logistic model to describe gadolinium kinetics in breast tumors," *J Magn Res Imaging*, vol. 22, pp. 467-473, 2004.
Szabo, B. K. et al., "Dynamic MR Imaging of the Breast: Analysis of Kinetic and Morphologic Diagnostic Criteria," *Acta Radiology*, vol. 44, pp. 379-386, 2003.
Kaiser, W. A, et al., "MR imaging of the breast: fast imaging sequences with and without Gd-DTPA. Preliminary observations," *Radiology*, vol. 170, pp. 681-686, 1989.

(56) References Cited

OTHER PUBLICATIONS

Buadu, L. D. et al., "Breast Lesions: Correlation of Contrast Medium Enhancement Patterns on MR Images with Histopathologic Findings and Tumor Aniogenesis," *Radiology*, vol. 200, pp. 639-649, 1996.

Ikeda, O. et al., "Characterization of Breast Masses by Dynamic Enhanced MR Imaging. A Logistic Regression Analysis," *Acta Radiology*, vol. 40, pp. 585-592, 1999.

Liao, Y. P. et al., "Assessment of Physiological Parameters Estimated by DCE MRI with Delayed or Dispersed Anterial Input Function," *Proc. Intl. Soc. Mag. Reson. Med.*, vol. 15, pp. 1435, 2007.

Fisher R. A., "Theory of Statistical Estimation," *Mathematical Proceedings of Cambridge Philisophical Society*, vol. 22, pp. 700-725, 1925.

Green, D. M. et al., "Signal Detection Theory and Psychophysics," Wiley & Sons, New York, 1966.

Shiraishi, J. et al., "Experimental Design and Data Analysis in Receiver Operating Characteristic Studies: Lessons learned from Reports in Radiology from 1997 to 2006," *Radiology*, vol. 253, pp. 822-830, 2009.L.

Gatsonis, C. A., "Reciever Operating Characteristic Analysis from the Evaluation of Diagnosis and Prediction," *Radiology*, vol. 253, pp. 593-596, 2009.

Fawcett, T., "An introduction to ROC analysis," *Pattern Recognition Letters*, vol. 27, pp. 861-874, 2006.

Bølviken, E. et al., *Lectures in applied statistics*, Kompendium for STK4900, Universitetet i Oslo, 1994.

Borgan, Ø., Lecture notes in STK4900 (programs 1-11), Forelesningsnotater for STK4900, Universitetet i Oslo, 2009.

Altman, D. G., *Practical Statistics for Medical Research*, First edition, London, Chapman & Hall, 1991.

Brix, G. et al., "Microcirculation and Microvasculature in Breast Tumors: Pharmacokinetic Analysis of Dynamic MR Image Series," *Magnetic Resonance in Medicine*, vol. 52, pp. 420-429, 2004.

Miyati, T. et al., Dual dynamic Contrast-Enhanced MR Imaging, *JMRI*, vol. 7, pp. 230-235, 1997.

Barbier, E. L. et al., "A model of the Dual Effect of Gadopentetate Dimeglumine on Dynamic Brain MR Images," J Magn Res Imaging, vol. 10, pp. 242-253, 1999.

Moon, M. et al., "Dynamic Contrast-Enhanced Breast MR Imaging," *Magn Reson Imaging Clin N Am*, vol. 17, pp. 351-362, 2009.

O'Connor, J. P. B. et al., "DCE-MRI biomarkers in the clinical evaluation of antiangiogenic and vascular disrupting agents," *British Journal of Cancer*, vol. 96, pp. 189-195, 2007.

Leach, M. O. et al., "The assessment of antiangiogenic and antivascular therapies in early-stage clinical trials using magnetic resonance imaging: issues and recommendations," *British Journal of Cancer*, vol. 92, pp. 1599-1610, 2005.

Walker-Samuel, S. et al., "Evaluation of response to treatment using dce-mri: the relationship between initial area under the gadolunium curve (IAUGC) and quantitative pharmacokinetic analysis," Physics in Medicine and Biology, vol. 51, pp. 3593-3602, 2006.

Kvistad, K. A. et al., Breast Lesions: Evaluation with Dynamic contrast-enhanced T1-weighted MR Imaging and with T2*-weighted First-Pass Perfusion MR Imaging. *Radiology*, vol. 216, pp. 545-553, 2000.

Mussurakis, S. et al., "Dynamic MR Imaging of the Breast Combined with Analysis of Contrast Agent Kinetics in the Differentiation of Primary Breast Tumours," *Clinical Radiology*, vol. 52, pp. 516-526, 1997.

Furman-Haran, E. et al., "Magnetic Resonance Imaging Reveals Functional Diversity of the Vasculature in Benign and Malignant Breast Lesions." *American Cancer Society*, vol. 104, pp. 708-718, 2005.

Yankeelov, T. E. et al., "Quantitative pharmacokinetic analysis of DCE-MRI data without an arterial input function: a reference region model," *Magn Res Imaging*, vol. 23, pp. 519-529, 2005.

Pintaske, J. et al., "Relaxivity of Gadopentelate Dimeglumine (Magnevist), Gadobutrol (Gadovist), and Gadobenate Dimeglumine (MultiHance) in Human Blood Plasma at 0.2, 1.5 and 3 Tesla," *Investigative Radiology*, vol. 41, pp. 213-221, 2006.

Haacke, E. M. et al., "Fast NMR Imaging: Techniques and Clinical Applications," *AJR*, vol. 155, pp. 951-964, 1990.

Haase, A. et al., "FLASH Imaging. Rapid NMR Imaging Using Low Flip-Angle Pulses," *Journal of Magnetic Resonance*, vol. 67, pp. 258-266, 1986.

Emblem, K. E., "Glioma Grading by Using Histogram Analysis of Blood Volume Heterogeneity from MR-derived Cererbral Blood Volume Maps," *Radiology*, vol. 247, pp. 808-817, 2008.

World Health Organization, International Agency for Research on Cancer, World Cancer Report 2008, edited by Peter Boyle and Bernard Levin, 2008.

"Cancer in Norway 2008: Cancer incidence, mortality, survival and prevalence in Norway," *Cancer Registry of Norway*, Institute of Population-based Cancer Research, 2008.

Folkman, J., "Tumor Angiogenesis: Therapeutic Implications," *N Engl J Med*, vol. 285, pp. 1182-1186, 1971.

Kuhl, C. K. et al., "Dynamic Bilateral Contrast-enhanced MR Imaging of the Breast: Trade-off between Spatial and Termporal Resolution," *Radiology*, vol. 236, pp. 789-800, 2005.

Veltman, J et al., "Contrast-enhanced magnetic resonance imaging of the breast: the value of pharmacokinetic parameters derived from fast dynamic imaging during initial enhancemetn in classifying lesions," *Eur Radiol*, vol. 18, pp. 1123-1133, 2008.

Kuhl, C. K. et al., "Healthy Premenopausal Breast Parenchyma in Dynamic Contrast-enhanced MR Imaging of the Breast: Normal Contrast Medium Enhancement and Cyclical-phase Dependency," *Radiology*, vol. 203, pp. 137-144, 1997.

Mouridsen, K. et al., "Automatic Selection of Arterial Input Function Using Cluster Analysis," *Magnetic Resonance in Medicine*, vol. 55(3), pp. 524-531, 2006.

Barbier, E.L. et al., "Proceedings of the International Society for Magnetic Resonance in Medicine," Sixth Scientific Meeting and Exhibition : Sydney, Australia, vol. 3, p. 2157, Apr. 18-24, 1998.

* cited by examiner

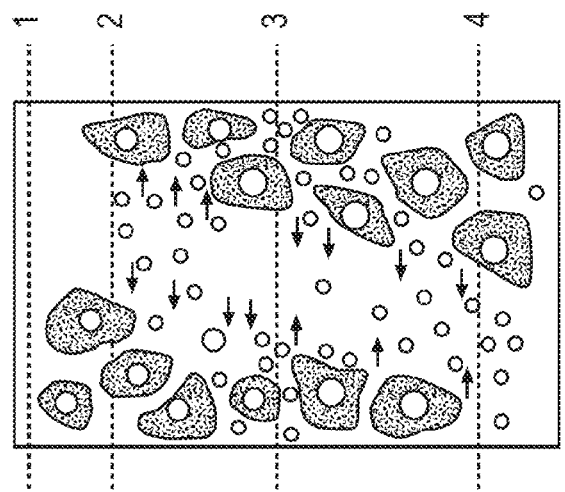
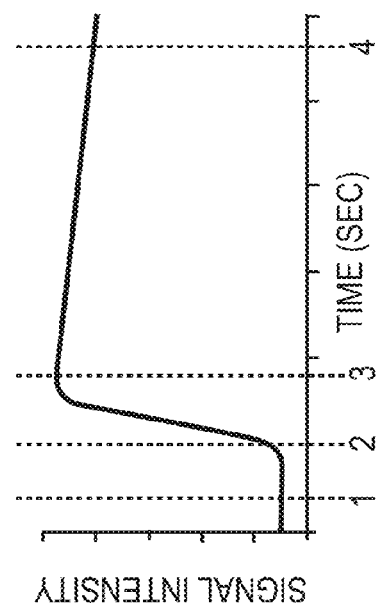
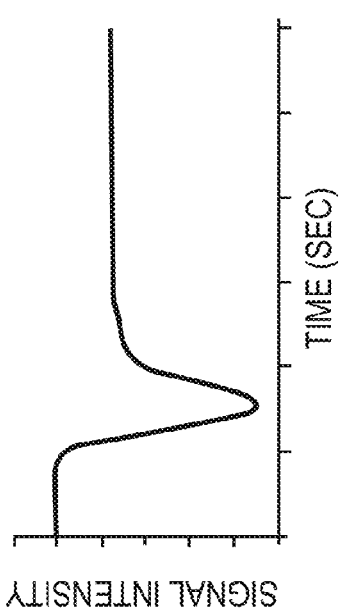
FIG. 1C
FIG. 1A
FIG. 1B

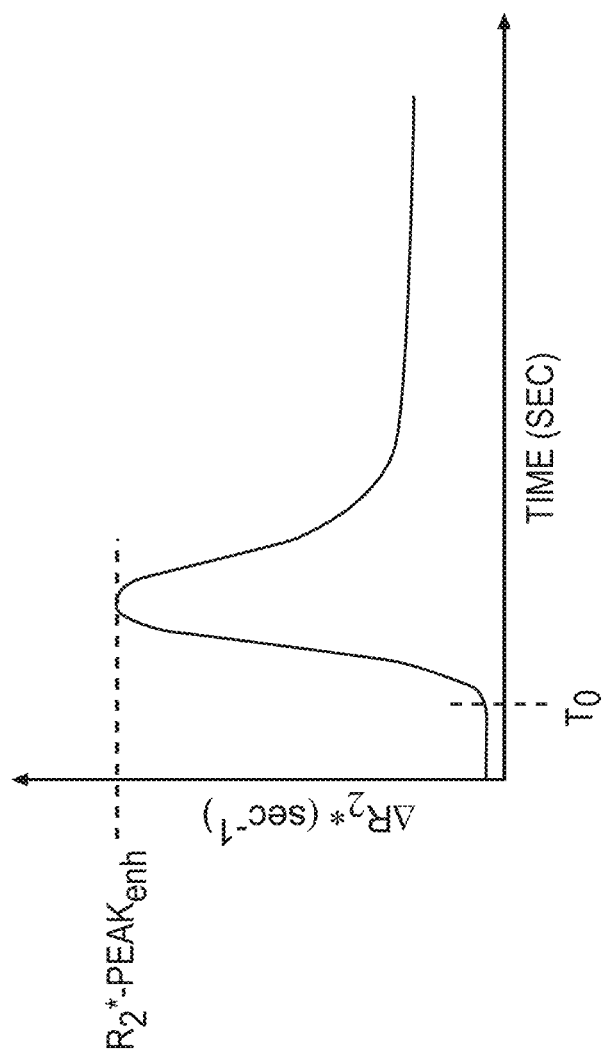

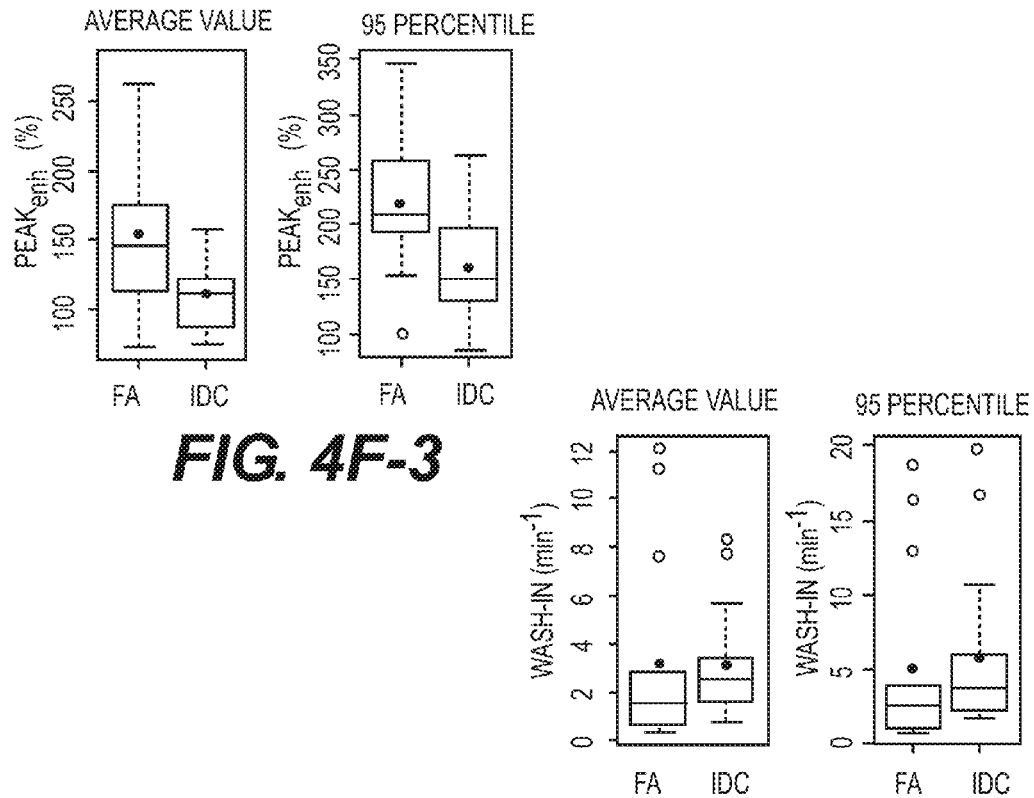
FIG. 4F-3
FIG. 4F-4
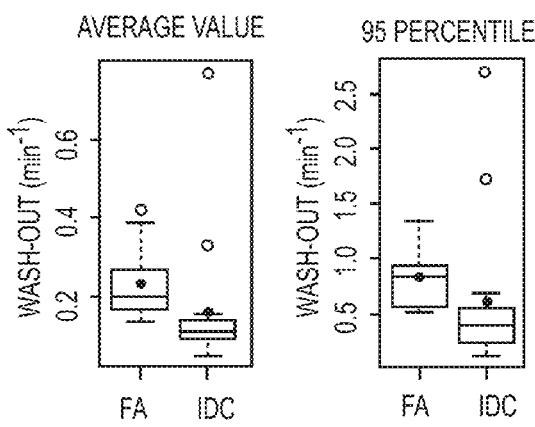
FIG. 4F-5

DYNAMIC MR IMAGING OF PATIENTS WITH BREAST CANCER—ESTABLISHMENT AND COMPARISON OF DIFFERENT ANALYTICAL METHODS FOR TISSUE PERFUSION AND CAPILLARY PERMEABILITY

RELATED APPLICATIONS

The present application is a continuation of application Ser. No. 13/941,652, flied Jul. 15, 2013, pending, which is a continuation of application Ser. No. 13/900,266, filed May 22, 2013, abandoned, which is a continuation in part of, and claims priority to Patent Application No. PCT/NO2011/000330, filed Nov. 22, 2011 (published as WO 2012/070951), pending, which claims priority to Norwegian application NO/20101638, filed Nov. 22, 2010, pending. The contents of each of these applications are incorporated by reference herein.

BACKGROUND OF THE INVENTION

Globally, breast cancer is the cancer that affects most women, and radiological imaging using mammography and ultrasound are currently the primary tools for detection and characterization of this type of cancer. However, these radiological image modalities demonstrate limitations with respect to the diagnostic performance and show a generally low specificity, particularly when evaluating young women.

Dynamic contrast-enhanced MR imaging has in recent decades emerged as a promising method for the evaluation of patients with breast cancer. This success is due to the methods ability to identify physiological differences in different cancer tissue through the description of distribution of the contrast agent in the tissue over time.

Dynamic contrast-enhanced MR imaging (DCE MR) is a diagnostic tool for examining tissue such as breast tissue and particularly breast cancer, and is under constant development, wherein the dynamic contrast-enhanced curves obtained from T1-weighed pictures have been proved to be predictive for tumor malignity (Kuhl et al., *Radiology* 1999; 211: 101-110). A significant diagnostic accuracy has also been obtained from qualitative examinations of signal loss in $T2^*$-weighed imaging by using dynamic susceptibility contrast (DSC) MRI (Kuhl et al., *Radiology* 1997; 202: 87-95; Kvisatd et al., Acta Radiol. 1999; 40: 45-51).

Some of the disadvantages of the prior art has, however, been that it has proven to be difficult to distinguish between benign and malign tumors by contrast-enhanced MR imaging. The reason for this has been inter alia that previously there has not been any coupling between the interpretation of data from DCE-MRI and DSC-MRI, and neither has there been any intermittent measurements of these two imaging types during one and the same data collection procedure.

SUMMARY OF THE INVENTION

Generally, the present invention relates to a process for diagnosing and characterizing benign and malign cell transformations in tissues from mammals particularly humans Furthermore, the present invention relates to a process/method for such diagnosing/characterization by using and comparing biomarkers collected from MR-imaging of tissues, and particularly by collecting such markers from MR-imaging of tissues by using contrast substances.

By analyzing this dynamic distribution through the relevant kinetic models, one can estimate the physiological-associated biomarkers that can contribute to an improved characterization of breast lesions. Image-based biomarkers that demonstrate a significant ability to differentiate between different types of lesions can assist the diagnostic evaluation of patients with breast cancer and thereby increase the diagnostic performance compared with conventional methods.

This work presents preliminary data from an ongoing study. The study is accepted by the regional ethics committee and has a limit of 50 patients with known lesions in the breast, of which 25 are likely benign and 25 are likely malignant. This presentation includes 19 benign and 22 malignant breast lesions, representing 76% and 88%, respectively, of the study's overall framework. In this work a high temporal dynamic contrast-enhanced MR imaging sequence of 40 patients with a total of 41 breast lesions were evaluated. Different acquisition methods and kinetic models were evaluated. The dynamic contrast sequence was described by two different methods: 1) descriptive evaluation of signal intensity's dynamic enhancement pattern and 2) by a quantitative evaluation of contrast agent time-dependent distribution. Histopathological diagnosis was available for all patients.

In the quantitative description of breast lesions physiological and anatomical characteristics, a mathematical modeling of the observed contrast sequence using a pharmacokinetc two-compartment model was carried out. This modeling requires determination of the individual contrast enhancement in the patient's blood plasma by using an arterial input function (AIF). The model allows a quantitative estimation of transfer coefficients $K^{trans}$ and $k_{ep}$, the volume fractions of plasma and the extravascular extracellular space ($v_p$ and $v_e$). As it turned out that an AIF estimation was difficult to achieve in all patients, the analysis with the use of an idealized patient-independent AIF was also performed.

In the descriptive evaluation features of lesions contrast progress through five different biomarkers were identified. These include the 1) dynamic signal curve time to the maximum value (TTP), 2) area under the curve (AUC), 3) maximum signal enhancement ($peak_{enh}$), 4) signal curve wash-in rate, and 5) washout rate (Wash-in and Wash-out).

The use of a double-echo pulse sequence allows the estimation of tissue transversal relaxation rate, $R_2^*$, assuming a mono-exponential signal change as a function of echo time. In this work, the dynamic $R_2^*$-curve was evaluated by estimating the maximum $R_2^*$-gain based on the tissue pre contrast value.

The different biomarkers were analyzed and compared to histological pathology by applying statistical significance tests with respect to their predictive power, as well as diagnostic tests in terms of their sensitivity, specificity, and diagnostic accuracy. In addition, logistic regression was performed to achieve an optimal fit between patients' histology and the biomarkers estimated values.

An important hypothesis in work was that tumor heterogeneity is an important factor in the diagnostic evaluation of breast lesions. In a heterogeneous tumor, the estimated average biomarker ignores regional differences, and thus the most aggressive and clinically important regions of the tumor. In this work, the different biomarkers were, therefore, estimated from various parts of the tumor volume value distribution. This involves the estimation of the average biomarker value of the tumor volume and a number of percentile values. In this way, possible small malignant areas in a large heterogeneous tumor could be identified. It was here found that a significantly higher predictive ability can be achieved by identifying the regions of the tumor that demonstrates the most abnormal properties.

In this work, it was found that malignant breast lesions demonstrated a significantly shorter TTP compared with benign breast lesions. In addition, as demonstrated, the quantitative biomarker $v_p$ is a significantly higher value in malignant breast lesions as compared with benign breast lesions. By identifying tumor volume of the 95-percentile of the quantitative biomarker $k_{ep}$, this biomarker demonstrated a significantly higher value in malignant breast lesions as compared to benign breast lesions. Among the qualitative biomarkers, $k_{ep}$ demonstrated a significantly higher value in malignant breast lesions as compared with benign breast lesions. If all fibroadenoma (FA) and invasive ductal carcinoma (IDC) are considered separately, the qualitative $v_e$ factor demonstrated a significantly higher value for the FA. It was also found that malignant breast lesions demonstrated a significantly higher $R_2^*$-enhancement compared to benign breast lesions. The result shows that these biomarkers can be used as diagnostic predictors for the evaluation of patients with breast cancer.

Based on tumor the volume 95-percentile, multivariate regression models through backward stepwise elimination process of significant biomarkers were established. This analysis showed that the combination of the three biomarkers $R_2^*$-peak$_{enh}$, TTP, and the quantitative $v_p$ gave the most optimal diagnostic performance. Regression demonstrated a diagnostic accuracy of 93% with respect to differentiating between malignant and benign breast lesions. This corresponds to the sensitivity and specificity of 80% and 100%, respectively. If the FA and IDC are considered separately, they achieved a diagnostic accuracy of 98%. This corresponds to a sensitivity and specificity of 93% and 93%, respectively.

A quantitative estimation of pharmacokinetic biomarkers requires an accurate measurement of the arterial input function (AIF). This proved to be very difficult to measure in all patients, leading to a dispersion and inaccuracy in the quantitative biomarkers. A normalization method was therefore introduced in which the pharmacokinetic relationship between the different patients' parenchymal tissue and tumor tissues were identified. This method was developed for the purpose of reducing errors by the pharmacokinetic analysis due to an insufficient AIF. The normalized $K^{trans}$ was identified as the most predictive biomarker, and demonstrated a significantly higher value in malignant breast lesions compared with benign breast lesions. By introducing the normalized $K^{trans}$ as a substitute for the quantitative pharmacokinetic contribution in the logistic regression model, a diagnostic accuracy of 96%, regarding the differentiation of benign and malignant breast lesions, was achieved. This corresponds to a sensitivity and specificity of 90% and 94%. If the FA and IDC are considered separately, the multivariate regression model successfully differentiated all of these.

The results showed that the dynamic image information acquired from the high temporal images, introduces valuable information that can assist the diagnostic evaluation of patients with breast cancer.

The present invention concerns an ex vivo process for diagnosing tumors in tissues of mammals, particularly in humans, but in other mammals as well, such as household animals, pets, useful animals, etc. The process according to the invention may also be used for studying organ functions and the verification/diagnosing of normal and/or abnormal functions thereof as well as the diagnosing of lesions and their severity. The invention concerns particularly such a process used for diagnosing different types of tumors in soft tissues such as breast tissue, and even more particularly, the invention relates to such a use for distinguishing between benign and malign tumors in breast tissue, especially human breast tissue. The process according to the invention is founded on the collection of data by examining the relevant tissue by magnetic resonance imaging (MRI), and particularly such a collection of data by the aid of contrast-substance assisted MRI. As a contrast substance it is preferably used gadolinium (Gd), but also other contrast substances providing a measurable magnetic signal that may be separated into a high-temporal and a high-spatial imaging may be used; it is preferred to use Gd and Gd-based contrast substances.

In the process it is preferable to use a T1 and T2/T2* truncating chemical substance ("MRI contrast substance) which is administered to the relevant patient or to the relevant tissue, e.g. intravenously, intraarterially, or intralymphatically. The process is best performed through the administration of the contrast substance as a bolus, providing a high contrast substance concentration over a short period of time. Alternatively, the contrast substance may be administered as smaller intermittent boluses, but a bolus-administration is preferred. The contrast substance may be administered manually by a physician or by the aid of a machine ("contrast injector"). The process for ex vivo diagnosing, according to the invention, is performed by collecting MRI signals prior to, during, or after the passage of the contrast substance bolus through the region/tissue of interest and comparing the parameters founded on this signal basis. The foundation for the invention is thus based on the collection and post-treatment of data collected from the MRI signals.

The process, according to the invention, preferably uses a dynamic contrast substance enhanced (DCE) MRI method wherein two distinct MR pulse sequences repeated several times prior to, during, or after the administration of MRI contrast substance is collected, wherein these two pulse sequences are denoted as sequence 1 and sequence 2. Sequence 1 is formed to give sharp anatomic ("spatial") details for the region of interest, wherein this sequence may be repeated one or more times for increasing the reliability of the measurements. Sequence 2 is constructed to provide picture information with the highest frequency possible ("high temporal dissolution"). This sequence may also be repeated one or more times for increasing the reliability of the measurements. Sequence 1 and sequence 2 may be performed alternatingly, and this alternating embodiment may be performed in a ratio of 1:1 (so that there are equally many of sequence 1 and sequence 2) or up to a ratio of 1:100 (so that there is 100 times as many of sequence 2 than sequence 1) or 100:1 (so that there is 100 times as many of sequence 1 as sequence 2). It is preferred that there is more of sequence 2 than sequence 1. The ratios are, however, not meant to be absolute, so that a ratio between the number of sequence 1 and sequence 2 may vary beyond the specified limits as well. In the process, sequence 1 is T1-weighed. Sequence 2 gives two gradient echoes wherein the first echo in sequence 2 is T1-weighed. Sequence 2 gives two gradient echoes wherein the first echo in sequence 2 is T1-weighed and the second echo in sequence 2 is T2*-weighed.

In the process according to the invention there may be used signals for any type of contrast substance giving a signal within MRI and that additionally is physiologically acceptable, e.g. it is preferred that a gadolinium-based (Gd) contrast substance is used.

Furthermore the invention concerns a data program based on the relevant parameters from the MRI signals being compared/combined with each other. The data program is adjusted to collect data from DCE-MRI and DSC-MRI signals and generates measurement-marker-data selected from: 1) the area under the curve (AUC=Area under the curve); 2) time and maximum signal enhancement/TTP=Time to peak);

3) maximum relative signal enhancement ($P_{enh}$=relative peak enhancement); 4) the pour-in of the curve (Wash-in rate), 5) the pour out of the curve (Wash out rate); 6) plasma volume ($v_p$=plasma volume); 7) volume transfer constant 1 ($K^{trans}$=Volume transfer coefficient from the plasma volume $v_p$ to the extracellular extravascular space $v_e$); 8) extracellular extravascular volume ($v_e$=extracellular extravascular space); 9) volume transfer constant 2 ($k^{ep}$=volume transfer coefficient from the extracellular extravascular space $v_e$ to the plasma volume $v_p$), and 10) the transversal relaxivity rate R2*(Transversal relaxation rate R2'), preferably T1 and T2/T2* and R2 for then comparing said data with standard values for malign and benign tumors of a corresponding type of tissue for distinguishing between benign and malign tumor types, for further displaying the generated results on a screen or onto a physical medium such as paper.

The disclosed invention includes methods, apparatus, and computer-based systems for identifying benign and malign tumors in tissues such as soft tissues, and particularly breast tissue, through the registration and comparison of measurement data from dynamic contrast-enhanced magnetic resonance imagining (DCE-MRI) and dynamic susceptibility contrast-enhanced magnetic resonance (DSC) imaging of the tumors. Disclosed embodiments encompass two dynamic MRI pulse sequences in intercalating mode during parenteral? administration of an MR contrast substance, wherein one of said pulse sequences is optimized for spatial information and the other pulse sequence is adjusted for high temporal resolution; the high-temporal resolution sequence further comprising a double echo-collection for both DCE-MRI and DSC-MRI for generating biomarker data such as pharmacokinetic biomarker data, descriptive DCE biomarkers and descriptive DSC biomarkers, and subsequently normalizing and comparing said data with corresponding data from corresponding benign and malign tumors, respectively.

One of the features of the present invention is introducing the transversal relaxation rate R2*, obtained from a double echo dynamic DSC sequence, as a quantitative bio-marker for distinguishing between malign and benign tumors, particularly in breast tissue.

One of the advantages with the process, according to the present invention, is that through connecting these two contrast medium-based methods (DCE-MRI and DSC-MRI) it is only necessary with one injection of contrast substance, as opposed to two or more when the methods are performed separately. By using one injection only of a Gd-based contrast substance, the following will be achieved:

1. Lower probability of movement during the imaging. One contrast substance injection for first registering data with a high spatial solution and then a new injection for collecting data with high temporal solution (as being done previously) leads to a higher probability for an inferior coregistration of the two sets of data.

2. Two (or more) doses of injected Gd-based contrast substaces increase the probability for "nephrogenic systemic fibrosis/nephrogenic fibrosing dermopathy" (NSF/NFD) being a potentially deadly disease developed primarily among patients with reduced kidney function.

Other advantages of the process, according to the present invention, are:

The use of "split dynamics" (i.e. splitting two image sequences and performing these sequences at different frequencies) provides image information with both high temporal solution and high spatial solution.

The fastest image sequence generates pictures from two different echo times. With this information a new quantitative picture data set may be generated based on absolute R2*-values.

BRIEF DESCRIPTION OF THE DRAWINGS

FIG. 26 is a 90° RF-pulse excites the spin system and rotates the magnetization vector 90° into the transversal plane. In this example the excitation is observed in the rotating frame of reference.

FIG. 3E illustrates the initial situation where the delay contrast is visually measured and is given by T0,VOI–T0, AIF. FIG. 3F illustrates the corrected situation where contrast agent arrival occurs simultaneously in the arterial vowels' and the tissue of interest.

Box plots depict the group marker distribution in first to fourth quartile. In addition, the distribution median value and average value are presented with solid lines and red markers, respectively, Any outliers are illustrated as individual point outside the distribution. The figure presents box plots for (A) $K^{trans}$, (B) $k_{ep}$, (C) $v_e$, and (D) $v_p$

DETAILED DESCRIPTION OF THE INVENTION

Figures 1, 2A:
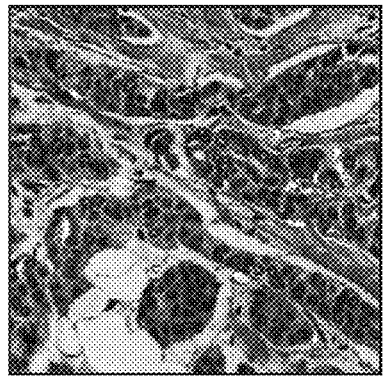
FIG. 1 is an illustration of the contrast enhancement in cancer tissue, and has been re-drawn into three separate figures FIG. 1A through FIG. 1C. The curves to the left demonstrate the tissue signal intensity (SI), with respect to T1 and T2/T2*-effect, as a function of the contrast agent time-dependent movement through the observed tissue. The figure illustrates the intravascular T2*-effect assuming there is no leakage of the contrast agent.
FIG. 2A is the histology of normal and abnormal breast tissue, and has been re-drawn into five separate figures FIG. 2A-1 through FIG. 2A-5. (A) Invasive ductal carcinoma (IDC) is defined as the most frequent malignant breast tumor and is characterized by a destroyed glandular barrier. (B) A lobular carcinoma in situ (LCIS) is characterized by the proliferation of cancer cells in the most peripheral channel of the lobular unit. (C) Ductal carcinoma in situ (DCIS) is characterized by the fact that proliferation of cancers cells is restricted to the ductal parts of the breast. (D) Fibroadenoma (FA) is defined as the most frequent benign breast lesion. (E) Normal breast histology which illustrates (1) glandular tissue, (2) fatty tissue, and (3) fibrous tissue.
Figures 2, 2A:
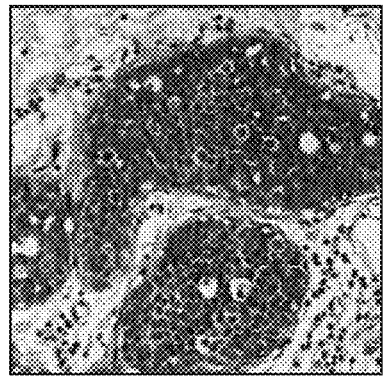

Worldwide, cancer is one of the most frequent causes of death, and more than 12 million new cases were detected in 2008 [61]. Among these were about 5,779,000 women, where breast cancer was diagnosed as the most common occurrence of cancer and cancer-related cause of death. A cancer tumor depends on vascular supply to grow. This is obtained through a process called the angiogenesis and involves the formation of blood vessels in the tumor. The development of new blood vessels in cancerous tissue happens in a more disordered and chaotic manner than compared to normal tissue, leading to cancer-specific pathophysiological changes. This includes in particular an increase in cancer tissue perfusion, blood volume and the capillary permeability. If these parameters can be measured, we can therefore characterize cancer tissue pathophysiology in comparison with the same parameters in normal tissue.

Although the prognosis among the different cancer types in general will vary, the chance of cure is far better if the disease is detected at an early stage. This has led to a national screening process for breast cancer among women. This process implies that all women between 50 and 69 years of age are invited for screening for breast cancer every two years by the use of x-ray mammography. However methods like mammography, ultrasound, and physical examination often demonstrate limited sensitivity and specificity with regard to diagnosis, especially among young women. The final diagnosis is almost invariably based on histopathological analysis of tumor tissue from the biopsy. The importance of tumor angiogenesis has long been known in clinical oncology, but traditional imaging methods are not able to measure the degree of angiogenesis.

Magnetic resonance imaging (MRI) today is increasingly used, for example, in preoperative grading, localization of multiple lesions, and screening of patients at high risk for cancer development, and represents an active field of research in the diagnostic world. MRI of the breast was first initiated in the 1980s, and the introduction of contrast medium led to an expansion of MRI-based breast diagnostics. Using MRI-based measurement of the dynamic contrast medium course in breast tissue, it was possible to achieve a higher specificity for the detection of malignant tumors due to a significantly higher contrast uptake compared with surrounding tissue. The significant importance of generating dynamic information from contrast-enhanced MR imaging was first introduced by Kaiser and Zeitler in 1989 [34]. This study suggested that malignant breast lesions demonstrate a characteristic enhancement pattern that differs from normal tissue and benign breast lesions, an observation which is now verified by a number of other studies [11-17]. The dynamic contrast enhancement will reflect the tissue underlying physiological factors and can therefore be used to differentiate between tumors with different pathophysiology.

The cancer tissue signal change can be described non-invasively by using dynamic contrast-enhanced MR imaging (DCE-MRI) and/or dynamic susceptibility MR imaging (DSC-MRI). These methods represent rapid imaging methods executed before, during, and after administration of a paramagnetic contrast agent, with the purpose of following its distribution in the tissue of interest over time. By injecting the contrast agent intravenously, it is transported by the vascular system into the tumors capillary network. On arrival, the contrast agent immediately begins to leak out through the capillary walls and accumulate in the extravascular, extracellular space (EES). Depending on the distribution of the contrast agent in cancer tissue, and properties on the capillary network, two mechanisms could be observed. These are referred to as the contrast agent T1- and T2/T2*-effect, and is regarded as complementary mechanisms. The degree of these effects are highly dependent on the pulse sequence used, which thus often is referred to as T1- and T2/T2*-weighed sequences.

It is important to note that it is not the contrast agent itself, but the transient effect of the contrast agent that leads to changes in signal intensity, and the contrast agent leads to both T1 and T2/T2* values are reduced. FIG. 1 illustrates the change in tissue signal intensity (SI), with respect to T1 and T2/T2*-effect, as a function of the contrast agent time-dependent movement through the observed tissue. If the contrast agent is homogeneously distributed, T1-effects will be dominant, as this effect is associated with the contrast agent direct interaction with free water molecules in the tissue. The presence of contrast agent in this case leads to an increased signal intensity in the observed tissue when T1-weighed series are used. The signal change rate and magnitude depends on the capillaries and tissue anatomical and physiological characteristics. Tissue contrast enhancement, as a result of contrast agent T1-effect, can be observed by DCE-MRI. Accumulation of contrast agent in the EES results in a reversed contrast agent flux through the capillary walls, resulting in a washout of contrast agent from the extracellular space back into the intravascular compartment. All contrast media used for MRI mammography is water soluble molecules that are distributed in the extracellular space and excreted renally with a half-life of approx. 60 minutes. The renal excretion results in a continuous reduction of the contrast agent tissue concentration, and thus a continuous washout of contrast agent from the EES. In DCE-MRI, this leaching is observed as a gradual reduction in cancer tissue signal intensity.

In addition, the contrast agent passage through capillary network will produce local field inhomogeneity between the intravascular and extravascular components. These susceptibility effects will lead to a transient signal that depends on the anatomical structure of the capillaries and tissue blood flow (perfusion). A signal loss will also be observed if the contrast agent is distributed heterogeneously. This will generate a dominant $T2/T2^*$-effect as the associated susceptibility effect possesses a larger effective interaction range compared to T1-effects. The corresponding signal loss will accordingly depend on capillary and tissue anatomical and physiological characteristics. Tissue signal reduction, as a result of the contrast agent $T2/T2^*$-effects can be observed with DSC-MRI. It is important to note that the relative degree of T1- and $T2/T2^*$-effects is determined by the physiological conditions listed above.

The dynamic SI curves obtained from DCE- and DCS-MRI will be related to tissue contrast agent concentration, and by evaluating these curves one can extract physiological or physiologically relevant biomarkers that allow for a characterization of the studied cancer tissues, and thus can help increase the diagnostic performance in differentiating between benign and malignant breast lesions. Dynamic MRI imaging of the breast is currently preferred using high spatial resolution and demonstrates generally a high sensitivity. In addition, the dynamic information can be used to differentiate between various breast lesions and thus contribute to an increased specificity. However, specificity represents a major challenge, since the spatial resolution comes at the expense of the image sampling time (temporal) resolution. As a result, the images sampled do not provide an adequate description of the dynamic contrast enhancement patters, and thus ignore differences in lesions physiological properties.

In this study a protocol that executes a high temporal and high spatial sequence in an alternating pattern after administration of a contrast agent is used. In this way, a good representation of both lesions morphology and their dynamic contrast gradient is obtained. In this study, the high temporal sequence is evaluated. This is performed with particularly high temporal resolution in relation to what is common today. The reason for this is the hypothesis that a measurement of the early phase of contrast distribution in the tissue may lead to better tumor differentiation, which requires a higher temporal resolution than that achieved with present day standard sequences. Both DCE and DSC recordings with high temporal resolution were performed in 40 patients with a total of 41 confirmed breast lesions. All patients were diagnosed on the basis of the tissue sample obtained from cytology or histological fine needle biopsy. The patients' dynamic images in this study are evaluated by analyzing and characterizing signal intensity's temporal change pattern (descriptive biomarkers), and by modeling the contrast agent time-dependent motion in the tissue, also called pharmacokinetics, through mathematical pharmacokinetic models (quantitative biomarkers). The different biomarkers are further evaluated and compared to the patients' histology by applying statistical analysis and diagnostic tests.

Dynamic MR imaging is currently the most routinely used MRI technique for the evaluation of breast lesions, and has also proven the most accurate imaging technique in terms of detecting and characterizing breast lesions. But even if the sensitivity is generally good using present days' techniques, the specificity remains a challenge. The aim of this study is to apply a dynamic double-echo sequence with high time resolution to estimate a range of qualitative, quantitative and descriptive kinetic parameters, referred to as biomarkers. Then further develop statistical models and analysis strategies to identify biomarkers that best differentiate malignant from benign breast lesions, with the aim to increase the diagnostic performance.

1. Breast Cancer and Angiogenesis

In Norway breast cancer is the most common cancer related female disease with more than 2700 new cases being registered in 2008 [62]. The risk for breast cancer increases with age and about 80% of those struck by it is over the age of 50. The causes behind the disease are not well understood, but genetic risk factors are known along with choice of lifestyle and diet. The breast contains a mixture of glandular, fatty and fibrous tissue. Breast cancer is a malignant tumor that usually caused by glandular tissue small export times and in the glandular end-pieces. Cancer of the breast is, in a more general term, part of a family of diseases called carcinomas. This condition is in a more general term. The most common type of breast cancer originates from tubular endothelial cells. The second most frequent type is lobular carcinoma which originates from glandular end-pieces. In addition to these two types of breast cancer, many additional breast cancer types exist with varying degrees of aggressiveness, and prognosis is based upon stage and cancer type. In common for all types of malignant breast disease is an uncontrolled cell division in the breast tissue that is explained by abnormalities in the genetic material of the transformed cell. This uncontrolled growth will often proliferate and form a mass (tumor). The developing tumor goes through stages of variable length. For long periods of time the proliferation can be limited to encapsulated glandular tissue. This stage is called an "in situ cancer". Sooner or later, depending on the tumor's aggressiveness, cancer cells will break the glandular barrier and spread into the surrounding fibrous tissue. We then have an "invasive cancer". At this stage the patient is at risk for having cancer cells spreading to lymph nodes in the armpit and by the blood stream to the rest of the body. This can cause new tumors to appear and the patient has a metastatic disease. The prognosis of the patient depends on the tumor stage, and the time of detection and diagnosis of breast cancer is therefore of vital importance.

Cancer cells as well as normal cells consume oxygen as part of the metabolism. In solid tumors proliferation over a distance of 1 to 2 mm will not take place without a vascular supply since this distance represents the diffusion length for nourishment and residual products from the capillaries. Sprouting and the formation of new blood vessels are therefore a prerequisite for growth. This process is called angiogenesis and is activated through stimulation of nearby vessels that will branch out to the tumor, and by this supply the tumor with oxygen and nourishment. The stimulation of angiogenesis happens when the tumor cells emit promoting substances into the surrounding normal tissue. These signals activate a certain gene in the normal tissue which leads to the production of angiogenesis promoting proteins. The strong angiogenic promoting factor in breast cancer is called the vascular endothelial growth factor (VEGF). Blood vessels that are shaped by this factor often possess a high degree of permeability and demonstrate a chaotic anatomy and physiological properties that diverge substantially from normal tissue. In addition the cancerous tissue will also display high capillary density and is often heterogeneously distributed. FIGS. 2A-1 through 2A-5 demonstrate the histology of the most common types of malignant and benign breast lesions and also normal tissue. The figures illustrate the differences in anatomical structures between normal endothelial cells found in glandular tissue and abnormal endothelial cells found in cancerous tissue.

2. Basic MR-Theory

Figures 2, 2A, 3:
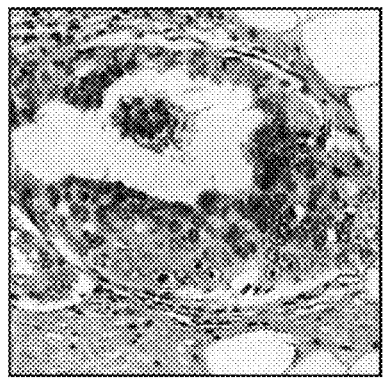
Figures 2, 2A, 3, 4:
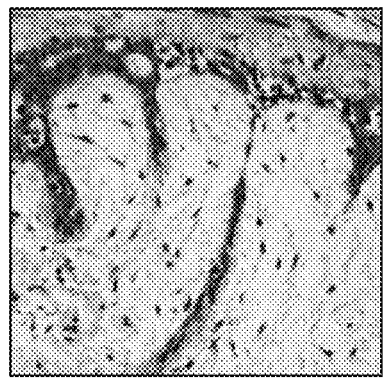
Figures 2, 2A, 3, 4, 5:
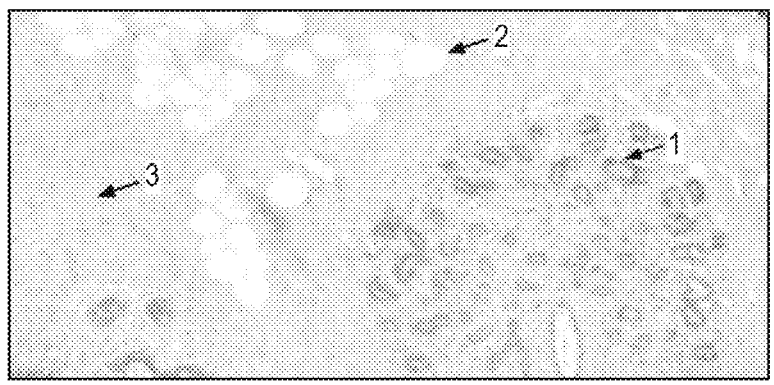
Figure 2B:
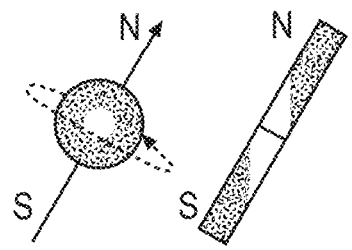
FIG. 2B is the proton magnetic moment compared to a magnetic bar.

Biological material mostly consists of unbound water. The water molecule contains one oxygen atom and two hydrogen atoms. Magnetic resonance imaging (MRI) is a non-invasive imaging modality that exploits the magnetic properties of the hydrogen nucleus to generate images of the biological material. The hydrogen nucleus consists of one proton which is an elementary particle with a positive electric charge. The proton has a property called spin implying that the proton rotates around its own axis. The positive electric charge associated with the proton follows this motion. Through its spin and electric charge the proton possesses what is called the magnet moment, μ. For simplification the magnetic moment can be compared to the property of a magnetic bar as illustrated in FIG. 2B.

Figure 2C:
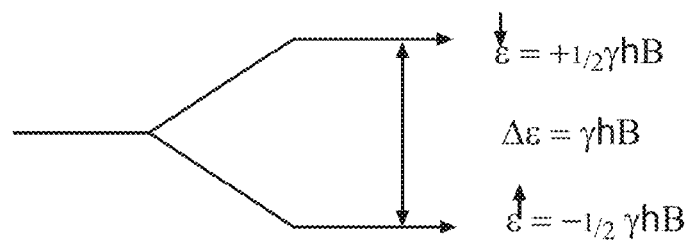
FIG. 2C is the energy levels for a Y spin system associated with the Zeeman effect, where the magnetic moment in an external magnetic field causes the nucleus to split into two energy levels. The spin is oriented parallel to the external field B0 in its lowest energy level.

The physical phenomenon called magnetic resonance is based on the fact that the atomic nucleus of the hydrogen is magnetic. Without any external forces the protons will orient themselves in a random fashion, but if experiencing a strong external magnetic field, $B_0$, as found in an MR scanner, the protons' magnetic moment will interact and orient itself along the magnetic flux lines. More exact, the protons' magnetic moment has two possible orientations: either parallel or anti-parallel to the external magnetic fields. These orientations are named spin up, $N^\uparrow$, and spin down, $N^\downarrow$. The two orientations indicate two energy levels, and where the anti-parallel orientation represents the higher energy level for the proton, the energy for each of the two levels is given by:

$$\epsilon = \mu \cdot B = \gamma \hbar l \cdot B$$

where l is the quantum number for the angular momentum, given by ±½ for protons, $\hbar$ is the Planck constant divided by $2\pi$ and $\gamma$ is the gyromagnetic ratio which has unique values depending on the atomic nucleus. FIG. 2C presents a schematic illustration of the two separate energy levels and the energy difference.

In this case, as is the case in so many other places in nature, the lowest energy level is preferred. The relative number of spins with different orientations is given by the Boltzmann equation:

$$\frac{N^\uparrow}{N^\downarrow} = e^{\Delta\epsilon/kT} = e^{\gamma \hbar B_0/kT} \qquad (2\text{-}2)$$

where k is the Boltzmann constant and T is the temperature measured in degrees Kelvin. At the body temperature and in a magnetic field of 1.5 T the value of $\gamma \hbar B_0$ will be small compared to kT and a Taylor expansion can be used. This gives us:

$$\frac{N^\uparrow}{N^\downarrow} = 1 + \frac{\gamma \hbar B_0}{kT} = 1 + 3.7 \cdot 10^{-6} \qquad (2\text{-}3)$$

This minor difference in proton population between the two energy levels represents the net magnetization and is called $M_0$. Note that only two variables can change the value of; the magnetic field strength and the temperature. Because the body temperature is relatively constant, only the magnetic field strength can influence the net magnetization. The surplus of protons in the lower energy state can look tiny but as there are an estimated $10^{22}$ protons per $cm^3$ in living biological tissue, this net magnetization is measurable.

Figure 2D:
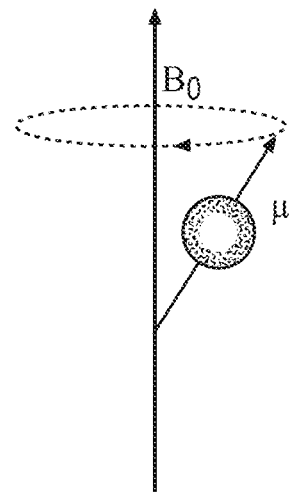
FIG. 2D is a geometric illustration of the magnetic moments, µ, precession around the magnetic field, B0.

Protons that are positioned in an external magnetic field will, as already told, be split into two separate orientations. However, it is important to note that these protons are not at rest but will move in a fashion called precession. Precession is per definition a circular movement of the rotation axis of a rotating sphere around another stationary axis. The movement is caused by the application of the angular momentum in the processional direction. The interaction between the proton spin and the magnetic field creates this angular momentum, which results in precession of the protons' magnetic moment around a stationary axis. This is illustrated in FIG. 2D.

Precession is a classical physics description of a quantum mechanical proton spin movement. The use of Newtonian physics can be defended by looking at a simple but important relationship between precession and the energy difference illustrated in FIGS. 2B and 2C. The difference between the two achievable orientations is given by $\Delta\epsilon = \gamma \hbar B$. De Broglie's wave equation tells us that the frequency associated with this energy is given by:

$$\Delta\epsilon = \hbar \omega \qquad (2\text{-}4)$$

and the precession frequency can be described by:

$$\hbar \omega_0 = \gamma \hbar B_0 \qquad (2\text{-}5)$$

$$\omega_0 = \gamma B_0 \qquad (2\text{-}6)$$

The equation is formulated with the index 0 to indicate that this is the Larmor frequency also called the resonance frequency along with the applied external magnetic field $B_0$. The equation is also called the Larmor equation, named after the Irish physicist and mathematician Joseph Larmor. At the magnetic field strength commonly used in today's MR images, the hydrogen nuclei will have a resonance frequency in the frequency range of radio waves (42.58 MHz at 1 Tesla).

Figure 2E:
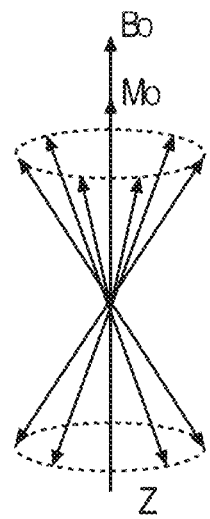
FIG. 2E is the precision in a spin system. The spins are either parallel or anti parallel and rotates around the B0-field at a random phase. The net magnetization, M0, which is the sum of all components, is oriented along the external magnetic field, B0.

In a system containing multiple protons exposed to a magnetic field, $B_0$, these protons will either orient themselves parallel or anti-parallel to the field with a surplus in the parallel direction. In addition each proton will precess at a certain angle relative to the magnetic field. The net magnetization will despite this always point in the direction as the $B_0$-field. The explanation for this is that the protons rotate at a random phase and are therefore evenly distributed. If all components of the magnetization are added together, this will result in a net magnetization in the same direction as the external magnetic field. This is illustrated in FIG. 2E, where the net magnetization vector is shown as $M_0$.

For practical reasons the direction of the external magnetic field is called the z-direction. In conjunction with the protons' precessional movement and frequency, we introduce a few elementary concepts to describe these mechanisms.

3. The Bloch Equation and Excitation

Magnetic resonance is a quantum mechanics process and should therefore be treated as such. But because the coupling of the nuclei is mutual and weak in relation to the surrounding material, a classical approach is acceptable

3.1 The Bloch Equation

It is valid to describe the behavior of the magnetization vector, as a result of magnetic interaction, in classical terms using the Bloch equation:

$$\frac{dM}{dt} = \gamma(M \times B)$$

M represents the spin system magnetization vector and B the magnetic field strength. The vector product, M×B gives us a vector that is perpendicular to both M and B, with an amplitude given by |M| |B|sin α, where α is the angle between M and B. The Bloch equation tells us that the vector dM/dt is always oriented perpendicular to the plane defined by B and M. However, it is important to note that a spin system in thermal equilibrium always will possess a magnetization vector that points in the same direction as the main field. The amplitude of the magnetization vector in the z-direction is called $M_z$.

3.2 Excitation

Figure 2F:
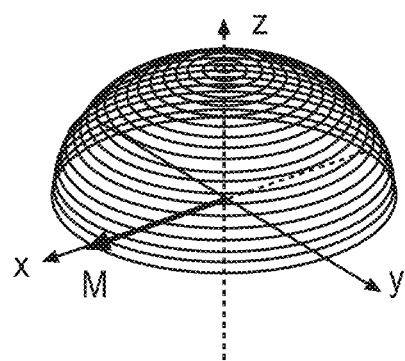
FIG. 2F is the movement pattern of the magnetization vector during the application of an excitation pulse. As the figure tells us this is done in a spiral fashion seen from the laboratory frame of reference. This example shows an excitation that rotates the magnetization vector 90° into the xy-plane.

It is the spin system net magnetization represented by its vector M, that gives rise to the MR-signal and the detection of M is the basic prerequisite for obtaining MR-Images. But, to get information from M, movement of the magnetization vector x- and y-components are necessary. This implies that M one way or the other has to be forced from its equilibrium position along B, and also oscillate in time to induce a measurable current in a coil positioned perpendicular to the z-direction. In today's MR scanners this is done by applying a second magnetic field, $B_1$, perpendicular to the external main magnetic field, $B_0$. The secondary magnetic field is generated through induction of radio waves that are transmitted using a coil positioned in the transversal plane (the xy-plane). This field is called an RF-pulse or an excitation pulse. When the frequency of this field corresponds to precession frequency of the proton, called the Larmor frequency, these protons will be excited. By this we mean a modification or change in the proton energy level and spin face. In terms of quantum mechanics, it implies that the protons jump from one energy level to another, that is from an anti-parallel to a parallel orientation. The consequence of this is that the magnetization vector is flipped away from the z-direction and into the transversal plane. This is done in a spiral fashion as illustrated in FIG. 2F.

The motion of the magnetization vector, with the presence of both $B_0$ and $B_1$ can be described as:

$$\frac{dM}{dt} = \gamma M \times (B_0 \times B_1)$$

If the frequency of the $B_1$-field corresponds to the Larmor frequency, i.e. $\omega = \omega_0$:

$$\omega = \omega_0 = \gamma B_0$$

and further:

$$B_{\mathit{eff}} = B_1$$

Described by words, this implies that the effective magnetic field, as felt by the protons, only consists of the secondary $B_1$-field. The interaction between the rotating field and the spins can over time be neglected and the consequence of applying the RF-field $B_1$, will then be a precession of the net magnetization, M, with an angular frequency given by:

$$\omega_1 = -\gamma B_1$$

A B1-field applied at the resonance frequency during a defined time is called an "RF-pulse". If one assumes that the RF-pulse is coupling to the magnetization M in the direction of the x-axis applying a constant B1-value during a time interval tr, M will rotate at an angle α relative to the z-axis and towards the transversal plane. This angle is called the RF-pulse "flip-angle" as is given by:

$$\alpha = \gamma B_1 t_r = \omega_1 t_r$$

Figure 2G:
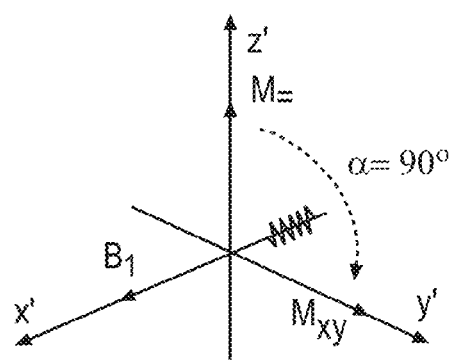
FIG. 2H is the typical FID-signal observed after the application of an excitation pulse.
FIG. 2I is the return of longitudinal magnetization after the application of a excitation pulse. The relaxation rate is defined by T1.
FIG. 2J shows that after the excitation of the spin system the spins at different locations will experience macroscopic field inhomogeneities caused by the main magnetic field and local magnetic fields from neighboring spins. This results in a cumulative loss of phase coherence.
FIG. 2K is the decay of the transversal magnetization caused by loss of phase coherence has the shape of a negative exponential curve. The degree of the decay is determined by T2.
FIG. 2L is a schematic illustration of a classical gradient echo sequence. During excitation a slice selective gradient is applied defining the slice orientation and thickness. The reversed polarity of this pulse just after excitation is done to rephrase the spins in the slice thickness direction. Further, two gradient pulses are applied orthogonally to the slice selection gradient and also orthogonal to each other. One is called the phase encoding gradient and the other is the first of the bipolar gradients that leads to the formation of the gradient echo.
FIG. 2M is the chemical structure of the gadolinium based contrast agents Magnevist™ Gd-DTPA (left) and Omniscan.
FIG. 2N is a pharmacokinetic two compartment model. It modulates the transport of a contrast agent between the plasma volume and the extravascular extracellular space (EES) in a unity tissue volume.
FIG. 2O is an idealized mono-exponential input function $C_p(t)$. The relative plasma volume is given by the Initial step-increase in the tissue concentration curve $C_t(t)$.

The RF-pulse is frequently named after the number of degrees M rotates relatively to its initial stating point. For example, an RF-pulse that flips the net magnetization vector 90-degrees away from the z-axis is called a 90° RF-pulse, or just a 90°-pulse. This is illustrated in FIG. 2G. The 90°-pulse is here shown as an example, and in today's modern scanners a variety of pulse-angles and pulse combinations are used. The 180°-pulse is worth mentioning as this pulse inverts the magnetization and is applied in combination with a 90°-pulse in the frequently used spin echo (SE) sequences.

After the application of an RF-pulse, the magnetization vector will gain a transversal magnetization component, $M_{xy}$. Along with the longitudinal component, $M_z$, this will now represent the total magnetization of the system. The transversal component makes it possible to detect the magnetization due to its oscillation around the external magnetic field and as it will induce a current in a pickup coil. The physical principal behind the detection of the MR-signal is derived from Faradays' law for electromagnetic induction. This law tells us that an electromotive force (emf) will be generated in a coil by altering the magnetic flux:

$$\mathrm{emf} = -\frac{d\Phi}{dt}$$

Figure 2H:
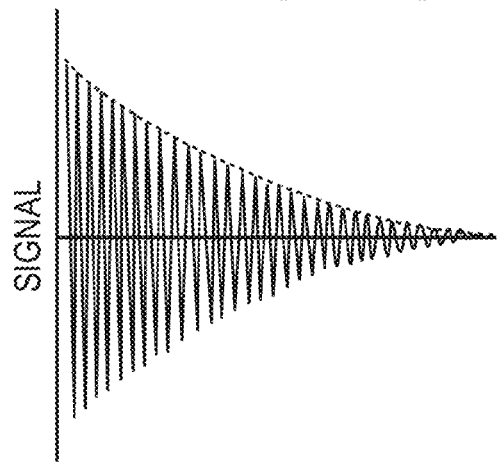

Φ represents the flux through the coil. The time dependent shape of this signal carries all the information that is necessary to create an MR-image. This signal is called "free induction decay" (FID). A typical FID-signal observed after the application of an excitation pulse is illustrated in FIG. 2H. The expression "decay" refers to the rapid loss of signal strength due to so-called proton relaxation mechanisms, which is the topic for the next sectional chapter.

4. Relaxation

Assume that the equilibrium state of the magnetization is altered, for example by using an RF-pulse. The existence of the persisting external magnetic field, $B_0$, will result in restitution of the magnetization back to equilibrium trough the processes generally referred to as proton relaxation. These processes result from proton-proton interaction and lead to the loss of excitation energy. The relaxation is caused by the combination of two separate mechanisms:

$T_1$-relaxation, longitudinal relaxation or spin-gitter relaxation; and $T_2$-relaxation, transversal relaxation or spin-spin relaxation.

4.1 $T_1$-Relaxation

Longitudinal relaxation is caused by the exchange of quantum energy between exited protons and their environmental surroundings termed "the gitter". This energy exchange can happen through spontaneous emission or through stimulated emission. However, only stimulated emission is important with regard to MR imaging. This process is dependent on protons experiencing a fluctuating magnetic field that consists of frequency components equal or dose to the Larmor frequency. In biological material such magnetic fields will be generated by various processes, most important of these being the dipol-dipol interactions and chemical shift interactions. The macroscopic effect of this energy exchange is the gradual recovery of the longitudinal magnetization component, $M_2$. The rate of this recovery can be described by temporal parameter $T_1$, and is defined as the time it takes for the longitudinal component to regain to 63% of its initial value. The inverse of the longitudinal relaxation time $1/T_1$ is referred to as the longitudinal relaxation rate $R_1$. The values of the time parameter $T_1$ spans over several thousand milliseconds for protons in biological material, and the value of $T_1$ will characterize the tissue. Differences in tissue $T_1$ give rise to image contrast between tissues by applying MR pulse sequences that are sensitive to $T_1$ variations. These sequences are called $T_1$-weighed sequences and where short $T_1$-valuese will cause higher signal intensity (SI) than longer $T_1$.

Figure 2I:
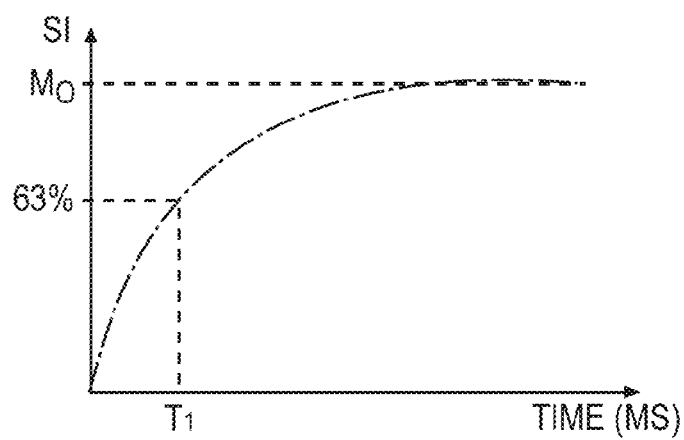

After the application of an RF-pulse the longitudinal magnetization will follow an exponential development that depicts the change from its initial value $M_2(0)$ until its equilibrium value $M_0$. An illustration of this is seen in FIG. 2I. This relaxation process can be expressed through the following differential expression:

$$\frac{dM_2}{dt} = \frac{M_z - M_0}{T_1}$$

If one assumes that the relaxation processes can be neglected during the RF-excitation (the excitation time is much shorter than the relaxation times), the effect of the relaxation of the longitudinal magnetization component can be derived from solving equation in (2-14). This gives us:

$$M_z(t) = M_z(0)e^{-t/T_1} + M_0(1-e^{-t/T_1})$$

4.2 $T_2$-Relaxation

Figure 2J:
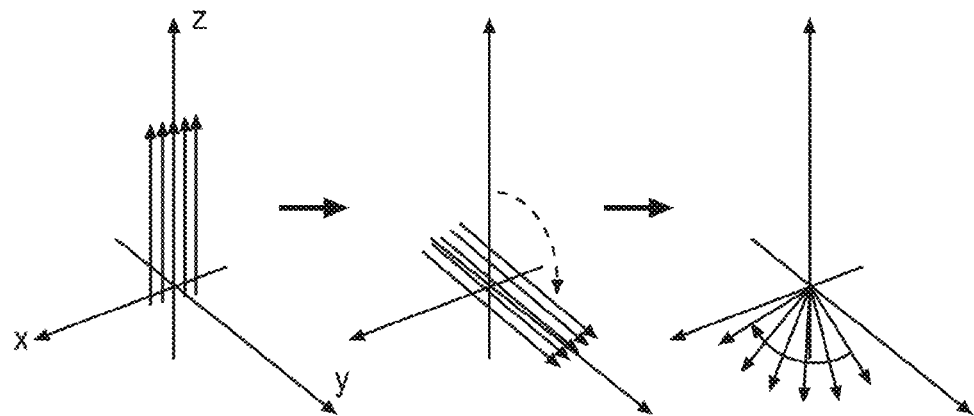

Transverse relaxation is the result of spins losing their phase coherence. Moving spins will experience both the main magnetic field and also local magnetic fields variations due to the effect of neighboring spins. These macroscopic field inhomogeneities will create spatial dependent precession frequencies resulting in a cumulative loss of phase coherence. As the signal depends on the sum of all spin vectors, the loss in phase coherence will result in loss of the MR signal. FIG. 2J illustrates this mechanism.

Figure 2K:
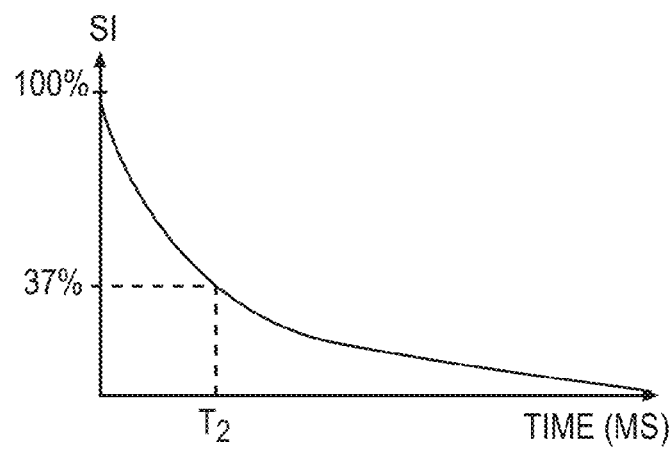

The reduction of transverse magnetization is mathematically described by the exponential curve characterized by the relaxation parameter $T_2$. This parameter is defined by the time it takes the transverse magnetization to lose 63% of its initial value. See FIG. 2K for illustration. The inverse relaxation time, $1/T_2$ is referred to as the transversal relaxation rate $R_2$.

Similar to $T_1$, $T_2$ is also tissue specific. $T_2$ is in general longer in liquid than in tissue and variations in $T_2$-values are often used to detect pathology because several pathological processes are associated with increased level of free fluid.

In real life there exists a second factor that causes the spins to lose phase coherence, that is inhomogeneities in the external magnetic field. The reduction in transverse magnetization caused by magnetic field errors is given a separate time constant $T_2'$. The actual relaxation rate, named $R_2^*$, is given as the sum of both the internal and external relaxation rate:

$$R_2^* = R_2 + R_2'$$

The equivalent expression of the total relaxation time is given by:

$$\frac{1}{T_2^*} = \frac{1}{T_2} + \frac{1}{T_2'}$$

However, the loss of transverse magnetization due to external field inhomogeneities can be restored. This is done by applying a second RF pulse after the initial RF pulse that is designed to regain phase coherence. This process is similar to the formation of an echo used for decades in Nuclear Magnetic Resonance (NMR) techniques and is called spin echo (SE). The loss of signal due to internal effects is irreversible because these effects are caused by local, random and time-dependent field strength variations.

The transversal relaxation process can, with a high degree of accuracy, be described by the following differential equation:

$$\frac{dM_x}{dt} = -\frac{M_x}{T_2} \quad og \quad \frac{dM_y}{dt} = -\frac{M_y}{T_2}$$

By assuming that the relaxation process can be neglected during RF excitation, the effect relaxation on the transversal magnetization can be presented as:

$$M_{xy}(t) = M_{xy}(0)e^{-t/T_2}$$

By combining the two relaxation processes, $T_1$ and $T_2$, expressed by the differential equations (2-14) and (2-18), the motion of the magnetization vector M in an external magnetic field can be described by the vector equation:

$$\frac{dM}{dt} = \gamma M \times B_0 + \frac{1}{T_1}(M_0 - M_z)\hat{z} - \frac{1}{T_2}M_{xy}$$

This is again the empirical Bloch equation but with relaxation terms included. The transversal component of magnetization is given by:

$$M_{xy} = M_x\hat{x} + M_y\hat{y}$$

The theory that lies behind the MR-imaging technique is comprehensive and will not be described in detail. Only fundamental principles and main elements that are relevant for this thesis and for dynamic MR-imaging are presented. For a more detailed description of basic MRI principles see *Magnetic Resonance Imaging* of Vlaardingerbroek et al. [8], and also *Magnetic Resonance Imaging: Physical Principles and Sequence Design* by Haacke et al. [9].

A single MR image is often presented as a axial slice of the object with a given slice thickness. The anatomic area covered by the slice is referred to as "Field Of View" (FOV), usually defined in terms of $mm^2$. The slice is further divided into volume elements referred to as "voxels'". A voxel represents a value in the three dimensional space which correlates to the spin density, and further, the magnetization vector in that volume element. The magnitude of this vector will, for each voxel, correspond to a given value on a grey scale or color scale and also a spatial position in the final image. The respective squares are elements in the image called "pixels" and all these elements add up to the final MR-image. However, it is not the mere spin density in a voxel that is commonly of most interest when forming an MR-image, but mainly the effects of relaxation mechanisms. It is these effects that make MR imaging unique and a very informative diagnostic method.

For best make use of the relaxation processes in the imaging technique, temporary field gradients are applied. When done correctly, optimal image contrast in the final image can be obtained. The combination of RF pulses and magnetic field gradients is called a pulse-sequence and this is the topic for the next section.

5. Pulse-Sequences

A pulse-sequence is defined as a pre-described set of RF pulses and field gradient pulses carefully timed and spaced with the aim to generate an MR image. MR imaging is a very advanced imaging technique that has high demand on the technical specification of the hardware. Technical innovation has for the last 30 years led to great improvement in image quality and in image acquisition time. As a result of this progress, today's scanners include a very long list of possible pulse sequences. Irrespective of which pulse-sequence chosen, the objective is the same: to optimize image contrast and do this as fast as possible with the minimum amount of image artifacts and at an acceptable signal-to-noise level.

The pulse-sequences can be divided into two separate groups, depending on how the NMR signal is formed. These are:
1. Spin Echo sequences (SE)
2. Gradient Echo sequences (GRE)

Many versions and variations of these two families of pulse-sequences have been developed, mainly to optimize SNR and contrast between tissues but also to reduce acquisition time and tailor sequences for specific clinical applications. Pulse-sequences based on gradient echo formation are highlighted in this thesis, as this family of sequences is most commonly used in our study.

5.1 Gradient Echo Sequences

Figure 2L:
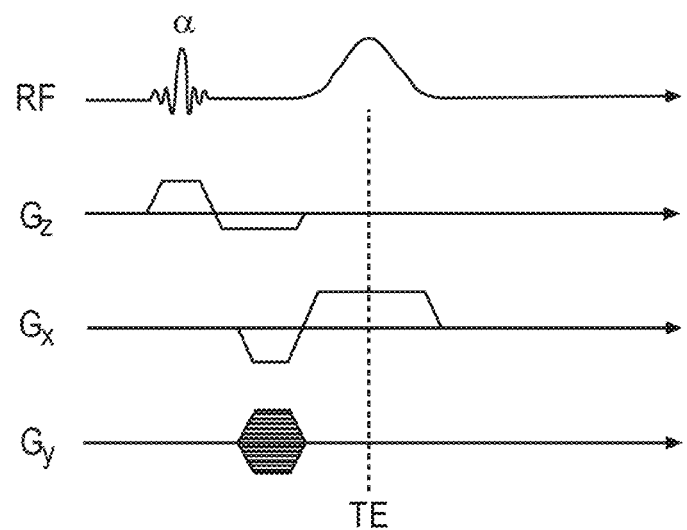

A classical gradient echo sequence generates its echo by applying bipolar gradient pulses between successive excitation pulses. The application of these gradient pulses along with using just a single RF pulse for each repetition of the pulse-sequences sets gradient echo sequences apart from spin echo sequences. In SE imaging one or several 180° refocusing pulses are used between each excitation. A temporal pulse sequence diagram of a classical GRE-sequence is presented in FIG. 2L. The excitation pulse that is used in a gradient echo sequence is referred to as an α-pulse. This pulse rotates the magnetization into the transverse plane at an angle α, commonly with a value between 0° and 90°. The flip angle decides the fraction between longitudinal and transversal magnetization where the amplitude of transversal component will decide the strength of the MR-signal in the pick-up coil. The flip angle along with the magnitude of the initial longitudinal magnetization will be the primary cause for image contrast in a gradient echo. Just after the excitation bipolar gradients are applied. The first gradient pulse will effectively dephase the spins while the second pulse of opposite polarity will rephase the spin and by this generate a gradient echo. During the application of the first part of the refocusing gradient, the spins will gain phase coherence towards a maximum level of coherence at echo time and then dephase again. This gradient pulse is also referred to as the "read-out" pulse as signal sampling is performed during the deployment of this gradient pulse. The time from the excitation pulse to the maximum echo signal is referred to as the echo time (TE) for the pulse sequence, and the time between each excitation is called the sequence repetition time (TR).

The application of a low flip angle results in faster return of the magnetization back to its equilibrium value. This implies that shorter successive repetition times between each excitation pulse can be used. The use of bipolar gradient for echo formation will simultaneously shorten the minimum possible TR and also make the sequence faster compared to SE sequences where additional RF pulses are used. The consequence of these time reducing efforts is shorter imaging time compared to SE sequences. The absence of refocusing RF pulses in gradient echo imaging also have its drawback as it makes the gradient echo sequences more sensitive to magnetic field inhomogeneities. The relaxation measured in a GRE-sequence caused by these field homogeneities will therefore not be reversed and the loss of signal is therefore due to $T_2^*$-effects.

The image contrast in gradient echo based sequences is therefore $T_2^*$-weighed instead of $T_2$-weighed in SE-sequences, and where $T_2^* < T_2$. Because of this a GRE-sequence will be more sensitive to susceptibility caused artifacts compared to SE-sequences.

In gradient echo sequences the short TR leads to residual transverse magnetization between each TR-interval. If not dealt with, this can lead to image artifacts. To eliminate this possibility, two main approaches are used. The first one is to make $TR \gg T_2$ but this gives us long imaging times. The second approach is to carefully design the pulse sequence so that the residual transverse magnetization does not cause artifacts. This is done using two very different methods:
1. Spoiled GRE: A phase varying RF-pulse (α-pulse) is applied along with spoiler gradients preventing the build-up of transverse magnetization.
2. Steady State GRE: Conserves the residual transverse magnetization which adds to the MR-signal. A steady signal state is established after a given number of TR intervals.

The signal intensity (SI) in a GRE-sequence is proportional to the net transverse magnetization and mathematically given by:

$$SI_{GRE} \propto M_T(TR, TE, \alpha) = M_0 \frac{\sin(\alpha)(1 - e^{-TR/T_1})}{1 - e^{-TR/T_1}\cos(\alpha)} e^{-TE/T_2^*}$$

This is the expression for the signal intensity in a spoiled GRE-sequence. As already mentioned, the steady state magnetization will depend on the flip angle. From equation (2-22) one can observe that for a given $T_1$ and TR, there will exist a flip angle that generates maximum signal strength. This flip angle is referred to as the Ernst angle, $\alpha_e$, named after the Swiss chemist Richard Ernst, and is given by:

$$\cos(\alpha) = e^{-TR/T_1}$$

The contrast properties associated with GRE-sequences and with regard to sequence parameters can be summarized as following:
1. $T_1$-weighed image: Short TR (TR/T1≪1) and short TE combined with a large flip angle.
2. $T_2^*$-weighed image: Long TR (TR/T1=1) and long TE combined with a small flip angle.

6. Contrast Agent in MRI

Sufficient contrast to separate normal from pathologic tissue is a prerequisite in all diagnostic imaging modalities. MR has excellent soft tissue contrast but this can be further improved by the use of contrast agents. Exogenous MR-compatible contrast agents were introduced in the 80's and today is in use in a substantial number of MR exams. The contrast agent itself is not directly visible in the images but its influence on tissue specific parameters is what can be observed. Existing contrast agents cause reduction in $T_1$, $T_2$ and $T_2$* relaxation times in the tissue. If this leads to an increased contrast between healthy and pathologic tissue, both the sensitivity and specificity of the exam can be increased.

6.1 Relaxitvy

As already discussed a time varying field caused by thermal motion will induce spin energy exchange between the protons and their surroundings (spin-gitter relaxation, $T_1$). These oscillation magnetic fields are amplified with the presence of a paramagnetic contrast agent causing an increase in the relaxation rate $R_1$, which implies that $T_1$ is reduced. In analogy to image contrast, this will lead to an increase in contrast in $T_1$-weighed images. A basic assumption for this is that all water molecules have equal access to the contrast agent. This is referred to as "fast exchange" and is not necessarily fulfilled close to the capillary walls or in voxels containing several divisions separated by membranes. The change in longitudinal relaxation rate is linear if the condition for fast exchange is fulfilled. If $T_{1,0}$ represents the tissue real $T_1$ and $T_1(C)$ is its new value due to the effect of the contrast agent, we can show that:

$$R_1(C) = \frac{1}{T_1(C)} = \frac{1}{T_{1,0}} + r_1 C \equiv R_{1,0} + r_1 C$$

Here the proportional constant $r_1$ is called longitudinal relaxivity, a property of the contrast agent that depends on its composition.

In addition to dipolar relaxation effects that results in increased $R_1$, the contrast agent will also increase the relaxation rate $R_2$. This is the consequence of two $T_2$-effects: one dipolar $T_2$-effect equivalent to $T_1$-relaxivity, and one susceptibility induced $T_2$*-effect that has a long interaction range and is independent of the dipolar relaxivity. Similar to $R_1$, the degree of increased transversal relaxation rate $R_1$ will also be proportional to the concentration of the contrast agent:

$$R_2(C) = \frac{1}{T_2(C)} = \frac{1}{T_{2,0}} + r_2 C \equiv R_{2,0} + r_2 C$$

Here $r_2$ represents the transversal relaxivity of the contrast agent. This effect is commonly referred to as the susceptibility-induced relaxation. Note that the equations (2-24) and (2-25) have linear dependency between the concentration of the contrast agent and the increase relaxation rate. However, in real life this is not always the case. Contrary, it shows that the so called "dose-signal response" in general is not linear, which causes great difficulties when one tries to quantify the effects of the contrast agent.

6.2 Contrast Agent Categories

After contrast agents became commercially available in 1988, gadolinium (Gd) based contrast agents have dominated the market. However, today several other substances exist and are used depending on the type of study. MR contrast agents are categorized according to magnetic properties and biological distribution.

Figure 2M:
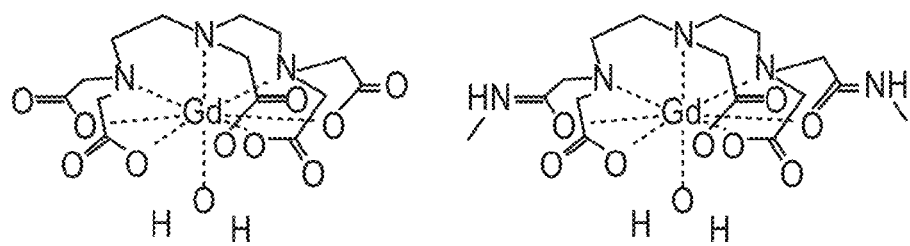

Based on their magnetic properties, the contrast agents are divideded into two groups: paramagnetic and super paramagnetic compounds. The best known contrast agent consists of Gd ions ($Gd^{3+}$) and belongs to the paramagnetic group. Atoms and molecules from paramagnetic metals have permanent magnetic moments caused by the spin of an unpaired electron in the outer shell of the atom/molecule. Because of this, magnetic dipoles are created when paramagnetic metals are exposed to a magnetic field. Gadolinium has seven unpaired electrons each containing a magnetic moment that is 700 times larger than for a single proton. These paramagnetic ions induce a large fluctuating field that the nearby protons experience causing a significant amplification of the proton relaxation. However, the free gadolinium is very toxic. Before clinical usage, the Gd ion has to be incorporated into a ligand that prevents the gadolinium from binding to endogenous anions. Attached to the ligand, the Gd ion forms a stable chelate that is used in contrast enhanced MR. The most commonly used gadolinium chelates are Magnevist™ Gd-DTPA and Omniscan™ Gd-DTPA-BMA. The chemical structures of these compounds are illustrated in FIG. 2M. Gd-based contrast agents show bi-exponentlal kinetics.

In addition, superparamagnetic contrast agents based on insoluble iron oxide crystals are often referred to as nano particles. Each of these nano particles consists of several thousand paramagnetic iron ions. Today there exist two types of contrast agents based on iron oxide crystals: SPIO ("Super-Paramagnetic Iron Oxide") and USPIO ("Ultrasmall Super-Paramagnetic Iron Oxide"). Superparamagnetic contrast agents are dominated by a $T_2/T_2$* relaxation effect due to their large magnetic moment.

The biological distribution of a contrast agent describes how the substance is distributed in the tissue after an intravenous administration. Based on this contrast, agents can be categorized into three groups:

1. ECF-CA—A small paramagnetic contrast agent that diffuses from the plasma volume and is distributed in the extravascular extracellular space (EES). DCF-KM shows bi-exponential kinetics with a tissue distribution half-life of about 3-5 minutes and an excretion half life (via the kidneys) of 50-60 minutes.
2. Intravascular-CA—A larger molecular contrast agent that causes a prohibitive leakage and therefore remains intravascular.
3. Tissue specific-CA—A specially designed contrast agent that accumulates in a predetermined organ or tissue type.

7. Dynamic MR Imaging

Dynamic MR-imaging has through several studies proved to be a method well suited for studying physiological factors associated with tumor angiogenesis. A number of studies have demonstrated that the dynamic signal pattern resulting from the administration of an intravenous contrast agent is predicative for tumor malignancy, and that tumors in general have deviating contrast enhancement compared to normal tissue. [11]-17). This reflects underlying physiological factors associated with angiogenesis as malignant tissue commonly possesses increased vascularity and also increased endothelial permeability compared to normal tissue and tissue in benign lesions.

7.1 Dynamic Contrast Enhanced MRI

Dynamic contrast enhanced MRI (DCE-MRI) is an imaging technique designed for T1-weighed perfusion imaging. DCE-MRI uses a rapid temporal imaging technique before, during and after the administration of a paramagnetic contrast agent. The objective is to observe over time the distribution of the contrast agent in the tissue. The contrast agent is intravenously injected in a peripheral vein where it is transported by the vascular system to the imaged tissue. The contrast agent will immediately start leaking through the capillary wall and accumulate in the extracellular extravascular space (EEC) by passive diffusion effects driven by the contrast concentration difference over the capillary wall (Ficks law). Since the contrast concentration in the plasma volume is decreasing due to leakage, this concentration will after a given time be less than in the EES, resulting in a wash-out of the contrast agent from the EES and back into the plasma volume. Execration through the kidneys will lead to a continuous decrease in plasma concentration until all the contrast is eliminated [18]. The leakage rate through the capillary wall will depend on physiological factors such as capillary permeability, capillary area and perfusion. Because the MR-signal is assumed to be proportional to the contrast concentration, the time dependent signal intensity curve will contain underlying mechanisms that describes physiological factors and also the vascularity in the tissue of interest [18, 19].

A detailed anatomical imaging sequence is performed prior to the dynamic imaging sequence. Before the administration of the contrast agent a single or several sets of pre-contrast images of the object are registered, referred to as "baseline images". Then the MR dynamic signal change due to the contrast agent is monitored by the use of a rapid imaging technique and where the time interval between each acquired image set decides the temporal resolution of the imaging pulse sequence. To model the tissue specific change in the relaxation rate caused by transient contrast agent effects, one needs to know the concentration of the contrast agent at each measuring point during the data acquisition.

For a qualitative approach it is helpful to convert the signal intensity to relative signal intensity (RSI) [20-22]. The relationship between the concentration of the contrast agent and the relative increase in signal intensity can be derived from the Bloch equations [9] for any pulse sequence. By using a spoiled gradient echo sequence and further assuming that the contrast agent does not have an effect on the proton density and that TE is short compared to the $T_2^*$ effects, then the change in signal intensity is due to $T_1$ effects alone. But at the same time the use of a short sequence repetition times the relationship between the signal intensity and the relaxivity, $1/T_1$, will be approximate linear:

$$SI \approx \frac{g\rho TR}{T_1}$$

By assuming that the signal intensity is proportional to the relaxivity $1/T_1$, one gets from equations (2-24) and (2-26) that:

$$\frac{S(t) - S(t_0)}{r_1 \rho TR} \approx \left(\frac{1}{T_1} - \frac{1}{T_{1,0}}\right) = r_1 C(t)$$

If this expression is divided by the precontrast signal one gets:

$$RSI(t) = \frac{S(t) - S(t_0)}{S(t_0)} = r_1 T_{1,0} C(t)$$

The relative signal intensity after the administration of a contrast agent will be proportional to the concentration, spin-gitter relaxivity and the underlying tissue specific $T_1$-relaxation time. This approximation will not be exact if the contrast concentration is too high. The signal intensity will then vary in a non-linear fashion as a function of concentration. This will however only be true in the vascular system and not in the leakage space. The relative signal intensity will, as already mentioned, represent a qualitative measure for the contrast concentration in the tissue. The exact concentration cannot be estimated without knowledge of the tissue specific $T_1$-time. In this study the contrast concentration is not quantified but hemodynamic parameters are based on the assumption that the relative contrast agent concentration can be estimated. This is done by applying pharmacokinetic models, models that are presented later in this chapter.

7.2 Dynamic Susceptibility Contrast MRI

Dynamic susceptibility contrast MR (DSC-MRI) is acquisition technique for $T_2$- or $T_2^*$-weighed perfusion imaging based on either SE- or GRE-sequences. Similar to the DCE-MRI technique, this method also applies a rapidly repeating imaging technique before, during and after the injection of a paramagnetic contrast agent to monitor the contrast agent distribution in the imaged tissue. However, the effect of the contrast agent on these relaxation times is based on different mechanisms. The signal enhancement in $T_1$-weighed images can only be observed in regions directly in contact with the contrast agent while the reduction $T_2^*$ values and the signal loss due to this can be observed in a larger area. This can be explained by the dephasing of the spins due to susceptibility-induced local field gradients surrounding the paramagnetic contrast agent.

The $T_1$- and $T_2$-effects can be looked upon as complimentary effects. In a volume where the contrast agent is homogenously distributed, the $T_1$-effect will be dominating because the complete volume will be in contact with the contrast agent. The $T_2^*$-effect will then be weak because of negligible intrinsic field gradients. Furthermore, an inhomogeneous distribution of the contrast agent will give rise to limited $T_2$-effects (depending on the distribution volume in each voxel of the contrast agent) but will cause a substantial $T_2^*$-effect [23].

Similar to DCE, the DSC sequence is applied prior to injecting the contrast agent for the purpose of getting baseline images then continued during and after contrast administration. The purpose of this strategy is again to observe the distribution of the contrast agent in the selected anatomic volume over time and its transient effect on the measured signal intensity. The time dependent signal intensity curve will be equally modulated due to the changes in the transversal relaxation rate as function of tissue specific physiological factors. DSC-MRI is most commonly applied in cerebral perfusion imaging where physiological information is derived from a concept referred to as tracer kinetic modeling. This model is based on the central volume principle that states that the blood volume (BV) in a given tissue is equal to the blood flow (BF) multiplied by the mean transit time (MTT):

$$BV = BF \cdot MTT$$

The central volume principle assumes a pure intravascular contrast agent distribution and can therefore not be applied if the blood-brain barrier (BBB) is altered or destroyed or when analyzing non-cerebral organs. In the case of an extravascular contrast agent distribution, the signal enhancement due to $T_1$-reduction will be much more profound than the signal loss due to $T_2^*$-effects (24). An alternative way to prevent contamination due to $T_1$ signal enhancement is to apply a double echo $T_2^*$-weighed sequence, assuming a monoexponential signal change as a function of echo time. In this way one can directly quantify the transversal relaxation rate $R_2^*$, without any assumptions regarding $T_1$:

$$\Delta R_2^*(t) = \frac{\ln\left(\frac{S_1(t)}{S_2(t)}\right) - \ln\left(\frac{S_{1,pre}}{S_{2,pre}}\right)}{TE_2 - TE_1}$$

where $S_k(t)$ is the signal intensity for echo k at the time t, and $S_{k,pre}$ is the corresponding signal intensity before the administration of the contrast agent [47, 48]. A quantification of the physiological dependent parameters BV, BF and MTT for this case requires a modification of the kinetic model to include the contribution from contrast agent leakage. The registration of two echo signals will however increase the sequence repetition time causing fewer slices to be acquired in a given imaging time.

7.3 Pharmacokinetic Theory

Pharmacokinetic is a quantitative description of the time-dependent movement of a tracer in tissue based on mathematical modeling. Many pharmacokinetic models have been proposed and applied for the analysis of DCE-MRI data, and almost every one of these models use curve approximation for the purpose to estimate physiological parameters. Because Gd-based contrast agents are distributed in the extracellular space the applied model has to be considered to contrast agent concentration in several compartments. It is common that a tissue structure is divided into three compartments: the vascular plasma space, the extracellular extravascular space (EES), and the total intracellular space [25].

All MR compatible contrast agents in clinical use will however not penetrate into the intracellular space. A pharmacokinetic two-compartment model will therefore represent a good approximation when describing the contrast concentration in the tissue for each voxel. Before continuing to explore this model in detail, it can be appropriate to define the unity tissue volume, $v_t$, consisting of the volume fractions plasma volume, $v_p$, extravascular extracellular volume, $v_t$, and the intracellular volume. $v_t$ will represent a partial volume of the observed tissue.

The contrast agent pharmacokinetics in a two-compartment model can be described as following: The contrast agent is initially distributed in the vascular plasma compartment, represented by $v_p$. Gradually the contrast agent diffuses through the capillary walls into the extracellular, extravascular compartment, represented by $v_e$. The leakage rate is described by the time dependent volume transfer constant, $K^{trans}$, and is defined as the transfer rate from the plasma to the EES per $v_t$ (min$^{-1}$).

Figure 2N:
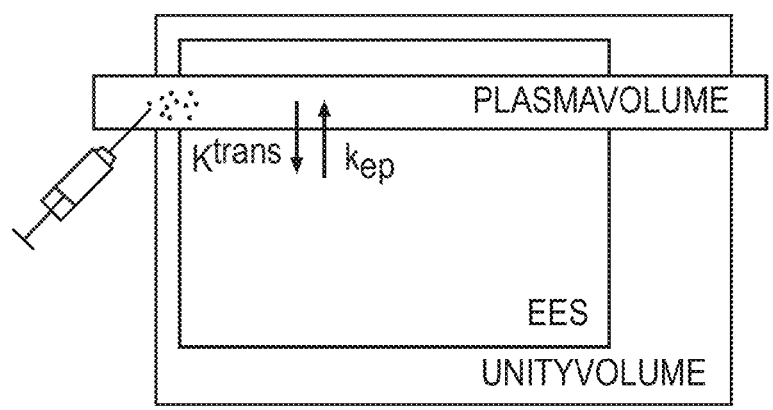
Figure 2O:
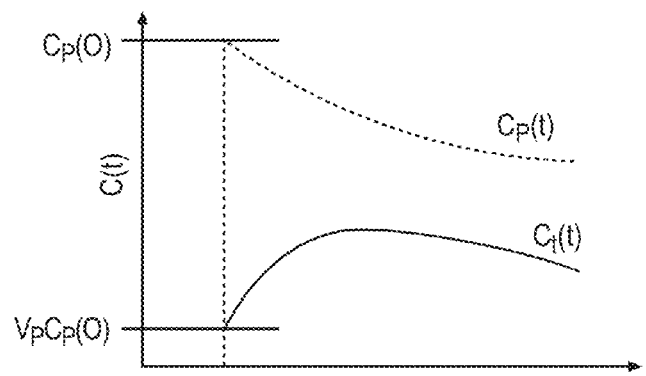

The accumulation of the contrast agent in EES leads to a reversed concentration density across the capillary wall which leads to a wash out of the contrast agent from the EES. The leakage rate of this wash out process is described by the rate constant, $k_{ep}$, defined as the transfer constant between EES and the plasma space per $v_p$ (min$^{-1}$). The model assumes a homogenous distribution of the contrast agent in each of the compartments and that a "fast exchange" approximation is fulfilled. The two-compartment model is illustrated in FIG. 2N. In normal tissue the vascular volume will represent a small fraction of the total unity volume and one can therefore assume that the contrast concentration in the unity volume $C_t$, exclusively originates from EES [26]:

$$C_t = v_e C_e$$

where $C_e$ is the contrast agent concentration in EES and $v_e$ can be described as the non-dimensional relationship between the unity volume and the EES. The exception from this approximation is in highly vascular tissue where the varying contribution from the contrast agent in the vasculature can be observed.

The transfer constant $K^{trans}$ and the EES volume fraction $v_e$ are related to basic physiological tissue properties, while the rate constant $k_{ep}$ is given as the relationship between the transfer constant and EES:

$$k_{ep} = \frac{K^{trans}}{v_e}$$

This equation tells us that if no cells are found in the unity volume, i.e. $v_e = 1$, then $k_{ep} = K^{trans}$.

In 1951 Kety developed a model for blood flow limiting tracer uptake in tissue. The model was developed to study the transport of gasses in the lungs, and represented a generalized kinetic model that has been modified by many, among those Tofts and Kermode in 1991 [26], with the purpose of DCE-MRI application. The time dependent tissue concentration of the contrast agent $C_t$ (mmol contrast agent per unity volume) is assumed to have a permeability limited constant transfer rate between the plasma volume and the EES, and can be described by the differential equation: [25]

$$\frac{C_t(t)}{dt} = K^{trans}\left(C_p - \frac{C_t}{v_e}\right) = K^{trans} C_p - k_{ep} C_t$$

where $C_p$ and $C_t$ represent the concentration in the tissue of the contrast agent in the plasma space and the unity space, respectively. The solution to the time dependent pharmacokinetic transport equation (2-33), using the initial conditions that $C_p = C_t = 0$ at $t=0$, is:

$$C_t(t) = K^{trans} \int C_p(\tau) e^{-k_{ep}(t-\tau)} d\tau$$

$K^{trans}$ here represents the slope for the initial change in contrast concentration, i.e. the amount of contrast agent that leaks into the EES per unit time, and $k_{ep}$ represents the wash-out rate of the contrast agent from EES into the plasma space. The solution (2-34) is identical to a folding integral, and the exponential term $\exp(-k_{ep}\cdot t)$ can be seen as a response function to the contrast agent concentration in the plasma space.

To get a quantitative estimation of the kinetic parameters based on the two-compartment model, it is necessary to measure and incorporate the time dependent contrast behavior in the plasma space $C_p(t)$, something the general two-compartment model does not describe. If both, the plasma and the tissue concentration, can be estimated temporarily, then the transfer function $K^{trans}$ can be determined by using a standard mathematical deconvolution. In the original model developed by Tofts and Kermode in 1991 [26], the temporal plasma concentration theoretically described by a bi-exponential curve made possible an analytical solution to $C_t(t)$. However, studies demonstrated that the original TK-model neglected the vascular contribution which leads to an overestimation of the transfer constant $K^{trans}$ [27]. Later, people have suggested a more versatile approach to the plasma term where the time dependent contrast concentration in the capillaries $C_p(t)$ is related to an arterial input function (AIF) [46]. This implies the registration of the time dependent signal intensity in an artery using at fast dynamic MR sequence, and then converting the relative signal intensity curve to a dynamic concentration curve assuming an approximate linear dose response and also assuming that the "fast exchange" condition is met. This makes a quantitative analysis of the pharmacokinetic two-compartment model possible. By including the contribution from the capillary volume fraction $v_p$, the solution to the transport equation is as follows:

$$C_t(t) = K^{trans} \int_0^t C_p(\tau) e^{-k_{ep}(t-\tau)} d\tau + v_p C_p(t)$$

The first term in the folding integral (2-35) describes leakage of contrast agent, and the second term describes the intravascular effect.

The plasma concentration, represented by the AIF, can be difficult to measure due to the lack of distinct arteries in the object or limited spatial resolution. Simultaneously, a solution to the folding integral requires that the AIF is described. As a simplified alternative, one can then assume that the plasma concentration follows at a certain temporal curve. Depending on the temporal resolution, the plasma concentration can be approximated using an idealized mono- or bi-exponential input function and with a half-life equal to the contrast agent half-life. An idealized mono-exponential input function is illustrated in FIG. 2N.

If the plasma concentration is modeled as:

$$C_p(t) = C_p(t_0) e^{(-t/T_{1/2})}$$

where $T_{1/2}$ represents the half life of the contrast agent in plasma, one gets:

$$\frac{dC_t(t)}{dt} = K^{trans} C_p(t_0) e^{(-t/T_{1/2})} - k_{ep} C_t(t)$$

This is a non-homogenous equation with the solution:

$$C_t(t) = \frac{K^{trans} C_p(t_0)}{T_{1/2} - k_{ep}} \left( e^{(-k_{ep} t)} - e^{(-t/T_{1/2})} \right)$$

which assumes a linear dose response. If $C_{p,0}$ and $T_{1/2}$ are assumed to be constant, then the transfer constants can be estimated by applying standard non-linear least squares quadratic curve fitting of the dynamic data and the theoretical idealized input curve.

A list of expressions and parameters, along with corresponding definitions and units, are presented in table 2-1. The terminology used follows the convention described by Tofts et al., 1999 [25].

TABLE 2-1

Abbreviations of pharmacokinetic variables

| Symbol: | Definition: | Unit: |
| --- | --- | --- |
| EES | Extracellular Extravascular Space | None |
| $K^{trans}$ | The volume transfer constant between the plasma and the EES | min$^{-1}$ |
| $k_{ep}$ | Rate constant between EES and the plasma | min$^{-1}$ |
| $v_e$ | EES volume per unit volume tissue | None |
| $v_p$ | Plasma volume per unit volume tissue | None |
| $C_e$ | The contrast agent concentration in EES | mmol |
| $C_p$ | The contrast agent concentration in arterial blood plasma | mmol |
| $C_t$ | The contrast agent concentration in unit tissue volume | mmol |

8. Introduction

The method's main objective is to apply a dynamic double-echo pulse sequence with high temporal resolution to estimate a variety of quantitative, qualitative and descriptive bio-markers and, during the same sampling time interval, also sample image data of high spatial resolution. Based on the dynamic Images, the method aims to develop statistical models and analytical strategies to identify those bio-markers that are best suited to differentiate between malignant and benign breast lesions.

Most breast lesions are heterogeneous in nature. It is therefore of importance to be aware of this by studying small volume segments of the defined lesion. The different bio-markers are therefore estimated on a voxel-by-voxel basis throughout the three-dimensional lesion. Post processing of the dynamic image data is without exception being done using the software package nordicICE (version 2.3.0, NordicNeuroLab, Bergen, Norway).

A fundamental issue, during the acquisition of dynamic MR-data, is the compromise between spatial and temporal resolution. In our method a unique sequence protocol was developed where the dynamic image-series is split into several segments alternating between high temporal resolution and high spatial resolution. This sequence protocol was developed by Kjell-Inge Gjesdal (Ph.D, Sunnmøre MR-klinikk, Ålesund, Norway). Most of the data used for analysis is from the high temporal segments which best describes the dynamic properties in the observed volume of tissue. In this chapter we present the applied sequence, the acquisition of the dynamic image date, and also the applied image processing.

Statistical analysis is applied to evaluate the various bio-markers' ability to predict the correct diagnosis. The statistical analysis is performed using Excel (Microsoft Corporation, version 12.0) and the software package R (R Foundation for Statistical Computing, version 2.10.0, Vienna, Austria).

9. Patients

The method here presented has been applied to ~50 patients with known breast lesions, after the study was accepted by the regional ethics committee.

In premenopausal women a significant contrast signal enhancement can occur in healthy glandular tissue during the part of the menstrual cycle where epithelial proliferation is most significant.

To avoid problems related to this phenomenon, it is recommended that the MR exam is performed between day 5 and day 15 in the menstrual cycle. Imaging of postmenopausal women that receives estrogen substitution treatment should by same reasoning postpone the treatment a time before the MR study.

Fifty-two patients having 53 breast lesions underwent a dynamic MR exam at the Stavanger University Hospital in Norway. The exams were accomplished in the period from March 2008 until August 2009. The patients were recruited from a clinical collective (patients with the most common symptom of a lump in the breast) and a screening collective (patients without symptoms being a part of the national mammography study) based on mammography and ultrasound findings. The patients were included in the study based on the finding of a solid lesion. Other criteria for inclusion were: above 18 years of age, no contra indication for MRI and contrast injection, and a written consent. The reported diagnosis was confirmed on the basis of tissue sample from cytology or histological needle biopsy. In addition, all patients went through surgery.

The retrospective analysis included 40 patients with 41 verified lesions divided into one of the following subgroups:

| 1. | Invasive ductal carcinoma (IDC): | n = 16 lesions |
|---|---|---|
| 2. | Fibroadenoma (FA): | n = 14 lesions |
| 3. | Invasive lobular carcinoma: | n = 3 lesions |
| 4. | Papilloma: | n = 3 lesions |
| 5. | Mucinous carcinoma: | n = 2 lesions |
| 6. | Benign phylloides: | n = 1 lesions |
| 7. | Tubular adenoma: | n = 1 lesions |
| 8. | Inflammatory carcinoma: | n = 1 lesions |

A total of 12 patients were excluded from the study due to different reasons: no visible tumor found by MRI, histology not showing a solid tumor, image artifacts due to movement of the patient, patients not able to go through the MR exam, and a failed contrast injection.

The study analyzed the breast lesions based on two group strategies:

Group strategy 1:
1. Benign (n=19)
2. Malignant (n=22)

Group strategy 2:
1. FA (n=14)
2. IDC (n=16)
3. Relictbenign (n=5)
4. Relictmalignant (n=6)

The analysis of group strategy 2 is performed mainly using fibroadenomas and invasive ductal carcinomas since the two relics groups were not considered statistically robust. The patient population is presented in Table 3-1.

TABLE 3-1

Presentation of the patient population and the chosen group strategies.

| | FA | Relictbenign | IDC | Relictmalignant |
|---|---|---|---|---|
| Number | 14 | 5 | 16 | 6 |

| | Benign | Malignant |
|---|---|---|
| Number | 19 | 22 |

A more detailed list presenting all the patients included in the retrospective analysis with age, histology and tumor volume is shown in Table A.1 (Lesion Card File).

TABLE A-1

Lesion card file. The table presents histology, tumor volume and patient age.

| Patient no.: | Type | Tumor volume (cm$^3$) | Age |
|---|---|---|---|
| 1 | IDC | 1.82 | 55 |
| 2 | Papilloma | 0.98 | 47 |
| 3 | IDC | 2.55 | 60 |
| 4 | ILC | 0.25 | 56 |
| 5 | IDC | 0.86 | 49 |
| 6 | IDC | 1.34 | 56 |
| 7 | FA | 0.32 | 40 |
| 8 | FA | 1.02 | 39 |
| 9 | IDC | 5.29 | 38 |
| 10 | Papilloma | 0.1 | 31 |
| 11 | FA | 0.36 | 53 |
| 12 | FA | 1.84 | 48 |
| 13 | IDC | 3.33 | 49 |
| 14 | IDC | 2.05 | 46 |

TABLE A-1-continued

Lesion card file. The table presents histology, tumor volume and patient age.

| Patient no.: | Type | Tumor volume (cm$^3$) | Age |
|---|---|---|---|
| 15 (Lesion 1) | FA | 0.89 | 25 |
| 15 (Lesion 2) | FA | 0.31 | 25 |
| 17 | IDC | 5.58 | 25 |
| 18 | IDC | 1.66 | 46 |
| 19 | IDC | 0.27 | 36 |
| 20 | IDC | 0.86 | 42 |
| 21 | Benign Phylloides | 3.03 | 40 |
| 22 | FA | 3.15 | 47 |
| 23 | Tubular Adenoma | 0.76 | 50 |
| 24 | FA | 2.73 | 20 |
| 25 | ILC | 4.1 | 44 |
| 26 | FA | 1.97 | 32 |
| 27 | IDC | 1.1 | 65 |
| 28 | FA | 0.39 | 44 |
| 29 | IDC | 2.66 | 51 |
| 30 | IDC | 1.64 | 37 |
| 31 | FA | 12.84 | 18 |
| 32 | ILC | 2.2 | 49 |
| 33 | FA | 1.01 | 27 |
| 34 | FA | 3.35 | 43 |
| 35 | IDC | 1.98 | 53 |
| 36 | Mucinous Carcinoma | 10.96 | 24 |
| 37 | IDC | 3.33 | 47 |
| 38 | Mucinous Carcinoma | 3.28 | 38 |
| 39 | Papilloma | 0.41 | 45 |
| 40 | FA | 1.18 | 35 |

10. Tumor Volume Estimation

A pharmacokinetic analysis of tumor tissue requires a well defined tumor volume to avoid contamination from surrounding normal tissue. Contribution from normal tissue can result in errors estimating the different tumor bio-markers. Because of this, the method used for tumor volume estimation is important. Today there are no standardized methods for volume estimation, but most researchers define a volume surrounding the lesion using high spatial resolution contrast enhanced images and, at the same time, omitting necrotic and normal surrounding tissue. Some researchers apply data assisted tumor determination, while others use manual assigning of the tumor volume. Sampling the whole tumor is preferred as this makes possible the evaluation of tumor heterogeneity.

In our study a two-dimensional region of interest (ROI) defined in each slice includes the lesion. This work was manually performed by an experienced radiologist. The sum of the ROI's represented the volume of interest (VOI). The tumor volume was defined on the basis of the high spatial contrast enhanced images using the THRIVE pulse sequence. This is advantageous because of the excellent image contrast and histological information from the actual tumor volume. During the definition of tumor volume, earlier breast exams by ultrasound and mammography should be made available.

The actual tumor volume is defined in nordicICE. The software package grants the radiologist the required liberty to manipulate the images, and by doing so defining the tumor volume precisely. NordicICE stores the defined tumor volume in a binary file format referred to as the ROI-buffer. This descriptive file contains information regarding the coordinates of the volume and which ROI's are defined in each slice. The ROI-buffers used in our study describe the drawing of the tumor in each slice as a polygon, i.e. a geometrical figure consisting of a number of straight lines between an equal number of points in a plane. The tumor location is described by the coordinates of the polygon corners, which corresponds to the position of the tumor in the MR-scanner. This makes possible a geometric comparison to other MR pulse sequences in the same MR exam.

11. Data Collection

The patient is positioned in the prone position on the patient table and with the breasts placed in a 7 channel bilateral breast coil (In Vivo). During the dynamic MR exam, it is of vital importance that the patient does not move because movement can cause artifacts and misregistration in the dynamic image data. To avoid patient motion is in general a challenge during dynamic MR imaging, and this can be further be made difficult if lying in the prone position is uncomfortable or if the patient is claustrophobic. During the exam the breasts are lightly compressed by applying foam cushions to reduce motion artifacts. Motion artifacts can be further reduced by a comforting technician and by short scan times.

Figure 3A:
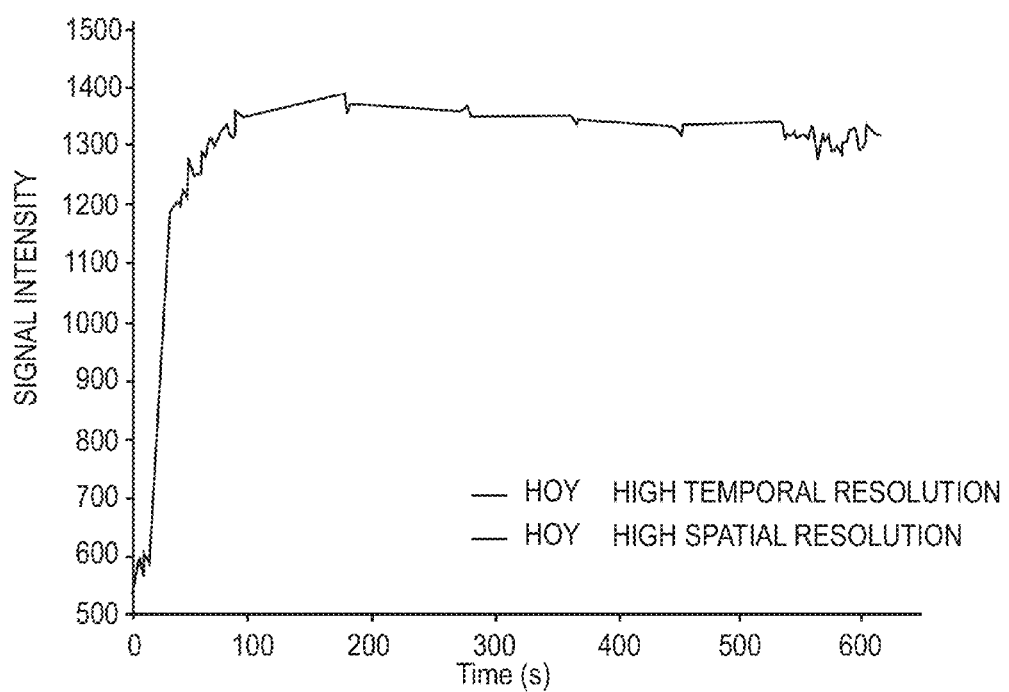
FIG. 3A is a dynamic split strategy: The dynamic contrast course is split into one sequence with high temporal resolution and one with high spatial resolution. The high spatial resolution is also applied before the administration of the contrast agent (not shown) for image reference purposes. During the first ~90 seconds of image acquisition only the high temporal pulse sequence is applied as this part is vital for the post processing of the data.

The MR exams were performed on a 1.5 Tesla Philips Achieva MR scanner (Philips Medical Systems, Best, Nederland) with NOVA field gradients. All the images were acquired in the axial direction. The dedicated dynamic acquisition method developed inhouse applying alternating periods with high spatial and high temporal resolution is referred to as a "spilt dynamic" strategy illustrated in FIG. 3A. The spatial resolution represents the sequence ability to image details. This parameter is important when the intention is to evaluate small structures also called morphology. The sequence temporal resolution describes how frequent an MR image is registered and high temporal resolution is chosen when studying dynamic changes in the imaged volume.

This study consists of a $T_1$-weighted pulse sequence with high spatial resolution (THRIVE) applied for tumor identification and morphological evaluation and a $T_1/T_2^*$-weighted sequence with high temporal resolution end double echo sampling (Multi-echo EPI) for dynamic and pharmacokinetic evaluation. These two sequences were applied in an alternating fashion before, during, and after the administration of Gd-BOPTA, 0.2 mmol/kg body weight (MultiHance, Milan, Italy).

The registered MR-images are stored in the DICOM (Digital imaging and COmmunications in Medicine) file format developed by NEMA (Notional Electrical Manufacturers Association). The is a file format standard containing relevant patient information, acquisition method including pulse sequence parameters, image dimensions, scantime information, and technical data regarding the MR scanner. Furthermore, the DICOM-format contains information regarding the patient's position relative to the scanner's iso-center making it possible to relate each imaging sequence to the patient's position.

11.1 Multi-Echo EPI

The EPI (Echo Planar imaging) is the fastest MR acquisition method in MR imaging (less than 100 ms/slice). The EPI-sequence is based on an initial excitation pulse followed by a continuous train of gradient echoes. This allows the sampling of the entire k-space (single-shot EPI) or parts of the k-space (multi-shot EPI) in one or a few TR-intervals, depending on the EPI-factor. The EPI-factor is used to specify the number of k-space profiles acquired per excitation. To create the train of gradient echoes, the read out gradient is switched in an alternating fashion between positive and negative polarity. In combination with short phase encoding gradient pulses called "blips", the k-space is sampled line by line. The main purpose for this image acquisition is to collect data as fast as possible (high temporal resolution). There are several options to increase the image sampling rate even further.

Reducing the number of phase encoding steps will also reduce scan time. One way of achieving this is to apply a rectangular field of view (FOV) including just the anatomy in question, and also use optimal EPI and SENSE factors (Sensitivity Encoding). Note that a high EPI-factor can cause image geometric distortion artifacts. The high temporal image series in this study is generated by a 3-dimensional T1- and T2*-weighed multi-shot EPI sequence with a double-echo system. The first echo is generated as quickly as possible as it requires a robust T1-weighing. The second echo is generated later in the TR interval to detect T2*-related contrast changes.

The images were acquired with a repetition time (TR) of 42 ms, echo time (TE) 5.5 ms/23 ms, a flip angle of 28°, voxel size=1.69×1.48×4 mm3, the number of slices equal to 30 and a temporal resolution of 2.7 seconds per image volume with a total of 77 dynamic data points. At the same time PROSET fat suppression prepulses were applied together with a SENSE factor of 2.5 and an EPI factor of 9. The multi-echo EPI-sequence is schematically illustrated with a pulse diagram in FIG. 3B.

11.2 Thrive

The THRIVE sequence (T1-weighted High Resolution Isotropic Volume Examination) is a spoiled GRE sequence that is optimized for fast T1-weighed 3-dimensional imaging. This sequence combines SENSE, high volume coverage and fat suppression. The THRIVE sequence is performed with low flip angles, short TR and TE in a multi-shot mode. The purpose of this sequence is to achieve high spatial resolution MR images. Any T2 contamination is prevented by phase modulation of the RF pulse (RF spoiling). This implies that magnetization is flipped into different positions in the xy plane for every sequence repetition sequence.

The high spatial image series in this study is generated with a repetition time (TR) of 5.4 ms, echo time (TE) 2.7 ms, a flip angle of 10°, voxel size=0.85,×0.85×1.25 mm3, the number of slices equal to 125 and a temporal resolution of 63 seconds. At the same time a spectral fatsuppresion prepulses (SPAIR) were used and a SENSE factor of 2.5 was chosen. The THRIVE sequence is schematically illustrated with a pulse diagram in FIG. 3C.

12. Analysis of Dynamic Data

The tracing of the contrast agent seen as dynamic image series can be evaluated either by analyzing the signal of intensity changes with descriptive parameters and/or quantitative analysis of the contrast agent dynamic concentration distribution by using the pharmacokinetic model parameters. As a common term, one can also refer to the parameters as descriptive and quantitative biomarkers. Overall in this study 10 different biomarkers were evaluated, each of which describes various characteristics of the contrast agent interaction with the tissue. These properties are explained in detail later in the current chapter. All biomarkers were calculated voxel-by-voxel, a method that takes into account tumor heterogeneity. However, it is important to note that this analysis assumes zero significant movement of the individual voxels. Depending on voxel size, even the smallest physiological motion has significant influence on the estimated biomarkers. On this basis, it is very important that the original dynamic image series are thoroughly inspected to identify potential sources of error-like patient motion and image artifacts.

The various biomarkers are estimated on the basis of the dynamic signal intensity curve in the individual vowels depicted in the object. However, one only wishes to estimate the values of the voxels showing contrast enhancement. This is done by applying a lower limit for inclusion of voxels, also called the noise limit. The noise threshold is determined manually through visual inspection of the dynamic image series for each patient. Voxels with an intensity value below the specified noise limit will be excluded in the analysis. With this procedure it is of course very important to ensure that voxels in the defined tumor volume are included the estimation. At the same time, a temporal smoothing of the dynamic curve by application of a low-pass filter is carried out. This reduces the effect of noise and spikes in the dynamic curve. A high temporal smoothing will reduce the algorithm's ability to detect rapid signal changes, but improves the quality of curve fitting process significantly. It is therefore appropriate to find a compromise in the choke of temporal smoothing. In this study a relative filtration factor, being the same for all patients, is specified.

12.1 Descriptive DCE-MRI Analysis

Figure 3B:
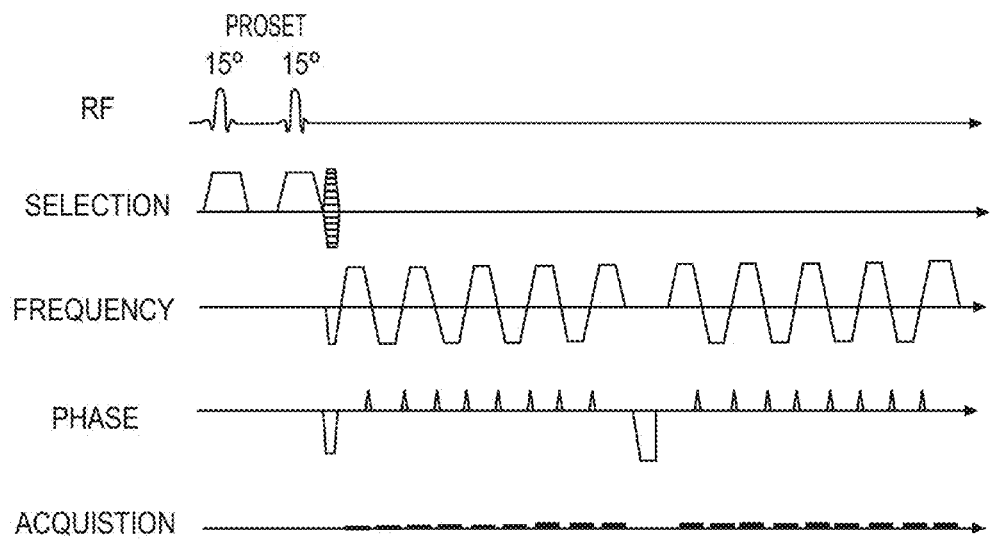
FIG. 3B is the pulse sequence diagram for multi-echo EPI-sequence
Figure 3C:
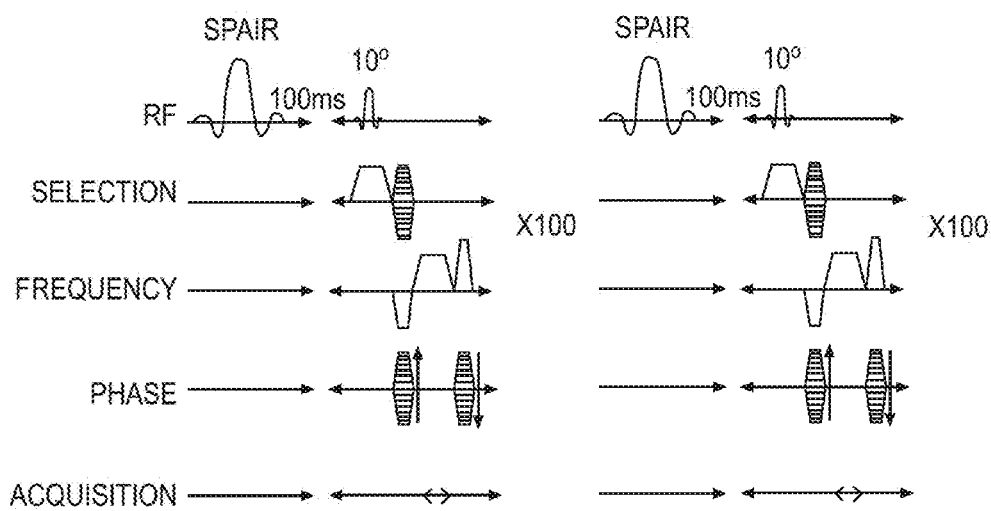
FIG. 3C is the pulse sequence diagram for the THRIVE-sequence
Figure 3D:
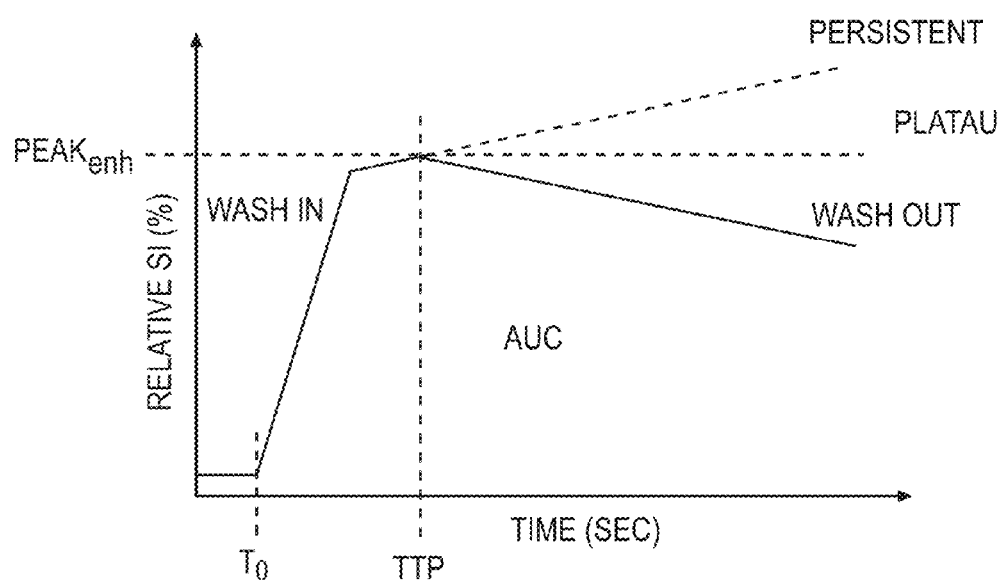
FIG. 3D demonstrates a schematic illustration of a typical temporal SI curve following administration of a contrast agent. The chart shows how the curves are characterized in the current study. In the case where voxel curve shows a plateau or persistent pattern in the late post-contrast phase the wash-out value for the current voxel is set to 0 (ie no washout).

The current clinical practice regarding the analysis of dynamic data is to use descriptive biomarkers that provide a simple indirect description of the underlying physiological factors. In order to compare the different descriptive biomarkers between patients, it is important to define the arrival time of the contrast agent into the tumor tissue. This is performed manually by inspection of the lesions' dynamic curves and the extent of the baseline. Arrival time is defined as $T_0$, and is illustrated in FIG. 3D. At the same time it is required that the time interval between the various data points' and data series' temporal ranges are similar for the different patients.

The descriptive biomarkers evaluated in this study are:
5. Area under the curve, AUC [31,32]
6. Time to peak enhancement, TTP [33]
7. Maximum signal intensity, $P_{enh}$ [34]
8. Wash-in rate, Wash-in [32,35]
9. Wash-out rate, Wash-out [36]

Figure 3F:
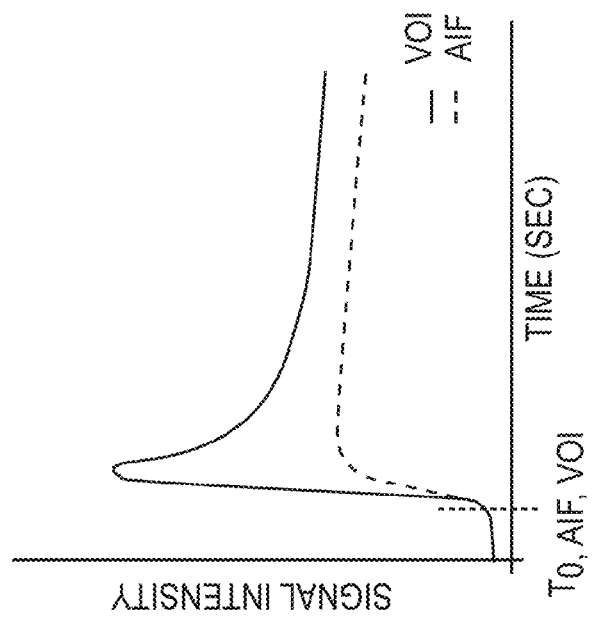
FIG. 3E and FIG. 3F demonstrate the registration of the contrast delay between the measured AIF signal and the VOI signal.
Figure 3E:
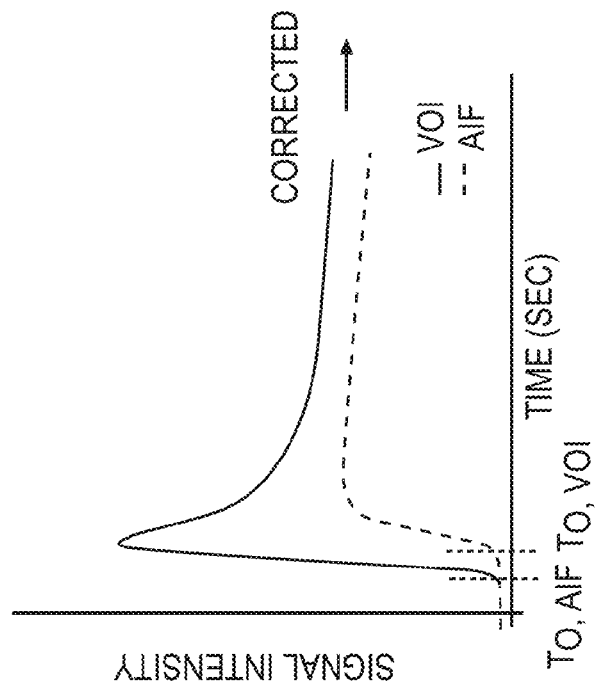

The various biomarkers are estimated on the basis of the relative SI change and illustrated in FIGS. 3E and 3F. Estimations are produced through the generation of parametric maps where the pixel value represents the magnitude of the various biomarkers.

The relative SI value at a given time will only represent a snapshot of relative contrast agent concentration in the corresponding tissue. The biomarker AUC gives a picture of the system contrast media exposure, or rather, the change relaxation rate over time. AUC is estimated by integrating the temporal SI curve:

$$AUC(t) = \int_0^t SI(t)dt \quad 1.$$

Furthermore, the biomarker TTP is estimated by measuring the time interval between contrast agent initial arrival time and the time the maximum enhancement occurs. Maximum contrast enhancement $P_{enh}$ which occurs at the time TTP is estimated by measuring the temporal SI curve's highest relative value calculated on the basis of the individual voxels pre-contrast value. The wash-in of the contrast agent is observed in the time interval between contrast agent arrival time and TTP. As TTP can occur late in the post-contrast phase due to persistent contrast uptake or artifacts, the wash-in interval is defined manually by visual evaluation. This ensures that the curve wash-in rate is estimated from the appropriate data points. Wash-in is estimated through a standard linear regression on the basis of the dynamic data points in the defined wash-in interval, and is given as the slope of the regression line. Furthermore, the curve wash-out is estimated. This parameter is calculated in the time interval between TTP and the last temporal data point. The wash-out rate is estimated in a similar way by a standard linear regression on the basis of the dynamic data points in that time interval, and is given as the absolute slope of the regression line. For voxel-curves showing a plateau or persistent pattern in the late post-contrast phase, the wash-out value for the current voxel is set to 0 (i.e. no wash-out).

12.2 Quantitative and Qualitative DCE-MRI Analysis

As previously mentioned, the contrast uptake observed by DCE-MRI is dependent on a number of physiological factors like tissue perfusion, blood volume, the shape and size of the blood vessels, endothelial permeability, endothelial surface area, and size of the extracellular extravascular space (EES). The optimal analysis of dynamic contrast-enhanced data will form a basis for identifying specific quantitative physiological biomarkers that characterize precisely the micro vascularity in the tissue observed. The main advantage of quantification is the ability to directly compare patients. In this study the dynamic contrast-enhanced data is analyzed with a model-based method. The model used is a two-compartment model developed by Toft et al. [25]. This model allows quantitative estimates of transfer coefficients $K^{trans}$ and $k_{ep}$, and volume fractions $v_p$ and $v_e$ under the assumption that a specific arterial input function (AIF) is determined for each patient.

The provision of an individual AIF is often very difficult, and errors in the measured AIF will be transferred to the error in the estimated pharmacokinetic biomarkers. On this basis of this it is very important that the measured AIF is meticulously reviewed before it is applied in the analysis. In this study the individual AIF is determined by a semi-automatic clustering technique. This technique includes an algorithm that automatically scans individual slices searching for a current average of pixel lines that meet certain criteria relating to the curve shape (rapid initial wash-in, sharp peak, smooth curve) and temporal constraints (the contrast bolus arrival time, time to peak) [67]. The AIF query is specified by defining a 3-dimensional volume where the arterial voxels existence is known. The defined search volume includes the internal thoracic artery supporting breast tissue with approx. 60% of the arterial blood. For each patient the AIF is determined on the basis of 20-30 pixel lines from 3 different slices where an arterial signal is observed. All the pixel curves are evaluated visually and, where curves that differ significantly, are excluded from the analysis. The applied AIF is given as the average of the included pixel curves. However, it is important to note that the arterial pixel curves contain a signal from the total blood volume, while the applied model assumes that the signal is solely a contribution from the plasma concentration of the contrast agent. Because of this the measured arterial signal is scaled in relation to blood hematocrit factor (Hct), such that;

$$C_{AIF} = (1-Hct)C_p \quad 2.$$

where the hematocrit factor is specified to 0.4 and describes the percentage of blood volume that are occupied by red blood cells. This factor can vary between individuals, and especially between the sexes, but in this study is the constant for all patients.

When the final AIF is determined, equation (2-33) can be solved by using the folding integral $$C_t(t) = K^{trans}\int_0^t C_p(\tau)e^{(t-\tau)}d\tau + v_p C_p(t) \quad 3.$$

This is previously described in Section 7.3. The contrast agent concentration C(t), as previously mentioned, cannot be measured directly by MRI imaging but by assuming that the change in signal intensity is proportional to the contrast agent concentration, with the same proportionality constant (relaxivity) in both tissues and plasma, one will achieve a quantitative approach of the pharmacokinetic biomarkers $K^{trans}$, $k_{ep}$, $v_p$, and $v_e$. Quantitative analysis also requires knowledge of the tissue density (g/ml) and any water-exchange effects in the tissue.

In the applied model, one assumes that the contrast agent arrives in the arterial voxels and the tissue of interest simultaneously. In reality, however, there exists a delay between the AIF and the arrival of the contrast agent in the tissue. The magnitude of this contrast delay (CD) will depend on the location of the measured arterial voxels relative to the tissue and physiological factors that vary between individual patients. Investigators have previously shown that the deconvolution method can be very sensitive to large CD in the tissue [37)], and that this can lead to estimation errors in the pharmacokinetic analysis. In this study this delay is corrected manually in all patients by measuring the contrast agent arrival time in the registered AIF and VOI, and then the contrast delay between them is determined. Registration of delayed arrival of the contrast agent is illustrated in FIGS. 3E and 3F. The recorded data for the AIF and VOI is fitted to the measured CD and the corrected signal data used in the pharmacokinetic model.

The CD between registered AIF signal and VOI-signal is a source of error as previous investigators have been aware of, but that is not corrected for in conventional practice. To evaluate the influence of this delay has on the different pharmacokinetic biomarkers, these biomarkers are also estimated without CD-correction. The different pharmacokinetic biomarkers are compared with and without correction of contrast delay.

In addition to an individual AIF specification, the pharmacokinetic analysis is also performed based on an idealized mono-exponential AIF, which gives a qualitative description of the observed tissue pharmacokinetic properties. This is done to evaluate the importance of an individual AIF. Application of an idealized mono-exponential AIF requires that the sequence's temporal resolution is high relative to the equilibrium time of contrast agent in the plasma compartment. This means that the temporal resolution must be significantly higher than the time for contrast agent first passage in the tissue imaged. Despite the fact that the applied sequence has a temporal resolution of 2.7 seconds, it has not observed any significant first pass in the tissue. The plasma concentration curve is now described by:

$$C_p(t) = C_p(t_0) e^{(-t/T_{1/2})} \qquad 4.$$

Here, $T_{1/2}$ represents the plasma space half-life of the contrast agent. Equation 2-37 can now be solved by including the expression of plasma concentration in folding integral:

$$C_t(t) = \frac{K^{trans} C_p(t_0)}{K_{el} - k_{ep}} (e^{(-k_{ep}(t-T_0))} - e^{(-K_{el}(t-T_0))}) + C_p(t_0) v_p e^{(-K_{el}(t-T_0))}, \qquad 5$$

$t \geq T_0.$ $K_{el}$ is referred to as the elimination rate is the inverse of the plasma half-life space of the contrast agent $1/T_{1/2}$. By determining the contrast agent half-life this equation can be solved with respect to the measured DCE signal using a nonlinear least square method (NLLSQ).

Once again, a linear relationship between the measured signal change and the change contrast agent concentration is assumed, or rather, the change the longitudinal relaxation rate caused by the transient effect of the contrast agent. Equation (3-5) contains many model variables which can lead to unrealistic estimates of the pharmacokinetic biomarkers. Because of this, the selected variables are given constant value during curve fitting. Since it is foreseen that the imaging is performed in the initial distribution phase of the contrast agent into the tissue, it is primarily sensitive to contrast agent half-life in the tissue distribution. In this study $T_{1/2}$ is therefore set at 5 minutes for all patients. At the same time $v_p=0$ by assuming that the intravascular fraction the tissue unit volume can be neglected relative to the total unit volume, such that $C_t(0)=0$. In this way the method allows for qualitative estimates of transfer coefficients $K_{trans}$ and $k_{ep}$ and estimation of the volume fraction $w_{oe}$ under the assumption that an idealized mono-exponential AIF is used.

12.3 Quantitative DSC-MRI Analysis

The acquisition of a double-echo system allows a quantification of the $R_2^*$ without assumptions regarding the underlying $T_1$. The change in the temporal transversal relaxation rate $\Delta R_2^*$ is calculated on the basis of the measured DCE signal from a double-echo system:

$$\Delta R_2^*(t) = \frac{\ln\left(\frac{S_1(t)}{S_2(t)}\right) - \ln\left(\frac{S_{1,pre}}{S_{2,pre}}\right)}{TE_2 - TE_1} \qquad (3\text{-}6)$$

under the assumption of a mono-exponential dependent-signal change between the two echo times. The respective echoes acquired at TE1=5.5 ms and TE2-23 ms. S1(t) and S2(t) in equation (3-6) represent the signal intensity, respectively, from echo 1 and echo 2, while S1,pre and S2,pre are the corresponding signal intensity before contrast administration. FIG. 3G shows a typical temporal R2*-curve following the administration of a contrast agent. By using equation (3-6) a voxel level temporal series of images are generated where the pixel intensity in each slice represents the quantitative transversal relaxation rate.

With the purpose to differentiate between benign and malignant breast lesions, it is appropriate to evaluate the dynamic R2*-curves by measuring the temporal change observed. The temporal effect of the contrast agent on cancer tissue transversal relaxation rate demonstrates a fast transient pattern. It is therefore important to register this trend with a descriptive biomarker. On this basis, parametric maps where pixel intensity represents the absolute maximum $R_2^*$-amplification, $R_2^*$-peak$_{enh}$ are generated and estimated by measuring the $R_2^*$-curve highest absolute value, calculated on the basis of the individual vowels' precontrast value. $R_2^*$-peak$_{enh}$ is illustrated in FIG. 3G. This biomarker will reflect the effect of the intravascular contrast agent in tissue. It may also be that other measurements of the dynamic $R_2^*$-curve may be descriptive, such as the area under the $R_2^*$-curve. In this study, however, only biomarker $R_2^*$-peak$_{enh}$ is used to describe the dynamic $R_2^*$-curve.

13. Improved Diagnostic Performance of Dce-Mri by Normalization of Pharmacokinetic Biomarkers The applied model-based analysis allows a quantitative description of the observed tissue pharmacokinetic properties, provided that an individual AIF is described for each patient. This assumes that a distinct artery is included in the imaging field of view (FOV). To increase the accuracy of the pharmacokinetic model, it is appropriate that the applied AIF is extracted from an artery close to the tissue of interest.

In this study, the applied AIF is best measured from the internal thoracic artery, which provides breast tissue with approx. 60% of the arterial blood. In addition, quantitative acquisition of pharmacokinetic biomarkers requires an adequate description of the applied AIF. This can only be achieved by using sequences with sufficient temporal resolution to detect the contrast agent arrival and passage of the arterial system. The realization of the necessary temporal resolution will be at the expense of the sequence's spatial resolution, which in turn increases the dimensional requirements for the included arteries. As a result of low spatial resolution, the signal in the arterial voxels is affected by partial volume effect (PVE), which in practice will result in an underestimation of the amplitude of the plasma curve. PVE, together with arterial motion in the dynamic series, the inflow effects and flow artifacts, will reduce the AIF curve accuracy, thereby increasing the uncertainty of the estimated biomarkers.

An accurate determination of the AIF is often problematic and represents an active field of research. In this study we have developed a method to reduce the estimation error caused by inaccurate AIF extraction, by normalizing the pharmacokinetic biomarkers with corresponding values in normal breast parenchyma, which is thought to have normal vascularity and a constant leakage component. The parenchyma region where the "normal" pharmacokinetics is extracted is defined by the radiologist. The hypothesis behind this method is that any error in the pharmacokinetic marker values in cancer tissue, caused by an insufficiency AIF, will also be applicable for marker values in parenchyma tissue, as these will likewise be scaled with the same AIF. By applying a normalization strategy, one will estimate the relationship between pharmacokinetics in parenchyma tissue and in cancer tissue. Any errors in the applied AIF will be cancelled in this operation, since this error is evident in both tissues. The result will thus represent the real pharmacokinetic relationship between parenchyma tissue and in cancer tissue, regardless of insufficiency in the extracted AIF. The normalized biomarker, quotient, is generally given by:

$$\beta_{quotient} = \frac{\beta_{cancer}}{\beta_{parenchyma}}. \qquad 1$$

The normalization method in this study is tested on the applied model four quantitative biomarkers $K_{trans}$, $k_{ep}$, $w_{oe}$ and $v_p$, and further evaluated for their diagnostic performance.

14. Statistical Analysis

Statistics is the mathematical science of collecting, organizing and interpreting the processing of numeric data related to a group of individuals or experiments. In this study statistical methods are used to evaluate the information obtained from DCE-MRI and DSC-MRI, and the different biomarkers ability to differentiate between benign and malignant breast lesions. By using statistical methods to the different biomarkers, their predictive ability will be summarized and evaluated, with the purpose of establishing multi-spectral models for increased diagnostic accuracy using DCE-MRI and DSC-MR-mammography.

Under the estimation of biomarkers, a global filtering of the object marker values is used. This filtering is done by excluding the 2% highest marker values in the object from the data. After this estimation, a local filtering of the VOI markers' values are performed in that 2% of the highest and lowest marker values are excluded from the data. This was done to systematically exclude so-called statistical outliers, extreme observations that represent abnormal and deviant values. This filtering operation can be justified by recognizing the statistical outliers' location at the edges of the data series' distribution function. If there are statistical outliers in a data series, the filtration process will exclude these and a normal distribution will be met. If a data series does not contain statistical outliers and the original is normally distributed, however, a normal distribution will be applicable even after the filtration process.

14.1 Statistical Significance

A result is called statistically significant if it is unlikely that it occurred by chance. The amount of evidence required to accept this argument is referred to as level of significance or critical p-value. In another way, it can be said that the significance level represents the amount of error allowed in the current test. Generally a null hypothesis is rejected if the estimated p-value is less than the significance level, as the estimated p-value indicates how likely it is that the null hypothesis is true in the current analysis. The level of significance is chosen in advance of the analysis, and is determined depending on the study conducted. In this study a significance level of 5% is selected, which corresponds to a critical p-value of 0.05, a significance level that is recommended by the man behind the phrase "test of significance," R. A. Fisher [38].

14.2 Evaluation of the Statistical Properties of Parameter Distribution

After the generation of parametric maps these are transferred as an overlay to the high resolution image series (THRIVE). During this process the parametric maps are coregistered manually in the 3-dimensional space relative to the corresponding TRIVE images. Then the specific patient VOI is loaded for the extraction of the marker values tumor volume. For each biomarker all voxel values are extracted that are included in the patients' VOI, but excluded in the filtered values. The biomarkers VOI-values are organized in ranked cumulative tables, where elementary statistical estimations are performed. This includes:
1. Average value
2. Maximum value
3. Percentile values
   1. 50-percentile (median)
   2. 60-percentile
   3. 70-percentile
   4. 80-percentile
   5. 85-percentile
   6. 90-percentile
   7. 95-percentile The basic statistical quantities are further used in the statistical analysis. In this way, several parts of biomarkers' value distribution can be evaluated. The average value and median value represent good indicators of the distribution system's main tendency. These are routine values used to describe the mean or the typical value from a data series. At the same time, these two values are used to evaluate the distribution of the biomarkers in the corresponding VOL. The average value and median value, however, represent only the distribution's main trend. As the goal of this study is to evaluate the different biomarkers ability to differentiate between malignant and benign breast lesions, it is diagnostically useful to study the lesion most malignant region. This is especially important since many breast lesions are naturally heterogeneous, and may thus possess small regions with highly divergent pharmacokinetic properties. These regional characteristics can be overlooked if only the lesion's central distribution tendency is examined. On the basis of this issue, the various percentile values, listed above, of the lesion volume marker values are estimated. The estimated percentile values are evaluated separately in the statistical analysis. The exception to this is the biomarker TTP, for which percentile values 50, 40, 30, 20, 15, 10 and 5 are evaluated. The reason for this is that in malignant breast tissue a shorter TTP is expected than in benign breast tissue.

14.3 Evaluation of Biomarkers Predictive Ability of the Mann-Whitney U Test

The Mann-Whitney U test, also referred to as the Wilcox rank sum test, is a non-parametric equivalent student's t-test. In the same way as the parametric t-test, the Mann-Whitney U test is used to check if a significant difference exists between the average values of two defined groups. The main reason for using a Mann-Whitney U test is that it does not make any assumptions regarding the series data distribution. If a parametric significance test is used, this requires a certain sample size in the study, as a normal distribution is assumed. In this study the patient group sizes are not large enough to legitimize a normal distribution, and a Mann-Whitney U test is used to evaluate the predictive ability of the various biomarkers. Although no assumptions about the sample distribution are made, the following assumptions are made during the execution of a Mann-Whitney U test:

1. An observation drawn for the sampled population is random.
2. The groups under study are independent of each other and the observations in each group are mutually independent.

Assume one group X with $n_x$ observations $\{x_1, x_2, \ldots, x_n\}$ and one group Y with $n_y$ observations $\{y_1, y_2, \ldots, y_n\}$. By applying the Mann-Whitney U test all the observations $x_i$ in group X are compared with all the observations $y_j$ in group Y. The null hypothesis in a Mann-Whitney U test postulates that the observations are drawn from a single population, where the likelihood that a random observation from one group is larger than a random observation in the second group is equal to 0.5. The null hypothesis says that the different groups have the same probability distribution. The alternative hypothesis then postulates that one group stochastically tends towards larger observations than the other group:

$$H_0: P(x_i > y_i) = \frac{1}{2}. \quad\quad 1$$

$$H_A: P(x_i > y_i) \neq \frac{1}{2}. \quad\quad 2$$

Furthermore, the number of times a $x_i$-value counted from the group X is greater than a $y_i$ value from group Y. This number is referred to as $U_x$. Similarly, the number of times where $y_j$ is greater than $x_i$ is counted, and referred to as $U_y$. Under the null hypothesis, it is expected that $U_x$ and $U_y$ are approximately equal. If these differ significantly from each other, the null hypothesis can be rejected.

The procedure for the Mann-Whitney U test is as follows: all the observations from the two groups are arranged in a single series in which the observations are ranked regardless of their initial group affiliation. Furthermore, the ranked observations from the two groups are summed, respectively, and denoted $R_x$ and $R_y$, $U_x$ and $U_y$ are then given by:

$$U_x = R_x - \frac{n_x(n_x+1)}{2}. \quad\quad 3$$

$$U_y = R_y - \frac{n_y(n_y+1)}{2}. \quad\quad 4$$

The minimum value of $U_x$ and $U_y$ are used by consulting the significance tables, and during the acquisition of the corresponding p-value. If the smallest U-value is less than the critical value at a given level of significance, reject the null hypothesis.

14.4 Diagnostic Tests

Diagnosis is an essential part of all clinical trials, and represents the identification of a medical condition. Since this study is conducted to evaluate the ability of different methods for the diagnosis of breast lesions, it is appropriate to define tests that describe precisely the diagnostic performance of each method. The simplest case to consider is a grouping strategy with two respective groups, also called a binary classification, organized in accordance with the true results of a survey. The question of interest in this study is how good the information, obtained from DCE-MRI and DSC-MRI, is to differentiate between malignant and benign breast lesions. This question can be answered through the description of the methods' ability to diagnose the patient's true status by comparing the methodological diagnosis with the acquisition of cytology and histology.

One approach is to evaluate the diagnostic test, based on a binary indicator, by a direct comparison of the true presence or absence of a condition of interest, in our case abnormal breast pathology, with test results. Based on this, four different outcomes are formulated. These are illustrated in Table 3-2.

If the result of a prediction is positive, while the corresponding real result is positive, t is said that the result of prediction is "true positive" (A). If the actual result in the same case is negative, the predictive result is called "false positive" (B). In a similar way the two remaining outcomes are determined and referred to as "false negative" (C) and "true negative" (D). The proportion of the two groups who is correctly diagnosed by the predictive analysis is thus given by A/(A+C) and D/(D+B). These two parts are usually referred to as diagnostic parameters and is defined by:

Sensitivity (A/(A+C))—the proportion of positive results that is correctly identified by the predictive analysis. Sensitivity represents, in other words, the probability of a correct diagnosis of a positive disease state, in this case, the malignancy.

Specificity (D/(D+B))—the proportion of negative results that is correctly identified by the predictive analysis. The specificity represents the probability of a correct diagnosis of a negative medical condition, in this case benign.

The sensitivity and specificity of a diagnostic analysis can be visually evaluated by applying a so-called ROC (Receiver Operating Characteristic) analysis, a method developed by radar operators during World War II [39]. ROC was first introduced to radiology in the early 70's and is today a commonly used method for evaluation of radiology fundamental function in assessing diagnostic performance [40,41]. A ROC curve illustrates the tradeoff between sensitivity and specificity, as any increase in sensitivity will be accompanied by a reduction of specificity. The ROC curves are generated by applying logistic regression models based on diagnostic tables and a binary response function. The application of logistic regression models are discussed later in this chapter. The ROC curve represents a good visualization of a model's diagnostic performance, but has its clear strength by comparison of several models as this obtains significant information regarding the selection of the optimal model.

TABLE 3-2

The four outcomes are formulated in a 2 × 2 eventuality matrix. The terminology of positive and negative refers to the presence or absence, respectively, of a state of interest, here breast pathology.

|  |  | Real Result | |
|---|---|---|---|
|  |  | Positive | Negative |
| Predictive Result | Positive | A | B |
|  | Negative | C | D |

Figure 3H:
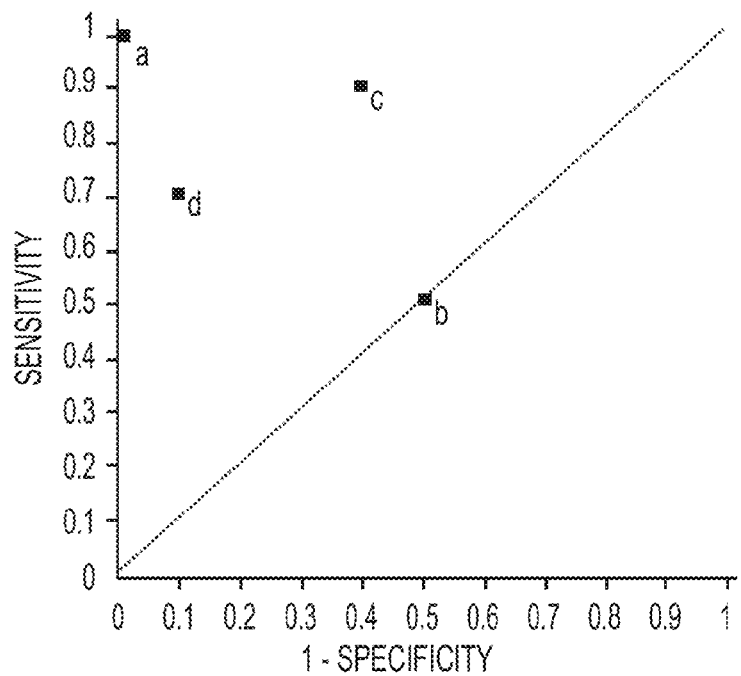
FIG. 3H is an illustration of the two-dimensional ROC space. The diagonal line represents the outcome of a completely random guess. This is called "line of no discrimination", and corresponds to the null hypothesis postulated by Mann-Whitney U test. Point c represents a predictive model with a sensitivity equal to 90% and specificity equal to 60%, while point d represents a sensitivity of 70% and a specificity of 90%.

Each predictive model can be represented by a unique point which indicates the model's sensitivity and specificity in the so-called ROC-space. A model that correctly predicts half of the positive and half of the negative conditions can be represented by the point (0.5, 0.5) in ROC space, which corresponds to a sensitivity and specificity of 50% and 50%, respectively. The optimal prediction model is represented by the coordinates (0.1) in ROC space, a point corresponding to 100% specificity (no false positive) and 100% sensitivity (no false negative). This point is also called a perfect classification. The ROC-space and the two points discussed are illustrated in FIG. 3H. The informative point in ROC-space based on the corresponding ROC curve is determined by defining a "cutoff" value. For every possible cut-off value, the applied model's sensitivity and specificity can be estimated. The provision of a cut-off value is not a statistical decision, but is selected according to the relative impact associated with the model's sensitivity and specificity. The optimal cut-off value is defined by the point that gives the best-balanced compromise between the model's sensitivity and specificity, and thus maximizes the sum of sensitivity and specificity.

In order to compare different models, it may be appropriate to reduce the ROC statistics to a single quantity that represents the expected diagnostic performance of a given model. A common method is to estimate the area under the ROC curve $AUC_{ROC}$. This quantity has a very important statistical property since it is equivalent to the probability that a method will rank a randomly chosen positive outcome higher than a randomly chosen negative outcome. This is again equivalent to the Mann-Whitney U test as described in Section 14.3. $AUC_{ROC}$ represents in this way the diagnostic accuracy of a test model. Since this quantity represents a fraction of the area of the two-dimensional ROC space (1×1), its value must always be in the range 0 to 1, where 1 represents the optimal predictive model.

14.5 Logistic Regression

A statistical regression analysis is a refined analysis of the relationship between a dependent variable called response y and one or more independent variables known as covariates x. This method is used especially to determine an approximate expression of how the model's response changes as a function of covariates. In this study the presence or absence of abnormal breast pathology represents the response variable, while biomarkers represent the explanatory covariates. The appropriate response variable is said to be dichotomous, as its possible values are binary (0 or 1). The values indicate whether the units in the survey have a particular property or not. In the current study, this corresponds to whether the lesions are benign (response equal to 0) or malignant (response equal to 1). The occurrence of a dichotomous response variable implies that an ordinary linear regression cannot be used, however, that a similar method called linear logistic regression can be applied, or just the logistic regression.

Figure 3I:
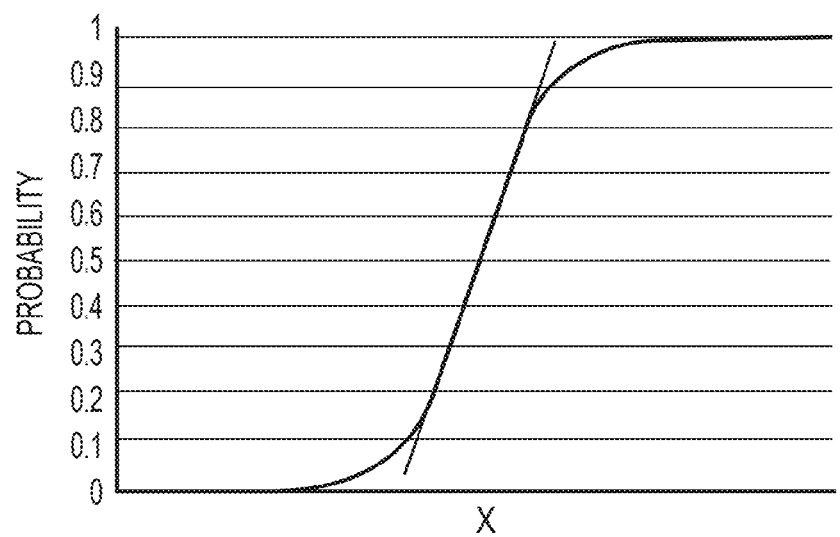
FIG. 3I is a schematic illustration of an S-curve relationship between the probability of an event occurring and the covariates.

By applying logistic regression the probability that the lesions in the different groups are malignant are modeled. The relationship between this probability and the explanatory covariates can be illustrated by a so-called S-curve, as shown in FIG. 3I. This curve describes that the relationship between probability and covariates is weak when the probability of malignancy is very low or very high. At the same time the S-curve describes that the probability will never reach its limits of 0 and 1. The S-curve shows a logistic relationship between covariates and the likelihood of malignancy occurring. FIG. 3I shows that the actual probability can have values between 0 and 1, and that similar restrictions are not applicable for covariates. The relationship the S-curve illustrates can, in other words, be used to transport a probability variable, ranging between 0 and 1, to a variable that is not limited to what values it can assume. This variable can again be used as a response variable in the regression. This is done by linking the probability of response $$E(y)=p=p(x) \tag{3-12}$$

and the linear predictor given by $$\eta(x)=\beta_0+\beta_1 x \tag{3-13}$$

with a relation called "logit transformation:"

$$\log\left(\frac{p(x)}{1-p(x)}\right) = \eta(x) = \beta_0 + \beta_1 x \tag{3-14}$$

By inverting the last expression and solving it with respect to p(x), the logistic function can be expressed by:

$$p(x) = \frac{e^{\eta(x)}}{1+e^{\eta(x)}} = \frac{e^{\beta_0+\beta_1 x}}{1+e^{\beta_0+\beta_1 x}}. \tag{3-15}$$

In this way the probability value is not modeled anymore, but rather a function of this. An advantage of this feature is that the estimated regression coefficient allows direct interpretation. This is done through the odds of the outcome of interest, which is given by:

$$\frac{p}{1-p} = e^{\beta_0+\beta_1 x}. \tag{3-16}$$

The odds express a proportion, i.e. the ratio between the probability of an outcome occurring (p) and the probability that there is no occurrence (1−p). If one further considers the relationship between the odds of two units with different values of the explanatory covariates x and x' and therefore also different probability values p and p', the so-called odds ratio is expressed by:

$$\frac{\frac{p}{1-p}}{\frac{p'}{1-p'}} = e^{\beta_1(x-x')}. \quad (3\text{-}17)$$

The value of regression coefficients describes how strong the effect a unit change in the relevant covariates has on the corresponding odds ratio.

As discussed previously, the logistic analysis is applied for the generation of diagnostic tests. This is performed by the logistic model generating a vector with the lesions predictive value, based on the applied covariates, which corresponds to the probability of malignancy occurring. This vector is tabulated against the real vector, which contains the true observations (0,1) for an n×2 table, where n is the number of unique predictive values. This table is used further to produce a diagnostic test table that represents the reverse cumulative probability of the two table columns. The information from the diagnostic table is used to plot the corresponding ROC curve. The area under the ROC curve $AUC_{ROC}$ is further estimated by adding the trapezes generated by the different parts of the ROC curve and the corresponding zero-horizontal lines.

The inclusion of multiple biomarkers into the statistical model is a simple extension, where the only change occurs in the linear predictor. This is replaced by the sum of the contributions of several biomarkers, i.e.:

$$\eta(x) = \beta_0 + \beta_1 x_1 + \beta_2 x_2 + \ldots + \beta_n x_n \quad (3\text{-}18).$$

The link between the probability and the response through the logit transformation will be similar to that described above. The likelihood of malignancy as a function of several biomarkers can generally be written in the form:

$$p(x) = \frac{e^{\eta(x)}}{1+e^{\eta(x)}} = \frac{e^{\beta_0+\beta_1 x_1+\beta_2 x_2+\ldots+\beta_n x_n}}{1+e^{\beta_0+\beta_1 x_1+\beta_2 x_2+\ldots+\beta_n x_n}}. \quad (3\text{-}19)$$

The adaptation of such a model is performed through the so-called maximum likelihood criterion, which means that the unknown parameters $\beta_0 + \beta_1 x_1 + \beta_2 x_2 + \ldots + \beta_n x_n$ is adapted to make the observed series of responses, $y_1, y_2, \ldots, y_n$, as likely as possible.

The significance of each covariate included in the logistic regression can be tested through a so-called Wald test, where the respective covariate's regression coefficient is divided by its estimated standard deviation. The quantity from a Wald test z is compared with values from a table of standard normal variable distribution. At a significance level of 5%, the null hypothesis is rejected $H_0$. $\beta=0$ (no effect from covariates) if:

$$z = \left|\frac{\beta}{se}\right| > 1.96. \quad (3\text{-}20)$$

However, several investigators have identified problems by the use of the Wald statistics. As an example, at high coefficient values, the standard error is inflated, resulting in a reduced Wald statistical value. Because of this, it is appropriate to conduct a so-called likelihood ratio test. The definition of this test is associated with a concept known as deviance D which in itself is very informative regarding a model's fit. The deviance is a quantity used in the logistic regression that is related to the square sum by linear regression. The deviance can be interpreted as a measure of lack of fit between model and data. However, the deviance is not usually interpreted directly but rather as a comparison between the deviance from different models. In this way, the deviance ranks different models with respect to the model's ability to fit the data.

In this study the deviance test is applied in the context of a model building strategy known as backward stepwise biomarker elimination. The 5 most significant biomarkers, based on the initial Mann-Whitney U test, are included in a logistic regression model. The information from the biomarker's respective regression coefficients are then used to estimate the z-values from the Wald-stats described above. On the basis of this test, the biomarker that has the lowest significant effect on the response is eliminated and a new model is adapted without the eliminated biomarker. To avoid any errors due to the Wald-statistic, the eliminated biomarker is also tested by evaluating the deviance between the two models. The difference in deviance denoted G is given by:

$$G = D_{post} - D_{pre} \quad 1.$$

where $D_{pre}$ and $D_{post}$ represent models with and without the eliminated biomarker, respectively. Note that G≥0, as the post model is built into the occupied pre model. In this context, the quantity G represents the loss of adaptation by limiting the logistic regression to no effect under the null hypothesis, and this is approximately the $\chi^2$-distributed with one degree of freedom (the difference in the number of covariates between the two models). This process ends in that the deviance test ascertains the elimination of a significant covariate. Along with this process, the number of included covariates must be legitimized with regard to the number of included patients in the statistical analysis. The inclusion of too many covariates will result in over adaptation in that the statistical model describes the random noise rather than the underlying relationships. To avoid this problem, an Information criterion is applied which penalizes the inclusion of covariates in the logistic model. In this study an Akaike information criterion (AIC) is estimated for each model selection. This information criterion tries at all times to balance the conflicting requirements regarding the model's accuracy (adaptation) and simplicity (low number of included covariates). The numerical value of AIC for a single model is highly descriptive. However, AIC is used to rank various model selections based on their dual criteria regarding fit and simplicity. The model selection with the lowest estimated AIC is preferred. This work results in the determination of the optimal regression model with respect to the observed data.

In summary, it is mentioned that a logistic regression model makes it possible to predict the likelihood that a given condition occurs in relation to several prognostic biomarkers. This means that one can distinguish between patients likely or unlikely to possess this condition, and thus act as a diagnostic subvention. Such statistical analysis can be referred to as a discriminant analysis, and may institute appropriate diagnostic tests with respect to sensitivity, specificity, and the total diagnostic accuracy.

15. Patient- and Image Base

In this paper a total of 52 patients with 53 breast lesions underwent dynamic MRI. Of these, 12 lesions were excluded on the basis of lack of visibility on MRI, motion artifacts, or that the final histological diagnosis demonstrated a non-solid lesion. This results in a retrospective patient base of 40 patients with a total of 41 lesions: 19 benign and 22 malignant. Table 4-1 shows the histological composition of benign and malignant groups. A atient's average age was 42 years, with a range of 18-65 years.

TABLE 4-1

The histological composition of benign and malignant lesion groups. The two most common solid lesions, fibroadenoma (FA) and invasive ductal carcinoma (IDC), have the highest frequency in the two groups.

| Benign (n = 19) | | Malignant (n = 22) | |
|---|---|---|---|
| Fibroadenoma | 14 | Invasive ductal carcinoma | 16 |
| Papilloma | 3 | Invasive lobular carcinoma | 3 |
| Benign phylloides | 1 | Mucinous carcinoma | 2 |
| Tubular adenoma | 1 | Inflammatory carcinoma | 1 |

Figure 4A:
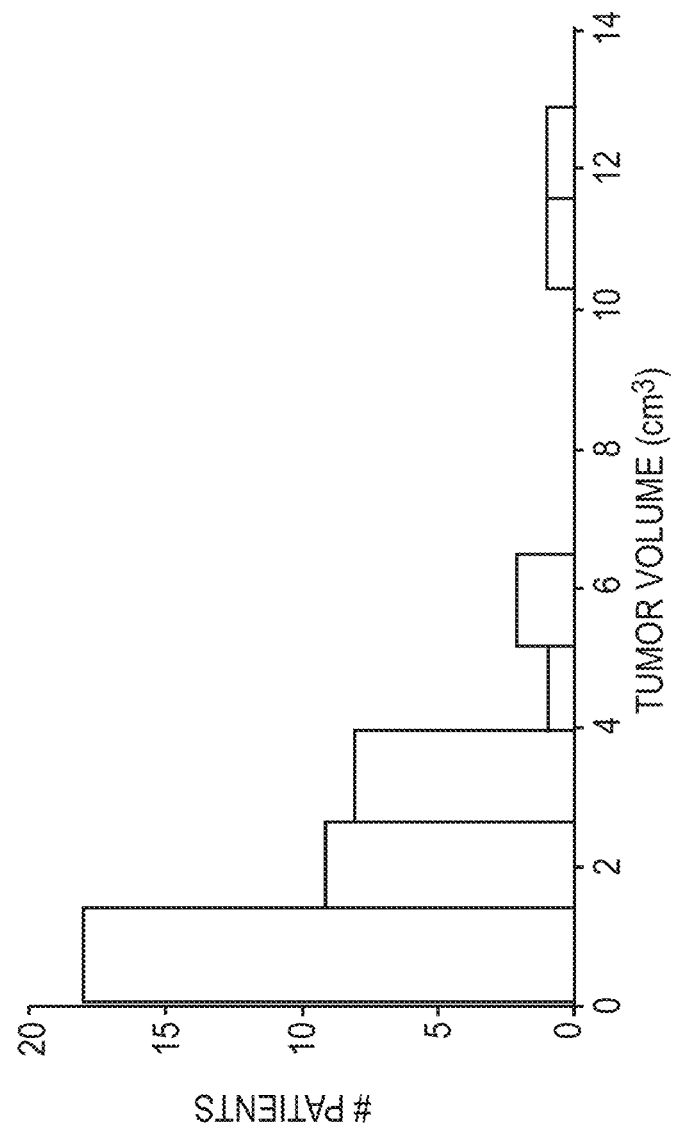
FIG. 4A shows the distribution of patients' tumor volume estimated from the plotted VOI. Two patients have a VOI greater than 10 cm3, with VOI at 10.96 and 12.84 cm3. These lesions are respectively mucinous carcinoma and fibroadenoma.

The tumor volume was estimated from the relevant drawings and shows an average tumor volume of 2.34 cm$^3$ with a range equal to 12.84 to 0.10 cm$^3$. Average tumor volume of malignant and benign lesions were respectively 2.72 cm$^3$ (10.96 to 0.25 cm$^3$) and 1.93 cm$^3$ (12.84 to 0.10 cm$^3$). FIG. 4A shows the distribution of the patient's tumor volume.

Figure 4B:
FIG. 4B from the top shows Axial slices of a 38-year-old woman with invasive ductal carcinoma (IDC) in the right breast. The pictures shown are, from left, a pre contrast image, a post contrast image 97 seconds after contrast administration, as well as the corresponding subtraction image. The images are centrally in the patient's tumor defined by the drawn ROI. Bottom: Axial slices of a 43 year old woman with fibroadenoma (FA) in the right breast, defined by the drawn ROI. Post contrast images are acquired 97 seconds after contrast administration.

As mentioned in Section 10, a region of interest (ROI) for each slice is defined by applying the polygon shapes which includes the actual lesion. The accumulated ROI-areas are consequently the lesion volume of interest (VOI). FIG. 4B illustrates two ROI examples from two different patients included in the retrospective group of patients. The image series shown is from the high resolution THRIVE(?) sequence and illustrates the pre- and post-contrast images with the ROI drawn and further subtracted images as used for the definition of the patient's tumor volume.

16. The Importance of Spatial Heterogeneity in Diagnostic Analysis of Tumor Characterization As mentioned in Section 8, the breast cancers are often naturally heterogeneous, and a spatial dependent evaluation is therefore essential for cancer diagnosis. In this study, this is done by evaluating the biomarkers' average value and a variety percentile values estimated from patients' tumor volume. These are again analyzed with regard to the histopathological diagnosis using the Mann-Whitney U test. In this study two grouping strategies are used as presented in Section 9. The estimated p-values for the grouping strategy 1 and 2 are presented in Tables 4-2 and 4-3, respectively. The result is considered statistically significant if the p-value does not exceed the critical p-value of 0.05.

From the grouping strategy 1, Table 4-2 shows a general increase of a biomarker's significance from median tumor volume value (50th percentile) to the 95-percentile. The biomarker that illustrates this spatial dependent differentiation ability dearly is $k_{ep}$. Median $k_{ep}$ demonstrates zero significance (p=0.9), while the biomarker 95-percentile demonstrates a statistically significant (p=0.06) with respect to the differentiation between benign and malignant breast lesions. At the same time it can be observed that the average value generally demonstrates a more robust differentiation between benign and malignant breast lesions relative to the lowest studied percentile values.

From the grouping strategy 2, Table 4C shows a similar trend of significance. An increase in the biomarker's percentile value generally offers a higher significance with respect to the differentiation between FA and IDC. Again, it is the biomarker $k_{ep}$ that demonstrates this trend clearly and, further, it is observed that the tumor volume's average value generally demonstrates a more robust predictive performance with regard to distinguishing between the FA and IDC compared to the lowest studied percentile values.

From both tables it can be observed that the biomarker's maximum value in some cases shows the highest significance. However, it should be noted that this value will be directly affected if any outliers are remaining after the global and local filtering presented in Section 14.

Figure 4C:
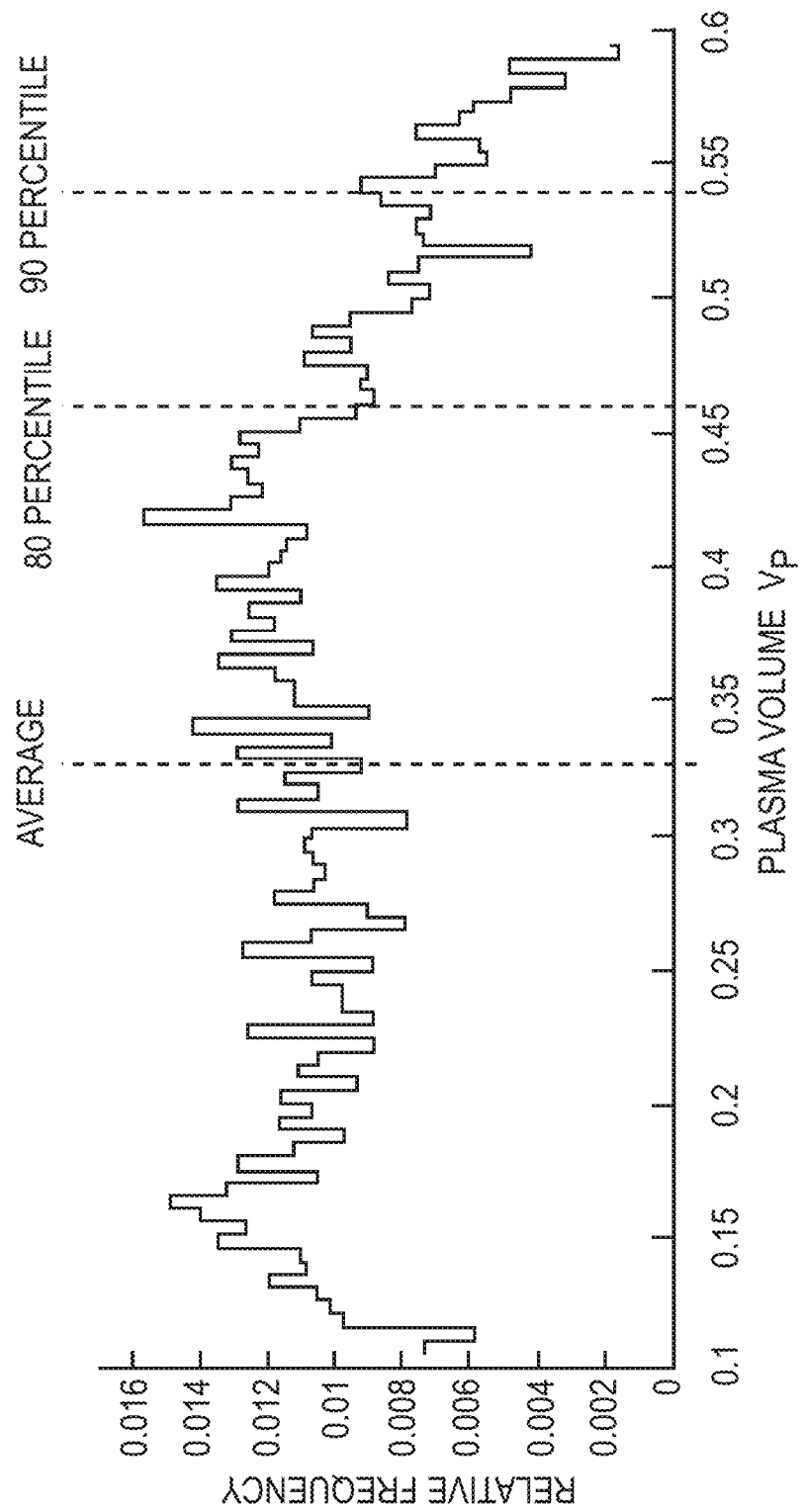
FIG. 4C demonstrates the histogram of biomarker vp in an IDC. The figure demonstrates the relative distribution of biomarkers in the patient's tumor volume. Illustrated are also three different scalar values of marker value distribution: the average value, 80 percentile and 95 percentile. For this specific case, these estimated to be 0.33, 0.46 and 0.54.

FIG. 4C shows the distribution of the plasma volume, $v_p$ in a patient with invasive ductal carcinoma (IDC). The figure is meant as an illustration of the biomarker's value distribution in a tumor volume, and shows three different values each representing a unique part of the markers value distribution. These average values of the biomarker, the 80 percentile and the 95 percentile, is in this case estimated to be 0.33, 0.46 and 0.54, respectively. The variation between these two values is directly dependent on the tumor's heterogeneity.

The observations made in this sub-study suggests that a significant improvement in the diagnostic differentiation can be achieved by identifying the tumor volume 5% region representing the lesion's most abnormal properties. As a result of this, the biomarker's 95 percentile is evaluated. At the same time the biomarker's average value is included since this represents an important statistical indicator of how a biomarker, and the physiology it represents, acts in the various tumors. Average VOI-value is also the most common value to study in this type of study.

TABLE 4-2 p-values estimated from the Mann-Whitney U lest by grouping stratrgy I. The table shows the different biomarkers p-values corresponding to the evaluated VOI-scalar.

| | Pharmacokinetic biomarkers | | | | | | |
|---|---|---|---|---|---|---|---|
| | Individual AIF Included | | | | With idealized mono-exponential AIF | | |
| | $K^{trans}$ | $k_{ep}$ | $V_p$ | $v_e$ | $K^{trans}$ | $k_{ep}$ | $v_e$ |
| Average value | 0.8064 | 0.6964 | 0.0261 | 0.6751 | 0.5735 | 0.0073 | 0.3611 |
| 50 percentile | 0.9424 | 0.9069 | 0.0305 | 0.6192 | 0.5394 | 0.0184 | 0.6653 |
| 60 percentile | 0.8722 | 0.8285 | 0.0205 | 0.6964 | 0.4364 | 0.0184 | 0.4364 |
| 70 percentile | 0.7397 | 0.3495 | 0.0165 | 0.7616 | 0.4262 | 0.0263 | 0.2154 |
| 80 percentile | 0.7148 | 0.1284 | 0.0112 | 0.9434 | 0.3755 | 0.0802 | 0.1690 |
| 85 percentile | 0.7179 | 0.0493 | 0.0103 | 1.0000 | 0.3611 | 0.0137 | 0.1170 |
| 90 percentile | 0.6761 | 0.0361 | 0.0105 | 0.9654 | 0.3334 | 0.0127 | 0.0630 |
| 95 percentile | 0.5311 | 0.0058 | 0.0094 | 0.9195 | 0.3900 | 0.0033 | 0.1301 |
| Max value | 0.4258 | 0.0012 | 0.0261 | 0.9885 | 0.3053 | 0.0013 | 0.0631 |

TABLE 4-2-continued p-values estimated from the Mann-Whitney U lest by grouping stratrgy I.
The table shows the different biomarkers p-values corresponding to the evaluated VOI-scalar.

| | Descriptive and quantitative curve markars | | | | | T2*-weighted |
|---|---|---|---|---|---|---|
| | T1-weighted | | | | | |
| | Wash-in | Wash-out | AUC | TTP | $peak_{enh}$ | $R_2^*\text{-}peak_{enh}$ |
| Average value | 0.1235 | 0.0116 | 0.2363 | 0.0037 | 0.1170 | 0.0008 |
| 50 percentile | 0.1375 | 0.0736 | 0.3300 | 0.0116 | 0.1866 | 0.0044 |
| 60 percentile | 0.0989 | 0.0098 | 0.3471 | 0.0010 | 0.2257 | 0.0013 |
| 70 percentile | 0.1170 | 0.0142 | 0.2585 | 0.0013 | 0.2055 | 0.0007 |
| 80 percentile | 0.1046 | 0.0217 | 0.2257 | 0.0007 | 0.1304 | 0.0002 |
| 85 percentile | 0.1235 | 0.0136 | 0.2155 | 0.0006 | 0.1107 | 0.0001 |
| 90 percentile | 0.1304 | 0.0159 | 0.2472 | 0.0008 | 0.0989 | 0.0001 |
| 95 percentile | 0.0989 | 0.0147 | 0.2821 | 0.0004 | 0.0933 | 0.0001 |
| Max value | 0.0933 | 0.0252 | 0.3334 | 0.0012 | 0.1304 | 0.0001 |

TABLE 4-3 p-values estimated from the Mann-Whitney U lest by grouping stratrgy I.
The table shows the different biomarkers p-values corresponding to the evaluated VOI-scalar.

| | Pharmacokinetic biomarkers | | | | | | |
|---|---|---|---|---|---|---|---|
| | Individual AIF Included | | | | With idealized mono-exponential AIF | | |
| | $K^{trans}$ | $k_{ep}$ | $V_p$ | $v_e$ | $K^{trans}$ | $k_{ep}$ | $v_e$ |
| Average value | 0.5068 | 0.3536 | 0.0016 | 0.7148 | 0.6670 | 0.0005 | 0.1306 |
| 50 percentile | 0.5613 | 0.6004 | 0.0019 | 0.7270 | 0.5799 | 0.0133 | 0.2572 |
| 60 percentile | 0.5045 | 0.4509 | 0.0013 | 0.7800 | 0.5799 | 0.0064 | 0.1794 |
| 70 percentile | 0.4253 | 0.1760 | 0.0019 | 0.8467 | 0.4726 | 0.0014 | 0.0426 |
| 80 percentile | 0.5045 | 0.0697 | 0.0009 | 0.9486 | 0.4475 | 0.0018 | 0.0213 |
| 85 percentile | 0.5045 | 0.0424 | 0.0006 | 1.0000 | 0.4984 | 0.0017 | 0.0069 |
| 90 percentile | 0.4509 | 0.0667 | 0.0008 | 0.9486 | 0.4984 | 0.0009 | 0.0021 |
| 95 percentile | 0.3314 | 0.0105 | 0.0008 | 0.8132 | 0.5611 | 0.0003 | 0.0062 |
| Max value | 0.2703 | 0.0037 | 0.0005 | 0.9486 | 0.6374 | 0.0002 | 0.0013 |

| | Descriptive and quantitative curve markars | | | | | T2*-weighted |
|---|---|---|---|---|---|---|
| | T1-weighted | | | | | |
| | Wash-in | Wash-out | AUC | TTP | $peak_{enh}$ | $R_2^*\text{-}peak_{enh}$ |
| Average value | 0.1536 | 0.0009 | 0.0576 | 0.0007 | 0.0245 | 0.0021 |
| 50 percentile | 0.1536 | 0.0045 | 0.1011 | 0.0015 | 0.0520 | 0.0052 |
| 60 percentile | 0.1103 | 0.0006 | 0.0925 | 0.0015 | 0.0576 | 0.0021 |
| 70 percentile | 0.1417 | 0.0012 | 0.0629 | 0.0009 | 0.0908 | 0.0039 |
| 80 percentile | 0.1417 | 0.0013 | 0.0906 | 0.0009 | 0.0172 | 0.0018 |
| 85 percentile | 0.1994 | 0.0009 | 0.0245 | 0.0009 | 0.0118 | 0.0011 |
| 90 percentile | 0.2062 | 0.0017 | 0.0306 | 0.0006 | 0.0091 | 0.0011 |
| 95 percentile | 0.1994 | 0.0011 | 0.0306 | 0.0008 | 0.0060 | 0.0007 |
| Max value | 0.2237 | 0.0028 | 0.0275 | 0.0021 | 0.0079 | 0.0007 |

17. Tumor Characterization by the Use of Descriptive DCE-MRI Biomarkers

Figures 1, 4D:
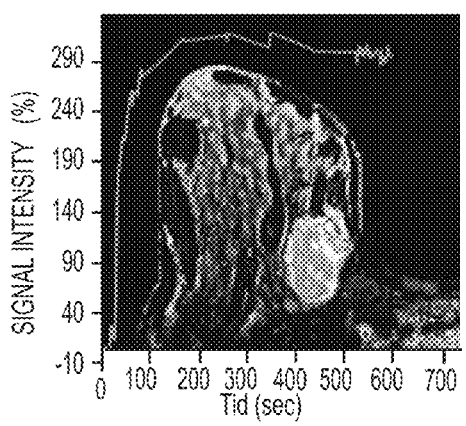
FIG. 4D is an illustrative case of descriptive T1-weighted biomarkers, separated as FIG. 4D-1 through FIGS. 4D-5 (A-E, respectively). Biomarkers that are presented are. (A) $\text{peak}_{enh}$ for a 18 year old woman with FA, (B) AUC for a 43 year old woman with FA, (C) TTP for a 46 years old woman with IDC, (D) Wash-in rate for a 38-year-old woman with IDC and (E) Wash-out rate for a 51 years old woman with IDC.
Figures 2, 4D:
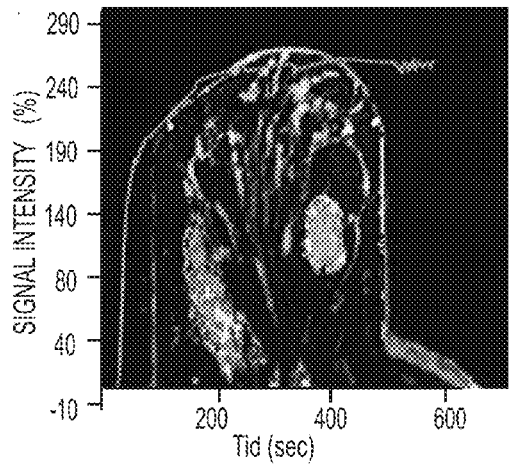
Figures 3, 4D:
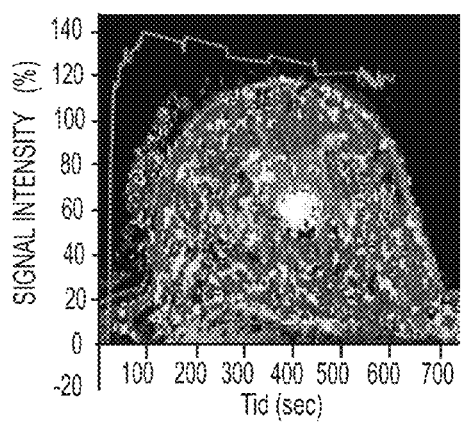
Figures 4, 4D:
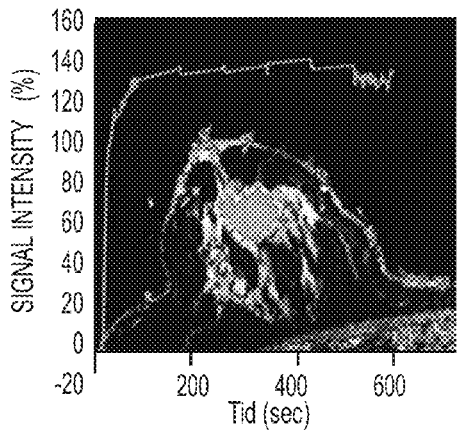
Figures 4, 4D, 5:
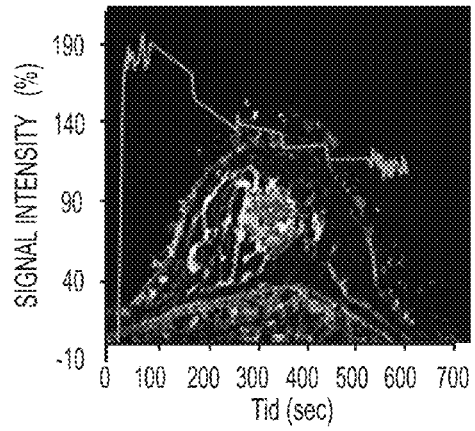

In this study the dynamic contrast sequence with five different descriptive biomarkers is evaluated, each of which describes a different characteristic of the lesions T1-weighed SI curve. These biomarkers are presented in Section 12.1. An illustrative example of the descriptive biomarkers is presented in FIG. 4D. The figure shows five different cases, where the dynamic SI curve of the tumor volumes is illustrated along with the estimated descriptive biomarkers. The biomarkers are presented as parametric maps superimposed onto a slice in the center of the tumor from the high resolution THRIVE series.

The main findings from the descriptive analysis is that biomarkers VOI-95 percentile in general demonstrates a higher predictive ability with regard to distinguishing malignant tissue from benign breast lesions, and in differentiating IDC and FA. Based on tumor volume of the 95-percentile the Mann-Whitney U test indicates that the biomarkers Wash-out and TTP show a significant correlation with malignancy, and that Wash-out, TTP and $peak_{enh}$ shows a significant ability to differentiate between invasive ductal carcinoma (IDC) and fibroadenoma (FA).

Figures 2, 4E:
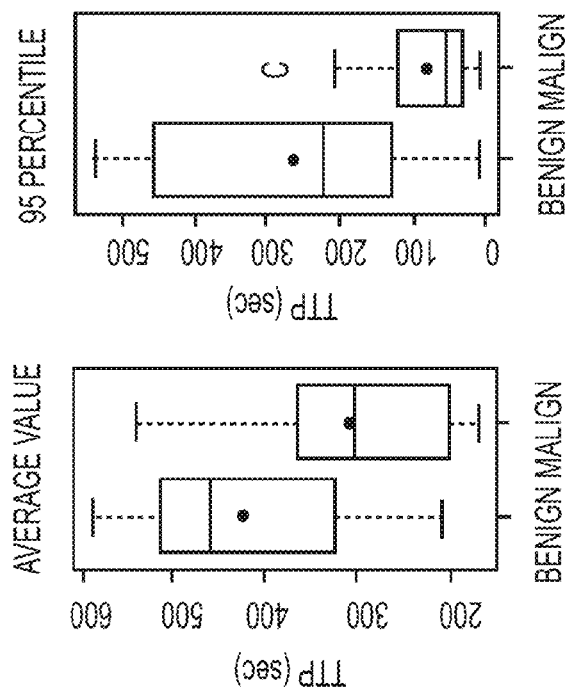
FIG. 4E illustrates box plots of the mean value and 95 percentile for the descriptive biomarkers corresponding to grouping strategy 1, separated as FIG. 4E-1 through FIG. 4E-4. The Box plot depicts the group marker distribution in first to fourth quartile. In addition, the distribution median value and average value are presented as solid line and red markers. Any outliers are illustrated as individual points outside the distribution. The figure presents box plots for (A) AUC, (B) TTP, (C) $\text{peak}_{enh}$, (D) Wash-in rate and (E) Wash-out rate.
Figures 1, 4E:
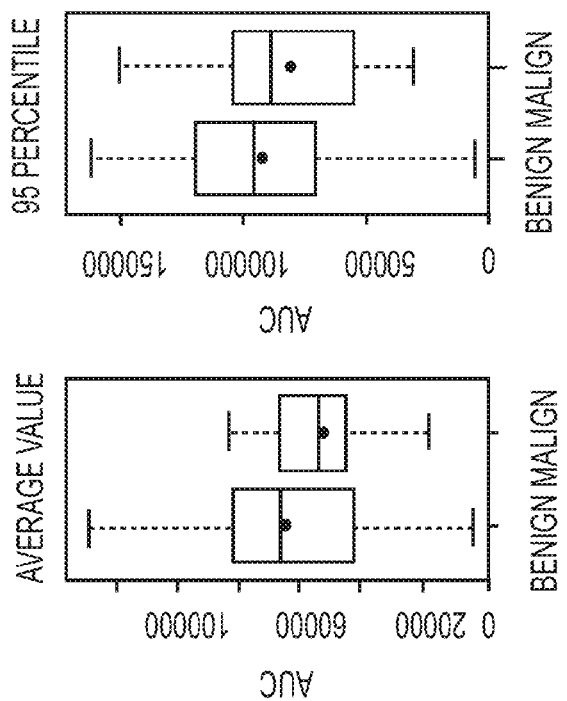
Figures 3, 4, 4E:
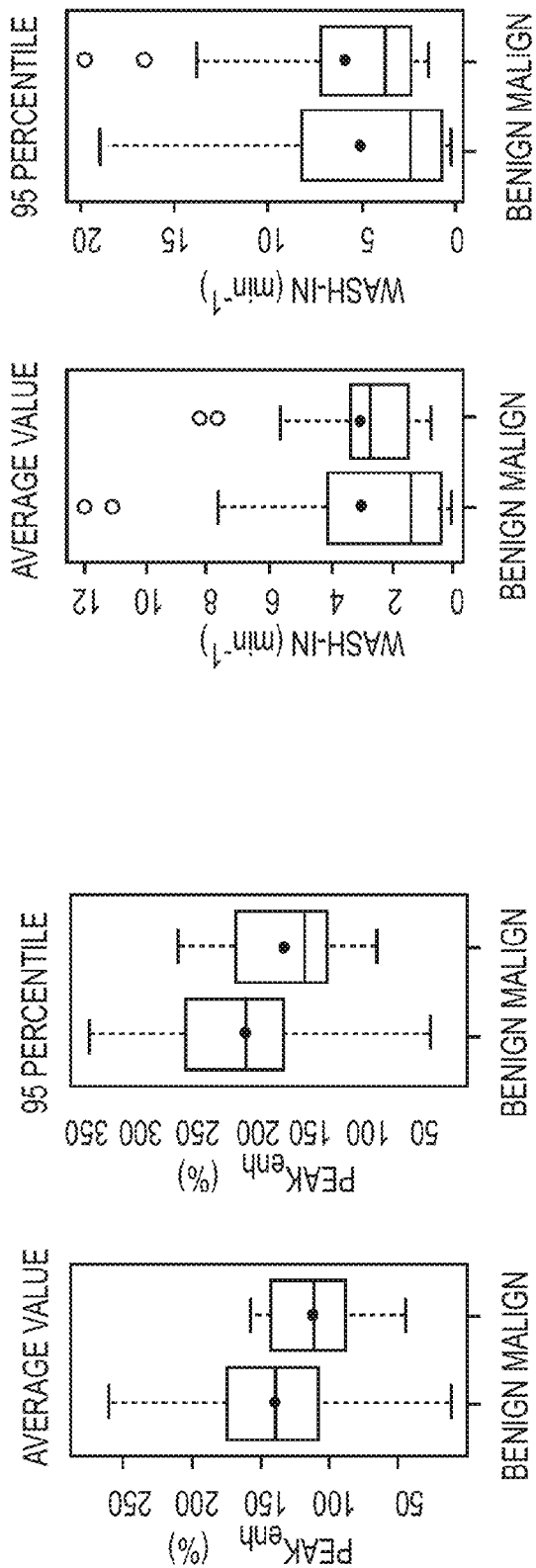
Figures 1, 2, 4F:
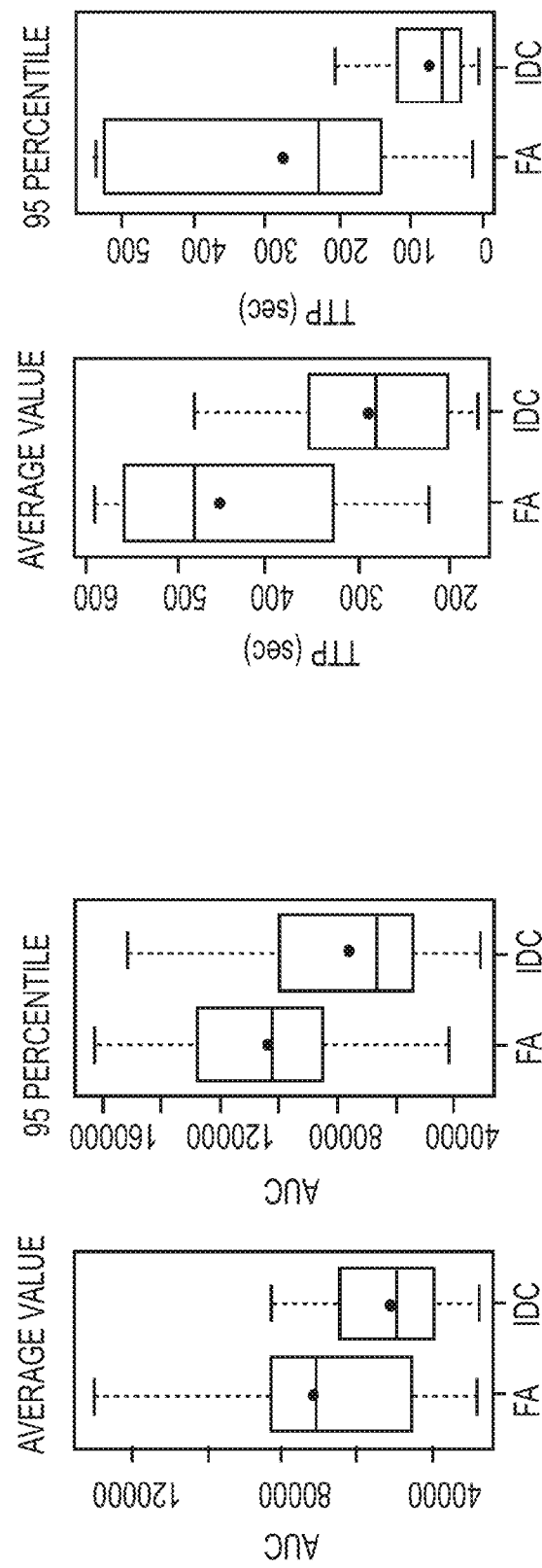
FIG. 4F illustrates box plots of the mean value and 95 percentile for the descriptive biomarkers corresponding to grouping strategy 2, separated as FIG. 4F-1 through FIG. 4F-5. The Box plot depicts the group marker distribution in first to fourth quartile. In addition, the distribution median value and average value are presented as solid line and red markers. Any outliers are illustrated as individual points outside the distribution. The figure presents box plots for (A) AUC, (B) TTP, (C) $\text{peak}_{enh}$, (D) Wash-in rate and (E) Wash-out rate.

Average VOI-value and VOI-95 percentile to the descriptive biomarkers are presented with box plots, as a function of the grouping strategy 1 and 2, in FIGS. 4E and 4F, respectively. The result of each descriptive biomarker is also presented with the group's mean value and standard deviation. The biomarkers demonstrate, in some cases, statistical outliers. It is important to note that this can have a profound influence on the group's estimated mean value and standard deviation.

17.1 Area Under the SI-Curve, AUC

VOI-Average—

The average AUC is estimated to be 53,018 (±17,395) for malignant lesions, and 64,187 (±34,652) for benign lesions. Furthermore, the mean AUC is estimated at 51,668 (±16,407) for the IDC, and 72,149 (±30,812) for the FA. Based on tumor volume, on an average the biomarker AUC shows no statistical significance regarding the differentiation of malignant and benign breast lesions (p=0.2363), as well as IDC and FA (p=0.0578). Box plots 4-S (A) shows that benign breast lesions demonstrate a slightly higher AUC compared with malignant breast lesions. This trend is more clearly presented in box plots 4-6 (A), where FA demonstrates a higher AUC compared with IDC. However, biomarker AUC demonstrates large overlap in both grouping strategies.

VOI-95 Percentile—

Average AUC is estimated to be 81,535 (±33,959) for the malignant lesions, and 92,627 (±42,053) for benign lesions. Furthermore, the mean AUC is estimated to be 75,735 (±32,768) for the IDC, and 103,323 (±32,784) for the FA. Based on tumor volume of the 95-percentile biomarker, AUC shows no statistical significance regarding the differentiation of malignant and benign breast lesions (p=0.2821). If the IDC and FA are considered independently, biomarker AUC demonstrates significantly higher value in FA (p=0.0308).

17.2 Time to Peak, TTP

VOI-Average—

Average TTP is estimated to 307 seconds (±105 seconds) for malignant lesions, and 423 seconds (±123 seconds) for benign lesions. Furthermore, the average TTP is estimated to be 287 seconds (±198 seconds) for the IDC, and 452 seconds (±120 seconds) for the FA. Based on tumor volume, on an average malignant breast lesions demonstrate a significantly shorter TTP compared with benign breast lesions (p=0.0037). If the IDC and FA are considered separately, IDC demonstrates a significantly shorter TTP (p=0.0007).

VOI-5 Percentile—

The average TTP is estimated to 83 seconds (±74 seconds) for malignant lesions, and 266 seconds (±189 seconds) for benign lesions. Furthermore, the average TTP is estimated to 78 seconds (±65 seconds) for the IDC, and 277 seconds (±184 seconds) for the FA. Based on tumor volume of the 95-percentile, malignant breast lesions demonstrate significantly shorter TTP compared with benign breast lesions (p=0.0004). If the IDC and FA are considered separately, IDC demonstrates a significantly shorter TTP (p=0.0003)

17.3 Peak Enhancement, $Peak_{enh}$

VOI-Average—

Average $peak_{enh}$ is estimated to be 114% (±31%) for malignant lesions, and 140% (±86%) for benign lesions. Furthermore, the average $peak_{enh}$ estimated at 111% (±27%) for IDC and 154% (±58%) for FA. From the box plots 4-S (FIG. 4E-3) it can be observed that benign breast lesions demonstrate a slightly higher average $peak_{enh}$, compared with malignant breast lesions. However, this difference is not statistically significant (p=0.117). If all the IDC and FA are considered separately, FA demonstrates a significantly higher $peak_{enh}$ (p=0.0245).

VOI-95 Percentile—

The average $peak_{enh}$ is estimated to be 172% (±57%) for malignant lesions, and 203% (±84%) for benign lesions. Furthermore, the average $peak_{enh}$ estimated to be 160% (±49%) for IDC and 222% (±62%) for FA. Based on tumor volume of the 95-percentile, the results show that benign breast lesions generally demonstrate a higher $peak_{enh}$ compared with malignant breast lesions. However, a large overlap is observed between the two groups with no statistically significant difference (p=0.0933). If all the IDC and FA are considered separately, FA demonstrates a significantly higher $peak_{enh}$ (p=0.006).

17.4 Wash-in Rate

VOI-Average—

The average Wash-in rate is estimated to be 3.13 $min^{-1}$ (±2.17 $min^{-1}$) for malignant lesions, and 3.07 $min^{-1}$ (±3.8 $min^{-1}$) for benign lesions. Furthermore, the average Wash-in rate is estimated to be 3.16 $min^{-1}$ (±2.22 $min^{-1}$) for the IDC, and 3.19 $min^{-1}$ (±4.03 $min^{-1}$) for the FA. Based on the average value for the tumor volume, the biomarker Wash-in rate demonstrates no significant difference regarding the differentiation of malignant and benign breast lesions (p=0.1235), as well as IDC and FA (p=0.1536). From the box plots FIG. 4E-4 and FIG. 4F-4 it can be observed that the different groups are affected by statistical outliers.

VOI-95 Percentile—

The average Wash-in rate is estimated to be 6.04 $min^{-1}$ (±5.4 $min^{-1}$) for malignant lesions and 5.16 $min^{-1}$ (±6.19 $min^{-1}$). Furthermore, the average Wash-in rate demonstrated is estimated to be 5.64 $min^{-1}$ (±5.47 $min^{-1}$) for the IDC and 5.03 $min^{-1}$ (±6.17 $min^{-1}$) for the FA. Based on the average value for the tumor volume, the biomarker Wash-in rate demonstrates no significant difference regarding the differentiation of malignant and benign breast lesions (p=0.0989), as well as IDC and FA (p=0.1934). Again box plots FIG. 4E-4 and FIG. 4F-4 show that the groups are affected by statistical outliers.

17.5 Wash-Out Rate

VOI-Average—

The average Wash-out rate is estimated to be 0.16 $min^{-1}$ (±0.16 $min^{-1}$) for malignant lesions, and 0.2 $min^{-1}$ (±0.1 $min^{-1}$) for benign lesions. Furthermore, the average Wash-out rate is estimated to be 0.16 $min^{-1}$ (±0.18 $min^{-1}$) for the IDC and 0.23 $min^{-1}$ (±0.09 $min^{-1}$) for the FA. The result shows that benign breast lesions possess a significantly higher Wash-out rate compared to malignant breast lesions (p=0.0116). In addition, the results show that FA possesses a significantly higher Wash-out rate compared to the IDC (p=0.0003). Box plots FIG. 4E-5 and FIG. 4F-5 shows that the different groups are affected by statistical outliers.

VOI-95 Percentile—

The average Wash-out rate is estimated to be 0.58 $min^{-1}$ (±0.6 $min^{-1}$) for malignant lesions and 0.72 $min^{-1}$ (±0.32 min-1) for benign lesions. Furthermore, the average Wash-out rate is estimated to 0.6 $min^{-1}$ (±0.67 $min^{-1}$) for the IDC and 0.84 $min^{-1}$ (±0.27 $min^{-1}$) for the FA. The result shows that the benign lesions possess a significantly higher Wash-out rate compared to malignant lesions (p=0.0147), and that FA possesses a significantly higher Wash-out rate compared to the IDC (p=0.0011). Again box plots FIG. 4E-5 and FIG. 4F-5 show that some groups are affected by statistical outliers.

18. Tumor Characterization by Use of Quantitative DCE-MRI Biomarkers

The quantitative biomarkers are estimated from the T1-weighed dynamic curves by using a pharmacokinetic two-compartment model [25]. This is presented in Section 7.3. The model here is affected on condition that an arterial input function (AIF) is directly measured in each patient.

Figure 4G:
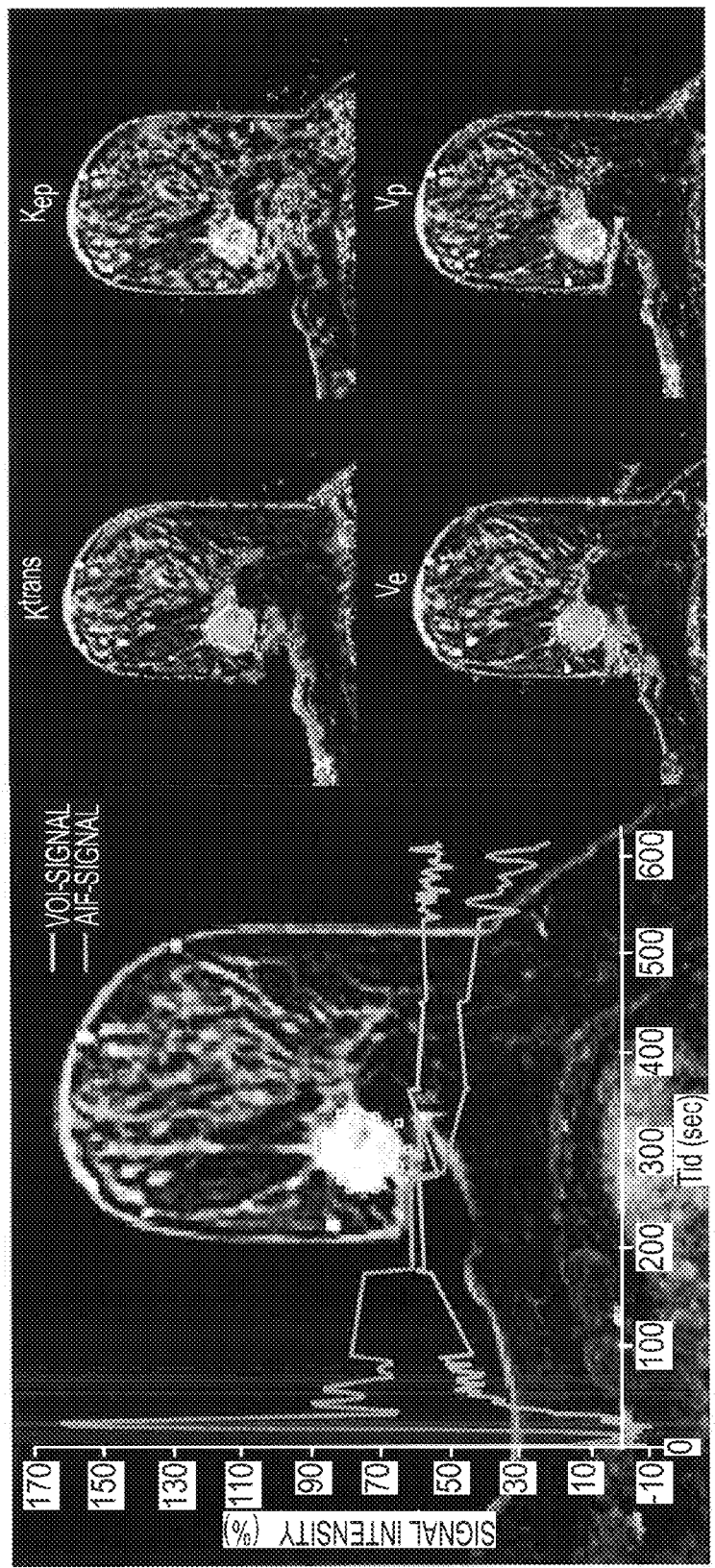
FIG. 4G is an illustration of quantitative DCE-MRI biomarkers for a 46 years old woman with IDC, as well as for the observed dynamic signal intensity from the selected ROI and the patient directly measured AIF. Estimation of the pharmacokinetic biomarkers is performed by modeling the signal from each voxel to the applied AIF. The degree of overlap between the AIF and the voxel signal is explained as plasma volume, and the discrepancy between the AIF and voxel signal is explained by leakage.

From the retrospective group of patients (n=40), 38 individual AIF are determined. In two patients, the AIF is not measurable because of an insufficiency condition with respect to the AIF curve's shape and temporal conditions. These patients are excluded from the quantitative analysis. An illustrative case of the quantitative biomarkers are presented in FIG. 4G. The figure shows an invasive ductal carcinoma (IDC) in a 46-year old woman and the patient's ROI and AIF signaling. The presented biomarkers are displayed as parametric maps superimposed onto a slice from the center of the tumor from the high resolution THRIVE series.

The result from the quantitative analysis shows that biomarkers VOI-95 percentile in general demonstrates a higher predictive ability with regard to distinguishing malignant tissue from benign lesions and dbetween IDC and FA. The VOI-95 percentile of the significant quantitative biomarkers is therefore used in further evaluations of the diagnostic performance. Based on the average value for the tumor volume of the 95-percentile, the Mann-Whitney U test designate $k_{ep}$ and $v_p$ as biomarkers that significantly correlate to malignancy and the ability to differentiate between FA and IDC.

Figures 1, 2, 4H:
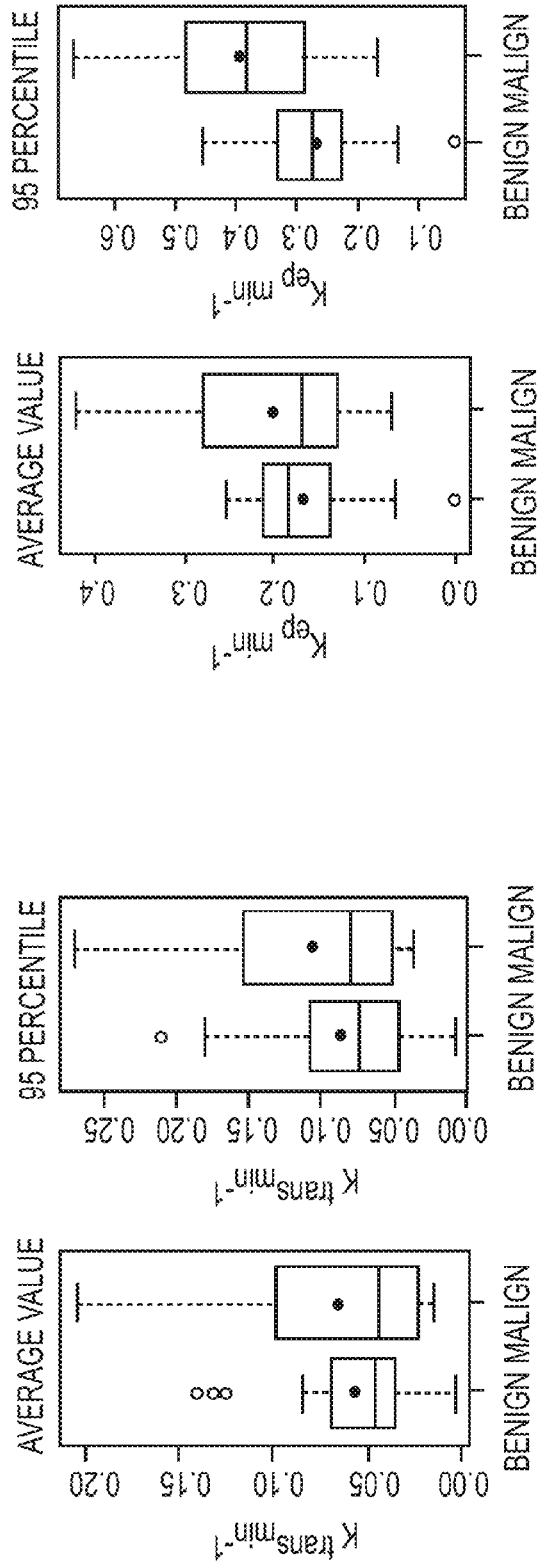
FIG. 4H illustrates box plots of the mean value and 95 percentile for the quantitative DCE-MRI biomarkers corresponding to grouping strategy 1, separate as FIG. 4H-1 through FIG. 4H-4. Box plots depict the group marker distribution in first to fourth quartile. In addition, the distribution median value and average value are presented as solid lines and red markers. Any outliers are illustrated as individual points outside the distribution. The figure presents box plots for (A) $K^{trans}$, (B) $k_{ep}$, (C) $v_e$, and (D) $v_p$.
Figures 3, 4, 4H:
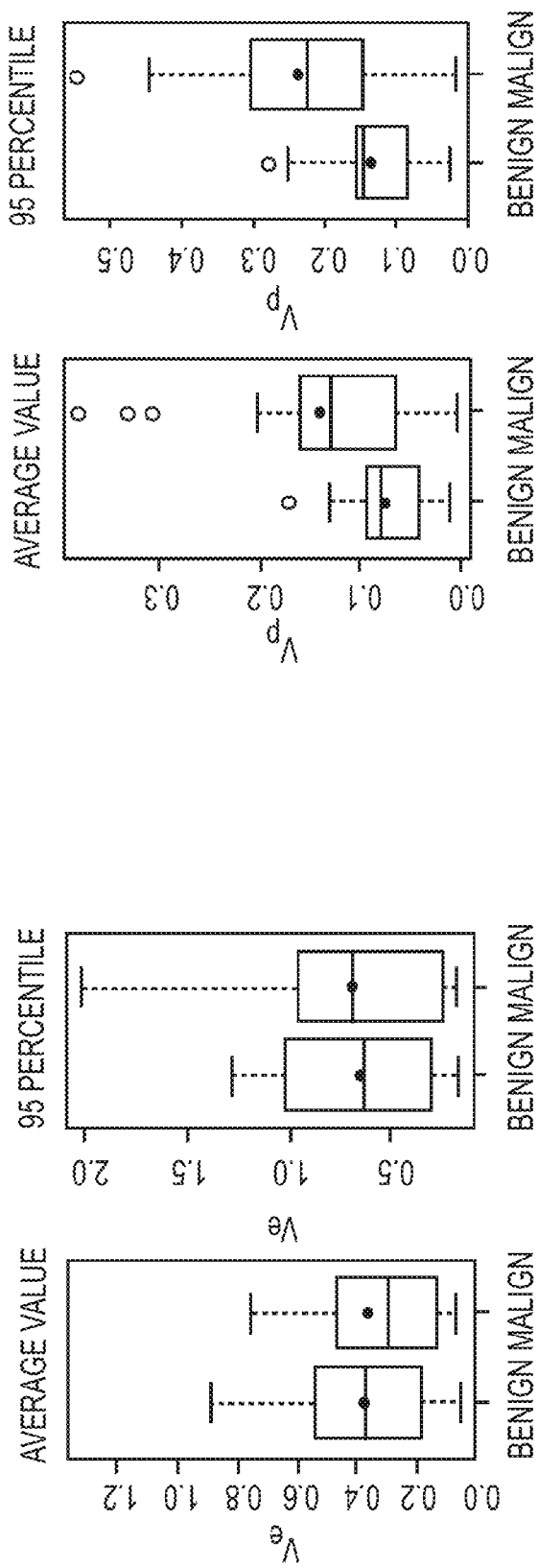
Figures 1, 2, 4I:
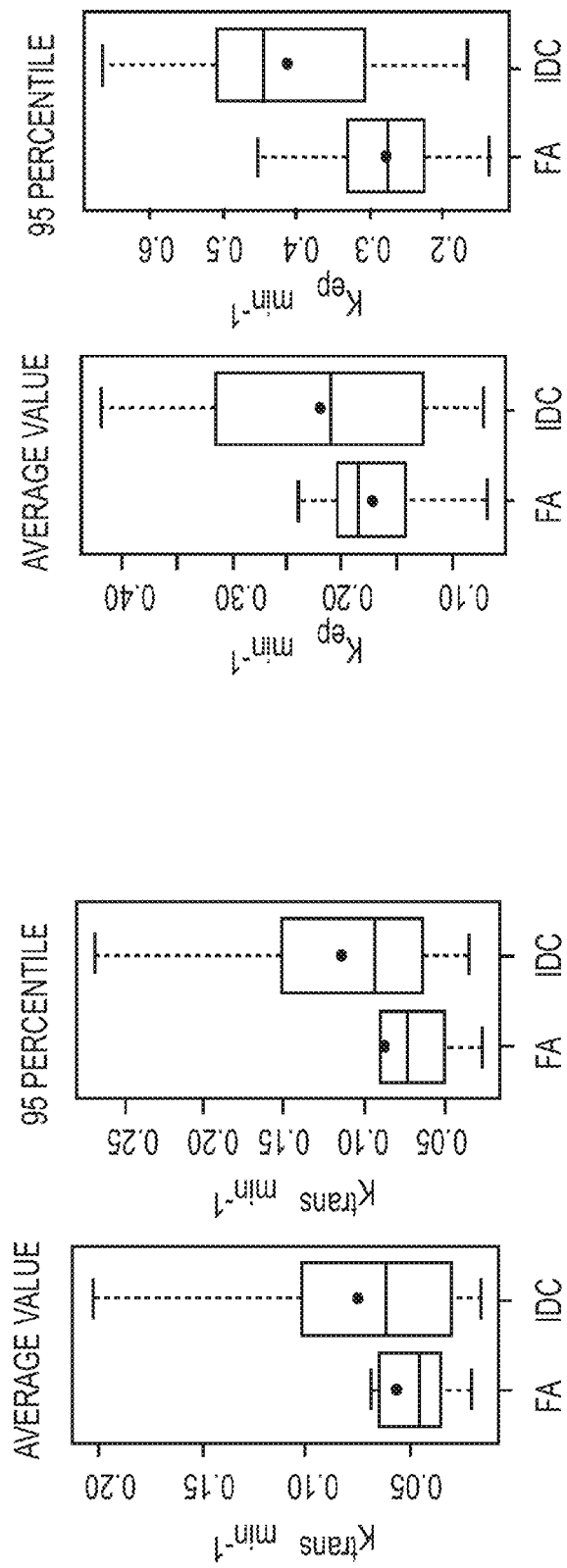
FIG. 4I illustrates box plots, separated as FIG. 4I-1 through FIG. 4I-4, of the average value and the 95 percentile for the quantitative DCE-MRI biomarkers corresponding to grouping strategy 2. Box plots depict the group marker distribution in first to fourth quartile. In addition, the distribution median value and average value are presented as solid lines and red markers. Any outliers are illustrated as individual points outside the distribution. The figure presents box plots for (A) $K^{trans}$, (B) $k_{ep}$, (C) $v_e$, and (D) $v_p$.
Figures 3, 4, 4I:
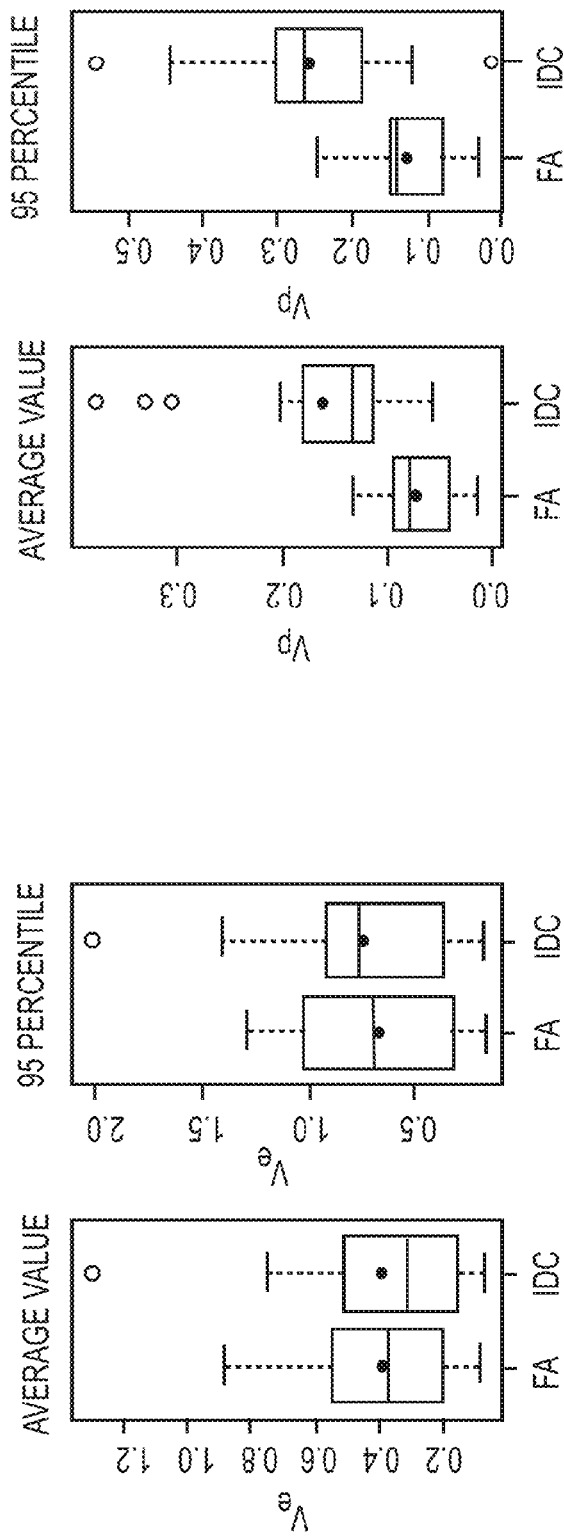

The average VOI-value and VOI-95 percentile of the quantitative biomarkers are presented with box plots, as a function of the grouping strategy 1 and 2, in FIGS. 4H and 4I, respectively. In addition, the results are presented in text form as the groups' mean value and standard deviation.

18.1 The Volume Transfer Coefficient $K^{trans}$

VOI-Average—

The average $K^{trans}$ is estimated to be 0.066 min$^{-1}$ (±0.053 min$^{-1}$) for malignant lesions and 0.057 min$^{-1}$ (±0.039 min$^{-1}$) for benign lesions. Furthermore, the average $K^{trans}$ is estimated to be 0.076 min$^{-1}$ (±0.057 min$^{-1}$) for the IDC and 0.056 min$^{-1}$ (f 0.033 min$^{-1}$) for the FA. Based on the average value for the tumor volume, the biomarker $K^{trans}$ shows no statistical significance regarding the differentiation of malignant and benign breast lesions (p=0.8264), as well as for the IDC and the FA (p=0.5268). The box plots FIG. H-1 and FIG. I-1 show that the benign group and the group of FA are affected by statistical outliers.

VOI-95 Percentile—

The average $K^{trans}$ is estimated to be 0.106 min$^{-1}$ (±0.068 min$^{-1}$) for malignant lesions and 0.088 min$^{-1}$ (±0.058 min$^{-1}$) for benign lesions. Furthermore, the average $K^{trans}$ is estimated to be 0.115 min$^{-1}$ (±0.069 min$^{-1}$) for the IDC and 0.089 min$^{-1}$ (±0.055 min$^{-1}$) for the FA. Based on the average value for the tumor volume of the 95 percentile, the biomarker $K^{trans}$ shows no statistical significance regarding the differentiation of malignant and benign breast lesions (p=0.5201), as well as for IDC and FA (p=0.3314). Similarly, box plots FIG. 4H-1 and FIG. 4I-1 show that the benign group and the group of the FA are affected by statistical outliers.

18.2 The Rate Constant, $k_{ep}$

VOI-Average—

The average $k_{ep}$ is estimated to be 0.203 min$^{-1}$ (±0.1 min$^{-1}$) for malignant lesions and 0.17 min$^{-1}$ (±0.065 min$^{-1}$) for benign lesions. Furthermore, the average $k_{ep}$ is estimated to be 0.221 min$^{-1}$ (±0.11 min$^{-1}$) for the IDC and 0.173 min$^{-1}$ (±0.049 min$^{-1}$) for the FA. Based on the average value for the tumor volume, the biomarker $k_{ep}$ shows no statistical significance regarding the differentiation of malignant and benign breast lesions (p=0.6964), as well as for the IDC and the FA (p=0.3536).

VOI-95 Percentile—

The average $k_{ep}$ shows is estimated to be 0.395 min$^{-1}$ (±0.145 min$^{-1}$) for malignant lesions and 0.267 min$^{-1}$ (±0.094 min$^{-1}$) for benign lesions. Furthermore, the average $k_{ep}$ is estimated to be 0.416 min$^{-1}$ (±0.157 min$^{-1}$) for the IDC and 0.275 min$^{-1}$ (±0.083 min$^{-1}$) for the FA. Based on the average value for the tumor volume 95-percentile malignant breast lesions demonstrate significantly higher $k_{ep}$ value compared to benign breast lesions (p=0.0058). The result also shows that the biomarker $k_{ep}$ is significantly higher in the IDC compared to the FA (p=0.0105).

18.3 EES Volum, $v_e$

VOI-Average—

The average $v_e$ is estimated to be 0.361 (±0.306) for malignant lesions and 0.372 (±0.243) for benign lesions. Furthermore, the average $v_e$ is estimated to be 0.4 (±0.334) for the IDC and 0.392 (±0.238) for the FA. Based on the average value for the tumor volume, the biomarker $v_e$ shows no statistical significance regarding the differentiation between malignant and benign breast lesions (p=0.6751), as well as for the IDC and the FA (p=0.7148).

VOI-95 Percentile—

The average $v_e$ is estimated to be 0.694 (±0.475) for malignant lesions and 0.651 (±0.375) for benign lesions. Furthermore, the average $v_e$ is estimated to be 0.746 (±0.495) for the IDC and 0.683 (±0.38) for the FA. Based on the average value for the tumor volume 95-percentile, the biomarker $v_e$ shows no statistical significance regarding the differentiation between malignant and benign breast lesions (p=0.9195), as well as for the IDC and the FA (p=0.8132).

18.4 Plasma Volume, $v_p$

VOI-Average—

The average $v_p$ is estimated to be 0.139 (±0.101) for malignant lesions, and 0.075 (±0.043) for benign lesions. Furthermore, the average $v_p$ is estimated to be 0.163 (±0.103) for the IDC, and 0.073 (±0.036) for the FA. The results show that malignant breast lesions demonstrates a significantly higher $v_p$-value compared to benign breast lesions (p=0.0261). If the IDC and the FA are considered separately, the IDC demonstrates a significantly higher $v_p$-value (p=0.0016). The box plots FIG. 4H-4 and FIG. 4I-4 show that the different groups are affected by outliers. This is especially true for the malignant group and the group of the IDC.

VOI-95 Percentile—

The average $v_p$ is estimated to be 0.236 (±0.135) for malignant lesions and 0.134 (±0.068) for benign lesions. Furthermore, the average $v_p$ is estimated to be 0.261 (±0.128) for the IDC and 0.43 (±0.058) for the FA. The result shows that malignant breast lesions demonstrate a significantly higher $v_p$-value compared to benign breast lesions (p=0.0094) and that the IDC demonstrates a significantly higher $v_p$-value compared to the FA (p=0.0008). Here, too, box plots FIG. 4H-4 and FIG. 4I-4 show that the group of IDC is somewhat affected by statistical outliers.

19. Tumor Characterization by Application of Qualitative DCE-MRI Biomarkers

The qualitative biomarkers are estimated using a pharmacokinetic two-compartment model. The applied AIF is determined by fitting an idealized mono-exponential input function. As the current model-based method does not require the provision of an individual input function, all patients are included in the analysis.

From the qualitative analysis, it is found that the biomarkers VOI-95 percentile, in general, demonstrates a higher predictive ability with regard to distinguishing malignant tissue from benign lesions, as well as for differentiation between the IDC and the FA. The Mann-Whitney U test designates $k_{ep}$ as the biomarker that significantly correlates to malignancy, as well as $k_{ep}$ and $v_e$ as biomarkers with significant ability to differentiate between the FA and the IDC.

Figures 1, 2, 4J:
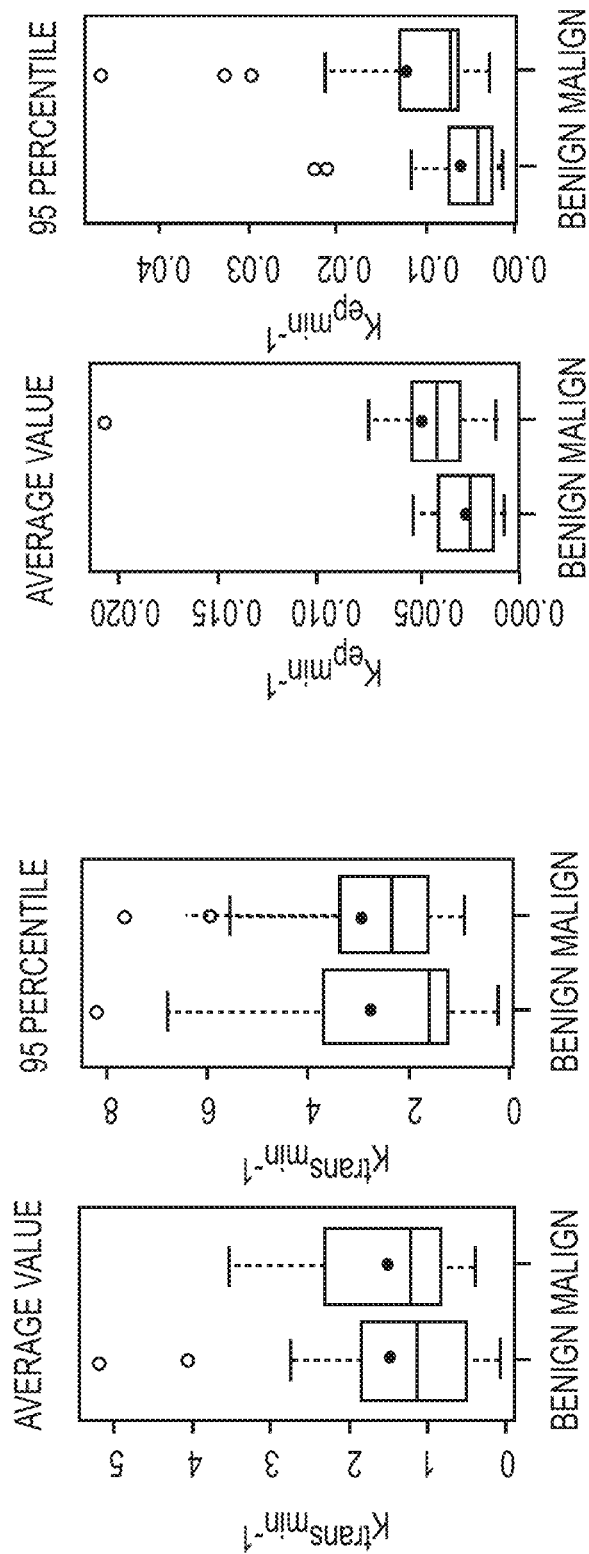
FIG. 4J illustrates box plots, separated as FIG. 4J-1 through FIG. 4J-6, of the mean value and 95 percentile for the qualitative DCE-MRI biomarkers corresponding to grouping strategy 1 and 2. Box plots depict the group marker distribution in first to fourth quartile. In addition, the distribution median value and average value are presented as solid lines and red markers. Any outliers are illustrated as individual points outside the distribution. The figure presents box plots for (A and D) for $K^{trans}$, (B and E) $k_{ep}$, (C) $v_e$, and (C and F) $v_e$.
Figures 3, 4, 4J:
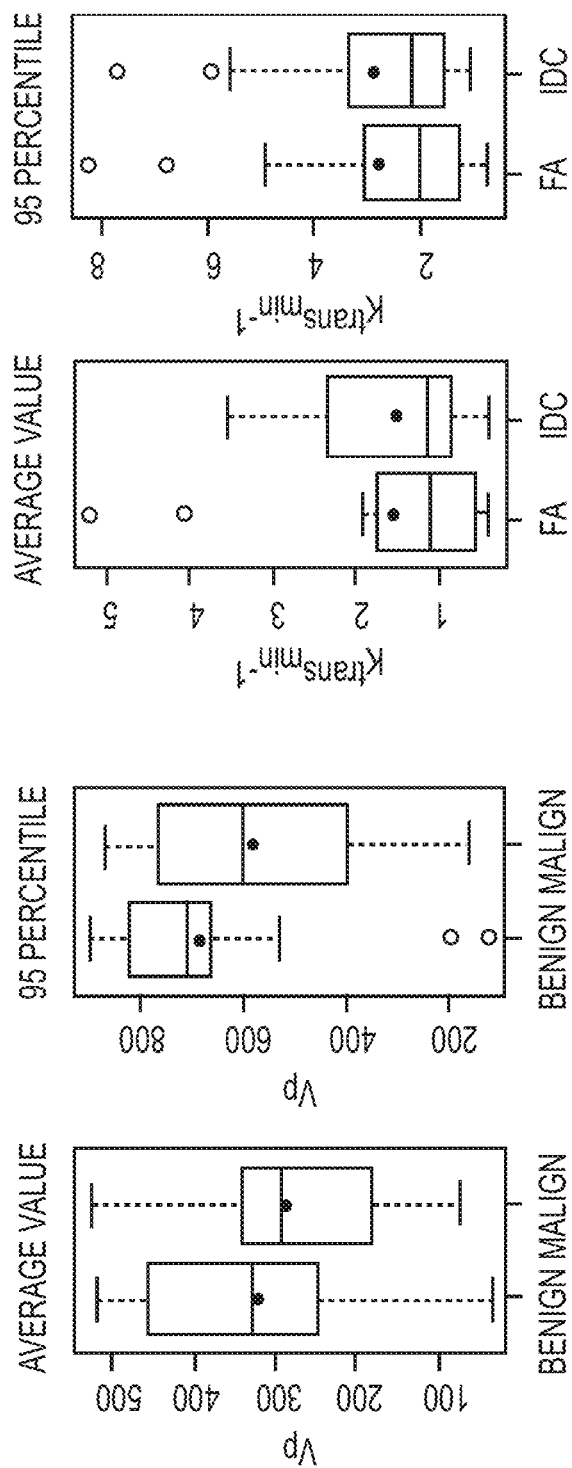

The average VOI-value and VOI-95 percentile for the qualitative DCE-MRI biomarkers are presented with box plots as a function of the grouping strategy 1 and 2 in FIG. 4J. The results for each the biomarker are also presented in the form of the respective group's mean value and standard deviation.

19.1 The volume Transfer Coefficient, $K^{trans}$

VOI-Average—

The average $K^{trans}$ is estimated to be 1.497 min$^{-1}$ ($\pm 0.872$ min$^{-1}$) for malignant lesions and 1.482 min$^{-1}$ ($\pm 1.348$ min$^{-1}$) for benign lesions. Furthermore, the average $K^{trans}$ is estimated to be 1.513 min$^{-1}$ ($\pm 0.911$ min$^{-1}$) for the IDC and 1.548 min$^{-1}$ ($\pm 1.424$ min$^{-1}$) for the FA. Based on the average value for the tumor volume, the qualitative biomarker $K^{trans}$ demonstrates no statistical significance regarding the differentiation of malignant and benign breast lesions (p=0.5735), as well as for the IDC and the FA (p=0.667). The box plots FIG. 4J-1 and FIG. 4J-4 show that the benign group and the group of the FA are affected by statistical outliers.

VOI-95 Percentile—

The average $K^{trans}$ is estimated to be 2.977 min$^{-1}$ ($\pm 1.85$ min$^{-1}$) for malignant lesions and 2.778 min$^{-1}$ ($\pm 2.334$ min$^{-1}$) for benign lesions. Furthermore, the average $K^{trans}$ is estimated to be 2.888 min$^{-1}$ ($\pm 1.891$ min$^{-1}$) for the IDC and 2.821 min$^{-1}$ ($\pm 2.277$ min$^{-1}$) for the FA. Based on the average value for the tumor volume 95-percentile, the qualitative biomarker $K^{trans}$ demonstrates no statistical significance regarding the differentiation of malignant and benign breast lesions (p=0.3902), as well as for the IDC and the FA (p=0.5521). The box plots FIG. 4J-1 and FIG. 4J-4 show that the different groups are affected by statistical outliers.

19.2 Rate Constant, $k_{ep}$

VOI-Average—

The average $k_{ep}$ estimated to 0.005 min$^{-1}$ ($\pm 0.004$ min$^{-1}$) for malignant lesions and 0.003 min$^{-1}$ ($\pm 0.002$ min$^{-1}$) for benign lesions. Furthermore, the average $k_{ep}$ is estimated to 0.005 min-1 ($\pm 0.004$ min$^{-1}$) for the IDC and 0.002 min$^{-1}$ ($\pm 0.001$ min$^{-1}$) for the FA. Based on the average value for the tumor volume, the results show that malignant breast lesions possess a significantly higher $k_{ep}$ value compared to benign breast lesions (p=0.0073), and that IDC possesses a significantly higher $k_{ep}$ value compared to the FA (p=0.0005). The box plots FIG. 4J-2 and FIG. 4J-5 show that the malignant group and the group of the IDC are affected by statistical outliers.

VOI-95 Percentile—

The average $k_{ep}$ is estimated to be 0.012 min$^{-1}$ ($\pm 0.011$ min$^{-1}$) for malignant lesions and 0.006 min$^{-1}$ ($\pm 0.006$ min$^{-1}$) for benign lesions. Furthermore, the average k, is estimated to be 0.014 min$^{-1}$ ($\pm 0.012$ min$^{-1}$) for the IDC and 0.004 min$^{-1}$ ($\pm 0.0003$ min$^{-1}$) for the FA. Based on the average value for the tumor volume 95-percentile, the results show that malignant lesions possess a significantly higher $k_{ep}$ value compared to benign breast lesions (p=0.0033), and that IDC possesses a significantly higher $k_{ep}$ value compared to the FA (p=0.0003). The box plots FIG. 4J-2 and FIG. 4J-5 also show the presence of statistical outliers in the different groups.

19.3 EES Volume $v_e$

VOI-Average—

Figures 4, 4J, 5, 6:
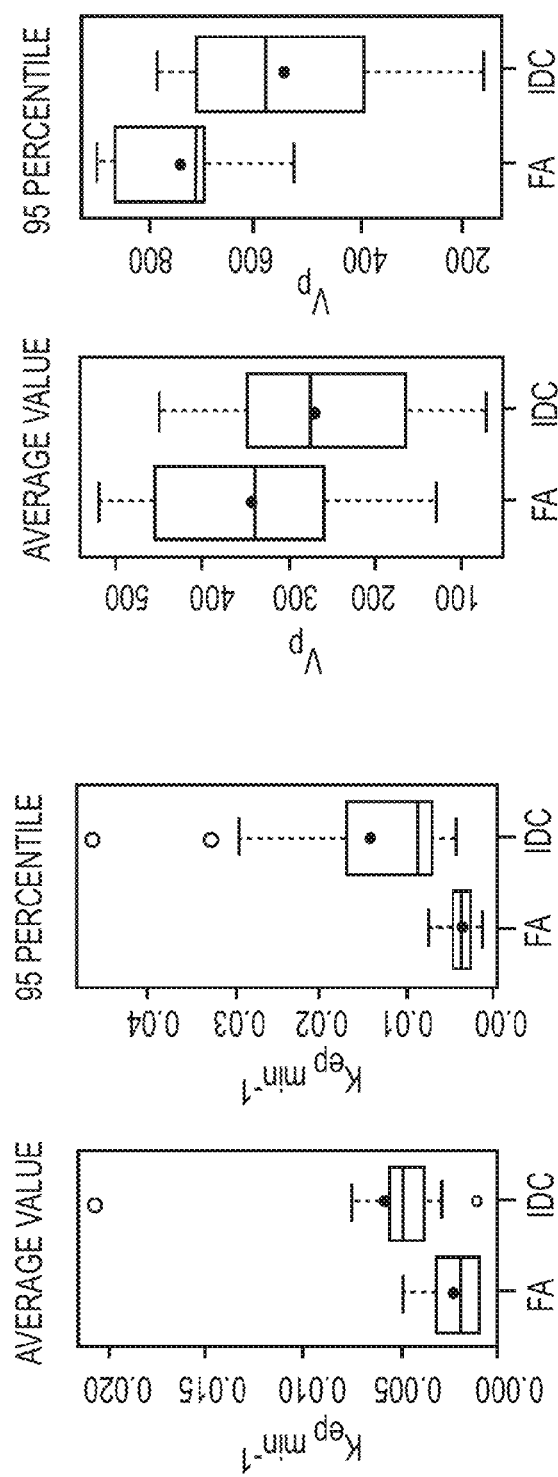

The average $v_e$ is estimated to be 283 ($\pm 117$) for malignant lesions and 321 ($\pm 147$) for benign lesions. Furthermore, the average $v_e$ is estimated to be 267 ($\pm 112$) for the IDC, and 341 ($\pm 115$) for the FA. Based on the average value for the tumor volume, the qualitative biomarker $v_e$ demonstrates no statistical significance regarding the differentiation of malignant and benign breast lesions (p=0.3611), as well as for IDC and FA (p=0.1306). The box plot FIG. 43-6 shows that the FA demonstrates a slightly higher $v_e$-value compared to the IDC, but that the values in these two groups largely overlap.

VOI-95 Percentile—

The average $v_e$ is estimated to be at 583 ($\pm 195$) for malignant lesions and 681 ($\pm 209$) for benign lesions. Furthermore, the average $v_e$ is estimated to be 545 ($\pm 187$) for the IDC and 743 ($\pm 104$) for the FA. The result shows that the benign lesions generally possess a higher $v_e$-value compared to malignant lesions. However, this difference is not statistically significant (p=0.1304). If the IDC and the FA are considered separately, the results show that the FA possesses a significantly higher ve-value (p=0.0052). Box plot FIG. 4J-3 shows that the benign group is influenced by two statistical outliers. These outlayers influence the group estimated average value and standard deviation.

20. Tumor Characterization by Use of Quantitative DSC-MRI Biomarker

The transversal relaxation rate is estimated on the basis of the measured DCE signal from a double-echo system under the assumption of a mono-exponential dependent signal change between the two echo times. The theory behind this method is presented in Section 12.3.

Figure 4K:
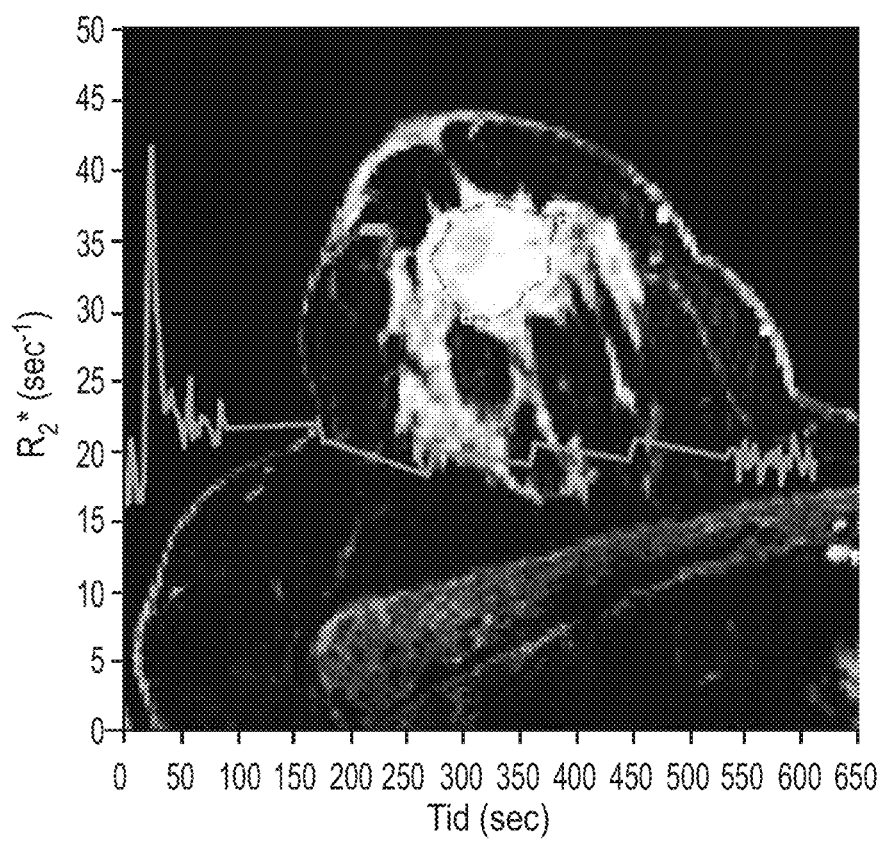
FIG. 4K is an illustration of the temporal transversal relaxation rate in a 38-year-old woman with invasive ductal carcinoma (IDC). The curve is extracted from the drawn ROI, and demonstrates a characteristic sharp peak in the early post-contrast phase, caused by the transient R2*-effect of the administered contrast agent.

An illustrative case of the dynamic transversal relaxation rate is presented in FIG. 4K. The figure shows the dynamic R2*-curve from a 38-year-old woman with an invasive ductal carcinoma (IDC), illustrated with the ROI.

From the patient's DSC capture, it is found in this study that the quantitative biomarker R2*-peak$_{enh}$ demonstrates a significant predictive ability with regard to distinguishing malignant tissue from benign lesions, as well as the differentiation of the IDC from the FA. R2*-peak$_{enh}$ demonstrates a high predictive ability when estimated from both the tumor volume average value and from the 95-percentile.

Figures 1, 4L:
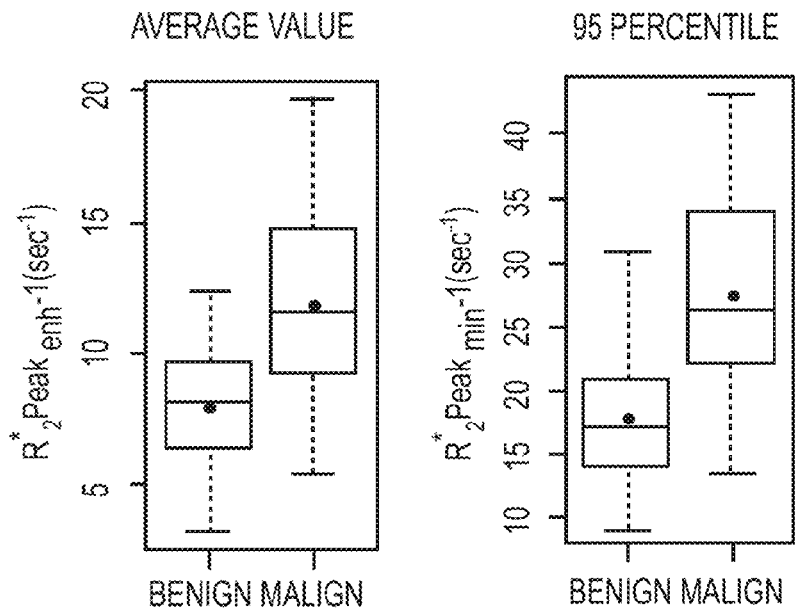
FIG. 4L illustrates box plots, separate as FIG. 4L-1 and FIG. 4L-2, of the mean value and 95 percentile for the quantitative DSC-MRI biomarker R2*-peak$_{enh}$ corresponding to grouping strategy 1 (A) and 2 (B). Box plots depict the group marker distribution in first to fourth quartile. In addition, the distribution median value and average value are presented with solid lines and red markers. Any outliers are illustrated as individual points outside the distribution.
Figures 2, 4L:
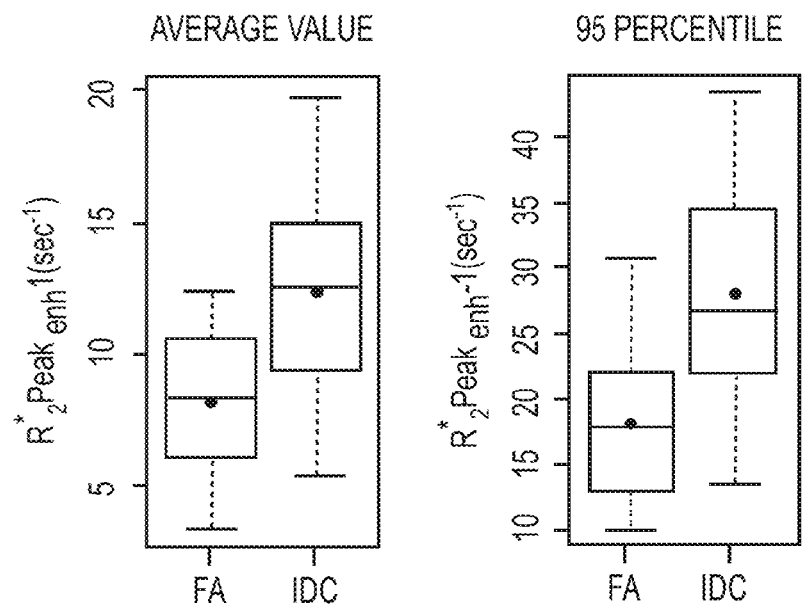

The tumor volume mean value and the 95-percentile for the quantitative DSC-MRI biomarker are presented as box plots, as a function of the grouping strategy 1 and 2 and in FIG. 4L. The results are also presented in the form of the respective group's mean value and standard deviation.

20.1 Maximum Transversal Relaxation Rate, R2*-Peak$_{enh}$

VOI-Average—

The average R2*-peak$_{enh}$ is estimated to 11.8 sec$^{-1}$ ($\pm 3.8$ sec$^{-1}$) for malignant lesions, and 7.9 sec$^{-1}$($\pm 2.3$ sec$^{-1}$) for benign lesions. Furthermore, the average R2*-peak$_{enh}$ is estimated to 12.3 sec$^{-1}$($\pm 3.9$ sec$^{-1}$) for the IDC, and 8.2 sec$^{-1}$ ($\pm 2.7$ sec$^{-1}$) for the FA. Based on the average value for the tumor volume malignant breast lesions demonstrate significantly higher R2*-peak$_{enh}$ compared to benign breast lesions (p=0.0008). The result also show that IDC possesses a significantly higher R2*-peak$_{enh}$ compared to FA (p=0.0021).

VOI-95 Percentile—

The average R2*-peak$_{enh}$ is estimated to 27.3 sec$^{-1}$ ($\pm 7.8$ sec$^{-1}$) for malignant lesions, and 17.6 sec$^{-1}$ ($\pm 5.7$ sec$^{-1}$) for benign lesions. Furthermore, the average R2*-peak$_{enh}$ is estimated to 27.8 sec$^{-1}$ ($\pm 8.1$ sec$^{-1}$) for the IDC and 18.0 sec$^{-1}$ ($\pm 6.0$ sec$^{-1}$) for the FA. Based on the average value for the tumor volume 95-percentile, malignant breast lesions demonstrate significantly higher R2*-peak$_{enh}$ compared to the benign breast lesions (p<0.0001). The results also show that the IDC possesses a significantly higher R2*-peak$_{enh}$ compared to the FA (p=0.0007).

Figure 4M:
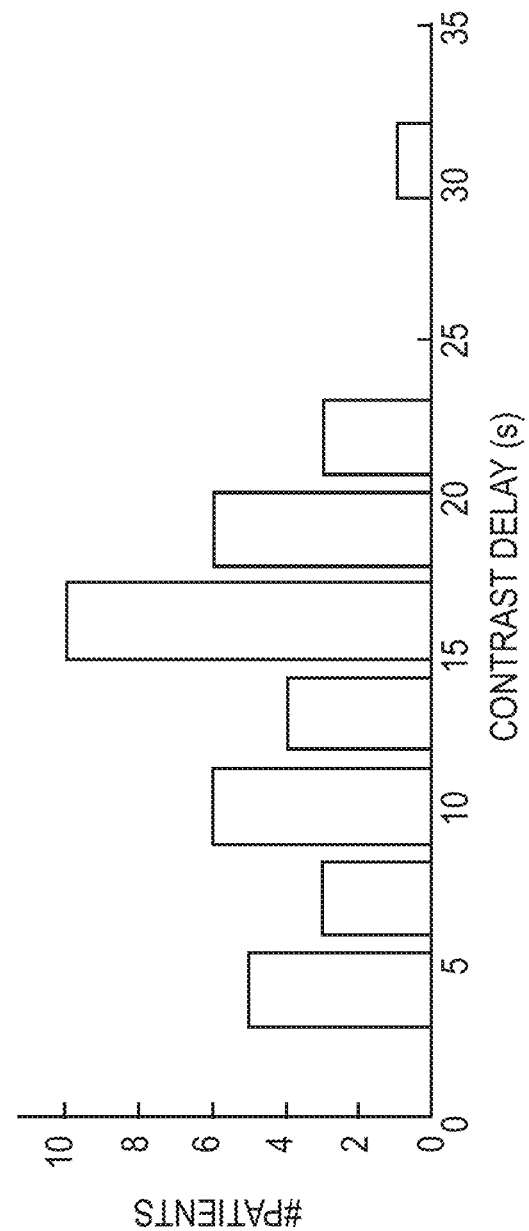
FIG. 4M is a histogram of patients' contrast delay, determined from the time interval between the contrast agents' arrival in the arterial voxels into the tissue of interest. One patient has a CD higher than 22 seconds, with a measured CD of 32.2 seconds.

21. The Importance of Contrast Delay in Diagnostic Evaluation of Pharmacokinetic Biomarkers As mentioned, the applied pharmacokinetic two-compartment model requires that the contrast agent arrives in the arterial voxels and into the tissue of interest at the same time. In this study it is found that there is a significant contrast delay (CD), and that this can lead to estimation errors and increased uncertainty of the models biomarker, if not corrected. The CD in this study is recorded individually for each patient by measuring the time interval between contrast agent's arrival in the arterial voxels and the tissue of interest. FIG. 4M shows the distribution of CD for the patients in this study. This figure shows that the CD is the variable for different patients, with an average value of 14 seconds and a variation width of 2.7 to 32.2 seconds.

Figures 1, 4N:
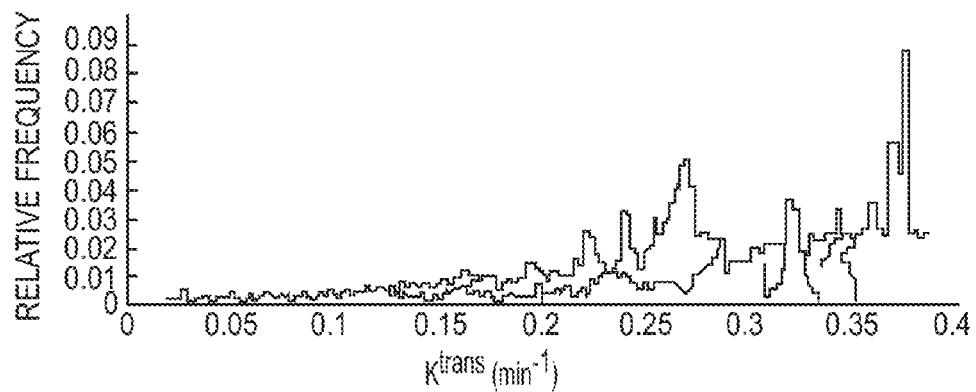
FIG. 4N, separated as FIG. 4N-1 through FIG. 4N-4, illustrates histograms of the pharmacokinetic biomarkers (A) $K^{trans}$, (B) $k_{ep}$, (C) $v_e$ and (D) $v_p$ for a 60 year old patient with IDC. The histograms illustrate the distribution of marker values calculated with CD-correction (blue line) and without KF-correction (red line).
Figures 2, 4N:
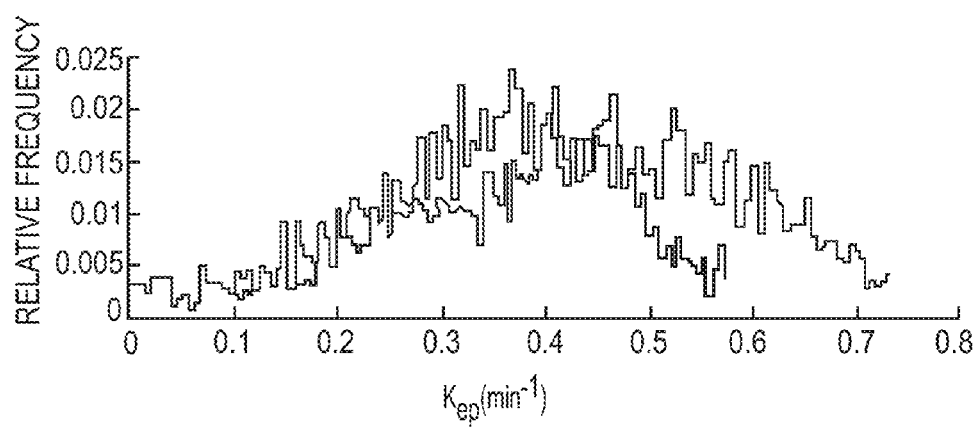
Figures 3, 4N:
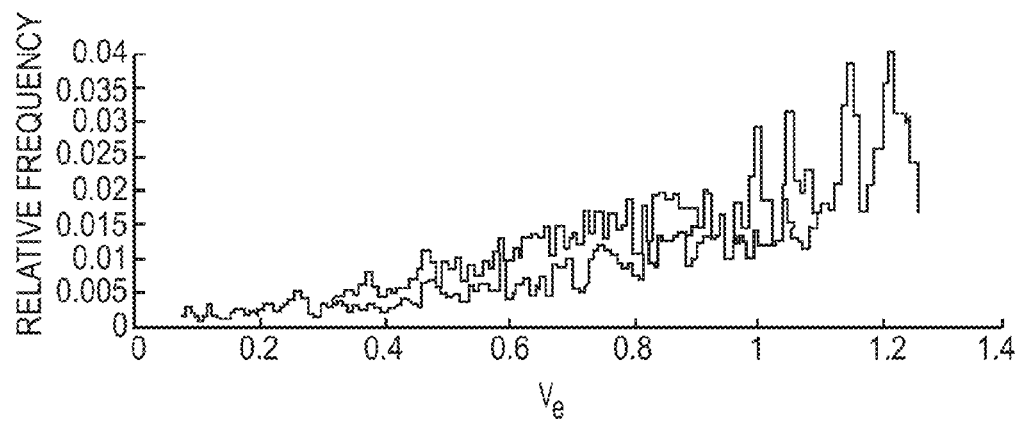
Figures 4, 4N:
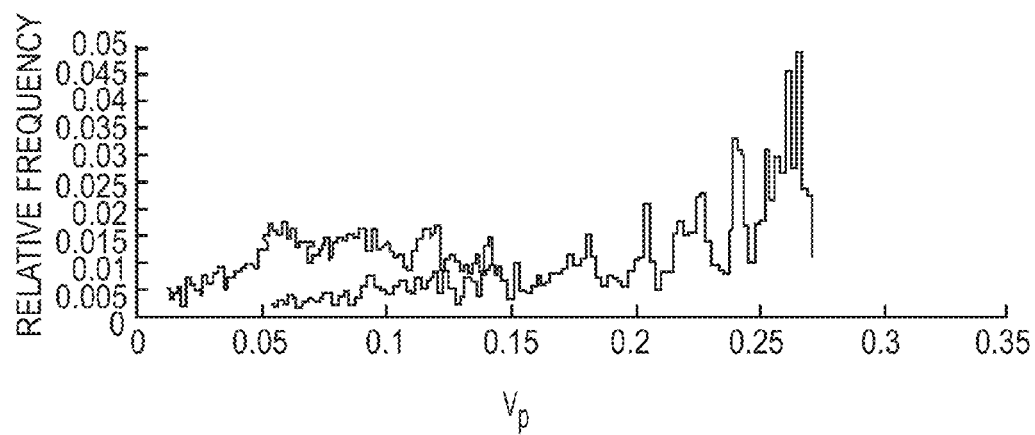
Figures 1, 2, 40:
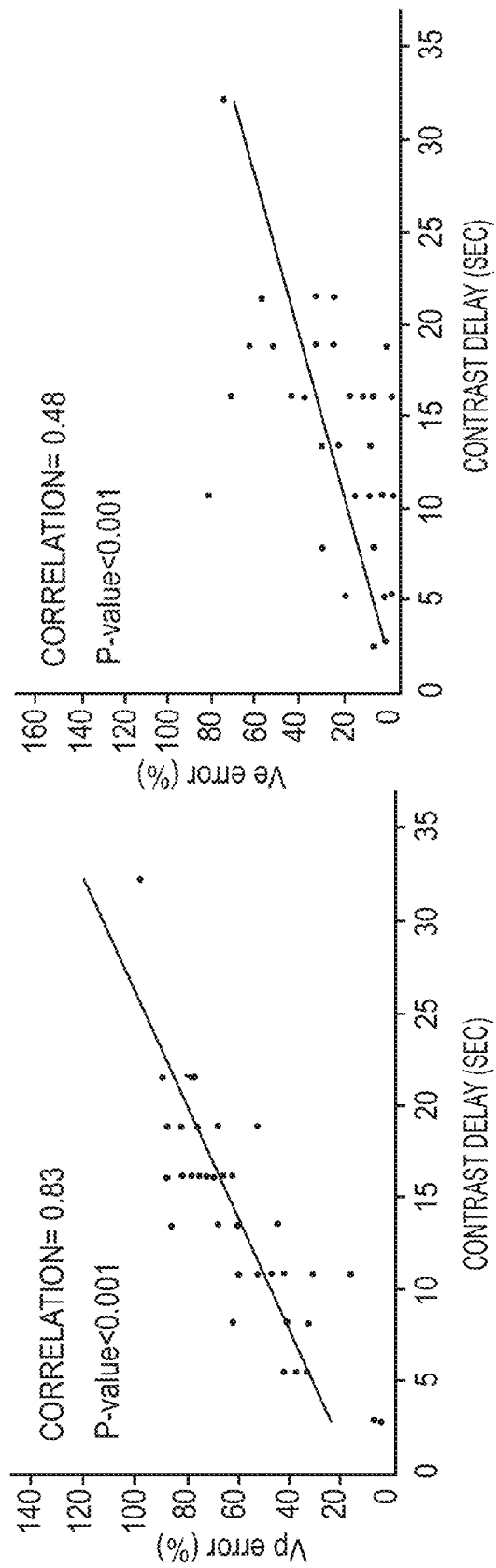
Figures 3, 4, 40:
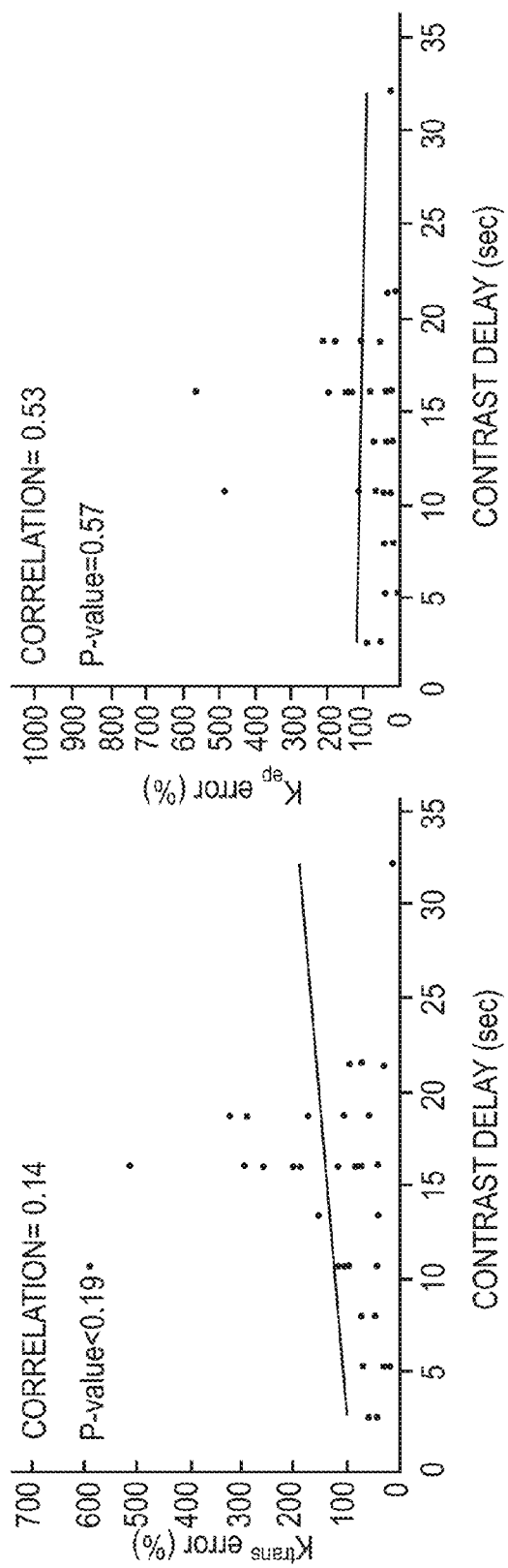
FIG. 3G is a schematic illustration of a typical temporal $\Delta R2^*$-curve following administration of a contrast agent. The dynamic change in $R2^*$ is evaluated with the quantitative biomarker $R2^*\text{-peak}_{enh}$.
FIG. 4O, separated as FIG. 4O-1 through FIG. 4O-4, demonstrates the relationship between the percentage of incorrect estimation of the pharmacokinetic biomarkers (A) $v_p$, (B) $v_e$, (C) $K^{trans}$ and (D) $k_{ep}$ as a function of contrast delay (CD). The study shows that transfer coefficients $K^{trans}$ and $k_{ep}$, and the volume fraction ve are estimated relative to the actual value if the CD is not corrected for. The study also shows that the volume fraction, $v_p$, is underestimated when CD is existing. Any outliers are displayed with a red point.
FIG. 4P, separated as FIG. 4P-1 through FIG. 4P-4, illustrates box plots of the initial and the normalized value of the quantitative DCE-MRI biomarkers, corresponding to the grouping strategy 1. Box plots depict the group marker distribution in first to fourth quartile. In addition, the distribution median value and average value are presented with solid lines and red markers, respectively, Any outliers are illustrated as individual point outside the distribution. The figure presents box plots for (A) $K^{trans}$, (B) $k_{ep}$, (C) $v_e$, and (D) $v_p$.
FIG. 4Q, separated as FIG. 4Q-1 through FIG. 4Q-4, illustrates box plots of the initial and the normalized value of the quantitative DCE-MRI biomarkers, corresponding with the grouping strategy 2.

To evaluate the importance of CD, the pharmacokinetic biomarkers are estimated from individually measured AIF, with and without CD-correction. FIG. 4N demonstrates the importance of the delay factor for the pharmacokinetic biomarkers in a patient. The figure shows the histogram distribution of the model's four biomarkers, estimated with and without CD-correction. In this particular case a contrast delay is registered between the arterial voxels and the tissue of interest of 10.7 seconds. The observations from FIG. 4N suggest an overestimation of the transfer coefficients $K^{trans}$ and $k_{ep}$, and the volume fraction $v_e$ if CD is occurring and an underestimation of the volume plasma fraction $v_p$.

The importance of CD in this study is evaluated using the patient's biomarker values estimated from the average tumor volume. In addition, it is assumed that the CD-corrected bio marker values represent a more accurate pharmacokinetic value. The CD-corrected average volume transfer constant $K^{trans}$ is estimated to be 0.066 min$^{-1}$ (±0.053 min$^{-1}$) for malignant lesions and 0.057 min$^{-1}$ (±0.039 min$^{-1}$) for benign lesions. Average $K^{trans}$ without CD-correction is estimated to be 0.13 min$^{-1}$ (±0.078 min$^{-1}$) for malignant lesions and 0.111 min$^{-1}$ (±0.066 min$^{-1}$) for benign lesions. This corresponds to a difference of 0.064 min$^{-1}$ for malignant lesions and 0.054 min$^{-1}$ for benign lesions, and is equivalent to a percentage of the overestimation error of 97 and 95%, respectively.

The CD-corrected average rate constant $k_{ep}$ is estimated to be 0.203 min$^{-1}$ (±0.101 min$^{-1}$) for malignant lesions and 0.17 min$^{-1}$ (±0.065 min$^{-1}$) for benign lesions. The average $k_{ep}$ without CD-correction is estimated to be 0.369 min$^{-1}$ (±0.169 min$^{-1}$) for malignant lesions and 0.289 min$^{-1}$ (±0.18 min$^{-1}$) for benign lesions. This corresponds to a difference of 0.166 min$^{-1}$ for malignant lesions and 0.119 min$^{-1}$ for benign lesions, and is equivalent to a percentage overestimation error of 82 and 70%, respectively.

The CD-corrected average volume fraction $v_e$ is estimated to be 0.361 (±0.306) for malignant lesions and 0.372 (±0.243) for benign lesions. The average $v_e$, without CD-correction, is estimated to be 0.445 (±0.324) for malignant lesions and 0.444 (±0.266) for benign lesions. This corresponds to a difference of 0.084 for malignant lesions and 0.072 for benign lesions, and is equivalent to a percentage overestimation error of 23 and 19%, respectively.

The CD-corrected average volume fraction $v_p$ is estimated to be 0.139 (±0.101) for malignant lesions and 0.075 (±0.043) for benign lesions. Average v, without CO-correction is estimated to be 0.074 (±0.093) for malignant lesions and 0.026 (±0.018) for benign lesions. This corresponds to a difference of 0.065 for malignant lesions and 0.049 for benign lesions, and is equivalent to a percentage overestimation error of 47 and 65%, respectively.

Assuming that the corrected marker values are more accurate, the results indicate that biomarkers $K^{trans}$, $k_{ep}$, and $v_e$ are overestimated if CD exists, and that $v_p$ is under estimated. FIG. 4O shows the correlation between the percentage of incorrect estimation of the pharmacokinetic biomarkers and CD. Any outliers are displayed as red plot markers. Biomarkers $v_p$ and $v_e$ show a significant positive correlation between CD-magnitude and percentage estimation errors. The correlation coefficients are estimated to be 0.83 and 0.48, respectively, which corresponds to a p-value of p<0.001 and p=0.001, respectively. This means that an increase of CD-magnitude will provide an increased estimation error of $v_p$ and $v_e$. Biomarker $K^{trans}$ and $k_{ep}$ show no significant correlation between the percentage estimation error and CD-magnitude. The correlation coefficients are estimated to be 0.14 and −0.03, respectively, which corresponds to a p-value of p=0.19 and p=0.57, respectively. However, the results suggest that the eventuality of CD will generate significant estimation errors of $K^{trans}$ and $k_{ep}$, and that the error estimation of $K^{trans}$ is increasingly affected by the CD-magnitude compared to $k_{ep}$.

CD and its relation to the estimation error can be explained by referring to the pharmacokinetic two-compartment model: If the CD exists, a smaller percentage of the measured tissue signal could be scaled with the AIF. Since the overlap between the VOI-curve and the AIF curve is explained as a plasma volume, this biomarker will be under estimated due to the CD. Furthermore, a greater proportion of VOI-curve will demonstrate a discrepancy with regard to the AIF curve, something the two-compartment model explains as leakage. The consequence of this is an overestimation of biomarkers $K^{trans}$ and $k_{ep}$, which describes the motion of contrast agent between the plasma compartment and EES. The EES volume $v_e$ is given as the ratio between $K_{trans}$ and $k_{ep}$. The result suggests that the error estimation of $K^{trans}$ is more affected by the CD-magnitude compared to $k_{ep}$. As a result the EES volume, $v_e$, is overestimated, with increasing CD-magnitude.

The result shows that the estimation of pharmacokinetic biomarkers are based on the two-compartment model and, assuming an individual measured AIF, is affected by CD between the arterial voxels and the tissue of interest. Attainment of robust pharmacokinetic biomarkers therefore requires a correction of CD between the arterial voxels and tissues of interest.

22. Improved Diagnostic Performance of DCE-MRI by Normalization of Pharmacokinetic Biomarkers The application of a quantitative pharmacokinetic evaluation of abnormally breast tissue requires a precise determination of the AIF. In this study it is found that an adequate measurement of the AIF is often very difficult and, in some cases, unattainable. As a result we have developed a method to reduce the estimation errors by normalizing the estimated biomarkers using pharmacokinetics properties in normal breast parenchyma. The method identifies the relationship between the pharmacokinetic properties of breast parenchymal tissue and cancer tissue. For the respective patients, the biomarkers VOI-95 percentile is normalized with respect to the average parenchymal value of the corresponding biomarkers.

This study shows that the application of a normalization method could potentially improve the diagnostic performance of the pharmacokinetic two-compartment model, by reducing the errors in the measured AIF. The Mann-Whitney U test designates the normalized $K^{trans}$, $k_{ep}$ and $v_p$ as biomarkers with significant correlation to malignancy and $Kt^{rans}$, $v_e$ and $v_p$ as biomarkers with significant ability to differentiate between the FA and the IDC.

Figures 1, 4P:
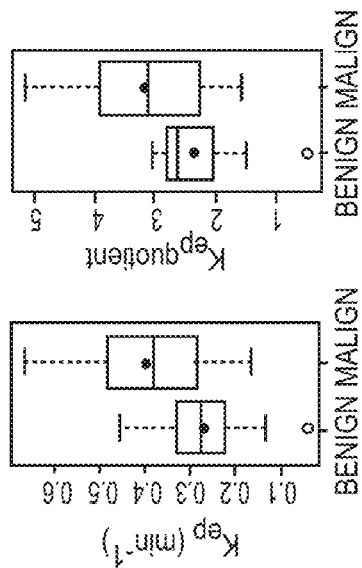
Figures 2, 4P:
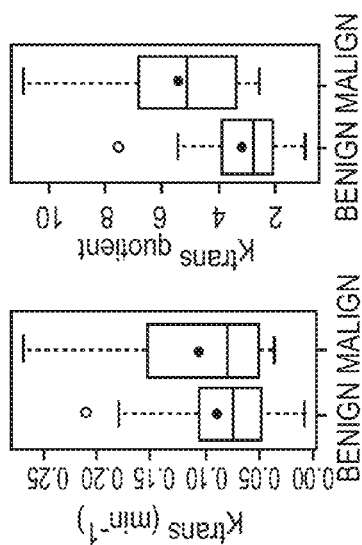
Figures 3, 4P:
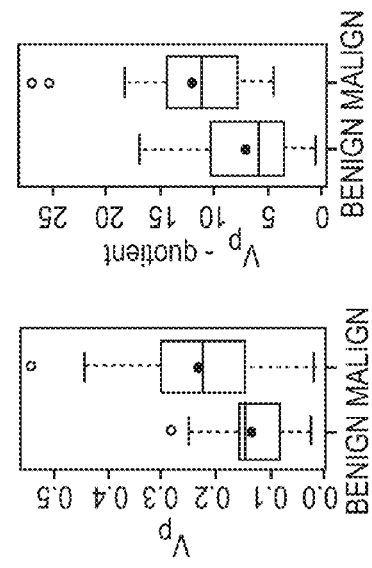
Figures 4, 4P:
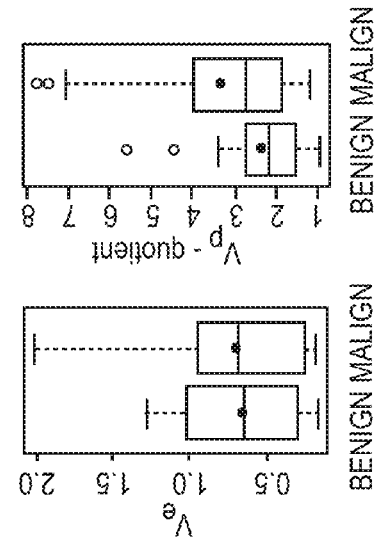
Figures 1, 4Q:
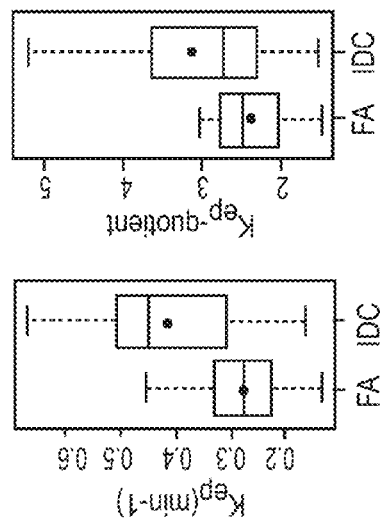
Figures 3, 4Q:
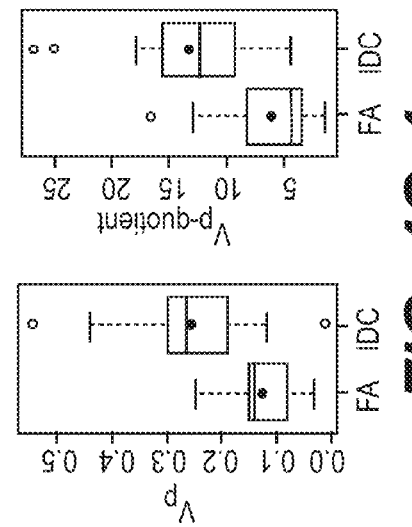
Figures 2, 4Q:
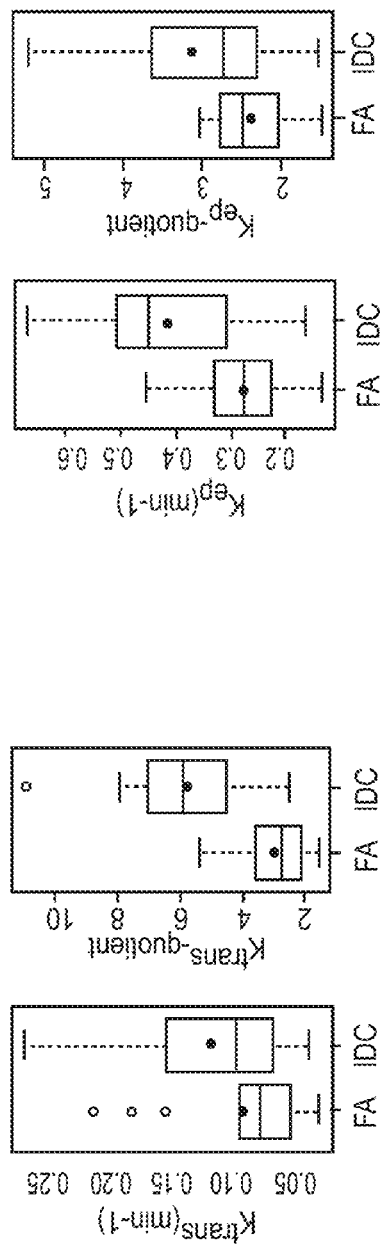
Figures 4, 4Q:
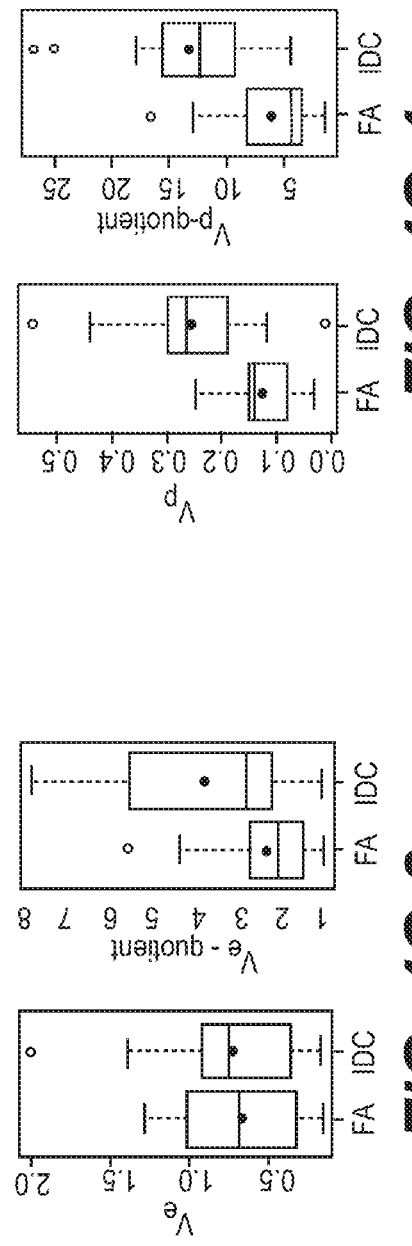

The initial and normalized value of the quantitative DCE-MRI biomarkers are presented with box plots, as a function of the grouping strategy 1 and 2, in FIGS. 4P and 4Q, respectively. The results are also presented in the form of the respective group's mean value and standard deviation.

22.1 Normalized $K^{trans}$

The average normalized $K^{trans}$-quotient is estimated to be 5.36 (±2.10) for malignant lesions and 3.17 (±1.57) for benign lesions. Furthermore, the average normalized $K^{trans}$-quotient is estimated to be 5.84 (±2.181 for the IDC, and 2.96 (±1.06) for the FA. The results show that malignant lesions possess a significantly higher $K^{trans}$-quotient compared with benign lesions (p=0.001). In addition, the result demonstrates that IDC possesses a significantly higher $K^{trans}$-quotient compared to FA (p=0.0002).

22.2 Normalized $k_{ep}$

The average normalized $k_{ep}$-quotient is estimated to 3.18 (±1.02) for malignant lesions and 2.37 (f 0.65) for benign lesions. Furthermore, the average normalized $k_{ep}$-quotient estimated at 3.11 (±1.11) for the IDC and 2.40 (±0.47) for benign lesions. The results show that malignant lesions possess a significantly higher $k_{ep}$-quotient compared with benign lesions (p=0.022). The IDC generally indicates a higher $k_{ep}$-quotient compared with the FA. However, the observed difference is not statistically significant (p=0.102).

22.3 Normalized $v_e$

The average normalized $v_e$-quotient is estimated to be 3.39 (±2.16) for malignant lesions and 2.40 (±1.17) for benign lesions. Furthermore, the average normalized $v_e$-quotient is estimated at 3.86 (±2.28) for the IDC and 2.45 (±1.28) for the FA. The results show that malignant lesions generally possess a higher $v_e$-quotient compared to FA. However, this biomarker demonstrates no statistical significance regarding the differentiation of malignant and benign lesions (p=0.167). If the IDC and the FA are considered separately, the IDC demonstrates a significantly higher $v_e$-quotient compared to the FA (p=0.041). Box plots FIG. 4P-3 and FIG. 4Q-3 show that some groups are characterized by statistical outliers.

22.4 Normalized $v_p$

The average normalized $v_p$-quotient is estimated to be 12.0 (±6.05) for malignant lesions and 6.99 (±5.03) for benign lesions. Furthermore, the average normalized $v_0$ quotient is estimated to 13.6 (±6.15) for the IDC and 6.33 (±4.60) for the FA. The normalized $v_p$-quotient shows a significantly higher value in malignant lesions compared with benign lesions (p=0.008) and a significantly higher value in IDC compared to the FA (p=0.0008). Box plots FIG. 4P-4 and FIG. 4Q-4 show that some groups are characterized by statistical outliers. This is especially true for the malignant group and the group of the IDC.

23. Diagnostic Tests of Significant Biomarkers Against Histologic Information In this study it is found that the different biomarkers, estimated from tumor volume of the 95-percentile, in general show the highest predictive ability. This distribution is considered, therefore, in the diagnostic analysis. The Mann-Whitney U test in this study is conducted to identify biomarkers that are significantly predictive with regard to distinguish one state from another. However, this test says little about how predictive the biomarkers are. This information may be obtained by performing diagnostic tests. This is presented in section 14.4. The diagnostic test performed by ROC analysis, and presented with the diagnostic accuracy in terms of area under the ROC curve $AUC_{ROC}$ and also estimated values of sensitivity and specificity, respectively.

23.1 Grouping Strategy 1

Based on the Mann-Whitney U test, a total of nine different biomarkers are found that possess a significant ability to differentiate between malignant and benign breast lesions. These are presented in Table 5-1. This table also presents the results of the diagnostic test. The estimated ROC curves for the significant biomarkers are displayed in FIGS. 7A-1-7H-3.

The result shows that the biomarker $R2^*$-$peak_{enh}$ demonstrating the highest diagnostic accuracy, with $AUC_{ROC}$ estimated to be 0.85. In addition, this biomarker has a high specificity of 84%, which represents a good prediction for benign lesions. From the descriptive image analysis the TTP demonstrates the highest predictive ability. Also this parameter shows high specificity. ROC analysis also shows that the normalized $K^{trans}$ possesses a good diagnostic accuracy, with $AUC_{ROC}$ estimated to be 0.81.

23.2 Grouping Strategy 2

If all the IDC and the FA are considered separately, the Mann-Whitney U test shows that a total of 12 biomarkers possess a significant predictive ability. These are presented in Table 5-2, together with the results from the diagnostic test. The estimated ROC curves for the significant biomarkers are displayed in FIGS. 7A-1-7H-3.

From the diagnostic test, it is found that the normalized $K^{trans}$ and qualitative $k_{ep}$ demonstrates the highest predictive ability. For these two parameters $AUC_{ROC}$ is estimated to be 0.89. With a specificity of 93%, the normalized $K^{trans}$ shows a good prediction for benign lesions, while the qualitative $k_{ep}$ shows a good prediction for malignant lesions with a sensitivity of 93%. With $AUC_{ROC}$ estimated at 0.87, the TTP shows again the highest predictive ability for descriptive image analysis. In addition, several biomarkers demonstrate good predictive ability with a diagnostic accuracy of over 0.8. The result shows that the diagnostic performance generally improved, if all the IDC and the FA are considered separately.

24. Logistic Regression with Several Biomarkers

Logistic regression is used to achieve an optimal fit between the patient's histopathological diagnosis and the values of the measured biomarkers. This is done with the purpose of identifying a refined modeling of the lesions respective probability for malignancy. In this study the logistic model is constructed with a backward stepwise elimination strategy of covariates, and involves the construction of an initial regression model that includes the five most significant biomarkers.

The model's starting point is determined on the basis of the biomarkers p-value, estimated by the Mann-Whitney U test, as well as the diagnostic performance evaluated by ROC analysis. Furthermore, the least significant biomarker is eliminated based on the Wald test. The elimination is audited by evaluating the deviance between the pre-eliminated and post-eliminated model. The elimination process is completed when the deviance test ascertains the elimination of asignificant covariates. In order to balance the conflicting requirements regarding the model's accuracy (adaptation) and simplicity (low number of included biomarkers), the Akaike information criterion (AIC) is estimated for each model selection. It is advantageous that the final selected regression model contains independent biomarkers, as there could be interactions between dependent biomarkers. In this study the quantitative biomarkers are preferred to qualitative biomarkers.

TABLE 5-1

Presentation of diagnostic accuracy, sensitivity, and specificity of biomarkers that demonstrate a significant predictive ability with regard to differentiating between malignant and benign breast lesions.

| Biomarker | $AUC_{ROC}$ | Sensitivity (%) | Specificity (%) |
|---|---|---|---|
| Wash-out | 0.72 | 71 | 84 |
| TTP | 0.81 | 71 | 84 |
| Quantitative $k_{ep}$ | 0.76 | 60 | 89 |
| Quantitative $v_p$ | 0.74 | 75 | 78 |
| Normalizied $K^{trans}$ | 0.81 | 70 | 83 |
| Normalizied $k_{ep}$ | 0.71 | 55 | 100 |
| Normalizied $v_p$ | 0.75 | 80 | 61 |
| $k_{ep}$ | 0.77 | 90 | 68 |
| $R_2^*$-peak$_{enh}$ | 0.85 | 76 | 84 |

TABLE 5-2

Presentation of diagnostic accuracy, sensitivity and specificity of biomarkers that demonstrate a significant predictive ability with regard to differentiating between the IDC and the FA.

| Biomarker | $AUC_{ROC}$ | Sensitivity (%) | Specificity (%) |
|---|---|---|---|
| Wash-out | 0.84 | 88 | 71 |
| TTP | 0.87 | 75 | 93 |
| AUC | 0.73 | 50 | 93 |
| peak$_{enh}$ | 0.79 | 75 | 79 |
| Normalized $K^{trans}$ | 0.89 | 80 | 93 |
| Normalized $v_e$ | 0.72 | 60 | 79 |
| Normalized $v_p$ | 0.85 | 93 | 72 |
| Quantitative $k_{ep}$ | 0.78 | 60 | 93 |
| Quantitative $v_p$ | 0.85 | 73 | 93 |
| Qualitative $k_{ep}$ | 0.89 | 93 | 79 |
| Qualitative $v_e$ | 0.79 | 69 | 93 |
| $R_2^*$-peak$_{enh}$ | 0.85 | 88 | 72 |

Logistic regression is used to model the relationship between the presence or absence of malignancy and the statistically significant biomarkers: Wash-out, TTP, quantitative $k_{ep}$ and $v_p$, and $R2^*$-peak$_{enh}$. This model is referred to as model selection 1, and is considered as the initial regression model with respect to the grouping strategy 1. The results from the different model selections in the backward stepwise elimination processes are presented in Table 5-11.

Model Selection 1

In the regression is biomarker $R2^*$-peak$_{enh}$ statistically significant (p=0.0372), while the remaining biomarkers showed no statistical significance with malignancy. Regression shows a residual deviance of 25,022 and an estimated AIC equal to 37.022. In the regression, the biomarker Wash-out rate is pointed out as the least significant (p=0.4134), thus is eliminated during next model selection.

Model Selection 2

With the biomarker Wash-out rate eliminated, a new logistic regression with the remaining biomarkers is performed. Regression shows a residual deviance of 25,697 and an AIC equal to 35.697. The eliminated biomarker Wash-out rate is tested by evaluating the deviance between model selection 1 and model selection 2. The difference in deviance between these two models, D2–D1=0.675, tells us that Wash-out rate does not have significant effect on response (p>0.05). In model selection 2 is again biomarker $R2^*$-peak$_{enh}$ statistically significant (p=0.0444), while the remaining biomarkers showed no statistical significance with malignancy. The least significant biomarker is $k_{ep}$ (p=0.3834), which is thereby eliminated.

Model Selection 3

Regression shows a residual deviance of 26,529 and an AIC equal to 34.529. The eliminated biomarker $k_{ep}$ is tested by evaluating the deviance between model selection 2 and model selection 3. The difference in deviance between these two models, D3–D2=0.832, says that $k_{ep}$ does not have a significant effect on the response (p>0.05). In model selection 3, biomarker $R2^*$-peak$_{enh}$ is statistically significant (p=0.0148). The remaining biomarkers showed no statistical significance with malignancy and where the least significant biomarker is $v_p$ (p=0.1306). This marker is eliminated at the next model adaptation.

Model Selection 4

Figure 5A:
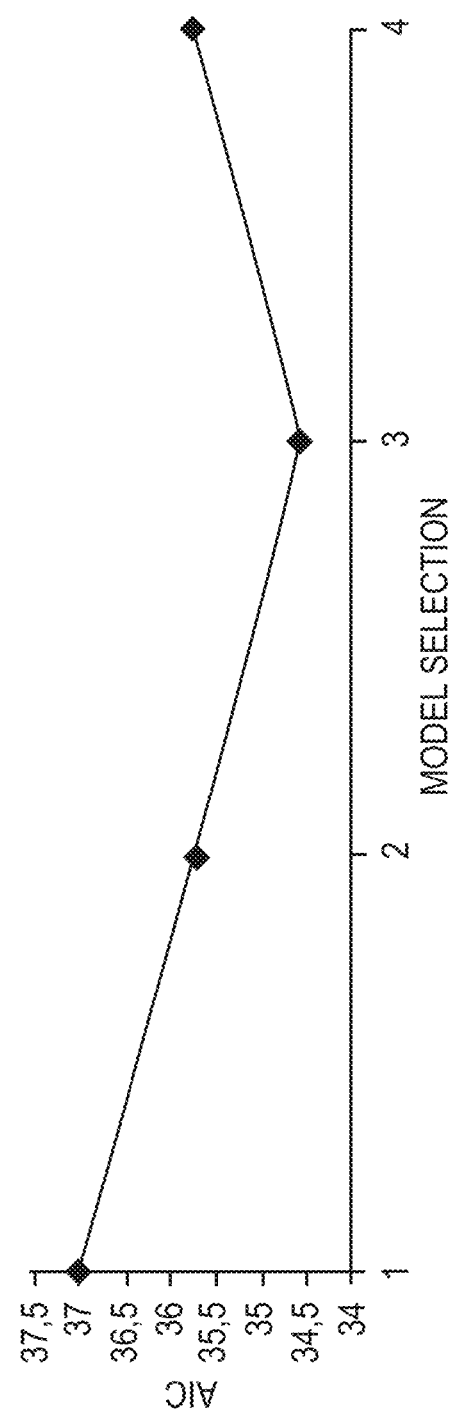
FIG. 5A is a plot of the estimated AIC value as a function of model selection. The plot indicates that the model selection 3 possesses the best balance between fit and simplicity.

Regression shows a residual deviance of 30,691 and an AIC equal to 35,691. The eliminated biomarker $v_p$ is tested by evaluating the deviance between model selection and 3 and model selection 4. The difference in deviance between these two models, D4–D3=4.162, verifies the elimination of a significant biomarker (p<0.05), and indicates the end of the elimination process of model selection 3. At the same time, the model selection 3 demonstrates the best balance between adaption and simplicity having the lowest observed AIC value. This is illustrated in FIG. 5A where the AIC values are plotted as a function of model selection.

TABLE 5-11

Backward stepwise model construction. The results of logistic regression is with grouping strategy 1 as response. Presented in the table are the biomarkers' regression coefficient β, standard error se, Wald statistical z-value, and the corresponding p-value.

| Biomarker | β | se | z-value | p-value |
|---|---|---|---|---|
| Model selection 1 | | | | |
| Wash-out | −1.107 | 1.354 | −0.818 | 0.4134 |
| TTP | −0.0065 | 0.0049 | −1.329 | 0.1839 |
| $k_{ep}$ | 5.548 | 5.786 | 0.959 | 0.3376 |
| $v_p$ | 6.158 | 6.072 | 1.014 | 0.3105 |
| $R_2^*$-peak$_{enh}$ | 0.21 | 0.101 | 2.084 | 0.0372 |
| Model selection 2 | | | | |
| TTP | −0.0071 | 0.0051 | −1.399 | 0.1619 |
| $k_{ep}$ | 4.938 | 5.665 | 0.872 | 0.3834 |
| $v_p$ | 8.411 | 6.002 | 1.401 | 0.1612 |
| $R_2^*$-peak$_{enh}$ | 0.18 | 0.09 | 2.01 | 0.0444 |
| Model selection 3 | | | | |
| TTP | −0.0081 | 0.0049 | −1.659 | 0.0970 |
| $v_p$ | 9.764 | 6.459 | 1.512 | 0.1306 |
| $R_2^*$-peak$_{enh}$ | 0.207 | 0.085 | 2.438 | 0.0148 |
| Model selection 4 | | | | |
| TTP | −0.0098 | 0.0045 | −2.165 | 0.0304 |
| $R_2^*$-peak$_{enh}$ | 0.208 | 0.085 | 2.437 | 0.0148 |

24.2 Diagnostic Evaluation of Model Selection 2 with Grouping Strategy 1

The backward stepwise elimination process nominates model selection 3 as the best logistical regression modeling between the lesions likelihood of malignancy and the studied biomarkers. This regression models the relationship between the presence or absence of malignancy and the statistically significant biomarkers TTP, $v_p$ and $R2^*$-peak$_{enh}$. In the logistic model the regression coefficients is estimated to be 0.207 for $R2^*$-peak$_{enh}$, 9764 for $v_p$, and −0.0081 for TTP. The positive regression coefficients for $v_p$ and $R2^*$-peak$_{enh}$, indicates that the probability of malignancy will be higher for higher values of these biomarkers. Similarly, the negative regression coefficients indicate for TTP that the likelihood of malignancy will be lower the higher values this biomarker possesses.

Figure 5B:
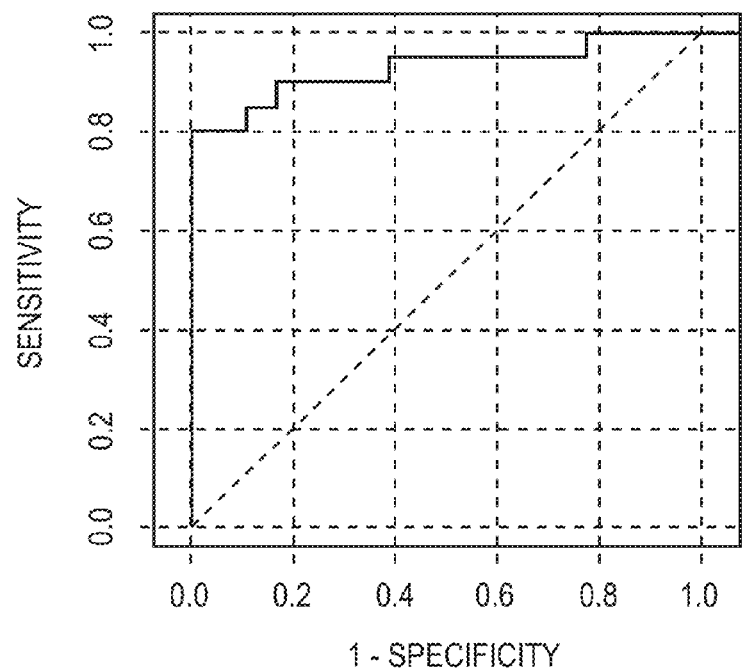
FIG. 5B is the ROC curve for logistic regression model selection 3 for grouping strategy 1. The area under the curve is estimated to be 0.93. This corresponds to a sensitivity and specificity of 80% and 100%, respectively.

In order to study the selected model's diagnostic performance, ROC-statistics are applied. The estimated ROC curve for model selection 3 is presented in FIG. 5B. The logistic regression model shows a good diagnostic accuracy with an area under the ROC curve of 0.93. This corresponds to a sensitivity and specificity of respectively 80% and 100%. The predictive and diagnostic table is presented in Table B.2.1

B.2 Predicitive and diagnostic table
B.2.1 Model selection 3, grouping strategy 1

| Predictive table | | | Diagnostic table | |
|---|---|---|---|---|
| Predicted prob | Non-diseased | Diseased | 1-Specificity | Sensitivity |
| 0.0017 | 1 | 0 | 1.00000000 | 1.00 |
| 0.0087 | 1 | 0 | 0.94444444 | 1.00 |
| 0.0100 | 1 | 0 | 0.88888889 | 1.00 |
| 0.0126 | 1 | 0 | 0.83333333 | 1.00 |
| 0.0342 | 0 | 1 | 0.77777778 | 1.00 |
| 0.0400 | 1 | 0 | 0.77777778 | 0.95 |
| 0.0448 | 1 | 0 | 0.72222222 | 0.95 |
| 0.0452 | 1 | 0 | 0.66666667 | 0.95 |
| 0.0479 | 1 | 0 | 0.61111111 | 0.95 |
| 0.0919 | 1 | 0 | 0.55555556 | 0.95 |
| 0.0994 | 1 | 0 | 0.50000000 | 0.95 |
| 0.2585 | 1 | 0 | 0.44444444 | 0.95 |
| 0.3468 | 0 | 1 | 0.38888889 | 0.95 |
| 0.3774 | 1 | 0 | 0.38888889 | 0.90 |
| 0.3922 | 1 | 0 | 0.33333333 | 0.90 |
| 0.3924 | 0 | 1 | 0.27777778 | 0.90 |
| 0.4434 | 1 | 0 | 0.22222222 | 0.90 |
| 0.4828 | 0 | 1 | 0.16666667 | 0.90 |
| 0.5302 | 1 | 0 | 0.16666667 | 0.85 |
| 0.6043 | 0 | 1 | 0.11111111 | 0.85 |
| 0.6484 | 1 | 0 | 0.11111111 | 0.80 |
| 0.7038 | 1 | 0 | 0.05555556 | 0.80 |
| 0.7175 | 0 | 1 | 0.00000000 | 0.80 |
| 0.7322 | 0 | 1 | 0.00000000 | 0.75 |
| 0.7429 | 0 | 1 | 0.00000000 | 0.70 |
| 0.7673 | 0 | 1 | 0.00000000 | 0.65 |
| 0.8632 | 0 | 1 | 0.00000000 | 0.60 |
| 0.8925 | 0 | 1 | 0.00000000 | 0.55 |
| 0.9071 | 0 | 1 | 0.00000000 | 0.50 |
| 0.9106 | 0 | 1 | 0.00000000 | 0.45 |
| 0.9648 | 0 | 1 | 0.00000000 | 0.40 |
| 0.9659 | 0 | 1 | 0.00000000 | 0.35 |
| 0.9705 | 0 | 1 | 0.00000000 | 0.30 |
| 0.9808 | 0 | 1 | 0.00000000 | 0.25 |
| 0.9810 | 0 | 1 | 0.00000000 | 0.20 |
| 0.9930 | 0 | 1 | 0.00000000 | 0.15 |
| 0.9937 | 0 | 1 | 0.00000000 | 0.10 |
| 0.9983 | 0 | 1 | 0.00000000 | 0.05 |
| | | | 0.00000000 | 0.00 |

24.3 Grouping Strategy 2

Logistic regression is used to model the relationship between the presence or absence of the IDC and the statistically significant biomarkers: Wash-out rate TTP, quantitative $k_{ep}$, $v_p$, and R2*-peak$_{enh}$. Similar to grouping strategy 1, this is considered as the initial regression model now with respect to grouping strategy 2. The results from the different model selections in the backward stepwise elimination process are presented in Table 5-11.

Model Selection 1

The regression shows a residual deviance in 6680 and an AIC equal to 18.680. It shows no significant biomarker ability to differentiate between the FA and the IDC. Again, the incremental elimination process is performed by eliminating the biomarker with the least significant response effect. In this particular case, that is the quantitative biomarker $k_{ep}$ (p=0.95). This biomarker is eliminated during the next model adaptation.

Model Selection 2

The regression shows a residual deviance in 6684 and an AIC equal to 16.684. The difference in the deviance between model selection 1 and model selection 2, D2−D1=0.004, tells us that $k_{ep}$ does not have a significant effect on response (p>0.05). In model selection 2 no biomarker shows significance during fitting of the model's response. The least significant biomarker is Wash-out (p=0.2970), which is thus eliminated.

Model Selection 3

The regression shows a residual deviance in 8423 and an AIC equal to 16.423. The difference in the deviance between model selection 2 and model selection 3, D3−D2=1.738, tells us that the Wash-out rate does not have a significant effect on response (p>0.05). In model selection 3 no biomarker shows significance during fitting of the model's response. The least significant biomarker is TTP (p=0.2970). This biomarker is eliminated during the next model adaptation.

Model Selection 4

Figure 5C:
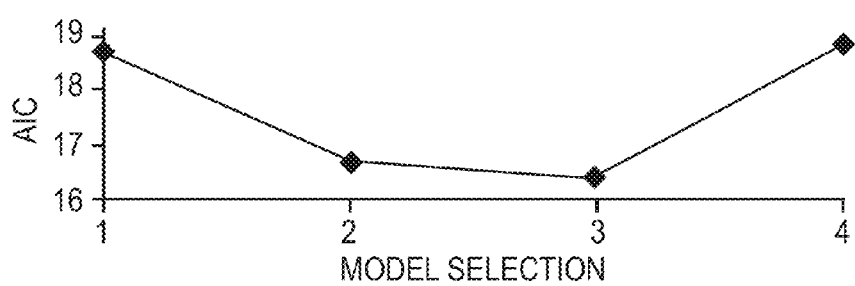
FIG. 5C is the plot of the estimated AIC value as a function of model selection. The plot indicates that the model selection 3 possesses the best balance between fit and simplicity.

The regression shows a residual deviance of 12,848 and an AIC equal to 18.848. The difference in the deviance between model selection 3 and model selection 4, D4−D3=4.425, states the elimination of a significant biomarker (p<0.05), indicating the end of the elimination process by model selection 3. Model Selection 3 demonstrates, at the same time, the best balance between fit and simplicity with the lowest observed AIC value. This is illustrated in FIG. 5C where the AIC values are plotted as a function of model selection.

TABLE 5-12

Backward stepwise model construction. Results of logistic regression with grouping strategy 2 as response. Presented in the table are biomarkers regression coefficient β, standard error se, Wald statistical z-value, and the corresponding p-value.

| Biomarker | β | Se | z-value | p-value |
|---|---|---|---|---|
| Model selection 1 | | | | |
| Wash-out | 5.932 | 5.634 | 1.503 | 0.2924 |
| TTP | −0.0671 | 0.0491 | −1.367 | 0.1716 |
| $k_{ep}$ | −0.816 | 13.006 | −0.063 | 0.9500 |
| $v_p$ | 110.951 | 72.505 | 1.530 | 0.1260 |
| $R_2^*$-peak$_{enh}$ | 0.762 | 0.474 | 1.606 | 0.1082 |
| Model selection 2 | | | | |
| Wash-out | 5.918 | 5.675 | 1.043 | 0.2970 |
| TTP | −0.0671 | 0.0496 | −1.352 | 0.1764 |
| $v_p$ | 110.368 | 72.589 | 1.520 | 0.1284 |
| $R_2^*$-peak$_{enh}$ | 0.752 | 0.444 | 1.691 | 0.0909 |
| Model selection 3 | | | | |
| TTP | −0.0298 | 0.0251 | −1.188 | 0.2349 |
| $v_p$ | 59.143 | 35.320 | 1.675 | 0.0940 |
| $R_2^*$-peak$_{enh}$ | 0.694 | 0.403 | 1.721 | 0.0852 |
| Model selection 4 | | | | |
| $v_p$ | 56.558 | 28.680 | 1.972 | 0.0486 |
| $R_2^*$-peak$_{enh}$ | 0.582 | 0.296 | 1.968 | 0.0490 |

24.4 Diagnostic Evaluation of Model Selection 3 and Grouping Strategy 2

Backward stepwise elimination process suggests that the model selection 3 provides the best balance between fit and simplicity regarding the ability to differentiate between the FA and the IDC using the studied biomarkers. This regression models the relationship between the presence of the FA or the IDC and the statistically significant biomarkers TTP, $v_p$ and $R_2^*$-peak$_{enh}$. In the logistic model, the regression coefficients are estimated to be 0.694 for $R_2^*$-peak$_{enh}$, 59,143 for $v_p$, and −0.0298 for TTP. The positive regression coefficients for $v_p$ and $R_2^*$-peak$_{enh}$ indicate that the probability of IDC will be higher the higher values these biomarkers possess. Similarly, the negative regression coefficients for TTP indicates that the likelihood for IDC will be lower the higher values this biomarker possesses.

Figure 5D:
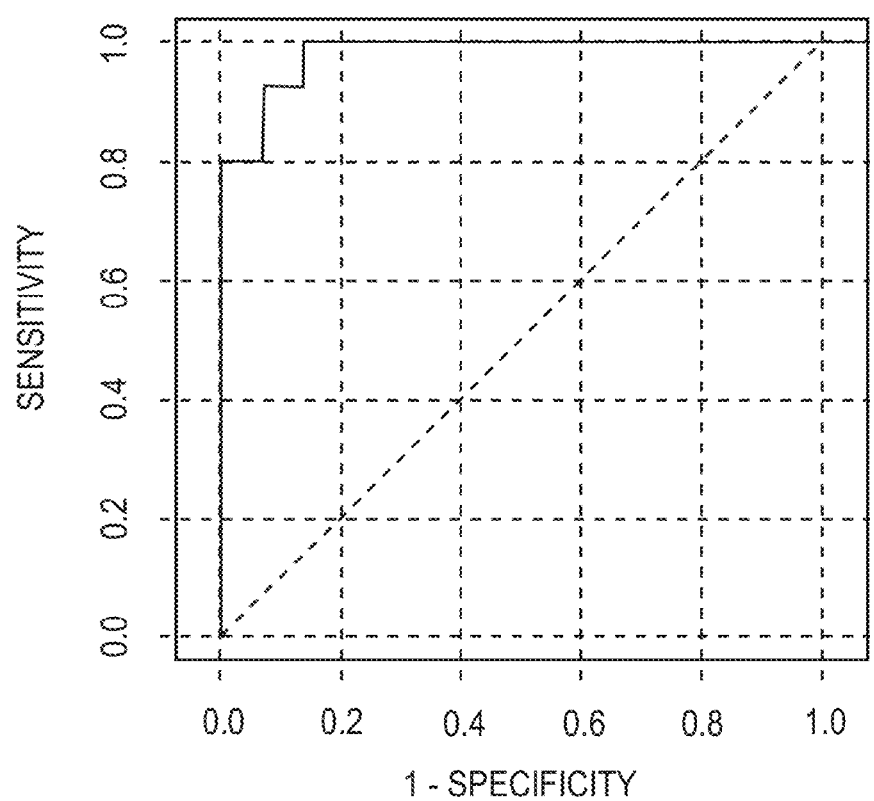
FIG. 5D is the ROC curve for logistic regression model selection 3 during grouping strategy 2. The area under the curve is estimated to be 0.98. This corresponds to a sensitivity and specificity of 93% and 93%, respectively.

In order to study the selected model's diagnostic performance, ROC-statistics are applied. The estimated ROC curve for model selection 3 is presented in FIG. 5D. The logistic regression model shows a good diagnostic accuracy with an area under the ROC curve of 0.98 and a sensitivity and specificity of respectively 93% and 93%. The predictive and diagnostic table is presented in Table B.2.2.

| B.2.2 Model selection 3, grouping strategy 2 | | | | | |
|---|---|---|---|---|---|
| Predictive table | | | Diagnostic table | | |
| Predicted prob | Non-diseased | Diseased | Predicted prob | Non-diseased | Diseased |
| 7.9809 | 1 | 0 | 1.00000000 | 1.00000000 |
| 1.1743 | 1 | 0 | 0.92857143 | 1.00000000 |
| 8.5783 | 1 | 0 | 0.85714286 | 1.00000000 |
| 1.7909 | 1 | 0 | 0.78571429 | 1.00000000 |
| 2.5742 | 1 | 0 | 0.71428571 | 1.00000000 |
| 7.9547 | 1 | 0 | 0.64285714 | 1.00000000 |
| 3.8117 | 1 | 0 | 0.57142857 | 1.00000000 |
| 5.8426 | 1 | 0 | 0.50000000 | 1.00000000 |
| 0.0056 | 1 | 0 | 0.42857143 | 1.00000000 |
| 0.0272 | 1 | 0 | 0.35714286 | 1.00000000 |
| 0.0304 | 1 | 0 | 0.28571429 | 1.00000000 |
| 0.0812 | 1 | 0 | 0.21428571 | 1.00000000 |
| 0.3417 | 0 | 1 | 0.14285714 | 1.00000000 |
| 0.5080 | 1 | 0 | 0.14285714 | 0.93333333 |
| 0.6508 | 0 | 1 | 0.07142857 | 0.93333333 |
| 0.7250 | 0 | 1 | 0.07142857 | 0.86666667 |
| 0.7536 | 1 | 0 | 0.07142857 | 0.80000000 |
| 0.9291 | 0 | 1 | 0.00000000 | 0.80000000 |
| 0.9603 | 0 | 1 | 0.00000000 | 0.73333333 |
| 0.9910 | 0 | 1 | 0.00000000 | 0.66666667 |
| 0.9962 | 0 | 1 | 0.00000000 | 0.60000000 |
| 0.9993 | 0 | 1 | 0.00000000 | 0.53333333 |
| 0.9999 | 0 | 1 | 0.00000000 | 0.46666667 |
| 0.9999 | 0 | 1 | 0.00000000 | 0.40000000 |
| 0.9999 | 0 | 1 | 0.00000000 | 0.33333333 |
| 0.9999 | 0 | 1 | 0.00000000 | 0.26666667 |
| 0.9999 | 0 | 1 | 0.00000000 | 0.20000000 |
| 0.9999 | 0 | 1 | 0.00000000 | 0.13333333 |
| 0.9999 | 0 | 1 | 0.00000000 | 0.06666667 |
| | | | 0.00000000 | 0.00000000 |

24.5 Inclusion of Normalized Pharmacokinetic Biomarkers in the Logistic Regression Analysis In Section 21 it is shown that the application of a normalization method could potentially improve the diagnostic performance of the pharmacokinetic two-compartment model, by reducing the errors in the measured AIF. Based on this observation, it is appropriate to include the normalized biomarkers in the logistic analysis. Since these are estimated to describe the pharmacokinetic relationship, compared to breast parenchyma they are directly dependent on the estimated pharmacokinetic biomarkers. On the basis of this, it is desired to include the normalized pharmacokinetic biomarkers as a substitute for the quantitative pharmacokinetic contribution in the logistic regression.

The Mann-Whitney U test designates the normalized $K^{trans}$ as the normalized biomarker with the most significant correlation with malignancy, and the highest significant ability to differentiate between the FA and the IDC. This is thus included in the model selection 3, for both grouping strategies 1 and 2, as a substitute for the quantitative contribution.

Grouping Strategy 1

Figure 5E:
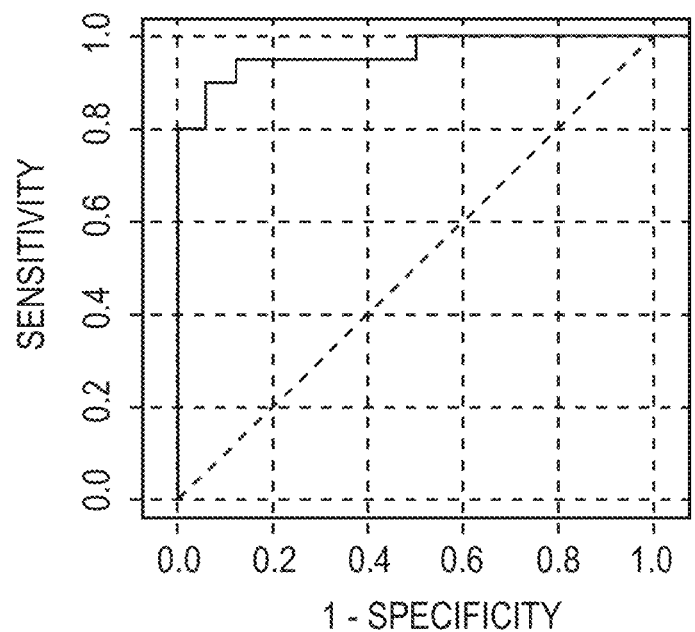
FIG. 5E is the ROC curve for logistic regression model selection 5 of the grouping strategy 1. The area under the curve is estimated to 0.96. This corresponds to a sensitivity and specificity of 90% and 94%, respectively.

A multivariable logistic regression is performed where the quantitative pharmacokinetic contribution in model selection 3 (Section 24.1) is replaced by the normalized pharmacokinetic biomarker $K^{trans}$. This is referred to as model selection 5. The estimated ROC curve for model selection 5 is presented in FIG. 5E. The regression shows a residual deviance at 19.01 and AIC equal to 27.01. This indicates that the inclusion of the normalized $K^{trans}$ produce a better modeling of the histopathological diagnosis compared with model selection 3 for grouping strategy 1. At the same time, the model selection 5 shows good diagnostic accuracy with an area under the ROC curve of 0.96 and a sensitivity and specificity of 90% and 94% (cut-off=0.60), respectively. The predictive and diagnostic table is presented in Table B.2.3.

| B.2.3 Model selection 5, grouping strategy 1 | | | | | |
|---|---|---|---|---|---|
| Predictive table | | | Diagnostic table | | |
| Predicted prob | Non-diseased | Diseased | Predicted prob | Non-diseased | Diseased |
| 4.2787 | 1 | 0 | 1.00000000 | 1.00 |
| 0.0005 | 1 | 0 | 0.94444444 | 1.00 |
| 0.0008 | 1 | 0 | 0.88888889 | 1.00 |
| 0.0009 | 1 | 0 | 0.83333333 | 1.00 |
| 0.0035 | 1 | 0 | 0.77777778 | 1.00 |
| 0.0048 | 1 | 0 | 0.72222222 | 1.00 |
| 0.0078 | 1 | 0 | 0.66666667 | 1.00 |
| 0.0196 | 1 | 0 | 0.61111111 | 1.00 |
| 0.0466 | 1 | 0 | 0.55555556 | 1.00 |
| 0.0481 | 0 | 1 | 0.50000000 | 1.00 |
| 0.0493 | 1 | 0 | 0.50000000 | 0.95 |
| 0.0597 | 1 | 0 | 0.44444444 | 0.95 |
| 0.1623 | 1 | 0 | 0.38888889 | 0.95 |
| 0.1849 | 1 | 0 | 0.33333333 | 0.95 |
| 0.2807 | 1 | 0 | 0.27777778 | 0.95 |
| 0.3818 | 1 | 0 | 0.22222222 | 0.95 |
| 0.4004 | 1 | 0 | 0.16666667 | 0.95 |
| 0.5474 | 0 | 1 | 0.11111111 | 0.95 |
| 0.6048 | 1 | 0 | 0.11111111 | 0.90 |
| 0.6304 | 0 | 1 | 0.05555556 | 0.90 |
| 0.7148 | 0 | 1 | 0.05555556 | 0.85 |
| 0.7205 | 1 | 0 | 0.05555556 | 0.80 |
| 0.7465 | 0 | 1 | 0.00000000 | 0.80 |
| 0.7653 | 0 | 1 | 0.00000000 | 0.75 |
| 0.8146 | 0 | 1 | 0.00000000 | 0.70 |
| 0.9368 | 0 | 1 | 0.00000000 | 0.65 |
| 0.9563 | 0 | 1 | 0.00000000 | 0.60 |
| 0.9568 | 0 | 1 | 0.00000000 | 0.55 |
| 0.9670 | 0 | 1 | 0.00000000 | 0.50 |
| 0.9932 | 0 | 1 | 0.00000000 | 0.45 |
| 0.9956 | 0 | 1 | 0.00000000 | 0.40 |
| 0.9985 | 0 | 1 | 0.00000000 | 0.35 |
| 0.9992 | 0 | 1 | 0.00000000 | 0.30 |
| 0.9993 | 0 | 1 | 0.00000000 | 0.25 |
| 0.9998 | 0 | 1 | 0.00000000 | 0.20 |
| 0.9999 | 0 | 1 | 0.00000000 | 0.15 |
| 0.9999 | 0 | 1 | 0.00000000 | 0.10 |
| 0.9999 | 0 | 1 | 0.00000000 | 0.05 |
| | | | 0.00000000 | 0.00 |

Figure 5F:
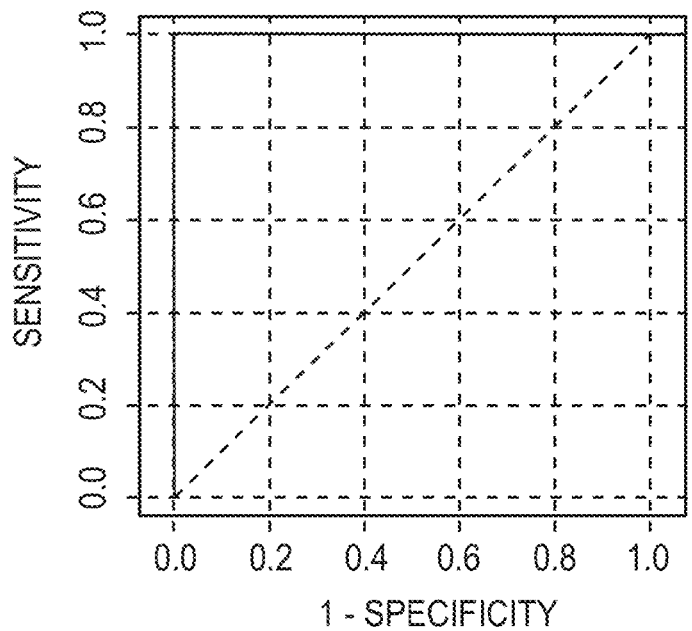
FIG. 5F is the ROC curve for logistic regression model selection 5 of the grouping strategy 2. The area under the curve is estimated to be 1. This corresponds to a sensitivity and specificity of 100% and 100%, respectively.

With the grouping strategy 2 in response, a multivariate logistic regression is performed in which the quantitative pharmacokinetic contribution in model selection 3 (Section 24.3) is replaced by the normalized pharmacokinetic biomarker $K^{trans}$. This is referred to as model selection S. The estimated ROC curve for model selection 5 is presented in FIG. 5F. Regression shows a residual deviance of $1.4^e$ and an AIC equal to 8. This indicates that the inclusion of the normalized $K^{trans}$ produce a better modeling of the histopathological diagnosis compared with model selection 3 in Section 24.1. At the same time the inclusion of the normalized $K^{trans}$ in model selection 5 demonstrates excellent diagnostic accuracy with an area under the ROC curve equal to 1. This corresponds to a sensitivity and specificity of 100% and 100%, which implies a correct differentiation of all the IDC and the FA. The predictive and diagnostic table is presented in Table B.2.4.

| B.2.4 Model selection 5, grouping strategy 2 | | | | | |
|---|---|---|---|---|---|
| Predictive table | | | Diagnostic table | | |
| Predicted prob | Non-diseased | Diseased | Predicted prob | Non-diseased | Diseased |
| 2.2204 | 12 | 0 | 1.00000000 | 1.0000000 |
| 1.0525 | 1 | 0 | 0.14285714 | 1.0000000 |
| 2.5467 | 1 | 0 | 0.07142857 | 1.0000000 |
| 0.9999 | 0 | 1 | 0.00000000 | 1.0000000 |
| 0.9999 | 0 | 1 | 0.00000000 | 0.9333333 |
| 0.9999 | 0 | 1 | 0.00000000 | 0.8666667 |
| 1.0000 | 0 | 12 | 0.00000000 | 0.8000000 |
| | | | 0.00000000 | 0.0000000 |

25. The Significance of DCE-MRI and DSC-MRI in the Diagnosis of Breast Cancer This study is conducted with the objective to establish and evaluate different methods for the analysis of perfusion and capillary permeability in breast cancer, based on dynamic MR imaging. DCE-MRI and DSC-MRI currently represent established methodologies for evaluation of cancer tissue and demonstrate a number of valuable clinical applications. The reason for this is the methods' ability to generate surrogate markers, also referred to as biomarkers that describe the physiological and anatomical characteristics of the observed tissue micro vascular system.

The current diagnostic practice utilizes a conventional high spatial imaging strategy to identify differences regarding tumors morphology. However, the morphological assessments represent an insufficient diagnostic accuracy, and additional methods are required. New advances in the development of pulse sequences have made it possible to combine a high spatial and high temporal sequence in an alternating pattern after administration of a contrast agent. This makes it possible to generate comprehensive assessments of both the dynamic contrast sequence and morphological characteristics of the studied tissue. This combination represents a gifted duo and demonstrates a potential improvement in the diagnosis of breast cancer. On this basis it is very important to evaluate different models for dynamic evaluation, and to establish analytical methodologies to optimize their robustness as well as dlinical and diagnostic usefulness.

In this study it is shown that the dynamic sequence with high temporal resolution generates a series of biomarkers that represent valuable information for the differentiation of benign and malignant breast lesions. In addition, it is observed that the acquisition of a second echo in the T1-weighed perfusion sequence with high temporal resolution, allows a separate evaluation of perfusion and permeability related biomarkers, and will improve the diagnostic performance of breast cancer through the acquisition of quantitative R2*-measurements. The result also suggests that a significant improvement of the diagnostic performance can be achieved by identifying regions in tumor volume that demonstrates the lesion most abnormal characteristics, and thus indicates the eventuality of heterogeneous cancer tissue in the breast.

In addition, this study shows that the application of the introduced normalization method could potentially improve the diagnostic performance of the pharmacokinetic analysis. This method allows the identification of the pharmacokinetic relationship between the respective patient parenchymal tissue and cancer tissue, and will thus reduce the possible errors in the measured AIF. Normalization method is proposed as an alternative strategy if there is suspicion of significant measurement errors of the AIF.

Based on the tumor volume 95-percentile, multivariate regression models through backward stepwise elimination process for the significant biomarkers are established. This method nominate $R_2^*$-peak$_{enh}$, TTP and the quantitative $v_p$ as the most predictive biomarkers regarding the differentiation for both benign and malignant breast lesions, as well as for FA and IDC. With regard to the grouping strategy 1 demonstrates the selected regression model a good diagnostic accuracy with an area under the ROC curve of 0.93. This corresponds to a sensitivity and specificity of respectively 80% and 100%. By introducing the normalized $K^{trans}$ as a substitution for the quantitative pharmacokinetic contribution in the logistic regression model, the diagnostic accuracy is improved and demonstrates an area under the ROC curve of 0.96. This corresponds to a sensitivity and specificity of 90% and 94%. With regard to the grouping strategy 2 demonstrates the selected regression model a good diagnostic accuracy with an area under the ROC curve of 0.98. This corresponds to a sensitivity and specificity of 93% and 93%, respectively. If the normalized $K^{trans}$ is included as a substitution for the quantitative pharmacokinetic contribution, will the multivariate regression model successfully differentiate between all the FA and IDC.

Reflecting on this result, it is important to consider the eventuality for over fitting the data when one includes multiple biomarkers in the model. However, this study is based only on the dynamic and pharmacokinetic biomarkers alone and do not include the morphological information obtained from the high-resolution images. This suggests that the dynamic image information, acquired from the high temporal images, introduces a valuable complement to the morphological information in the diagnosis of breast cancer.

As mentioned, the use of quantitative pharmacokinetic analysis allows the evaluation of dynamic contrast enhanced MRI in a physiological context. However, both the measurement process and data analysis introduce an uncertainty in the estimation of the various biomarkers. It is very important to address these uncertainties, as the diagnostic performance of quantitative physiological biomarkers can only be evaluated properly after an accurate and robust estimation is successfully performed.

26. Data Acquisition

Using dynamic MR imaging the picture quality is a compromise between the recording temporal and spatial resolution. In this study we have developed a method that combines both high temporal and high spatial resolution in a simple dynamic sequence. This is referred to as a split dynamic strategy. The high spatial sequence is performed for tumor identification and acquisition for morphological information, while the high temporal sequence is performed for a detailed description for contrast agent time-dependent distribution. An adequate description for the transient effect of the contrast agent can only be achieved with a sufficiently high temporal resolution, a requirement which is enhanced by quantification of the pharmacokinetic biomarkers through AIF deconvolution.

In this study, the images with high time resolution are acquired with a sequence that is optimized for fast imaging, and which detects a dynamic image in less than every three seconds. This fast image acquisition satisfies the requirement regarding temporal resolution and provides an adequate description of all the phases during the progression of the contrast agent. During image processing it was found that the images spatial resolution is not as good as desired, and that the imaging field of view (FOV) does not always include a distinct artery. This is a problem that is applicable to many patients and is especially problematic when the quantification of the pharmacokinetic biomarkers requires the provision of an individual AIF.

26.1 The Sequence Protocol: The Alternation of High Temporal and High Spatial Imaging The dynamic signal intensity curve is constructed from a series of high-temporal images. To optimize the mathematical fitting of the curve sufficiently high time resolution must be in the phases of the dynamic curve course in which changes are expected to be fastest. By identifying these parts of the curve one can allocate priority areas where the temporal requirement is higher. For cancer tissue this applies to the curve early post-contrast phase were the wash-in phase is located. In this part of the curve a high temporal sequence is therefore of priority. When the curve wash-in phase is described the high temporal sequence is alternated with a high spatial sequence in an alternating pattern which allows identification of both temporal and spatial information in one contrast agent administration. This splitting of the dynamic sequences is a new application in modern MRI scanners. After the dynamic split protocol is finished, the dynamic images are stitched together and presented to the observer as individual image series.

For identification of the wash-in phase of the signal curve in breast cancer a temporal resolution between 5 and 15 seconds [49] is required. Further requires quantification of the pharmacokinetic biomarkers provision of an individual AIF. As the observed signal waveforms from arterial voxels normally demonstrate a faster-changing pattern, the demand on the temporal resolution is further increased. There is currently no universal standard for which temporal resolution necessary for the determination of the AIF, but a proposal for two seconds was given by Tofts et al. in 1999 [25]. In generally a precise determination of the AIF requires higher temporal resolution than the signal acquisition in the tissue, and one can therefore say that the sequence's temporal resolution DCE-MRI is dictated by the AIF.

In this study, the temporal resolution was set to 2.7 seconds, which gives an adequate description of all contrast distribution phases in both cancer and arterial voxels. However, this high temporal resolution implies of a substantial loss of sequence's spatial resolution, which demonstrates a voxel size of $1.69*1.48*4$ mm$^3$. This spatial restriction increases the dimensional requirements for the included arteries. In several dynamic breast studies the aorta is included in the FOV for the determination of the AIF, as this can be done at a relatively low resolution. This study the FOV is limited to achieve higher temporal resolution, and also to exclude cardiac region to reduce image artifacts. Aorta is therefore not included in the FOV, and AIF is extracted from the internal thoracic artery (ITA), which supplements the arterial blood to the chest wall and breast. This artery has a diameter normally of 2-5 mm (personal communication). A robust extraction of AIF from the ITA requires a higher spatial resolution than the applied sequence can supplement. As a result, the signal in the arterial voxels is affected by a partial volume effect (PVE), which helps to reduce the applied AIF curve authenticity.

The current commercial MRI sequences do not allow an imaging protocol that satisfies the temporal requirements dictated by the AIF with an acceptable spatial resolution. In the clinical environment, it is today a universal agreement that an adequate spatial and temporal resolution is essential in MR mammography. However, there is little knowledge about what exactly constitutes the appropriate balance, and where the compromise between the spatial and temporal resolution should be set.

A study done recently investigated the clinical significance of the compromise between spatial and temporal resolution in MR mammography [64]. This study concluded that an increase of sequence's spatial resolution improves the diagnostic accuracy and that no diagnostic relevant dynamic information was lost by imaging with low temporal resolution. In the before mentioned study the high spatial and high temporal sequence were performed separately, which is common in current practice. However, our current study demonstrates that sequences with high temporal and high spatial resolution can now be combined in an interacting pattern during a single contrast injection, and that this allows the identification of morphological information, as well as dynamic and pharmacokinetic information through a variety of biomarkers. A study by Veltman et al. [65] in 2008 showed that combining the information acquired from a morphological and dynamic sequence results in a significant improvement of the diagnostic performance. Here is the dynamic information used as a supplement for breast lesions morphological character.

In the current study the diagnostic analysis is based only on the dynamic and pharmacokinetic biomarkers alone and does not include the morphological information obtained from the THRIVE sequence. The results obtained in this study suggest that the dynamic image information introduces a valuable complement to the morphological information in the diagnosis of breast cancer.

In this study it is found that the dynamic transversal relaxation rate, obtained from a double-echo recording, demonstrates a very rapid enhancement pattern in cancer tissue in the early post-contrast phase. It is also shown that the identification of this transient pattern gives very good diagnostic information. The provision of this Information, however, requires an adequate description of the $R_2^*$-curve, which is not possible if a high spatial sequence is used. The temporal requirement as dictated by the $R_2^*$-curve is discussed in more detail later in this chapter.

27. The Importance of Tumor Heterogeneity

As mentioned previously is cancer tissue in breast naturally heterogeneous, and a spatially dependent evaluation of biomarkers are therefore relevant for the diagnosis of breast cancer. To investigate which parts of biomarkers distribution in patients' VOI which is appropriate to evaluate further the diagnostic analysis, the average value of the biomarkers as well as a number percentile values are evaluated for each patient. The hypothesis behind this approach is that a high percentile value will identify the areas of the tumor that possesses the most abnormal pharmacokinetic properties. This allows for a diagnostic evaluation based on the most malignant tumors region and will, according to the present hypothesis, possess a higher predictive performance compared with lower percentile values. Since the purpose is to identify the most malignant regions of the tumor volume, the biomarkers distribution values are estimated on the basis of their expected malignant value. This means that for the biomarker $K^{trans}$, which is expected to demonstrate a higher value in malignant tissue, the percentile value is higher than the median estimate. Biomarker TTP is a special case, here it is expected that malignant tissue demonstrates a lower value, and that percentile values lower than the median are estimated.

The hypothesis used can be considered as a case: the average value and the median will describe the biomarkers distribution properties based on the total tumor volume, and its main trend. While high percentile values will describe the properties related to small regions of the tumor. If the considered tumor volume possesses a proportion of malignant cancer cells of 50% or more, the average value and all percentile values the median express this fact. But if the tumor volume of malignant cells constitutes only a proportion of 20% or less, will the average value and percentile values below the 80 percentile in a greater extent the tumor benign region, thus ignoring its real extent. Percentile values above the 80 percentile will, on the other hand, identify this region and thus demonstrate the real extent of the tumor.

In this study, the different biomarkers predictive ability are assessed using the Mann-Whitney U test, which tests the presence or absence of a significant difference between the marker values in the two defined groups. This test is performed for the biomarkers average value and all percentile values. The result suggests that a significant improvement in the diagnostic differentiation of benign and malignant lesions, as well as FA and IDC, can be achieved by identifying the tumor volume 5% region that demonstrates the lesion's most abnormal characteristics, and suggests the eventuality of heterogeneous cancer tissue in the breast. Based on this observation tumor volume 95 percentile is used in the further diagnostic and statistical analysis. In addition, biomarkers average VOI value is evaluated as this represents an important indicator of how a biomarker, and the physiology it represents, acts in the various lesions. Simultaneously, this is the most conventional distribution value to study for type of study.

Percutaneous biopsy is an increasingly used method for the acquisition of the histological diagnosis of breast lesions. The accuracy of this method depends on whether the tissue sample is representative of the entire lesion. In situations where breast lesions are heterogeneous, the tissue samples obtained by percutaneous biopsy do not necessarily represent the most aggressive and clinically important region of the lesion. Little is currently known about the histological heterogeneity of breast lesions. The information on this is potentially valuable as it may assist in determining whether it is advantageous to choose different regions of breast lesions by percutaneous biopsy. This study has shown that the estimation the various biomarkers voxel-by-voxel can demonstrate the most aggressive regions in the form of "hot spots" in the parametric maps. Based on a split dynamic strategy, different parametric maps used in conjunction with morphologic images can be used to determine which regions of the lesion that possesses the highest aggressiveness, and thus should be prioritized by percutaneous biopsy.

28. Descriptive Presentation of Dynamic Data

Signal gain as observed by a dynamic acquisition of T1-weighed images after administration of an intravenous contrast agent, can be described by two different methods: either by evaluating the change in the observed signal intensity and/or by quantifying the concentration change of the contrast agent in the observed tissue through pharmacokinetic modeling.

Shortly after administration, the contrast agent will primarily be distributed in the vascular system. Gradually the contrast agent diffuses through capillary walls and is distributed in the extravascular extracellular space (EES). The presence of contrast agent will change the signal intensity of the observed MR image through the effects described in Section 7. Note that it is not the contrast agent, but the transient effect of the agent that is leading to changes in signal intensity. The time-dependent pharmacokinetics of the contrast agent in the tissue is in this study described by a mathematical two-compartment model derived from Toft et al. In 1999 [25]. In this analysis it is assumed a linear relationship between contrast agent concentration and the observed signal intensity, an assumption which is valid if the "fast exchange" between the contrast agent and the hydrogen nuclei are met. The two-compartment model allows quantitative estimates of the transfer coefficients $K^{trans}$ and $k_{ep}$, volume fractions $v_p$ and $v_e$, provided that an individual AIF is determined. In addition, the pharmacokinetic biomarkers are described qualitatively by an idealized mono-exponential AIF.

The change in signal intensity is in this study described through 5 different descriptive biomarkers: Wash-in Wash-out, TTP, AUC and $peak_{enh}$. These are illustrated in FIG. 3B. The descriptive biomarkers are estimated by a voxel-by-voxel method on the basis of the individual voxels relative signal change.

28.1 Descriptive Analysis of DCE-MRI

Previous studies have shown that various properties of the dynamic signal intensity curve, generated from DCE-MRI, are predictive of tumor malignancy [11-17]. Descriptive markers have the advantage of being relatively easy to estimate, but possesses, however, a number of limitations. These limitations are mainly a consequence of the fact that biomarkers do not accurately reflect contrast medium concentration in the observed tissue and can therefore be affected by the scanner settings. This may in turn result in changes in tissue pre contrast values, and thus changes in the descriptive biomarker values. These methods can thus demonstrate significant differences between acquisition methods and Individual studies, making direct comparisons between different studies very difficult [50]. However, it is very unclear what these biomarkers reflect physiologically, and how robust they are about variations in patient-related factors not directly related to the physiology of tumors [51]. These circumstances help to limit the suitability of the descriptive biomarkers.

As mentioned, the descriptive biomarkers have no obvious physiological interpretation. However, they can relate to the signal curve underlying physiology and contrast agent kinetics. The area under the curve (AUC) will be related to the total amount of contrast agent that diffuses from the plasma compartment to the EES. The biomarker AUC would therefore represent a combination of contrast agent concentration in the plasma compartment and the transfer rate between the plasma compartment and EES [52]. The biomarker $peak_{enh}$ describes the contrast agent maximum transient effect, and will primarily be related to blood flow and the distribution and concentration of contrast agent in plasma volume and EES. Moreover, the first part of the post-contrast phase, the wash-in phase, is related to the uptake of contrast agent in the tumor, and the transfer rate from the plasma compartment to the EES. Thereafter the properties in the late post-contrast phase, Wash-out, will reflect the rate of the contrast agent returning from the EES to the plasma compartment. Time to peak enhancement (TTP) will be related to the combination of transmission rate of contrast agent between the plasma compartment and EES, and the return of contrast agent from the EES and plasma compartment.

Figure 6A:
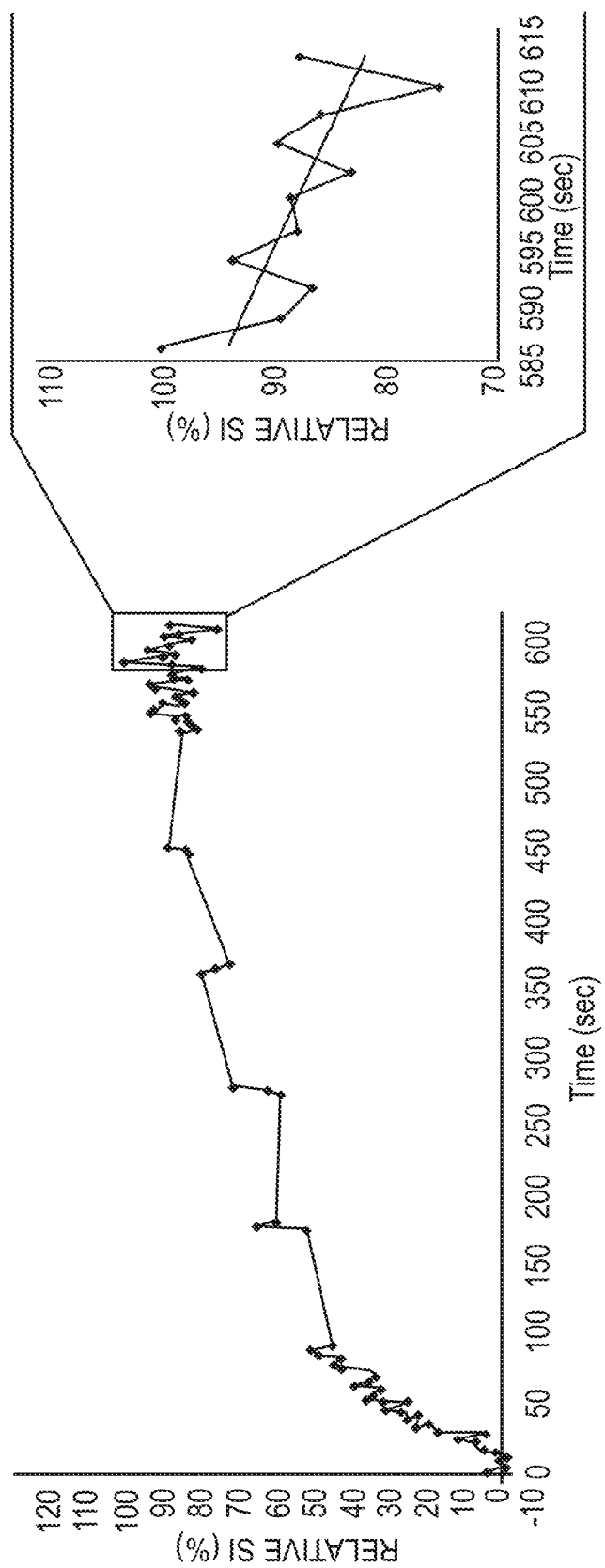
FIG. 6A is a dynamic SI curve after administration of a contrast medium. The data points are sampled with a high temporal resolution. The figure shows the signal from the FA with a 47-year-old woman. Lesion demonstrates a clear contrast continuous contrast uptake throughout the image series. The figure on the left highlights the curve's peak point occurs in a fluctuating phase. Lesion Wash-out is estimated from a linear regression, illustrated by a solid line, and is not representative of real contrast curve progress.

In this study it is observed that descriptive biomarkers contribute to a simple and good characterization of the cancer tissue contrast behavior. In addition, the results demonstrate that many descriptive biomarkers presents themselves as good diagnostic predictors with respect to the differentiation between benign and malignant breast lesions, as well as FA and IDC. The statistical analysis nominates Wash-out and TTP as biomarkers with significant correlation with malignancy, and wash-out, TTP and peak$_{enh}$ as biomarkers with significant ability to differentiate between FA and IDC. Among these, TTP is nominated as the most significant biomarker by both grouping strategies. The results indicate that malignant lesions (including IDC) possess a shorter TTP compared with benign lesions (including FA). This result corresponds with previous studies [33]. However, Wash-out and peak$_{enh}$ demonstrate unexpected results when it is suggested that benign lesions possess a higher Wash-out and peak$_{enh}$ compared with malignant lesions. Based on previous studies, it is expected that malignant lesions demonstrate a higher wash-out [36] and peak$_{enh}$ [53] compared with benign lesions. A study done by Mussurakis et al. 1997 [54] suggested that the relative change of the signal is higher in benign breast lesions compared with malignant breast lesions. While this study showed that benign lesions actually tend to possess a longer immanent $T_1$-time, and that they in fact show a less contrast uptake than malignant lesions. This case can also be applied to the current study, thus explaining the observed peak$_{enh}$ values. During image processing, a fluctuating pattern in the last part of the dynamic SI curve is observed. This behavior is consistent for many of the patients, and is especially problematic when the mathematical estimation of the Wash-out. A potential consequence of this problem is illustrated in FIG. 6A. This figure shows the dynamic SI curve after administration of a contrast medium for a 47-year-old woman with FA. Lesion demonstrates a clear contrast continuous recharge throughout the image series. However, a peak point occurs in the curve fluctuating phase, followed by the measurement point with considerably lower intensity. When Wash-out is estimated from a linear regression based on all points from the curve's height, a non-real Wash-out rate is identified which is not representative of real contrast curve progression. In FIG. 6A the regression line is illustrated as a solid line through the curve point after the peak point. This error is constructed due to an insufficient estimation algorithm, and the extent of the SI-curve fluctuating phase. Furthermore, it is observed that malignant lesions possess a significantly lower TTP compared with benign lesions. This indicates that the extent of the problem is largely applicable to benign lesions, when the fluctuating pattern occurs in the last part of post-contrast phase. In six out of 14 FA (43%) the tumor volume median value shows that curve's peak point occurs in the fluctuating phase. For these lesions it will mean that in 50% of tumor volume the peak of the voxel curve will occur in the fluctuating phase. For all of IDC curve's peak point occurs at an earlier time point. Reflecting over the results this may explain the unexpected observation that benign lesions demonstrate a higher wash-out compared with malignant lesions.

Figure 6B:
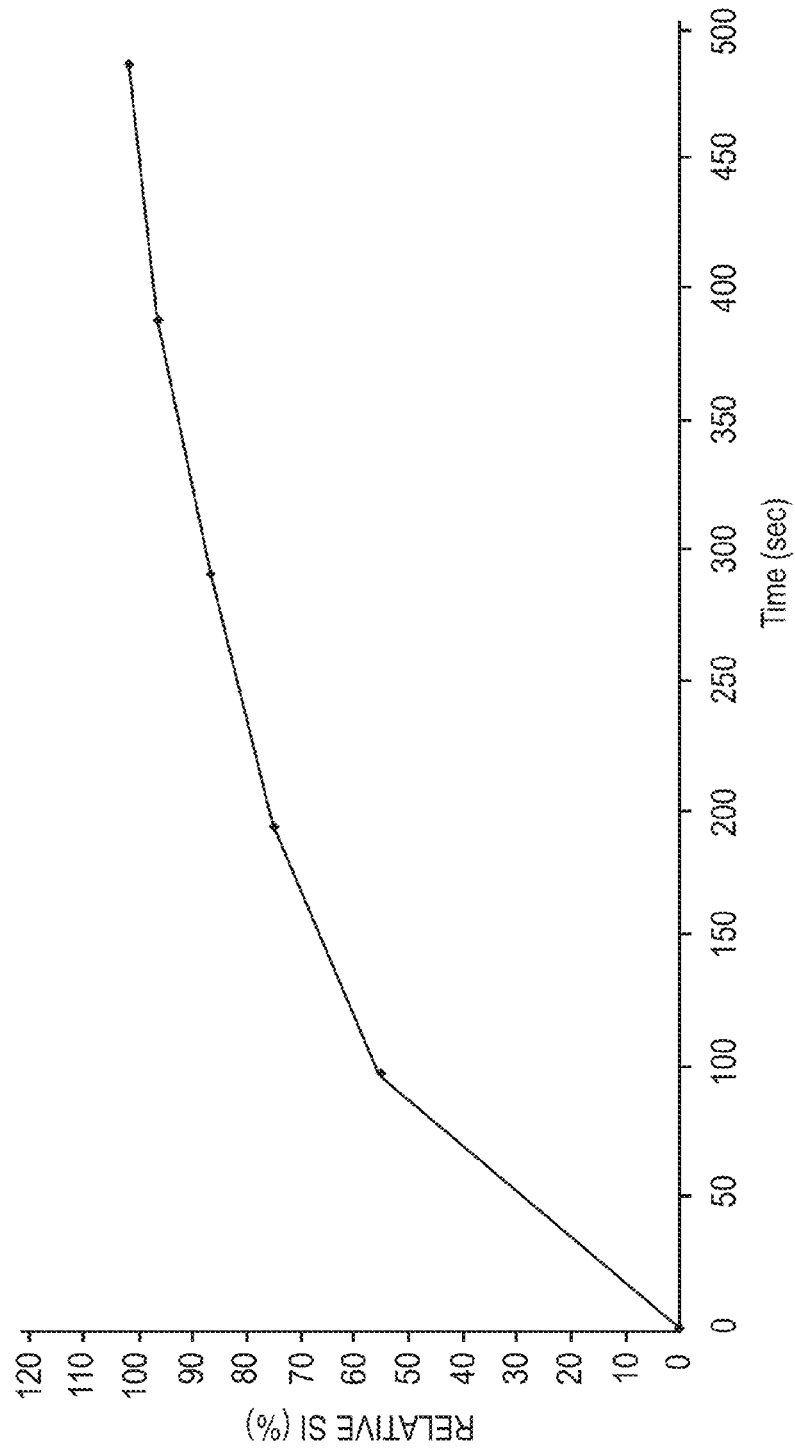
FIG. 6B is a dynamic SI curve after administration of contrast medium. The data points are sampled with a low temporal resolution. The SI-curve is obtained from the same lesion illustrated in FIG. 6-1. The lesion demonstrates a clear contrast continuous uptake throughout the image series, without being affected by a fluctuating phase. SI curve demonstrates no Wash-out.

In order to support the explanation given above, the lesion's Wash-out is also estimated from the dynamic THRIVE series. This possesses a lower temporal resolution, but will nevertheless demonstrate the progress tendency of the contrast agent. FIG. 6B illustrates the dynamic SI curve, obtained from THRIVE series, for the same lesion illustrated in FIG. 6A. Lesion demonstrates once again a clear contrast continuous charge throughout the image series. The SI curve is not affected by a fluctuating phase, and thus shows no wash-out. From the THRIVE series, and based on tumor volume on an average, the average Wash-out was estimated at 0.048 min$^{-1}$ for malignant lesions, and 0.010 min$^{-1}$ for benign lesions. The results suggest that malignant lesions possess a higher wash-out compared with benign lesions. However, the biomarker Wash-out demonstrates no statistical significance regarding the differentiation of benign and malignant lesions (p=0.065). Furthermore, the average Wash-out was estimated at 0.061 min$^{-1}$ for IDC, and 0.008 min$^{-1}$ for FA. The result indicates that the IDC possesses a significantly higher wash-out compared with FA (p=0.007). This confirms the expected result based on previous studies.

Besides Wash-out and peak$_{enh}$, the fluctuating pattern in the SI-curve does not affect the estimations of other biomarkers greatly. The problem can easily be solved by excluding the measuring points of the fluctuating phase, as enough dynamic information is sampled from the previous measurement points. However, this is not done in the current study.

Aside from their limitations descriptive biomarkers represent a diagnostic value in the differentiation of benign and malignant breast lesions. However, these biomarkers reflect a subjective description of contrast agent behavior, and a quantitative approach may be more appropriate.

28.2 Quantitative and Qualitative Analysis of DCE-MRI

To optimize the analysis of dynamic contrast enhanced imaging, a quantitative approach is applied. This includes the use of more complex modeling to describe the observed tissue contrast development. For this purpose, we used a pharmacokinetic two-compartment model developed by Toft et al. [25]. This is described in Section 7.3. The quantitative modeling acquire the ability to produce measurements that directly reflect the anatomical structure of the observed tissue micro vascular system, and physiological factors that affect the time-dependent movement of the contrast agent in the tissue. These include tissue perfusion, endothellal permeability, endothelial surface area and different volume fractions of tissue components. However, it should be noted that the signal intensity curves are only an Indicator of contrast agent distribution within one voxel. Even a small voxel is large in biological terms, and can contain various proportions of blood vessels, cells and the extravascular extracellular space (EES). Because of this, the dynamic signal curve reflects the contribution from the contrast agent distributed in blood vessels, the contrast agent that has leaked out in the EES, or a combination of these. The acquired signal curves can therefore not distinguish between voxels that contain few blood vessels, but with a rapid leakage of contrast medium in the EES, and voxels with little leakage but a large vascular fraction. This will consequently be more applicable at low spatial resolutions. In the quantitative modeling, will the linear approximation between the longitudinal relaxation rate and contrast agent concentration acting as an uncertainty factor. This is because the linear assumption is only valid for a limited amount of contrast agent concentration. This is discussed in more detail in Chapters 6-5.

A latent problem in the use of complex mathematical models is that the more complicated description of the curve there is and the more unknown parameters used to describe it, the more likely it will be for a number of different solutions to be found. This means that the less specific the acquired explanation is, the less accurate and reliable is the estimations of the underlying parameters. The application of a multi-parametric two-compartment model would therefore lead to instability in the analysis and increase the potentiality for error in the estimated model parameters, referred to as biomarkers.

This study shows the quantitative biomarkers $k_{ep}$ and $v_p$, based on the VOI-95 percentile, a significant differentiation ability of benign and malignant lesions, as well as FA and IDC. The results indicate that malignant lesions (including IDC) possess a higher $k_{ep}$- and $v_p$-value compared with benign lesions (including FA). This result corresponds with previous studies [55]. However, it is not found in previous studies of the fractional plasma volume of breast lesions, as this often is neglected in the pharmacokinetic two-compartment model. Several studies have previously nominated $K^{trans}$ as the most predictive pharmacokinetic biomarker regarding the differentiation of benign and malignant breast lesions [54, 55]. In this study, however, $K^{trans}$ show no significant correlation with malignancy (p=0.5268), and no significant ability to differentiate between FA and IDC (p=0.3314). This negative result is suspected to be related to the element of uncertainty regarding the kinetics model AIF deconvolution, as large uncertainties are associated with the measurement of the AIF.

In connection with the study of patients' contrast delay (CD), it was observed that the arterial input function temporal conditions greatly affect the estimated value of the pharmacokinetic biomarkers. It is therefore conceivable that the characteristics regarding the AIF curve shape and amplitude will also have a major influence on the estimation of the pharmacokinetic biomarkers. In this study, the AIF was extracted from the internal thoracic artery. This artery is distinct in the FOV but often require a higher spatial resolution than the applied sequence can supply. As a result, the signal in the arterial voxels is affected by partial volume effects (PVE), inflow effects and flow artifacts, which in practice will result in an underestimation of amplitude of the plasma curve. These factors, together with arterial motion in the dynamic range, are helping to reduce the AIF curve authenticity and thus increase the uncertainty of the pharmacokinetic biomarkers. In this study we have developed a method to reduce the estimation error caused by inaccurate AIF extraction, by normalizing the estimated biomarkers of pharmacokinetics in the breast parenchyma. This tissue is thought to have normal vascularity and a constant leakage component. The normalization method allows the estimation of the pharmacokinetic relationship between parenchymal tissue and cancer tissue. The statistical analysis designates the normalized $K^{trans}$, $k^{ep}$ and $v_p$ as biomarkers with significant correlation with malignancy, and the normalized $K^{trans}$, $v_e$ and $v_p$ as biomarkers with significant ability to differentiate between FA and IDC. Among these is the normalized $K^{trans}$ nominated as the most significant by both grouping strategies.

The pharmacokinetic values from breast parenchymal tissue are acquired from areas defined by the radiologist. These areas generally demonstrate a limited contrast uptake, and hence also low marker values. This is expected but may introduce a high uncertainty factor if high marker values in the form of blood vessels, are included in the defined parenchymal regions. This will result in an erroneous estimation of parenchymal tissue pharmacokinetics, and thus an erroneous estimation of the cancer tissue normalized pharmacokinetics. In addition, the patient's observed contrast delay (CD) is corrected for based on a manual measurement of contrast agent arrival in the arterial voxels and the defined tumor volume. This introduces an uncertainty for the estimated biomarkers in parenchymal tissue, as these are also corrected with the cancer-specific contrast delay. The magnitude of this uncertainty will depend on the difference between the contrast agent arrival in cancer tissue and in the parenchymal tissue. In spite of this, the result shows that the application of a normalization method could potentially improve the diagnostic performance of the pharmacokinetic analysis by reducing possible errors in the measured AIF, and can be used as an alternative strategy if there is suspicion of significant measurement errors of the AIF.

The parenchymal tissue contrast enhancement is often referred to as a background enhancement. A study by Kuhi et al. [66] demonstrates the variation of background enhancement in premenopausal women as a function of the survey conducted in menstrual cycle. This study showed that the background amplification occurs during all phases of the menstrual cycle, especially in week 1 and 4. The study also showed that background amplification was lowest in week 2. This indicates that if the normalization method is to be used, it is appropriate to examine all premenopausal patients in the same period of menstrual cycle. In addition, it is important to note that high background enhancement can occur, especially for young patients with high parenchymal density.

In the original version of Toft and Kermode [26] a bi-exponential input function was applied to the modeling of the contrast agent pharmacokinetics. This allowed for the application of a general non-linear fitting algorithm for the acquisition of the two qualitative kinetic biomarkers $K^{trans}$ and $k_{ep}$. In this model the contribution from the plasma volume is assumed to be small and therefore neglected. Buckley conducted in 2002 a comparison study [27] between pharmacokinetic models that neglect, and include, the contrast agent contribution from plasma. This study showed that if the vascular contribution is excluded from the model analysis, biomarkers $K^{trans}$ and $v_e$ be overestimated and not reflect the real physiological tissue properties. Apart from this, the original model to Toft and Kermode, with the application of a pre-defined plasma course, will still be appropriate in situations where the vascular contribution cannot be measured, or when the temporal resolution is not sufficient to identify the AIF curve peak.

In this study a qualitative description of the contrast agent pharmacokinetics is performed by applying an idealized mono-exponential input function. This is described in Section 11.2. The result shows that the qualitative biomarker $k_{ep}$, based on tumor volume of the VOI-95 percentile, demonstrates a significantly higher value in malignant lesions (including IDC), compared with benign lesions (including FA). This result corresponds with previous studies [55]. At the same time demonstrates the qualitative biomarker $v_e$, based on tumor volume of the vOI-95 percentile, a significantly higher value in FA compared with IDC, which corresponds with the previous study [55].

It is important to note that a pre-defined mono-exponential input function is missing details regarding the patient's true arterial contrast gradient, and therefore will produce less accurate and not reproducible kinetic biomarkers. This is because the arteries contrast signal development is related to a number of physiological factors including blood flow, vascular tone and renal function, and thus varies between patients over time [50]. The AIF will also be a function of injection timing and dose. A direct measurement of the AIF in each patient at each examination hence generate a more robust and reproducible description of the pharmacokinetic properties, and is thus preferred over a standard input function.

28.3 Quantitative Analysis of DSC-MRI

A double-echo system allows quantification of the transversal relaxation rate, $R_2^*$, without assumptions regarding the tissue underlying T1 properties. The dynamic $\Delta R_2^*$ is estimated from the double-echo system, assuming a mono-exponential dependent signal change between the two sampled echoes. The registration of two echoes will however lead to an extended recording time, which then limits the achievable spatial resolution and imaging FOV if an acceptable temporal resolution is to be maintained. In breast cancer, the analysis of DSC imaging is complicated by the direct $T_2^*$-effects from the extravascular contrast agent. Leakage of the contrast medium will not only cause an enhancement of the T1-weighed signal, but also introduce additional $T_2^*$-shortening in the tissue. Despite the recording of a double-echo system, which is not affected by the T1-changes, will the magnitude of the $T_2^*$-effect be unpredictable.

The estimated biomarker $R_2^*$-peak$_{enh}$ will be related to tissue perfusion, and probably also its micro vascular structure (vascular density, distribution of vessel diameter, etc.) This study indicates that malignant lesions (including IDC) possesses a higher $R_2^*$-peak$_{enh}$ compared with benign lesions (including FA). This result may indicate a greater heterogeneity in malignant breast tissue, as a non-homogeneous distribution of contrast agent will generate significant $T_2^*$-effects. This can be explained by the fact that the signal dephasing, which is associated with the susceptibility induced gradients surrounding the paramagnetic contrast agent, has a greater effective range compared to the contrast agent T1 effect. The statistical analysis nominate $R_2^*$-peak$_{enh}$ as the most predictive of all evaluated biomarkers with regard to differentiating between benign and malignant lesions, as well as FA and IDC. We found no previous studies of the quantitative transversal relaxation rate for breast studies, but Kvistad et al. [17] and Kuhi et al. [13] evaluated the relative signal loss in $T_2^*$-weighed images. These studies showed that malignant breast lesions demonstrate a significantly higher signal compared with benign breast lesions, which correlates with the observed results from the biomarker $R_2^*$-peak$_{enh}$.

Figure 6C:
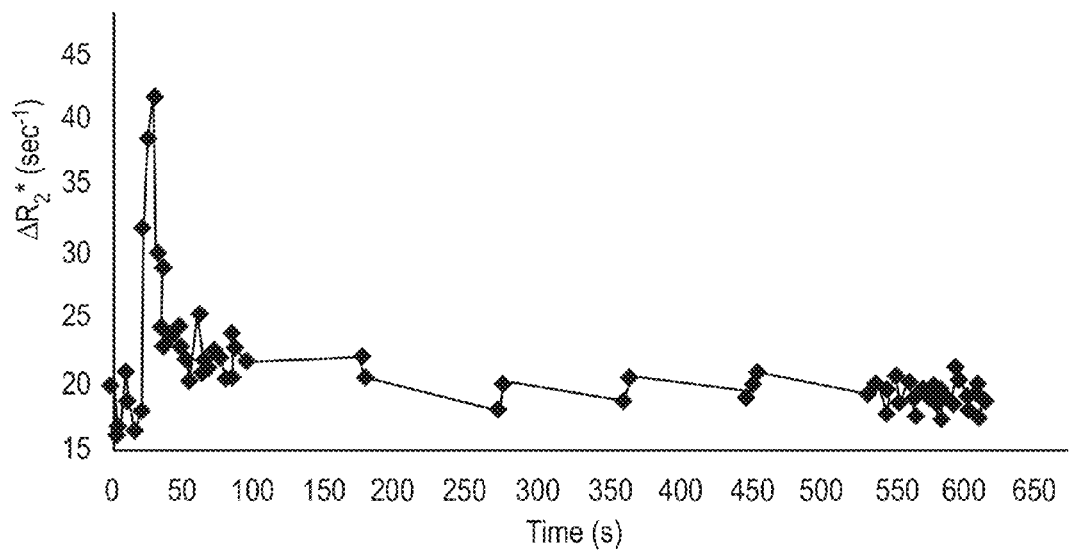
FIG. 6C is a dynamic acquisition of the transversal relaxation rate from a 38-year-old patient with IDC. The figure illustrates the narrow transient R2*-effect after administration of a contrast agent.

The dynamic change in the transversal relaxation rate demonstrates a limited transient pattern in the form of a narrow peak just after administration of contrast agent. This is illustrated in FIG. 6C. The figure illustrates a dynamic acquisition of the transversal relaxation rate in IDC. The identification of the characteristic peak requires a high temporal resolution, as $R_2^*$-effect of the contrast agent has been observed in a time interval of 16 seconds. For an adequate description of this transient susceptibility effect a temporal resolution of less than 3 seconds is proposed.

Acquisition of the dynamic $R_2^*$ can also be used to analyze the other perfusion related biomarkers. These include tissue blood volume (BV), blood flow (BF) and the mean transit time (MTT). This is described in Section 7.2. Although a double-echo method effectively removes the T1 contribution, a significant leakage of the contrast agent into the EES is in effect. This requires the use of modified and more complex kinetic models, including and adjusting for leakage contribution of the contrast agent. Such an analysis is not done in the current study.

In summary, this study shows that the registration of a second echo in a T1-weighted perfusion sequence with high temporal resolution, will improve the diagnostic accuracy of breast cancer through the acquisition of quantitative R2* measurements.

29. The Importance and Limitations of the Arterial Input Function

In this study contrast agent pharmacokinetics is modeled with a mathematical two-compartment model. Such modeling often requires a number of assumptions, which reflect the limitations of the applied model. Perhaps the most significant restriction of the various models is the ability to accurately measure an arterial input function (AIF) for each patient. From model used in the study (equation 3-3), it clearly states that the accuracy of the measured AIF directly affects the accuracy of the pharmacokinetic biomarkers. This issue represents a major technical challenge and is an active research area. An alternative solution of this restriction is the application of a pre-defined input function for all study subjects, such as an idealized mono-exponential input function. This allows for the execution of a qualitative analysis of the contrast agent pharmacokinetics when the true AIF is absence. However, such an input function is lacking details of the patient's true arterial contrast agent development, and will therefore produce less accurate and not reproducible kinetic biomarkers. The provision of an individual input function will hence produce a more robust and reproducible description of the pharmacokinetic properties.

Measurements of the AIF require the acquisition of a sequence with adequate temporal resolution at an acceptable spatial resolution and an image field of view that includes a distinct artery. The present study demonstrates the difficulty of this achievement by dynamic MR-mammography, and has Identified issues like insufficient spatial resolution, lack of arteries in the imaging volume and geometric motion of the exploit arteries in the dynamic image series. Uncertainty as a result of these factors is attempted minimized through a meticulous extraction of patients' final AIF: First is a manual search through the patient's average images performed for the identification of the most distinct arterial pixel signals. Then three sections are selected, of which 20-30 pixels are selected based on criteria relating the shape and temporal properties of the signal intensity curve. Each pixel curve is inspected manually by investigating and significantly aberrant individual curves are eliminated. The patient's final AIF is given by the average of the remaining arterial pixel curves.

To address the various challenges that arise when an insufficiency AIF is apparent, several methods have been proposed: Brix et al. [20] developed a method in 1991 that parameterized contrast sequence in the plasma compartment from the relative signal intensity (Brix model). In this model the measured input function is included as a free customized parameter. Another method is to measure the contrast agent concentration in the plasma compartment from a reference tissue, such as muscle tissue included in the imaging field of view, which is further used as an input function in the pharmacokinetic model. This method has been developed by TE Yankeelov [56] and is referred to as the RR model (Reference Region). In this study we have developed a method to reduce the estimation error in the applied model biomarkers as a result of an insufficient AIF extraction. This method is performed by normalizing the quantitative biomarkers with pharmacokinetics in the breast parenchyma, which is thought to have normal vascularity and a constant leakage component. The method will thus identify the relationship between the pharmacokinetic properties of breast parenchymal tissue and cancer tissue. Any errors in the pharmacokinetic marker values in cancer tissue, caused by an insufficient AIF will also be applicable for the marker values in parenchymal tissue, as these will likewise be scaled with the same AIF. The execution of the normalization method in this study shows a potential improvement of the diagnostic performance of the pharmacokinetic model, by reducing the actual error in the applied AIF.

In summary, an individual determination of the AIF allows a quantitative pharmacokinetic approach. This acquires a description of the physiological phenomenon that relates to a quantity or a range of patients, and can therefore be compared to a group of individuals. If such quantification is not feasible, the pharmacokinetic properties can be described by an idealized mono-exponential input function. This obtains a qualitative description of physiological phenomena related to the individual patient, and therefore cannot be compared to in a group. Qualitative and quantitative research is complementary methods that cannot be substituted for each other. Although most investigators currently recommend the determination of an individual AIF during a dynamic contrast-enhanced MRI, is the best method to use for the described purpose yet to be determined.

30. Sources of Error

Dynamic MRI-based mammography has several potential sources of error. Several of these have previously been discussed, but perhaps the biggest sources of error include the estimation of the arterial input function and the assumption regarding the linear relationship between the signal of intensity change and the contrast agent concentration. Other factors that may substantially affect the accuracy and precision of the dynamic analysis includes the definition process of tumor volume, patient movement during the dynamic study, the observed contrast, the delay between arterial voxels and the tissue of interest, insufficiency spatial resolution, the blood hematocrit factor (Hct), partial volume effect (PVE) and the observed tissue immanent $T_1$ value.

Improper selection or location of the tumor volume may result in the inclusion of contrast enhanced and necrotic or non-enhanced tissue components, and nearby blood vessels. The consequence of this would be an erroneous interpreting of the physiological properties of the cancerous tissue. In this study a two-dimensional ROI is defined in each section that includes the current lesion. The work is performed by a qualified radiologist with extensive experience in oncology and MR mammography. The volume is defined by drawing along the radial branches of the tumor, seen in a high spatial contrast-enhanced image series (THRIVE). Cancer tissue is separated from normal tissue because cancer usually takes up more contrast than the surrounding normal tissue. During image processing and analysis, it is found that the lesions volume is generally well defined and that this does not constitute a significant source of error.

Patient motion is generally a widespread problem in dynamic MR imaging. Since tumor contrast enhancement is often studied over several minutes, the potential for patient movement is great. This problem is made worse if the patient perceives the prone position as stressful or by patients with severe claustrophobia. The various biomarkers values are estimated using a pixel-by-pixel method in the acquired images, and a movement of the object will consequently result in estimation errors. In cases where this source of error is relevant mathematical algorithms for motion correction are applied. However, the breasts demonstrate a non-rigid motion, and therefore require the application of very complex correction algorithms. In this study the series of images with significant motion artifacts are eliminated from the retrospective analysis, but patient movement is an uncertainty factor that is difficult to avoid and which to some extent is applicable to all dynamic MRI recording. To minimize the uncertainty caused by patient movement the breasts are stabilize in the applied breast coil with foam pads or the like. In addition, patient motion is reduced by skilled and soothing radiographers.

Figure 6D:
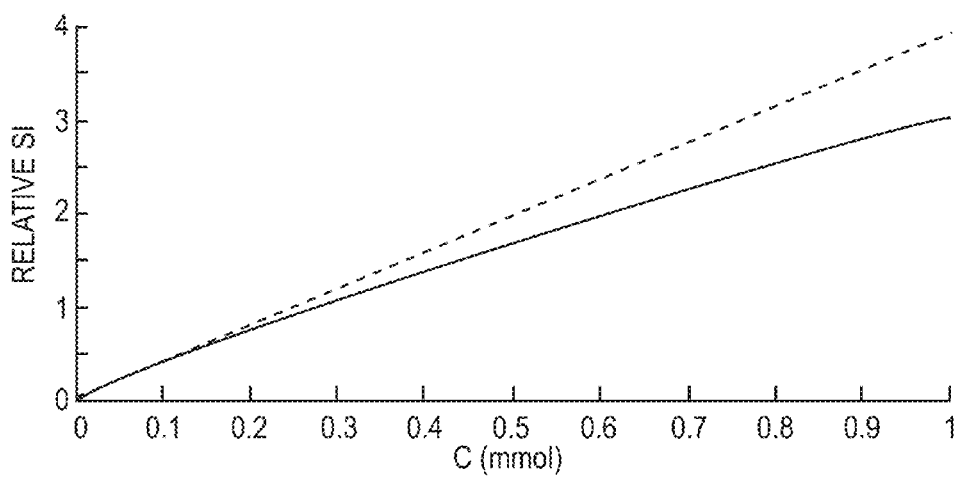
FIG. 6D is a plot of relative signal increase as a function of the contrast agent concentration using a GRE sequence. TR and T1 times are 80 ms and 1000 ms, respectively. The striped line demonstrates that linear approximation is assumed in this study.
Figures 1, 2, 7A:
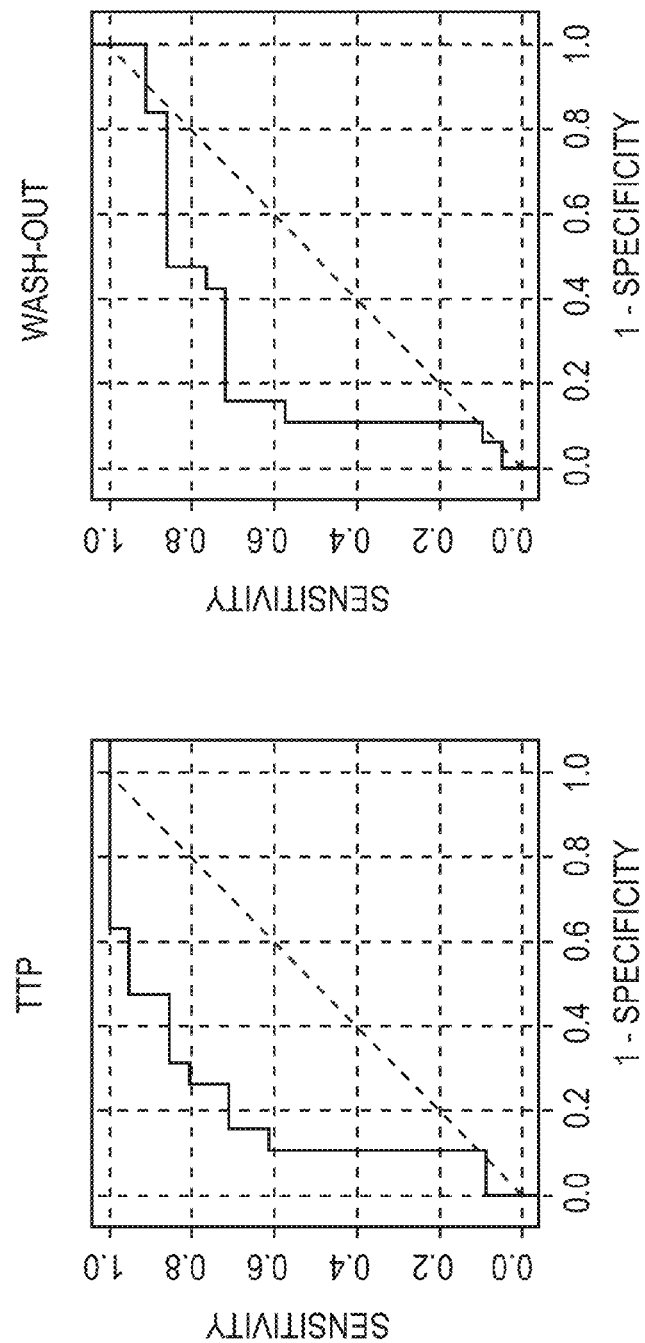
FIG. 7A, separated as FIG. 7A-1 through FIG. 7A-2, illustrates ROC curves. Semi-quantitative DCE-MRI biomarkers with significant correlation with malignancy. The area under the ROC curve and sensitivity and specificity are estimated to be 0.81, 71% and 84%, respectively for TTP, and 0.72, 71% and 84% for the Wash-out.
Figures 1, 7B:
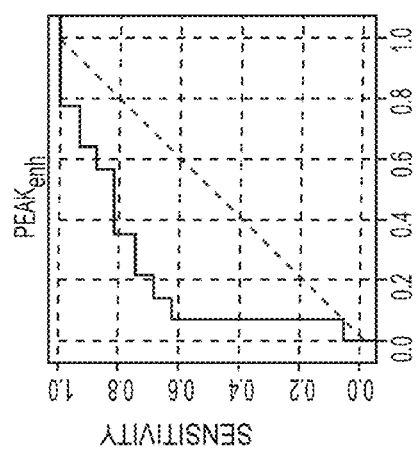
FIG. 7B, separated as FIG. 7B-1 through FIG. 7B-4, illustrates ROC curves. Semi-quantitative DCE-MRI biomarkers with significant ability to differentiate between FA and IDC. The area under the ROC curve and sensitivity and specificity are estimated to be 0.84, 88% and 71%, respectively for the Wash-out, 0.87, 75% and 93% for TTP, 0.73, 50% and 93% for AUC, and 0.79, 50% and 79% for peak$_{enh}$.
Figures 2, 7B:
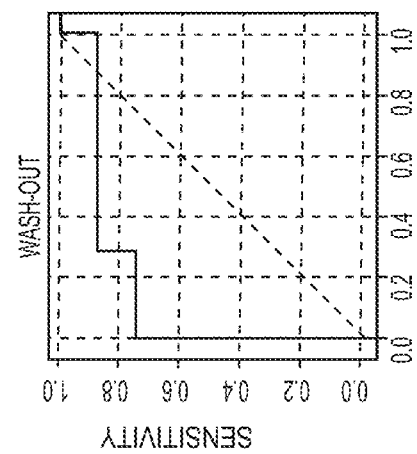
Figures 3, 7B:
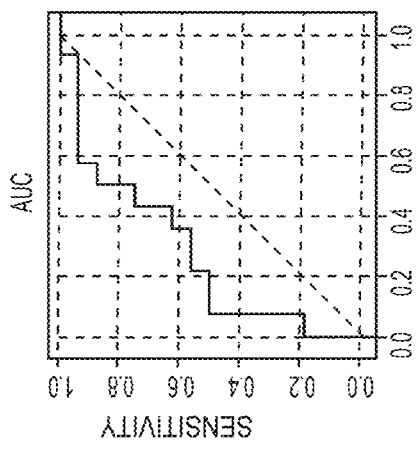
Figures 4, 7B:
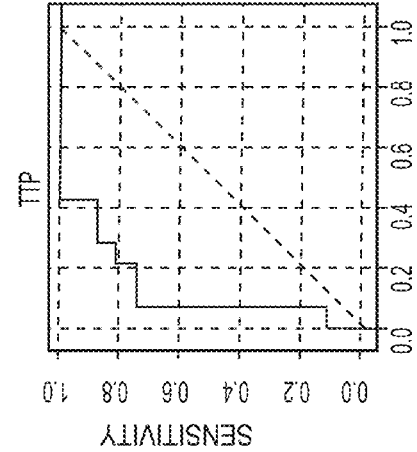
Figures 1, 2, 3, 7C:
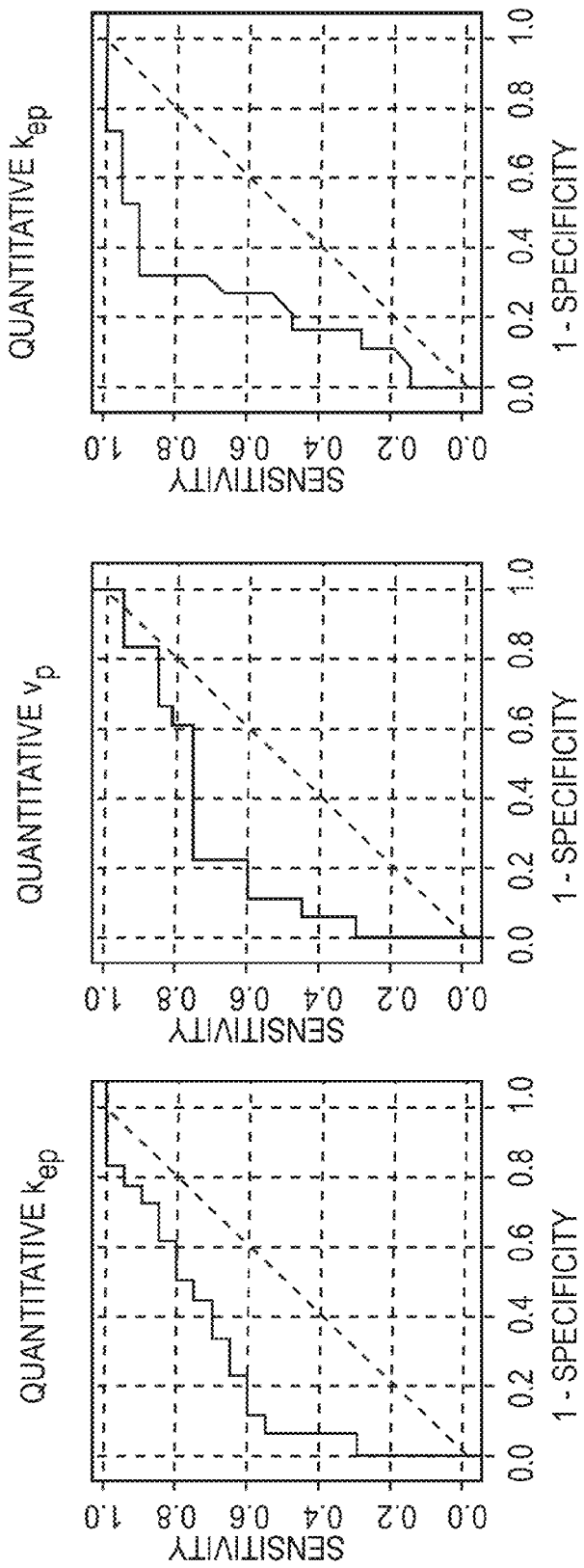
FIG. 7C, separate as FIG. 7C-1 through FIG. 7C-3, illustrates ROC curves. Quantitative and qualitative DCE-MRI biomarkers with significant correlation with malignancy. The area under the ROC curve and sensitivity and specificity are estimated to be 0.76, 60% and 89%, respectively for quantitative $k_{ep}$, 0.74, 75% and 78% for quantitative $v_p$, and 0.77, 90% and 68% for qualitative $k_{ep}$.
Figures 1, 7D:
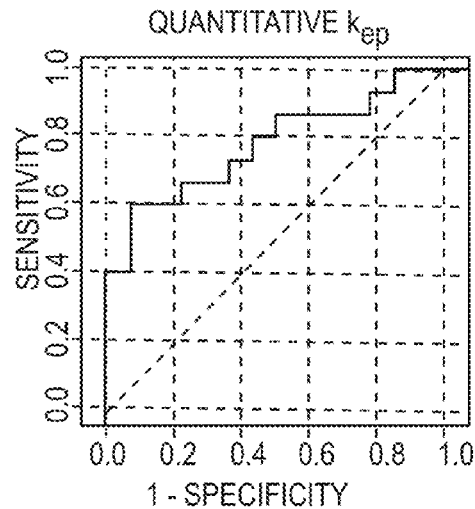
FIG. 7D, separated as FIG. 7D-1 through FIG. 7D-4, are ROC curves. Quantitative and qualitative DCE-MRI biomarkers with significant ability to differentiate between FA and IDC, the area under the ROC curve and sensitivity and specificity are estimated to be 0.78, 60% and 93%, respectively for quantitative $k_{ep}$, 0.85, 73% and 93% for quantitative $v_p$, 0.89, 93% and 79% for qualitative $k_{ep}$, and 0.79, 69% and 93% for qualitative $v_e$.
Figures 2, 7D:
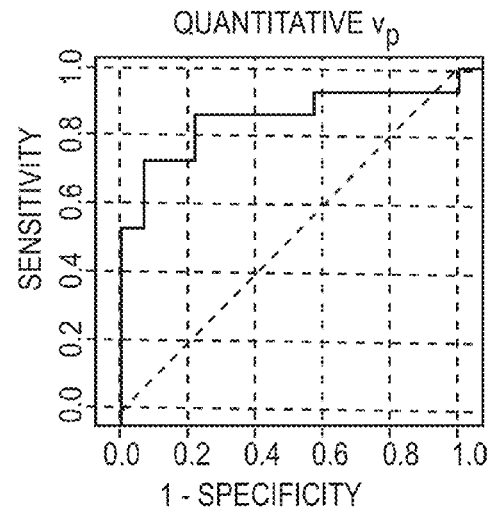
Figures 3, 7D:
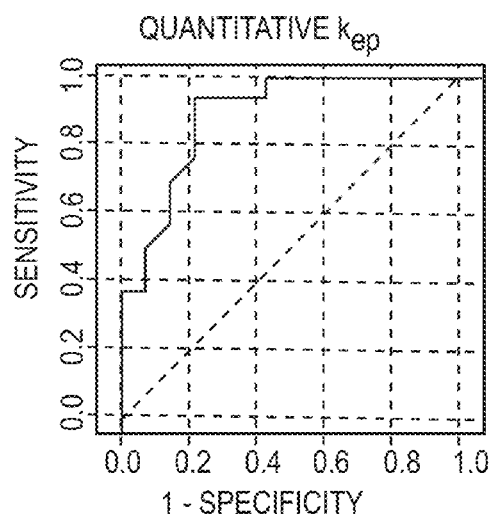
Figures 4, 7D:
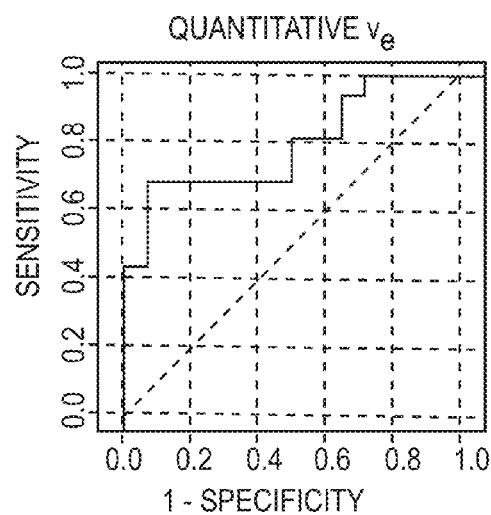
Figure 7E:
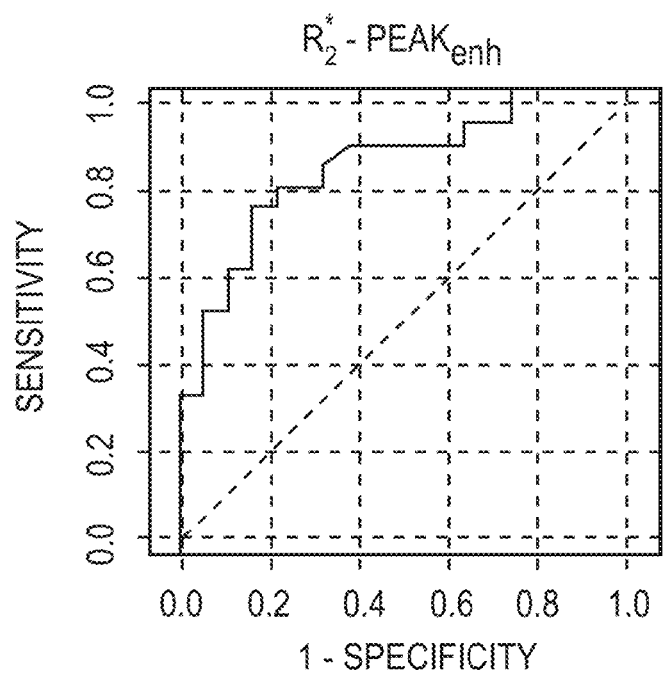
FIG. 7E illustrates ROC curves. Quantitative DSC-MRI biomarker with significant correlation with malignancy. The area under the ROC curve and sensitivity and specificity are estimated to be 0.85, 76% and 84%, respectively.
Figure 7F:
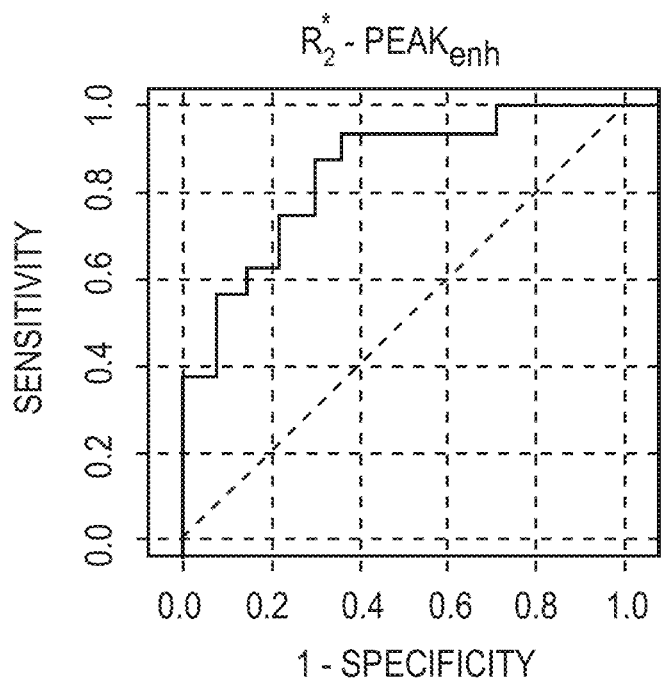
FIG. 7F illustrates ROC curves. Quantitative DSC-MRI biomarker with significant ability to differentiate between FA and IDC. The area under the ROC curve and sensitivity and specificity are estimated to be 0.85, 88% and 72, respectively.
Figures 1, 2, 3, 7G:
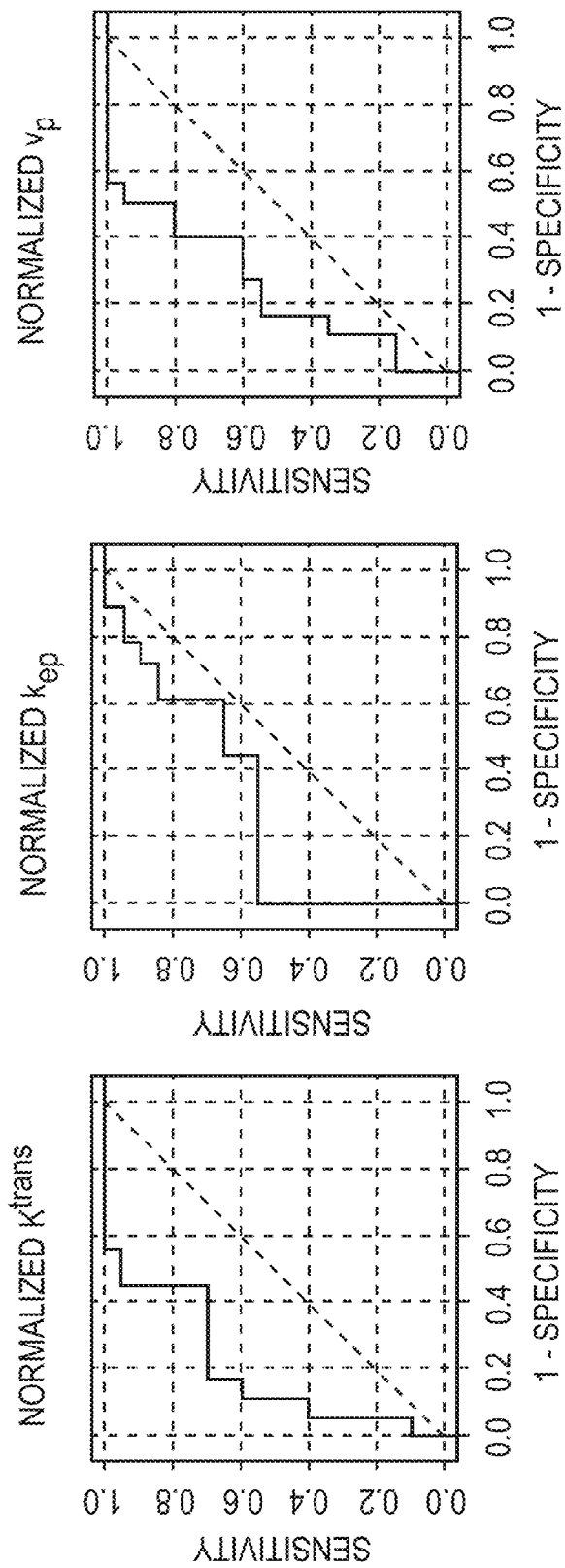
FIG. 7G, separated as FIG. 7G-1 through FIG. 7G-3, illustrates ROC curves. Normalized quantitative DCE-MRI biomarkers with significant correlation with malignancy. The area under the ROC curve and sensitivity and specificity are estimated to be 0.81, 70% and 83%, respectively for normalized $K^{trans}$, 0.71, 55% and 100% for normalized $k_{ep}$, and 0.75, 80% and 61% for normalized $v_p$.
Figures 1, 2, 3, 7H:
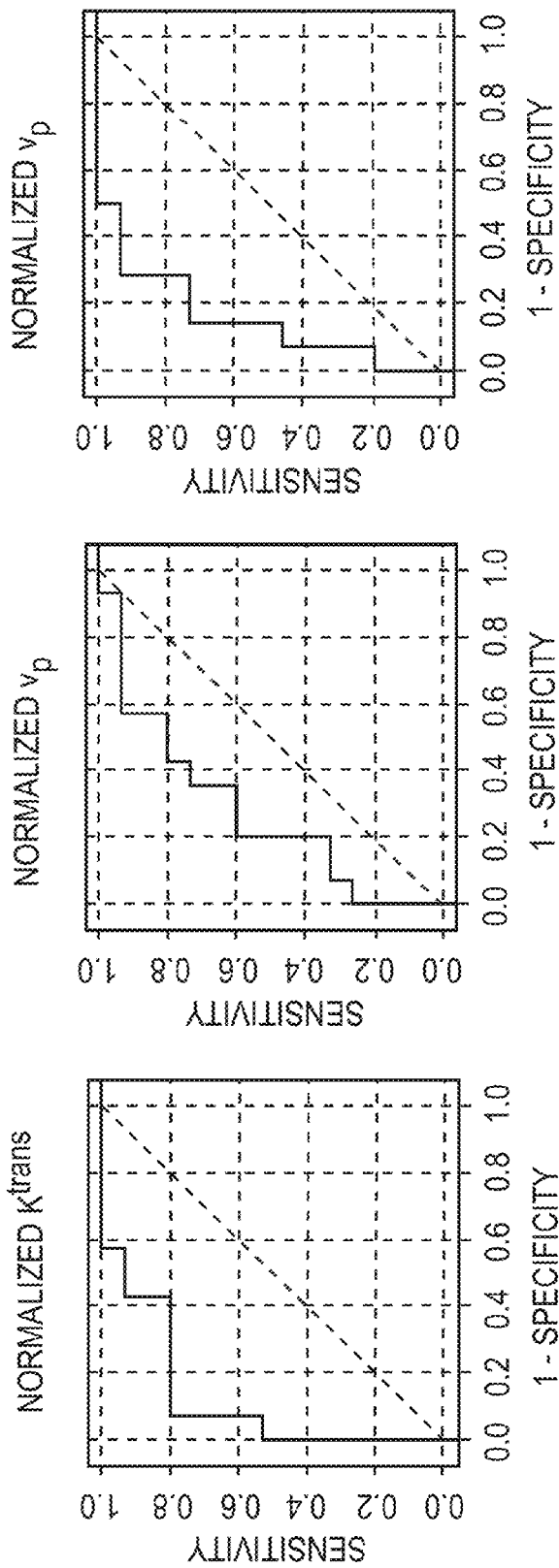
FIG. 7H, separated as FIG. 7H-1 through FIG. 7H-3, illustrates ROC curves. Normalized quantitative DCE-MR biomarkers with significant ability to differentiate between FA and IDC. The area under the ROC curve and sensitivity and specificity are estimated to be 0.89, 80% and 93%, respectively for normalized $K^{trans}$, 0.72, 60% and 79% for normalized $v_e$, and 0.85, 93% and 72% for normalized $v_p$.

Knowledge about the concentration of the contrast agent is required to extract physiologically relevant information from the observed tissue pharmacokinetic properties, in this study it is assumed a linear relationship between the longitudinal relaxation rate, $\Delta R_1$, and the concentration of the contrast agent, an assumption which is only approximately true for a limited amount of contrast agent concentration. This is illustrated in FIG. 6D, where the relative signal intensity is plotted as a function of the contrast agent concentration in a tissue with $T_1$ similar to 1000 ms. FIG. 6D is intended as an illustration, where 1000 ms is a representative relaxation time in soft tissue. The longitudinal relaxation time of the applied contrast agent Gd-DTPA is $3.9 \pm 0.2$ $s^{-1}$ $mmol^{-1}$ for an MRI unit with a stationary magnetic field strength of 1.5 T [57]. As illustrated in the figure, the deviation between the linear approximation and the actual signal change is very little for low concentration amounts, while for higher contrast agent concentration it will be more severe. The relationship between relaxation rate changes, as a result of the administered contrast agent, and signal change for a GRE sequence with short TE depends on several factors. These include the tissue relaxation rate before contrast medium injection, the applied sequence flip angle, the sequence repeat time and tissue proton density [58, 59]. In particular, the tissue immanent relaxation rate is a source of uncertainty. If this can be measured, it will allow a precise estimation of the relative signal intensity. This can be measured by using special MRI sequences, and require separate scans using different repetition times. Such MRI recording is not performed in this study, and it is therefore not possible to estimate the true relationship between the contrast agent concentration and the relative signal change. Apart from this limitation the linear approximation represents an accepted assumption for this study, provided that the $T_1$ times in cancer tissue and the injection rate and the amount of contrast medium does not vary between patients.

The blood hematocrit factor (Hct) plays an important role in the estimation of pharmacokinetic biomarkers, as the administered contrast medium is only distributed in the plasma fraction of the total blood volume. It is, therefore the contrast agent concentration in the plasma compartment that is studied instead of the total blood volume. Because of this the measured arterial signal is scaled in relation to the patient's Hct-factor, as shown in equation 3-2. However, the Hct factor varies between patients, which will lead to the wrong estimation of the quantitative biomarkers. Simultaneously, the Hct factor will vary between large blood vessels and the micro vascular system. This is because the collection of red blood cells is less dense in the capillaries, which then leads to a lower Hct factor. This study includes no explicit measurement of Hct, and a factor of 0.4 is generally assumed.

The partial volume effect (PVE) occurs if the signal from two or more tissue components combines to produce a single intensity value in the voxel. This is a result due to the limited spatial resolution of the system image acquisition, and usually occurs in areas adjacent to two or more tissues. As mentioned the high temporal image sequence causes a relatively low spatial resolution, as image quality is a compromise between these two factors.

This results in a larger point spread function (PSF) and accompanying larger voxels, and thus more likely to introduce significant PVE. In areas where the PVE is applicable, this will lead to the erroneous description of the specific tissue real contrast enhancement, which will introduce errors in the estimation of biomarkers. PVE is acting as an uncertainty factor in the quantification of the pharmacokinetic biomarkers, as the arterial voxels are potentially affected by the PVE. This is because the arteries included in the imaging field are relatively small compared with the acquired voxel size. If the AIF is measured in voxels where PVE is applicable, this will in practice result in a distortion and underestimation of the amplitude of the plasma curve. PVE may thus contribute to a poor accuracy and a low reproducibility of AIF measurements. In addition, PVE is more applicable for small lesions, since a larger proportion of the voxels in the tumor volume will be affected. A possible solution to this problem is the introduction of a lower volume limit as inclusion criteria. This is common practice in several studies where PVE is significant, for example, due to low spatial resolution.

In connection with the study of the quantitative pharmacokinetic description, it is observed that the estimated marker values are largely influenced by contrast delay (CD) between the arterial voxels and the tissue of interest. This is because the applied two-compartment model assumes that the contrast agent arrives in the arterial voxels and the tissue of interest at the same time. Assuming that the corrected marker values are correct, this study shows that a lack of correction of patient CD will result in an overestimation of biomarkers $K^{trans}$, $k_{ep}$, and $v_e$, and an underestimation of biomarker $v_p$. The observed contrast delay demonstrates the general large variability between patients. It is conceivable that the CD, as the arterial contrast course, is influenced by a number of physiological factors such as blood circulation and the vascular tone. However, some patients demonstrate unrealistic CD that cannot be explained by the examiner. Despite this, the patient variation indicates that a robust and reproducible pharmacokinetic analysis can only be achieved through an individual CD-correction. In FIG. 4O, existing outlayers are displayed with red plot markers. These are identified as three lesions that repeatedly appear as outliers. An observation made regarding the identified outliers is that they demonstrate a very clear washout pattern in the late post-contrast phase. This suggests that a pharmacokinetic analysis of lesions with distinct washout pattern to a greater extent will be affected by contrast delay and its magnitude.

31. Statistical Analysis

In this study, the statistical analysis is used to analyze the dynamic image information and compared to the diagnostic fact acquired from histology. In order to systematically exclude any statistical outliers a global and local filtering of biomarkers values have been made. The global filtering is carried out during the estimation of the various biomarkers. The filtering is performed by letting 2% highest marker values be excluded from the analysis. In addition, it conducted a local filtering after the tumor volume of the marker values is extracted. This is done by 2% of the highest and lowest marker values in the VOI being excluded from the analysis. The advantages of such a filtering process are seen when recognizing that the static outlayers are located at the edges of the marker value in the distribution function. If there are no outliers among the tumor volume marker values, will the filtering process not affect the analysis as it is performed at both ends of the distribution function. In this way can the tumor volume high percentile values be evaluated, and one can be sure that these are not greatly affected by the outliers.

To investigate which parts of biomarkers distribution in patients' VOI which is appropriate to evaluate further in the diagnostic analysis, is the significance between the two defined groups tested with the Mann-Whitney U test. Based on this test the null hypothesis is rejected if the estimated p-value is lower than the critical p-value of 0.05, which corresponds to a significance level of 5%. Statistically, this means that five out of 100 null hypotheses mistakenly are rejected if the tests are independent. This is a universally accepted level of significance that was recommended by RA Fisher (38).

In the statistical analysis it is performed a logistic regression analysis to achieve an optimal fit between the patients' proven histology and the dynamic image information. In this type of analysis it is very important to take into account the possibility for over adaptation. In multivariable regression analysis, a "small" number of events can affect the accuracy and precision of regression coefficients for the individual biomarkers and their associated tests of statistical significance. Under such circumstances, the regression analysis leads to unstable risk estimation and it is therefore misleading to a suggest relationships between the model response variable and the applied biomarkers. By analogy with type I error (false positive) the result may falsely reject the null hypothesis so that a biomarker cannot influence the outcome. By analogy with type II error (false negative), the model lacks the ability to identify the influence of an important biomarker. These are problems that can occur or get worse if the number of events is too small for the multivariate model, and means that the number of included biomarkers depends on the size of the data. A guideline for the number of biomarkers included in a logistic regression model is given by:

$$\text{The number of included biomarkers} = \frac{\text{The number(cases, non-cases)}}{10}$$

This means that if the study includes 20 lesions, these can be modeled with 2 biomarkers. In this study, the number of events in the grouping strategy 1 and 2, were 38 and 29, respectively. The selected regression models including both 3 biomarkers, which are accepted under the given guidelines.

32. Examples

In some embodiments, the spatial heterogeneity of breast cancer is displayed in a normalized histogram analysis of rationally selected biomarkers. This allows a direct measurement of tumor heterogeneity, the biomarker value distribution in tumor volume, and can be used as a separate biomarker in the diagnostic evaluation. Such a histogram analysis can be performed as follows: The histogram is generated for the selected biomarker values in the defined tumor volume with a predefined number of histogram bars. By normalizing the area under the resulting histogram as one, the biomarker relative frequency in the studied tumor volume is displayed. Simultaneously, it is appropriate to keep the biomarker values along the histogram x-axis constant. The breast cancer spatial heterogeneity can then be evaluated by measuring the relative frequency of the maximum normalized peak in the histogram distribution. The hypothesis behind this method is that the biomarker heterogeneity in tumor volume is related to tumor malignancy and inversely proportional to the height of the normalized marker distribution [60]. The investigator proposes a histogram analysis of the quantitative pharmacokinetic biomarkers, especially $v_p$ representing the cancer tissue fractional plasma volume. Tumor heterogeneity can also be measured by estimating the absolute difference between the histogram 25 percentile and 75 percentile. The hypothesis is that selected biomarkers for benign lesions show a narrow range due to lower heterogeneity, thus demonstrating a lower absolute difference between the histogram 25 percentile and 75 percentile, compared with malignant lesions.

Example I

Diagnosis of Breast Cancer

Forty-eight patients with confirmed lesions were subjected to breast MRI. The MR investigation was conducted with a Philips Achieva (1.5 T) system with NOVA providing both high spatial solution THRIVE sequence for tumor identification and a high 1-parameter quantification. The two sequences were conducted in an alternate manner (Multi-Hance 0.2 mmol/kg body weight, Milan, Italy). Images of high temporal solution in a 3D T1 multi shot EPI sequence with two echoes by using the following parameters: repetition time=42 ms, echo times 5.5 ms/23 ms, flip angle=28°, voxel size=1.69*1.48*4 mm$^3$, number of sections=30, temporal solution=2.8 s/picture volume with a total of 77 dynamic series collected. A PROSET fat suppression technique was used together with a SENSE factor of 2.5. The transversal relaxation rate, R2, was calculated on a pixel-per pixel basis by assuming a mono-exponential dependency of signal alteration in echo time and parametrical pictures representing the top alterations in R2* were generated. The volume of interest (VOI) identifying all lesions, was drawn manually be an experienced radiologist. Mann-Whitney U-tests and receiver operator characteristics (ROC) curve statistics were used on the 95 percentile value in each VOI for determining the significance and the diagnostic accuracy for establishing or excluding malignancy.

Results

Histology identified 22 lesions (54%) as malign and 19 (46%) as benign. The 95 percentile peak R2* value displayed a significant correlation towards malignancy (p<0.0001), and a good diagnostic accuracy with an area under the ROC-curve of 0.85. See FIGS. 8A-8C.

This example shows that the peak-change in the transverse relaxation velocity is a sensitive biomarker for tumor malignancy in DSC MR mammography. An additional echo in a T1-weighed perfusion sequence with a high temporal solution may consequently improve the diagnostic accuracy by allowing quantitative examination of tumor-specific changes in R2* after contrast substance administration.

Figure 8A:
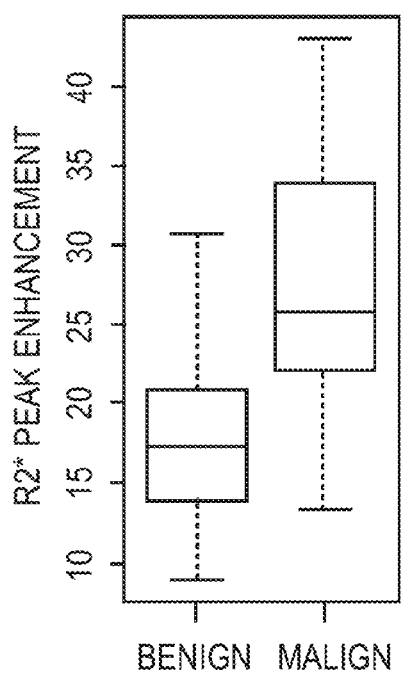
FIG. 8A is a box plot showing the four quartiles and the mean value of the R2*-peak enhancement for malign and benign tumors.
Figure 8B:
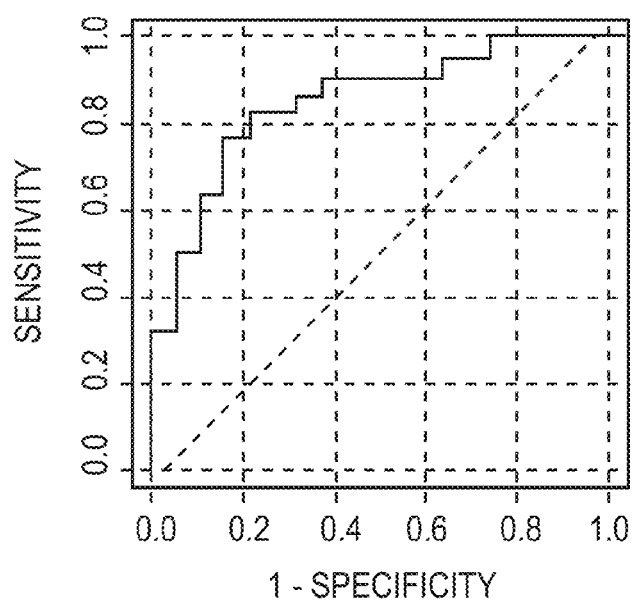
FIG. 8B is a receptor operator characteristics curve (ROC) for a 95 percentile R2* peak value. The area under the ROC curve was calculated to b 0.852.
Figure 8C:
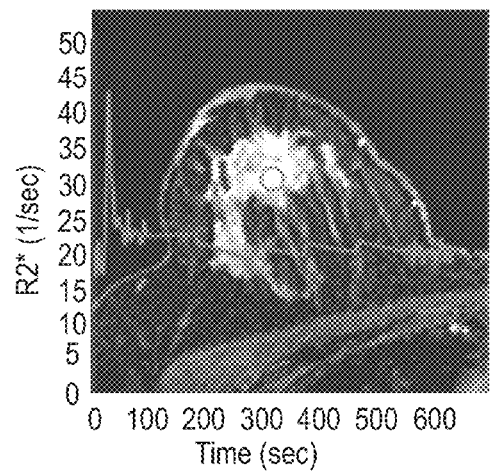
FIG. 8C is an invasive ductal carcinoma (IDC). The dynamic R2*-against-time curve of the illustrated RIO is shown as a superposition on a THRIVE-image. The distinct first passage R2* response is shown.

FIG. 8A presents a box-plot showing the four quartiles and the mean value of the R2*-peak enhancement for malign and benign tumors. FIG. 8B presents receptor operator characteristics curve (ROC) for a 95 percentile R2* peak value. The area under the ROC curve was calculated to b 0.852. FIG. 8C shows data for invasive ductal carcinoma (IDC). The dynamic R2*-against-time curve of the illustrated RIO is shown as a superposition on a THRIVE-image. The distinct first passage R2* response is shown.

As mentioned supra, the process according to the present invention uses biomarkers connected with the descriptive DCE-MRI analysis combined with pharmacokinetic biomarkers connected with the DCE-MRI analysis as well as pharmacokinetic biomarkers connected with the DSC-MRI analysis. This is illustrated infra where there is given as a non-limiting illustrational example a general theoretical DCE-MRI curve wherein the time from injection is present along the abscissa axis and relative SI-signal is given along the ordinate axis. The relevant biomarkers that are used in the process according to the invention are: 1: the area under the curve (AUC=Area under the curve); 2: Time to maximum signal enhancement (TTP=Time to peak); 3: Maximum relative signal enhancement ($P_{enh}$=relative peak enhancement); 4: The in-pouring of the curve (Wash-in rate) and 5: the Out-poring of the curve (Wash-out rate).

Figure 8D:
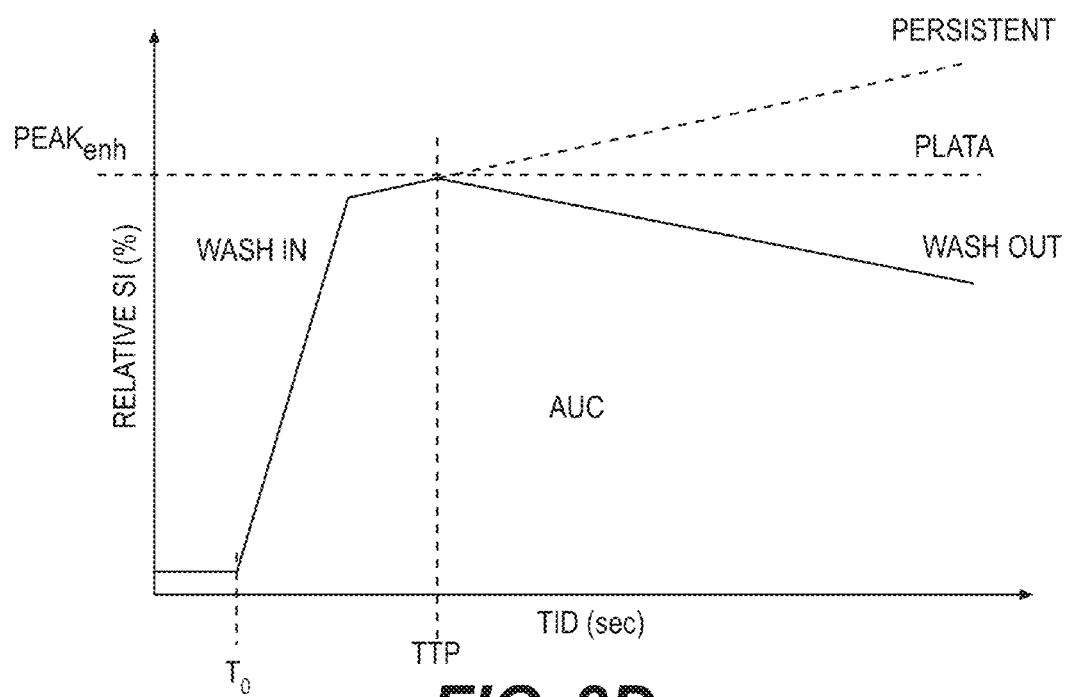
FIG. 8D shows relative SI (%) vs. lime (sec).

Furthermore it is illustrated infra the pharmacokinetic biomarkers that are connected to the DCE-MRI analysis. These biomarkers are: 6: The plasma volume ($v_p$=plasma volume; 7: The volume transfer constant 1 ($K^{trans}$=Volume transfer coefficient from the plasma volume $v_p$ to the extracellular extravascular space $v_e$); 8: The extracellular extravascular volume ($v_e$=extracellular extravascular space); 9: the volume transfer constant 2 ($k_{ep}$=volume transfer coefficient from the extracellular extravascular space $v_e$ to the plasma volume $v_p$). The pharmacokinetic biomarker being connected to the DSC-MRI analysis is: 10: The transversal relaxivity rate R2*(Transversal relaxation rate R2'). The relevant parameters are illustrated in the FIGS. 8D and 2N.

Statistical Method

The Mann-Whitney U-test is used for Identifying which biomarkers display a significant difference in the value between two defined groups (binary response variable) e.g. malign and benign breast lesions. It is recommended that a significance level between 0.05-0.01 is used. Biomarkers demonstrating a significant difference between the groups is further evaluated by using diagnostic tests, ROC-analysis (Receiver Operator Characteristics curve statistics) respectively. The diagnostic tests are evaluated on the basis of a binary indicator, e.g. the presence of absence of a condition of interest, e.g. normal or abnormal breast pathologies. From the ROC analysis there are estimated three different outputs that all to a different degree is a measurement for the diagnostic efficacy of the image-diagnostic method that is being used. These are:

I. The area under the ROC curve—represents the diagnostic accuracy of the diagnostic method II. Senstivity—The ratio of positive results that are correctly identified by the diagnostic method. The sensitivity represents the probability for a correct diagnosis of a positive disease condition, e.g. malignity.

III. Specifcity—The ratio of negative results that are correctly identified by he predictive analysis. The specificity represents the probability for a correct diagnosis of a negative disease condition, in this case benignity.

Based on the Mann-Whitney U-test and the ROC analysis the most predictive biomarkers with respect to differentiating between two different groups, e.g. positive or negative disease condition are identified. These are included in a multiple logistic regression making it possible to predict the probability for a given condition arising in relation to multiple prognostic biomarkers. This means that it is possible to distinguish those patients that probably or improbably possess this condition, and in this way assist as a diagnostic subvention.

In this method there is used a model assembly strategy a Wald reverse step-wise biomarker elimination. The first step in this strategy is to include all biomarkers with significant predictive ability. The information from the respective regression coefficients of the biomarkers is then used to estimate a "z-value" from Wald statistics. Based on this test the biomarker having the least significant effect on the response is eliminated, and a new model is adjusted without the eliminated biomarker. To avoid possible errors as a consequence of the Wald statistics, the eliminated biomarker is also tested by evaluating the deviance between the two models (deviance test). This process is concluded when the deviance test establishes the elimination of a significant covariant.

The inclusion of too many biomarkers in the model will result in an over-adjustment, by the statistical regression model describing random noise instead of basic relations. To avoid this problem there is used an information criteria punishing the inclusion of a biomarker in the logistic model is used. For this task the Akaike information criteria (AIC) may be used in every model selection. This information criteria attempts at any time to balance the conflict-ridden requirements concerning the accuracy of the model (adjustment) and simplicity (a low number of included biomarkers). However, AIC will here be used for ranging different model sections based on their double criteria concerning adjustment and simplicity. The model selection with the lowest estimated AIC is preferred. This process results in the determination of the optimal regression model (including the most descriptive biomarkers) with respect to the observed conditions.

Preliminary Result

From the study "Dynamic MR-imaging of patients with breast cancer: The establishment and comparison of different analytical methods for tissue perfusion and capillary permeability" the diagnostic efficacy of 10 different biomarkers is evaluated:

1: $K^{trans}$
2: $k_{ep}$
3: $v_e$
4: $v_p$
5: Wash-in
6: Wash-out
7: AUC
8: TTP
9: $peak_{enh}$
10: $R2^*\text{-}peak_{enh}$ with respect to two different binary grouping strategies:
1. Malign vs. benign breast lesions
2. Invasive ductal carcinoma (IDC) vs. fibroadenoma (FA)

In grouping strategy 1 the preliminary result shows that the biomarkers TTP, $R2^*\text{-}peak_{enh}$ and the normalized $K^{trans}$ are the most predictive biomarkers concerning differing between malign and benign breast lesions. The multiple regression with these biomarkers included display a good diagnostic accuracy with an area under the ROC-curve of 0.96, and a sensitivity and specificity of 90% and 94%, respectively.

In grouping strategy 2 the preliminary results show that the biomarkers TTP, $R2^*\text{-}peak_{enh}$ and the normalized $K^{trans}$ are the most predictive biomarkers with respect to distinguishing between IDC and FA. The multiple regression with these biomarkers included display an excellent diagnostic accuracy with an area under the ROC-curve equal to 1. This corresponds with sensitivity and specificity of 100% and 100%, respectively, representing a correct differentiation between all of the IDC and FA.

Diffusion Weighed Imaging (DWI)

Some embodiments further encompass the use of diffusion weighed imaging. In particular, DWI parameters related to tissue diffusion may act as an adjunct to the parameters obtained from the kinetic dynamic analysis. Parameters related to tissue diffusion may yield valuable and distinct information regarding pathology and may thus contribute to an improved sensitivity and specificity in the assessment of cancer tissue.

REFERENCES

1. Bloch, F. et al., *Nuclear Induction*. Phys Rev, vol. 70, pages 460-474, 1946.
2. Purcell, E. M. et al., *Resonance absorption by nuclear magnetic moments in a solid*, Phys Rev, vol. 69, page 37, 1946.
3. Proctor, W. G., et al., *The dependence of a nuclear magnetic resonance frequency upon chemical Compound*, Phy. Rev, vol. 77, page 717, 1950.
4. Damadian, R., *Tumor detection by nuclear magnetic resonance*. Science, vol. 171, pages 1151-1153, 1971.
5. Garroway, A. N. et al., *Image formation in NMR by a selective irradiative process*, J. Phys. C, vol. 7, pages L457-L462, 1974.
6. Kumar, D et al., *NMR Fourier Zeugmatography*, J Magn Res, vol. 18, side 69-83, 1975.
7. Mansfield, P., Multi-planar image formation using NMR spin echoes, J Phys C, Solid state phys., vol. 10, pages L55-L58, 1977.
8. Viaardingerbroek, M., et al., Magnetic Resonance Imaging. 2nd ed., Berlin, Springer, 1999.
9. Haacke, E. M., Magnetic resonance Imaging: Physical principles and sequence design, New York, Wiley, 1999
10. Bjørnerud, A., The physics of magnetic resonance imaging, Kompendium for FYS-KJM 4740, Universitetet i Osio, 2008.
11. Padhani, A. R. et al., Dynamic contrast-enhanced MRI studies in human tumours, Br J Radiol, vol. 72, sides 427-431, 1999.
12. Padhani A. R. et al. Dynamic contrast-enhanced MRI in clinical oncology: Current status and future directions. J Magn Res, 16, page 407-422, 2002
13. Kuhl, C. K. et al., Breast neoplasms: T2* susceptibility-contrast, first-pass perfusion MR imaging. Radiology, vol. 202, pages 87-95, 1997a.
14. Kuhl, C. K. et al., Do T2-weighted pulse sequences help with the differential diagnosis of enhancing lesions in dynamic breast MRI?, J Magn Res, vol. 9, pages-196, 1999.
15. Kuhl, C. K. et al., Dynamic breast MR imaging: Are signal intensity time course data useful for differential diognosis of enhancing lesions?, Radiology, vol. 211, pages 101-110, 1999.
16. Orel, S. G. et al., MR imaging of the breast for the detection, diagnosis, and staging of breast cancer, Radiology, vol. 220, pages 13-30, 2001.
17. Kvistad et al., Differentiating benign and malignant breast lesions with T2*-weighted first pass perfusion imaging, Acta Radiology, vol. 40, pages 45-51, 1999
18. Knopp et al., Pathophysiologic basis of contrast enhancement in breast tumors, J Magn Res, vol. 10(3), pages 260-266, 1999.
19. Bhujwaila, Z. M. et al., Tumor angiogenesis, vascularization, and contrast-enhanced magnetic resonance imaging, Top Magn Res Imaging, vol. 10(2), pages 92-103, 1999.
20. Brix, G. et al., Pharmacokinetic parameters in CNS Gd-DTPA enhanced MR imaging, J Comp Assist Tomogr, vol. 15(4), pages 621-628, 1991.
21. Buckley, D. L. et al., *Quantitative analysis of multi-slice Gd-DTPA enhanced dynamic MR images using on automated simplex minimization procedure*, Magn Res Med, vol. 32(5), pages 646.651, 1994.
22. Hoffmann, U. et al., Pharmacokinetic mapping of the breast: a new method for dynamic MR mammography, Magn Res Med, vol. 33(4), pages 506-514, 1995.
23. Villringer, A. et al., Dynamic imaging with lanthanide chelates in normal brain: contrast due to magnetic-susceptibility effects, Magn Res Med, vol. 6(2), pages 164-174, 1988.
24. Kassner, A. et al., Abnormalities of the contrast re-circulation phase in cerebral tumors demonstrated using dynamic susceptibility contrast-enhanced imaging: a possible marker of vascular tortuosity, J Magn Res Imaging, vol. 11(2), pages 103-113, 2000.
25. Tofts, P. S. et al., Estimating kinetic parameters from dynamic contrast-enhanced T (1)-weighted MRI of a diffusable tracer: standardized quantities and symbols, J Magn Res Imaging, vol. 10(3), pages 223-232, 1999.
26. Tofts, P. S. et al., G, Measurement of the blood-brain barrier permeability and leakage space using dynamic MR imaging. 1. Fundamental concepts, Magn Res Med, vol. 17(2), pages 357-367, 1991.
27. Buckley, D. L, Uncertainty in the analysis of tracer kinetics using dynamic contrast-enhanced T1-weighted MRI, Magn Res Med, vol. 47(3), pages 601-606, 2002.

28. Bjørnerud, A., Analyse av diagnostisk, dynamisk bildeinformasjon: Tracer-kinetikk, Forelesningsnotater for FYS-4780, Universitetet i Oslo, 2009.
29. Jackson, A. et al., Dynamic contrast-enhanced magnetic resonance imaging in oncology. Medical Radiology: Diagnostic imaging and radiation oncology, Berlin, Springer, 2005.
30. Reeder, S. B, et al., Magnetic resonance imaging clinics: Clinical Application of MR diffusion and perfusion imaging, vol. 12, No. 2, Pennsylvania, Saunders, 2009.
31. Evelhoch, J. L., Key factors in the acquisition of contrast kinetic data for oncology, J Magn Res imaging, vol. 10(3), pages 254-259, 1999.
32. Moate, P. J. et al., A modified logistic model to describe gadolinium kinetics in breast tumors. J Magn Res imaging, vol. 22(4), pages 467-473, 2004.
33. Szabo, B. K. et al., Dynamic MR imaging of the breast: Analysis of kinetic and morphologic diagnostic criteria, Acta Radiology, vol. 44(4), pages 379-386, 2003.
34. Kaiser, W. A, et al., *MR imaging of the breast: fast imaging sequences with and without Gd-DTPA. Preliminary observations*, Radiology, vol. 170, pages 681-686, 1989.
35. Buadu, L D. et al., Breast lesions: correlation of contrast medium enhancement patterns on MR images with histopathologic findings and tumor anglogenesis, Radiology, vol. 200, pages 639-649, 1996.
36. Ikeda, O. et al., Characterization of breast masses by dynamic enhanced MR imaging. A logistic regression analysis, Acta Radiology, vol. 40(6), pages 585-592, 1999.
37. Liao, Y. P. et al., Assessment of physiological parameters estimated by DCE-MRI with delayed or dispersed arterial input function, Magn Res Med, vol. 15, pages 1435, 2007.
38. Fisher R. A., Theory of statistical estimation, Proceedings of Cambridge Philosophical Society, vol. 22, pages 700-725, 1925.
39. Green, D. M. et al., Signal detection theory and psychophysics, New York, Wiley, 1966.
40. Shiraishl, J. et al., Experimental design and data analysis in receiver operating characteristic studies: Lessons learned from reports in radiology from 1997 to 2006, Radiology, vol. 253, pages 822-830, 2009.
41. Gatsonis, C. A., Receiver operating characteristic analysis for the evaluation of diagnosis and prediction, Radiology, vol. 253, pages 593-596, 2009.
42. Fawcett, T., An introduction to ROC analysis. Pattern Recognition Letters, vol. 27, pages 861-874, 2006.
43. Bølviken, E. et al., Lectures in applied statistics, Kompendium for STK4900, Universitetet i Oslo, 1994.
44. Borgan, Ø., Lecture notes in STK4900, Forelesningsnotater for STK4900, Universitetet i Oslo, 2009.
45. Altman, D. G., Practical statistics for medical research, First edition, London, Chapman & Hall, 1991.
46. Brix, G. et al., Microcirculatlon and microvasculature in breast tumors: pharmacokinetic analysis of dynamic MR image series, Magn Res Med, vol. 52(2), pages 420-429, 2004.
47. Miyati, T. et al., Dual dynamic contrast-enhanced MR imaging, J Magn Res imaging, vol. 7(1), pages 230-235, 1997.
48. Barbler, E. L. et al., *A model of the dual effect of gadopentetate dimeglumine on dynamic brain MR images, J Magn Res Imaging, vol.* 10, pages 242-253, 1999.
49. Moon, M. et al., Dynamic contrast-enhanced breast MR imaging, Magn Res Imaging Clinics of North America, vol. 17(2), pages 351-362, 2009.
50. O'Connor, J. P. B. et al., DCE-MRI biomarkers in the clinical evaluation of antiangiogenic and vascular disrupting agents, British J of Cancer, vol. 96(2), pages 189-195, 2007.
51. Leach, M. O. et al., The assessment of antiangiogenic and antivascular therapies in early-stage clinical trials using magnetic resonance imaging: issues and recommendations, British J of Cancer, vol. 92(2), pages 1599-1610, 2005.
52. Walker, S., S. et al., Evaluation of response to treatment using dce-mri: the relationship between initial area under the gadolinium curve (laugc) and quantitative pharmacokinetic analysis, Phys Med Biol, vol. 51(14), pages 3593-3602, 2006.
53. Kvistad, K. A. et al., Breast Lesions: Evaluation with dynamic contrast-enhanced T1-weighted MR imaging and with T2*-weighted first-pass perfusion MR imaging, Radiology, vol. 216, pages 545-553, 2000.
54. Mussurakls, S. et al., Dynamic MR imaging of the breast combined with analysis of contrast agent kinetics in the differentiation of primary breast tumours, Clinical Rad, vol. 52(7), pages 516-526, 1997.
55. Furman-Haran, E. et al., Magnetic resonance imaging reveals functional diversity of the vasculature in benign and malignant breast lesions, American Cancer Society, vol. 104(4), pages 708-718, 2005.
56. Yankeelov, T. E. et al., Quantitative pharmacokinetic analysis of DCE-MRI data without an arterial Input function: a reference region model, Magn Res imaging, vol. 23(4), pages 519-529, 2005.
57. Pintaske, J. et al., Relaxivity of gadopentetate dimeglumine (magnevist), gadobutrol (gadovist), and gadobenate dimeglumine (muitlhance) in human blood plasma at 0.2, 1.5 and 3 tesla, Invest Radiol, vol. 41(3), pages 213-221, 2006.
58. Haacke, E. M. et al., Fast MR imaging: techniques and clinical applications, American J of Roentgenology, vol. 155, pages 951-964, 1990.
59. Haase, A. et al., FLASH imaging. Rapid NMR imaging using low flip-angle pulses, J Magn Res, vol. 67(2), pages 258-266, 1986.
60. Emblem, K. E., Glioma grading by using histogram analysis of blood volume heterogeneity from MR-derived cerebral blood volume maps, Radiology, vol. 247(3), pages 808-817, 2008.
61. World Health Organization, International Agency for Research on Cancer, World cancer report 2008, 2008.
62. Institute of Population-based Cancer Research, Cancer Registry of Norway, Cancer in Norway 2008, 2008.
63. Foikman, J., *Tumor anglogenesis: therapeutic implications*, N Engl J Med, vol. 285, pages 1182-1186, 1971.
64. Kuhl, C. K. et al., Dynamic bilateral contrast-enhanced MR imaging of the breast: Tradeoff between spatial and temporal resolution, Radiology, vol. 236, pages 789-800, 2005.
65. Veltman, J et al., Contrast-enhanced magnetic resonance imaging of the breast: the value of pharmacokinetic parameters derived from fast dynamic imaging during initial enhancement in classifying lesions, Eur Radiol, vol. 18(6), pages 1123-1133, 2008.
66. Kuhl, C. K. et al., Healthy premenopausal breast parenchyma in dynamic contrast-enhanced MR imaging of the breast: Normal contrast medium enhancement and cyclical-phase dependency, Radiology, vol. 203, pages 137-144, 1997.

67. Mouridsen et al., Automatic selection of arterial input function using cluster analysis, Magn Res Med, vol. 55(3), pages 524-531, 2006.

What is claimed:

1. A method for imaging tumors in soft tissues, said method comprising:
    (a) administering an intravenous injection of contrast agent to a subject having a soft tissue tumor;
    (b) applying to the soft tissue tumor, with a magnetic resonance imaging (MRI) machine, two alternating dynamic magnetic resonance imaging (MRI) pulse sequences prior to, during, and after administration of the contrast agent,
        wherein one of said pulse sequences optimized for high spatial resolution and the other pulse sequence is optimized for high temporal resolution, and
        wherein the high temporal resolution sequence further comprises a double-echo collection for both dynamic contrast enhanced (DCE) magnetic resonance imaging and dynamic susceptibility contrast (DSC) enhanced magnetic resonance imaging; and
    (c) acquiring:
        (i) a T1-weighted MRI image data set for the soft tissue tumor from the high spatial resolution sequence,
        (ii) a T1-weighted MRI image data set for the soft tissue tumor from the dynamic contrast enhanced (DCE) echo of the high temporal resolution sequence, and
        (iii) a T2*-weighted MRI image data set for the soft tissue tumor from the dynamic susceptibility contrast enhanced (DSC) echo of the high temporal resolution sequence.

2. The method of claim 1 further comprising:
    (d) calculating:
        (i) descriptive biomarkers from the DCE high temporal T1-weighted image data set;
        (ii) quantitative pharmacokinetic biomarkers from the DCE high temporal T1-weighted image data set; and
        (iii) quantitative pharmacokinetic biomarkers from the DSC high temporal T2*-weighted image data set.

3. The method of claim 2, wherein the descriptive biomarkers are chosen from wash-in rate, wash-out rate, time to peak (TTP), peak enhancement ($peak_{enh}$), and area under the curve (AUC),
    wherein the quantitative pharmacokinetic biomarkers from the DCE high temporal T1-weighted image data set are chosen from $K_{trans}$, $k_{ep}$, $v_e$, and $v_p$, and
    wherein the quantitative pharmacokinetic biomarker from the DSC high temporal T2*-weighted image data set is absolute peak change in R2* ($R2^*\text{-}peak_{enh}$).

4. The method of claim 3, further comprising normalizing the calculated quantitative pharmacokinetic biomarkers from the DCE high temporal T1-weighted image data set to corresponding values collected from non-tumor parenchymal soft tissue.

5. The method of claim 1, wherein the soft tissue is breast tissue.

6. The method of claim 1, wherein the high temporal resolution is less than 3 seconds.

7. A method for distinguishing between benign and malignant breast tumors, said method comprising:
    (a) performing the method of claim 4;
    (b) comparing the calculated biomarkers with corresponding measurements from known benign breast tumors; and
    (c) identifying the tumor as malignant if:
        (i) the calculated time to peak (UP) is shorter than the corresponding TTP for known benign tumors;
        (ii) the calculated normalized $K^{trans}$ is higher than the corresponding normalized $K^{trans}$ for known benign tumors; and/or
        (iii) the calculated $R2^*\text{-}peak_{enh}$ is higher than the corresponding $R2^*\text{-}peak_{enh}$ for known benign tumors,
    wherein said method is at least 90% accurate for distinguishing between benign and malignant breast tumors.

8. The method of claim 7, wherein the high temporal resolution is less than 3 seconds.

9. The method of claim 7, wherein the benign tumor is a fibroadenoma (FA) and the malignant tumor is an invasive ductal carcinoma (IDC), and
    wherein said method is at least 98% accurate for distinguishing between the FA and IDC breast tumors.

10. The method of claim 9, wherein the high temporal resolution is less than 3 seconds.

* * * * *